US011622948B2

(12) United States Patent
McGowan et al.

(10) Patent No.: US 11,622,948 B2
(45) Date of Patent: Apr. 11, 2023

(54) BIOMARKERS FOR EFFICACY OF PROPHYLACTIC TREATMENTS AGAINST STRESS-INDUCED AFFECTIVE DISORDERS

(71) Applicants: The Trustees of Columbia University in the City of New York, New York, NY (US); Berg LLC, Framingham, MA (US); THE RESEARCH FOUNDATION FOR MENTAL HYGIENE, INC., Menands, NY (US)

(72) Inventors: Josephine Cecelia McGowan, New York, NY (US); Christine Ann Denny, Ho-Ho-Kus, NJ (US); Michael Kiebish, Framingham, MA (US)

(73) Assignees: The Trustees of Columbia University in the City of New York, New York, NY (US); Berg LLC, Framingham, MA (US); The Research Foundation for Mental Hygiene, Inc., Menands, NY (US)

( * ) Notice: Subject to any disclaimer, the term of this patent is extended or adjusted under 35 U.S.C. 154(b) by 11 days.

(21) Appl. No.: 16/761,548

(22) PCT Filed: Nov. 8, 2018

(86) PCT No.: PCT/US2018/059834
§ 371 (c)(1),
(2) Date: May 5, 2020

(87) PCT Pub. No.: WO2019/094596
PCT Pub. Date: May 16, 2019

(65) Prior Publication Data
US 2020/0261379 A1      Aug. 20, 2020

Related U.S. Application Data

(60) Provisional application No. 62/583,734, filed on Nov. 9, 2017.

(51) Int. Cl.
| | | |
|---|---|---|
| *A61K 31/135* | (2006.01) | |
| *A61P 25/22* | (2006.01) | |
| *A61P 25/24* | (2006.01) | |
| *A61K 9/00* | (2006.01) | |

(52) U.S. Cl.
CPC .......... *A61K 31/135* (2013.01); *A61K 9/0019* (2013.01); *A61K 9/0043* (2013.01); *A61K 9/0053* (2013.01); *A61P 25/22* (2018.01); *A61P 25/24* (2018.01); *G01N 2800/30* (2013.01); *G01N 2800/52* (2013.01)

(58) Field of Classification Search
CPC ............................ A61K 31/138; A61K 31/135
See application file for complete search history.

(56) References Cited

U.S. PATENT DOCUMENTS

| | | |
|---|---|---|
| 3,254,124 A | 5/1966 | Stevens |
| 6,727,231 B1 | 4/2004 | Page et al. |
| 8,785,500 B2 | 7/2014 | Charney et al. |
| 9,801,865 B2 | 10/2017 | Moran |
| 11,110,070 B2* | 9/2021 | Brachman .......... A61K 31/4245 |
| 2004/0067963 A1 | 4/2004 | Shapira et al. |
| 2004/0138298 A1 | 7/2004 | Mermelstein et al. |
| 2006/0116341 A1 | 6/2006 | Compan |
| 2009/0105222 A1 | 4/2009 | Kranzler et al. |
| 2009/0170899 A1 | 7/2009 | Debonnel et al. |
| 2011/0213219 A1 | 9/2011 | Bilello |
| 2011/0218213 A1 | 9/2011 | Royster, Jr. |
| 2013/0236573 A1 | 9/2013 | Singh et al. |
| 2014/0057988 A1 | 2/2014 | Weg |
| 2015/0342947 A1 | 12/2015 | Pollard et al. |
| 2016/0067196 A1 | 3/2016 | Charney et al. |
| 2016/0313355 A1 | 10/2016 | Aerts et al. |
| 2017/0007618 A1 | 1/2017 | Goosens et al. |
| 2017/0049780 A1 | 2/2017 | Wainer et al. |
| 2018/0325844 A1* | 11/2018 | Brachman ............ A61K 31/517 |
| 2019/0046506 A1 | 2/2019 | Friedhoff et al. |
| 2019/0046554 A1 | 2/2019 | Deisseroth et al. |
| 2019/0092809 A1 | 3/2019 | Runyon et al. |

FOREIGN PATENT DOCUMENTS

| | | |
|---|---|---|
| JP | 2012013415 A | 1/2012 |
| WO | 2003020275 A1 | 3/2003 |
| WO | 2008118785 A2 | 10/2008 |
| WO | 2013056229 A1 | 4/2013 |
| WO | 2013149102 A1 | 10/2013 |
| WO | 2014020155 A1 | 2/2014 |
| WO | 2014045023 A1 | 3/2014 |
| WO | 2014169272 A1 | 10/2014 |
| WO | 2014171826 A1 | 10/2014 |
| WO | 2015037248 A1 | 3/2015 |
| WO | 2015/121166 A1 | 8/2015 |
| WO | 2015121166 A1 | 8/2015 |
| WO | 2016025581 A1 | 2/2016 |
| WO | 2016/047677 A1 | 3/2016 |
| WO | 2016047677 A1 | 3/2016 |
| WO | 2017082103 A1 | 10/2016 |
| WO | 2017003935 A1 | 1/2017 |
| WO | 2017/082103 A1 | 5/2017 |
| WO | 2017/087691 A1 | 5/2017 |
| WO | 2018109935 A1 | 6/2018 |
| WO | 2018222781 A2 | 12/2018 |

OTHER PUBLICATIONS

McNulty et al. CAS: 158: 262504, 2012.*
Weckmann et al. Transl Psychiatry, 2014, 4, e481.*
Abdallah, C.G., Jiang, L., De Feyter, H.M., Fasula, M., Krystal, J.H., Rothman, D.L., Mason, G.F., Sanacora, G., 2014. Glutamate metabolism in major depressive disorder. The American journal of psychiatry 171(12), 1320-1327.

(Continued)

*Primary Examiner* — Rei Tsang Shiao
(74) *Attorney, Agent, or Firm* — Potomac Law Group, PLLC

(57) ABSTRACT

Biomarkers for assessing the efficacy of prophylactic treatments of stress-induced affective disorders are provided.

10 Claims, 53 Drawing Sheets

(56) References Cited

OTHER PUBLICATIONS

Amat, J., Dolzani, S.D., Tilden, S., Christianson, J.P., Kubala, K.H., Bartholomay, K., Sperr, K., Ciancio, N., Watkins, L. R., Maier, S.F., 2016. Previous Ketamine Produces an Enduring Blockade of Neurochemical and Behavioral Effects of Uncontrollable Stress. The Journal of neuroscience : the official journal of the Society for Neuroscience 36(1), 153-161.

Averill, L.A., Purohit, P., Averill, C.L., Boesl, M.A., Krystal, J.H., Abdallah, C.G., 2016. Glutamate dysregulation and glutamatergic therapeutics for PTSD: Evidence from human studies. Neuroscience letters.

Bartoli, F., Carra, G., Crocamo, C., Carretta, D., Clerici, M., 2013. Metabolic syndrome in people suffering from posttraumatic stress disorder: a systematic review and metaanalysis. Metabolic syndrome and related disorders 11(5), 301-308.

Diazgranados, N., Ibrahim, L., Brutsche, N.E., Newberg, A., Kronstein, P., Khalife, S., Kammerer, W.A., Quezado, Z., Luckenbaugh, D.A., Salvadore, G., Machado-Vieira, R., Manji, H.K., Zarate, C.A., Jr., 2010. A randomized add-on trial of an N-methyl-Daspartate antagonist in treatment-resistant bipolar depression. Archives of general psychiatry 67(8), 793-802.

Drew, M.R., Denny, C.A., Hen, R., 2010. Arrest of adult hippocampal neurogenesis in mice impairs single—but not multiple trial contextual fear conditioning. Behavioral neuroscience 124(4), 446-454.

Feder, A., Parides, M.K., Murrough, J.W., Perez, A.M., Morgan, J.E., Saxena, S., Kirkwood, K., Aan Het Rot, M., Lapidus, K.A., Wan, L.B., Iosifescu, D., Charney, D.S., 2014. Efficacy of intravenous ketamine for treatment of chronic posttraumatic stress disorder: a randomized clinical trial. JAMA psychiatry 71(6), 681-688.

Hasler, G., van der Veen, J.W., Tumonis, T., Meyers, N., Shen, J., Drevets, W.C., 2007. Reduced prefrontal glutamate/glutamine and gamma-aminobutyric acid levels in major depression determined using proton magnetic resonance spectroscopy. Archives of general psychiatry 64(2), 193-200.

Howlett JR, Stein MB (2016). Prevention of Trauma and Stressor-Related Disorders: A Review. Neuropsychopharmacology: official publication of the American College of Neuropsychopharmacology 41(1): 357-369.

Ionescu, D.F., Luckenbaugh, D.A., Niciu, M.J., Richards, E.M., Zarate, C.A., Jr., 2015. A single infusion of ketamine improves depression scores in patients with anxious bipolar depression. Bipolar disorders 17(4), 438-443.

Jinnah, H.A., Sabina, R.L., Van Den Berghe, G., 2013. Metabolic disorders of purine metabolism affecting the nervous system. Handbook of clinical neurology 113, 1827-1836.

Johnson, C.H., Ivanisevic, J., Siuzdak, G., 2016. Metabolomics: beyond biomarkers and towards mechanisms. Nature reviews. Molecular cell biology 17(7), 451-459.

Knoll AT, Meloni EG, Thomas JB, Carroll FI, Carlezon WA, Jr. (2007). Anxiolytic-like effects of kappa-opioid receptor antagonists in models of unlearned and learned fear in rats. The Journal of pharmacology and experimental therapeutics 323(3): 838-845.

Martinac, M., Pehar, D., Karlovic, D., Babic, D., Marcinko, D., Jakovljevic, M., 2014. Metabolic syndrome, activity of the hypothalamic-pituitary-adrenal axis and inflammatory mediators in depressive disorder. Acta clinica Croatica 53(1), 55-71.

McGowan, J.C., LaGamma, C.T., Lim, S.C., Tsitsiklis, M., Neria, Y., Brachman, R.A., Denny, C.A., 2017. Prophylactic Ketamine Attenuates Learned Fear. Neuropsychopharmacology : official publication of the American College of Neuropsychopharmacology.

Meyerhoff, D.J., Mon, A., Metzler, T., Neylan, T.C., 2014. Cortical gamma-aminobutyric acid and glutamate in posttraumatic stress disorder and their relationships to selfreported sleep quality. Sleep 37(5), 893-900.

Micheli, V., Camici, M., Tozzi, M.G., Ipata, P.L., Sestini, S., Bertelli, M., Pompucci, G., 2011. Neurological disorders of purine and pyrimidine metabolism. Current topics in medicinal chemistry 11(8), 923-947.

Miller, D.B., O'Callaghan, J.P., 2013. Personalized medicine in major depressive disorder—opportunities and pitfalls. Metabolism: clinical and experimental 62 Suppl 1, S34-39.

Murrough, J.W., Soleimani, L., DeWilde, K.E., Collins, K.A., Lapidus, K.A., Iacoviello, B.M., Lener, M., Kautz, M., Kim, J., Stern, J.B., Price, R.B., Perez, A.M., Brallier, J.W., Rodriguez, G.J., Goodman, W.K., Iosifescu, D.V., Charney, D. S., 2015. Ketamine for rapid reduction of suicidal ideation: a randomized controlled trial. Psychological medicine 45(16), 3571-3580.

Nelson, J.C., 2012. The evolving story of folate in depression and the therapeutic potential of l-methylfolate. The American journal of psychiatry 169(12), 1223-1225.

Pan, L., McKain, B.W., Madan-Khetarpal, S., McGuire, M., Diler, R.S., Perel, J.M., Vockley, J., Brent, D.A., 2011. GTP-cyclohydrolase deficiency responsive to sapropterin and 5-HTP supplementation: relief of treatment-refractory depression and suicidal behaviour. BMJ case reports 2011.

Pan, L., Vockley, J., 2013. Neuropsychiatric Symptoms in Inborn Errors of Metabolism: Incorporation of Genomic and Metabolomic Analysis into Therapeutics and Prevention. Current genetic medicine reports 1(1), 65-70.

Pan, L.A., Martin, P., Zimmer, T., Segreti, A.M., Kassiff, S., McKain, B.W., Baca, C.A., Rengasamy, M., Hyland, K., Walano, N., Steinfeld, R., Hughes, M., Dobrowolski, S.K., Pasquino, M., Diler, R., Perel, J., Finegold, D.N., Peters, D. G., Naviaux, R.K., Brent, D.A., Vockley, J., 2017. Neurometabolic Disorders: Potentially Treatable Abnormalities in Patients With Treatment—Refractory Depression and Suicidal Behavior. The American journal of psychiatry 174(1), 42-50.

Pan, X., Zeng, X., Hong, J., Yuan, C., Cui, L., Ma, J., Chang, Y., Hua, X., 2016. Effects of Ketamine on Metabolomics of Serum and Urine in Cynomolgus Macaques (Macaca fascicularis). Journal of the American Association for Laboratory Animal Science: JAALAS 55(5), 558-564.

Park, D.I., Doumes, C., Sillaber, I., Uhr, M., Asara, J.M., Gassen, N.C., Rein, T., Ising, M., Webhofer, C., Filiou, M.D., Muller, M.B., Turck, C.W., 2016. Purine and pyrimidine metabolism: Convergent evidence on chronic antidepressant treatment response in mice and humans. Scientific reports 6, 35317.

Pehrson, A.L., Sanchez, C., 2015. Altered gamma-aminobutyric acid neurotransmission in major depressive disorder: a critical review of the supporting evidence and the influence of serotonergic antidepressants. Drug design, development and therapy 9, 603-624.

Price, R.B., Nock, M.K., Charney, D.S., Mathew, S.J., 2009. Effects of intravenous ketamine on explicit and implicit measures of suicidality in treatment-resistant depression. Biological psychiatry 66(5), 522-526.

Ramaekers, V., Sequeira, J.M., Quadros, E.V., 2013. Clinical recognition and aspects of the cerebral folate deficiency syndromes. Clinical chemistry and laboratory medicine 51(3), 497-511.

Rotroff, D.M., Corum, D.G., Motsinger-Reif, A., Fiehn, O., Bottrel, N., Drevets, W.C., Singh, J., Salvadore, G., Kaddurah-Daouk, R., 2016. Metabolomic signatures of drug response phenotypes for ketamine and esketamine in subjects with refractory major depressive disorder: new mechanistic insights for rapid acting antidepressants. Translational psychiatry 6(9), e894.

Serchov, T., Clement, H.W., Schwarz, M.K., Iasevoli, F., Tosh, D.K., Idzko, M., Jacobson, K.A., de Bartolomeis, A., Normann, C., Biber, K., van Calker, D., 2015. Increased Signaling via Adenosine A1 Receptors, Sleep Deprivation, Imipramine, and Ketamine Inhibit Depressive-like Behavior via Induction of Homer1a. Neuron 87(3), 549-562.

Soumier, A., Carter, R.M., Schoenfeld, T.J., Cameron, H.A., 2016. New Hippocampal Neurons Mature Rapidly in Response to Ketamine but are Not Required for Its Acute Antidepressant Effects on Neophagia in Rats. eNeuro 3(2).

Van't Veer A, Carlezon WA, Jr. (2013). Role of kappa-opioid receptors in stress and anxiety-related behavior. Psychopharmacology 229(3): 435-452.

(56) References Cited

OTHER PUBLICATIONS

Weckmann, K., Labermaier, C., Asara, J.M., Muller, M.B., Turck, C.W., 2014. Timedependent metabolomic profiling of Ketamine drug action reveals hippocampal pathway alterations and biomarker candidates. Translational psychiatry 4, e481.
Zarate, C.A., Jr., Brutsche, N.E., Ibrahim, L., Franco-Chaves, J., Diazgranados, N., Cravchik, A., Selter, J., Marquardt, C.A., Liberty, V., Luckenbaugh, D.A., 2012. Replication of ketamine's antidepressant efficacy in bipolar depression: a randomized controlled add-on trial. Biological psychiatry 71(11), 939-946.
Zarate, C.A., Jr., Singh, J.B., Carlson, P.J., Brutsche, N.E., Ameli, R., Luckenbaugh, D.A., Charney, D.S., Manji, H.K., 2006. A randomized trial of an N-methyl-D-aspartate antagonist in treatment-resistant major depression. Archives of general psychiatry 63(8), 856-864.
Zheng, P., Wang, Y., Chen, L., Yang, D., Meng, H., Zhou, D., Zhong, J., Lei, Y., Melgiri, N.D., Xie, P., 2013b. Identification and validation of urinary metabolite biomarkers for major depressive disorder. Molecular & cellular proteomics: MCP 12(1), 207-214.
International Search Report and Written Opinion of corresponding International Application PCT/US2018/059834, dated Feb. 25, 2019.
Huang et al., "New treatment strategies of depression: based on mechanisms related to neuroplasticity": Neural Plast. Apr. 2017. Article ID 4605971.
Brachman et al. "Ketamine as a prophylactic against stress-induced depressive-like behavior": Biol Psychiatry. 2016, 79(9): pp. 776-786.
Khalid SA.: "Treatment-resistant depression: therapeutic trends, challenges, and future directions": Patient Prefer Adherence. 2012, 6: pp. 369-388.
Cieslak et al., "The roles of purinergic signaling in psychiatric disorders": Acta Biochim Pol. 2016, 63(1): pp. 1-9.
Yang et al.: "Potential metabolite markers of schizophrenia": Mol Psychiatry, vol. 18 / Issue 1, pp. 67-78, 2011.
Cattaneo et al.: "Absolute measurements of macrophage migration inhibitory factor and interleukin-1-β mRNA levels accurately predict treatment response in depressed patients": Int J Neuropsychopharmacol, 2016, vol. 19 / Issue 10: 1-10.
Watanabe et al.: "Gene expression-based biological test for major depressive disorder: an advanced study", Neuropsychiatr Dis Treat, vol. 13, pp. 535-541, 2017.
Kaddurah-Daouk et al: "Pretreatment metabotype as a predictor of response to sertraline or placebo in depressed outpatients: a proof of concept", Transl Psychiatry, vol. 1, No. e26, 2011.
Redei et al: "Blood transcriptomic biomarkers in adult primary care patients with major depressive disorder undergoing cognitive behavioral therapy", Transl Psychiatry, vol. 4, No. e442, 2014.
Tabak et al.: "Interaction of CD38 variant and chronic interpersonal stress prospectively predicts social anxiety and depression symptoms over six years", Clin Psychol Sci, vol. 1 / Issue 4, pp. 17-27, 2016.
Jha et al.: "Can C-reactive protein inform antidepressant medication selection in depressed outpatients? Findings from the CO-MED trial", Psychoneuroendocrinology, vol. 78, pp. 105-113, 2017.
Papakostas et al.: "L-methylfolate as adjunctive therapy for SSRI-resistant major depression: results of two randomized, double-blind, parallel-sequential trials": Am J Psychiatry, vol. 169 / Issue 12, pp. 1267-1274, 2012.
"Blood test unlocks new frontier in treating depression": Science Daily, Mar. 29, 2017.
Clinical trial sponsored by National Institute of Nursing Research: "An investigation of the biological and neuronal mechanisms of post traumatic stress disorder, depression and post-concussive syndrome onset following a traumatic brain injury", ClinicalTrials.gov identifier: NCT02019654. First Posted: Dec. 24, 2013. Actual Study Start Date: Feb. 3, 2015.
Clinical trial sponsored by University Hospital, Caen: "Effects of repeated short-term microgravity during parabolic flight conditions on neuro-endocrine, immune and metabolic changes (COSI@PFC)", ClinicalTrials.gov identifier: NCT02517190. First Posted: Aug. 6, 2015.

Wood et al., "Acute toxicity associated with the recreational use of the ketamine derivative methoxetamine", European Journal of Clinical Pharmacology, 68(5), 853-856, 2012.
Joo et al., "Chronic immobilization stress induces anxiety- and depression-like behaviors and decreases transthyretin in the mouse cortex", Neurosci Lett. 2009; 461(2): 121-5.
Kaddurah-Daouk et al., "Pretreatment metabotype as a predictor of response to sertraline or placebo in depressed outpatients: a proof of concept", Transl Psychiatry. 2011;1(7).
Kearns et al., "Early interventions for PTSD: a review", Depress Anxiety. Oct. 2012;29(10):833-42.
Kessler et al., "Posttraumatic stress disorder in the National Comorbidity Survey", Arch Gen Psychiatry. Dec. 1995;52(12):1048-60.
Kessler RC, Berglund P, Demler O, Jin R, Merikangas KR, Walters EE. Lifetime prevalence and age-of-onset distributions of DSM-IV disorders in the National Comorbidity Survey Replication. Arch Gen Psychiatry. 2005; 62(6): p. 93-602.
Kokras et al., "Sex differences in animal models of psychiatric disorders", Br J Pharmacol 2014; 171 (20): 4595-4619.
Kornstein SG, Schatzberg AF, Thase ME, Yonkers KA, McCullough JP, Keitner GI, et al. Gender differences in treatment response to sertraline versus imipramine in chronic depression. Am J Psychiatry_ 2000; 157(9): 1445-52.
Lagamma et al , "Antidepressant but Not Prophylactic Ketamine Administration Alters Calretinin and Calbindin Expression in the Ventral Hippocampus", Front Mol Neurosci. Nov. 6, 2018;11:404.
Maier SF, Seligman MEP (1976): Learned helplessness: Theory and evidence. J Exp Psychol 105:3-46.
Mastrodonato et al., "Ventral CA3 Activation Mediates Prophylactic Ketamine Efficacy Against Stress-Induced Depressive-like Behavior", Biol Psychiaty. 2018; 84(11): 846-856.
Mathew et al.: "Riluzole for relapse prevention following intravenous ketamine in treatment-resistant depression: a pilot randomized, placebo-controlled continuation trial", International Journal of Neuropsychopharmacology, vol. 13 / Issue 1. pp. 71-82, 2010.
Matt McMillen, Ketamine: The Future of Depression Treatment? WedMD.com, Depression Health Center, Sep. 23, 2014 [retrieved from https://www.webmd.com/depression/news/20140923/ketamine-depression#1].
McGhee LL, Maani CV, Garza TH, DeSocio PA, Gaylord KM, Black IH (2009): The effect of propranolol on posttraumatic stress disorder in burned service members. J Burn Care Res 30:92-97.
McGowan et al., "Prophylactic ketamine alters nucleotide and neurotransmitter metabolism in brain and plasma following stress", Neuropsychopharmacology 2018; 43 (9): 1813-1821.
McGowan JC, LaGamma CT, Lim SC, Tsitsiklis M, Neria Y, Brachman RA, et al. Prophylactic Ketamine Attenuates Learned Fear. Neuropsychopharmacology_ 2017; 42(8): 1577-89.
Mendez-David et al., "Rapid anxiolytic effects of a 5-HT(4) receptor agonist are mediated by a neurogenesis-independent mechanism", Neuropsychopharmacology 39 (6):1366-1378; 2014.
Mion et al., "Ketamine Pharmacology: An Update (Pharmacodynamics and Molecular Aspects, Recent Findings)", CNS Neurosci Ther. 2013; 19(6):370-80.
Muller JM, Morelli E, Ansorge M, Gingrich JA (2011): Serotonin transporter deficient mice are vulnerable to escape deficits following inescapable shocks. Genes Brain Behav 10:166-175.
Murrough et al, "Antidepressant Efficacy of Ketamine in Treatment-Resistant Major Depression: A two-site randomized controlled trial", Am. J. Psychiatry, 2013, vol. 1/0, Issue 10, pp. 1134-1142.
Murrough et al.: "Rapid and longer-term antidepressant effects of repeated ketamine infusions in treatment-resistant major depression": Biological Psychiatry, vol. 74 / Issue 4, pp. 250-256, 2013.
National Research Council. "Depression in parents, parenting, and children: Opportunities to improve identification, treatment, and prevention." (2009).
Nikiforuk Agnieszka et al: "Ketamine prevents stress-induced cognitive inflexibility in rats", Psychoneuroendocrinology, 2013, vol. 40, pp. 119-122.
Palomero-Gallagher et al., "AMPA, kainate, and NMDA receptor densities in the hippocampus of untreated male rats and females in estrus and diestrus", J Comp Neurol 2003; 459(4): 468-474.

(56) References Cited

OTHER PUBLICATIONS

Papakostas et al., "L-methylfolate as adjunctive therapy for SSRI-resistant major depression: results of two randomized, double-blind, parallel-sequential trials", Am J Psychiatry. Dec. 2012;169(12):1267-74.
Parise Eric M et al: "Repeated Ketamine Exposure Induces an Enduring Resilient Phenotype in Adolescent and Adult Rats", Biological Psychiatry, 2013, vol. 74, No. 10, pp. 750-759.
Paul et al., "(R,S)-Ketamine metabolites (R,S)-norketamine and (2S,6S)-hydroxynorketamine increase the mammalian target of rapamycin function", Anesthesiology_ 2014; 121(1): pp. 149-159.
Peselow et al., "Prophylactic efficacy of fluoxetine, escitalopram, sertraline, paroxetine, and concomitant psychotherapy in major depressive disorder: outcome after long-term follow-up". Psychiatry Res. Feb. 28, 2015;225(3):680-6.
Pham et al., "Common Neurotransmission Recruited in (R,S)-Ketamine and (2R,6R)-Hydroxynorketamine-Induced Sustained Antidepressant-like Effects", Biol Psychiatry 2018; 84 (1): e3-e6.
Piccinelli et al., "Gender differences in depression. Critical review", Br J Psychiatry. 2000; 177: pp. 486-492.
Pittig et al.. "The role of associative fear and avoidance learning in anxiety disorders: Gaps and directions for future research", Neurosci Biobehav Rev. May 2018;88:1 17-140.
Porsolt et al., "Depression: a new animal model sensitive to antidepressant treatments", Nature 1977; 266(5604): 730-732.
Rachel Yarmolinsky, Could a Dose of Ketamine Prevent Psychiatric Disorders Such as PTSD?, Columbia University Department of Psychiatry, Jul. 2, 2015 [retrieved from https://www.columbiapsychiatry.org/news/could-dose-ketamine-prevent-psychiatric-disorders-such-ptsd].
Ramirez et al., "Activating positive memory engrams suppresses depression-like behaviour", Nature 522, 335-339 (2015).
Rasmussen et al., "Serial infusions of low-dose ketamine for major depression", J Psychopharmacol. 2013; 27(5):444-50.
Reardon, Rave drug holds promise for treating depression fast, Nature, 517, 130-131 (2015).
Redei et al., "Blood transcriptomic biomarkers in adult primary care patients with major depressive disorder undergoing cognitive behavioral therapy", Transl Psychiatry. Sep. 16, 2014;4(9).
Richardson-Jones JW, Craige CP, Guiard BP, Stephen A, Metzger KL, Kung HF, et al. (2010): 5-HT1A Autoreceptor Levels Determine Vulnerability to Stress and Response to Antidepressants. Neuron 65(1): 40-52.
Rissman et al., "Estrogen receptors are essential for female sexual receptivity", Endocrinology_ 1997; vol. 138 (1):507-10.
Saland et al., "Hedonic sensitivity to low-dose ketamine is modulated by gonadal hormones in a ?ex-dependent manner", Sci Rep_ 2016; 6.
Saxe et al., "Ablation of hippocampal neurogenesis mpairs contextual fear conditioning and synaptic plasticity in the dentate gyrus", Proc Natl Acad Sci 2006; 103( 46): H501-17506.
Schiller D, Monfils MH, Raio CM, Johnson DC, LeDoux JE, Phelps EA (2010): Preventing the return of fear in humans using reconsolidation update mechanisms. Nature 463.49-53.
Serafini G, Howland RH, Rovedi F, Girardi P, Amore M. The Role of Ketamine in Treatment-Resistant Depression: A Systematic Review. Curr Neuropharmacol. 2014; 12(5):444-61.
Shansky et al., "Estrogen promotes stress sensitivity in a prefrontal cortex-amygdala pathway", Cerebral cortex (New York, NY: 1991) 2010; 20(11): 2560-2567.
Shin et al., "The neurocircuitry of fear, stress, and anxiety disorders", Neuropsychopharmacology. Jan. 2010;35(1):169-91.
Shirayama et al., "R-ketamine: a rapid-onset and sustained antidepressant without psychotomimetic side effects", Transl Psychiatry. Sep. 1, 2015;5(9):e632.
Singh et al., "Intravenous Esketamine in Adult Treatment-Resistant Depression: A Double-Blind, DoubleRandomization, Placebo-Controlled Study", Biol Psychiatly 2016; 80(6): 424-431.
Soldin et al., "Sex differences in pharmacokinetics and pharmacodynamics", Clin Pharmacokinet 2009; 48 (3): 143-157.
Soumier et al., "New Hippocampal Neurons Mature Rapidly in Response to Ketamine but are Not Required for Its Acute Antidepressant Effects on Neophagia in Rats", eNeuro_ 2016; 3(2).
Strom et al., "Ovariectomy and 17β-estradiol Replacement in Rats and Mice: A Visual Demonstration", Journal of Visualized Experiments, 2012 (64):e4013.
Sugiyama et al., "Systemic administration of a delta opioid receptor agonist, KNT-127, facilitates extinction learning of fear memory in rats", J Pharmacol Sci. Mar. 2019;139(3):174-179.
Abdallah et al., "Glutamate Metabolism in Major Depressive Disorder", The American Journal of Psychiatry, 171(12), 1320-1327, 2014.
Abdallah et al., "Ketamine and rapid-acting antidepressants: a window into a new neurobiology for mood disorder therapeutics", Annu Rev Med. 2015; 66: pp. 509-523.
Al Shirawi MI, Kennedy SH, Ho KT, Byrne R, Downar J. Oral Ketamine in Treatment-Resistant Depression: A Clinical Effectiveness Case Series. J Clin Psychopharmacol. 2017; 37(4):464-7.
Aleksandrova et al., "Antidepressant effects of ketamine and the roles of AMPA glutamate receptors and other mechanisms beyond NMDA receptor antagonism", J Psychiatry Neurosci 2017; 42(4): 222-229.
Alquraan et al., "Omega-3 Fatty Acids Prevent Post-Traumatic Stress Disorder-Induced Memory Impairment", Biomolecules. Mar. 12, 2019;9(3):100.
Altemus et al., "Sex differences in anxiety and depression clinical perspectives", Front Neuroendocrinol 2014; 35(3): 320-330.
Amat et al., "Previous Ketamine Produces an Enduring Blockade of Neurochemical and Behavioral Effects of Uncontrollable Stress", J Neuro_ 2016; 36(1):153-61.
Author Unknown, "Blood test unlocks new frontier in treating depression", UT Southwestern Medical Center, Mar. 29, 2017, last downloaded from https://www.sciencedaily.com/releases/2017/03/170329145732.htm on Nov. 23, 2021.
Autry AE, Adachi M, Nosyreva E, Na ES, Los MF, Cheng PF, et al. (2011): NMDA receptor blockade at rest triggers rapid behavioural antidepressant responses. Nature 475:91-95.
Bach et al., "Blocking human fear memory with the matrix metalloproteinase inhibitor doxycycline", Mol Psychiatry. Jul. 2018;23(7):1584-1589.
Baratta et al., "Stress Enables Reinforcement-Elicited Serotonergic Consolidation of Fear Memory", Biol Psychiatry. May 15, 2016;79(10):814-822.
Brachman et al, "Ketamine as a prophylactic against stress-induced depressive-like behavior", Biol Psychiatry. 2016, 79 (9): 776-786.
Brachman et al., "A single injection of ketamine confers robust, long-term protection against stress-induced depressive-like behaviors", Society for Neuroscience conference, Presentation Abstract on Nov. 17, 2014.
Brent Miles as told to Troy Farah, I Used Ketamine to Treat My Depression, Vice, Jan. 15, 2015 [retrieved from https://www.vice.com/en_us/article/4w7eyd/i-used-ketamine-to-treat-my-depression-122].
Browne CA, Lucki I. Antidepressant effects of ketamine: mechanisms underlying fastacting novel antidepressants. Front Pharmacol. 2013; 4.
Caddy C, Giaroli G, White TP, Shergill SS, Tracy DK (2014): Ketamine as the prototype glutamatergic antidepressant: Pharmacodynamic actions, and a systematic review and meta-analysis of efficacy. Ther Adv Psychopharmacol 4:75-99.
Carrier N, Kabbaj M. Sex differences in the antidepressant-like effects of ketamine. Neuropharmacology _ 2013; 170:27-34.
Cattaneo et al., "Absolute Measurements of Macrophage Migration Inhibitory Factor and Interieukin-1-β mRNA Levels Accurately Predict Treatment Response in Depressed Patients", Int J Neuropsychopharmacol. Sep. 30, 2016;19(10).
Chen et al., "Ovarian hormones mediate the prophylactic efficacy of (R,S)-ketamine and (2R,6R)-hydroxynorketamine in female mice", bioRxiv, 712752, Jul. 24, 2019.
Christine Denny, "Analysis of the role of hippocampal adult-born neurons in behavior and physiology", NIH Grant #: 5F31MH084529-03, Budget Start Jul. 1, 2011, Budget End Jun. 30, 2012.

(56) References Cited

OTHER PUBLICATIONS

Christine Denny, "Optogenetic dissection of hippocampal circuitry underlying Alzheimers disease", NIH Grant #: 1DP5OD017908-01, Budget StartSep. 19, 2013, Budget End Aug. 31, 2014.
Cieślak et al., "The roles of purinergic signaling in psychiatric disorders", Acta Biochim Pol. 2016;63(1):1-9.
ClinicalTrials.gov, Rapid Antidepressant Effects of Ketamine in Major Depression, National Institute of Mental Health (NIMH), Identifier: NCT00088699 [retrieved from https://clinicaltrials.gov/ct2/show/NCT00088699; First Posted: Aug. 2, 2004; Results First Posted: Oct. 12, 2018] [retrieved on Dec. 6, 2018].
Dalla et al., "Females do not Express Learned Helplessness like Males do", Neuropsychophamnacology _ 2007; 33(7): 1559-69.
Daly et al., "Efficacy and Safety of Intranasal Esketamine Adjunctive to Oral Antidepressant Therapy in Treatment Resistant Depression: A Randomized Clinical Trial", JAMA 2018, 75(2): 139-148.
David DJ, Samuels BA, Rainer Q,Wang JW, Marsteller D, Mendez I, et al. (2009): Neurogenesis-dependent and -independent effects of fluoxetine in an animal model of anxiety/depression. Neuron 62:479-493.
Davidson RJ, Pizzagalli D, Nitschke JB, Putnam K. Depression: perspectives from affective neuroscience. Ann Rev Psychology_ 2002; 53:545-74.
De Souza et al., "Posttraumatic stress disorder-type behaviors in streptozotocin-induced diabetic rats can be prevented by prolonged treatment with vitamin E", Behav Brain Res. Feb. 1, 2019 ;359:749-754.
Denny CA, Burghardt NS, Schachter DM, Hen R, Drew MR (2012): 4- to 6-week-old adult-born hippocampal neurons influence novelty-evoked exploration and contextual fear conditioning. Hippocampus 22:1188-1201.
Denny et al., "Hippocampal Memory Traces are Differentially Modulated by Experience, Time, and Adult Neurogenesis", Neuron. 2014; 83(1):189-201.
Dolzani et al., "Inhibition of a Descending Prefrontal Circuit Prevents Ketamine-Induced Stress Resilience in Females", eNeuro 2018; 5(1).
Domino, EF, "Taming the Ketamine Tiger," Anesthesiology, 2010, vol. 113, pp. 678-686.
Donahue RJ, Muschamp JW, Russo SJ, Nestler EJ, Carlezon WA Jr (2014): Effects of striatal deltaFosB overexpression and ketamine on social defeat stress-induced anhedonia in mice. Biol Psychiatry 76:550-558.
Dossat et al., "Behavioral and biochemical sensitivity to low doses of ketamine: influence of estrous cycle in C57BU6 mice", Neuropharmacology 2018; 130: 30-41.
Drew et al., "Arrest of adult hippocampal neurogenesis in mice impairs single- but not multiple-trial contextual fear conditioning", Behav Neurosci. 2010; 124(4):446-54.
Dulawa SC, Holick KA, Gundersen B, Hen R (2004): Effects of chronic fluoxetine in animal models of anxiety and depression. Neuropsychopharmacology 29:1321-1330.
Dunlop et al., "The hypothalamic-pituitary-adrenal axis in PTSD: Pathophysiology and treatment interventions", Prog Neuropsychopharmacol Biol Psychiatry. Mar. 8, 2019;89:361-379.
E.D. Ballard et al., Improvement in suicidal ideation after ketamine infusion: Relationship to reductions in depression and anxiety, J. Psychiatry Research vol. 58 pp. 161-166 Nov. 2014.
Elhabazi et al., "Assessment of morphine-induced hyperalgesia and analgesic tolerance in mice using thermal and mechanical nociceptive modalities", J Vis Exp. Jul. 29, 2014;(89).
Flory JD, Yehuda R. Comorbidity between post-traumatic stress disorder and major depressive disorder: alternative explanations and treatment considerations. Dialogues Clin Neurosci. 2015; 17(2):141-50.
Franceschelli et al.: "Sex differences in the rapid and the sustained antidepressant-like effects of ketamine in stress-naïve and "depressed" mice exposed to chronic mild stress", Neuroscience. Apr. 2, 2015;290:49-60.

Fukumoto et al., "Antidepressant Potential of (R)-Ketamine in Rodent Models: Comparison with (S)-Ketamine", J Pharmacol Exp Ther. Apr. 2017;361(1):9-16.
Gardier et al., "Ketamine as a prophylactic against stress-induced depressive-like behavior", Biol Psychiatry, vol. 79 (9), p. 776-86, May 2016.
Hammack SE, Cooper MA, Lezak KR (2012): Overlapping neurobiology of learned helplessness and conditioned defeat: Implications for PTSD and mood disorders Neuropharmacology 62:565-575.
Honack et al., "Sex differences in NMDA receptor mediated responses in rats", Brain Res 1993; 620(1): 167-170.
Huang et al., "New Treatment Strategies of Depression: Based on Mechanisms Related to Neuroplasticity", Neural Plast. 2017.
International Search Report and Written Opinion dated Feb. 3, 2017 corresponding to International Patent Application No. PCT/US16/62562, 16 pages.
International Search Report and Written Opinion of corresponding International Application PCT/US2018/060082, dated Jan. 24, 2019.
Janice B. Schwartz, "The influence of sex on pharmacokinetics", Clin Pharmacokinet 2003; 42(2): 107-121.
Jha et al., "Can C-reactive protein inform antidepressant medication selection in depressed outpatients? Findings from the CO-MED trial", Psychoneuroendocrinology, vol. 78, Apr. 2017, pp. 105-113.
Supplementary European Search Report in corresponding European Application EP 16867149.3, dated Nov. 6, 2019.
Suzuki, K., Nosyreva, E., Hunt, K. et al. Effects of a ketamine metabolite on synaptic NMDAR function. Nature 546, E1-E3 (2017).
Tabak et al., "Interaction of CD38 Variant and Chronic Interpersonal Stress Prospectively Predicts Social Anxiety and Depression Symptoms Over Six Years", Clin Psychol Sci. Jan. 1, 2016;4(1):17-27.
Thelen et al., "Repeated ketamine treatment induces sex-specific behavioral ?nd neurochemical effects in mice", Behav Brain Res_ 2016; 312:305-12.
Trouch S, Sasaki JM, Tu T, Reijmers LG (2013): Fear extinction causes target-specific remodeling of perisomatic inhibitory synapses. Neuron 80:1054-1065.
Watanabe et al., "Gene expression-based biological test for major depressive disorder: an advanced study", Neuropsychiatr Dis Treat. Feb. 21, 2017;13:535-541.
Waxman et al., "Sex differences in the expression of hepatic drug metabolizing enzymes", Mol Pharmacol 2009; 76(2): 215-228.
WHO. Depression Fact Sheet. World Health Organization. 2017.
Womble, AL, "Effects of Ketamine on Major Depressive Disorder in a Patient with Posttraumatic Stress Disorder," AANA Journal, Apr. 2013, vol. 81, No. 2, pp. 118-119.
World Health Organization. List of Essential Medicines. Adults: 19th Edition. Apr. 2015.
Yamaguchi et al., "(2R,6R)-Hydroxynorketamine is not essential for the antidepressant actions of (R)-ketamine in mice", Neuropsychopharmacology, 2018.
Yang et al. "Potential metabolite markers of schizophrenia." Molecular psychiatry vol. 18,1 (2013): 67-78. doi:10.1038/mp.2011.131.
Zanos et al., "NMDAR inhibition-independent antidepressant actions of ketamine metabolites", Nature_ 2016; 533 (7604):481-6.
Zarate et al, Ketamine for depression: evidence, challenges and promise, World Psychiatry. 2015;14(3):348-50.
Zarate et al. A randomized trial of an N-methyl-D-aspartate antagonist in treatment-resistant major depression. Arch Gen Psychiatry_ 2006; 63(8):856-64.
Zarate et al., "Relationship of ketamine's plasma metabolites with response, diagnosis, and side effects in major depression", Biol Psychiatry_ 2012; 72(4):331-8.
Zarate et al., "Replication of ketamine's antidepressant efficacy in bipolar depression: a randomized controlled add-on trial", Biol Psychiatry. 2012; 71 (11):939-46.
Zhang et al., "R (−)-ketamine shows greater potency and longer lasting antidepressant effects than S +)-ketamine", Pharmacol Biochem Behav_ 2014; 116:137-41.

\* cited by examiner

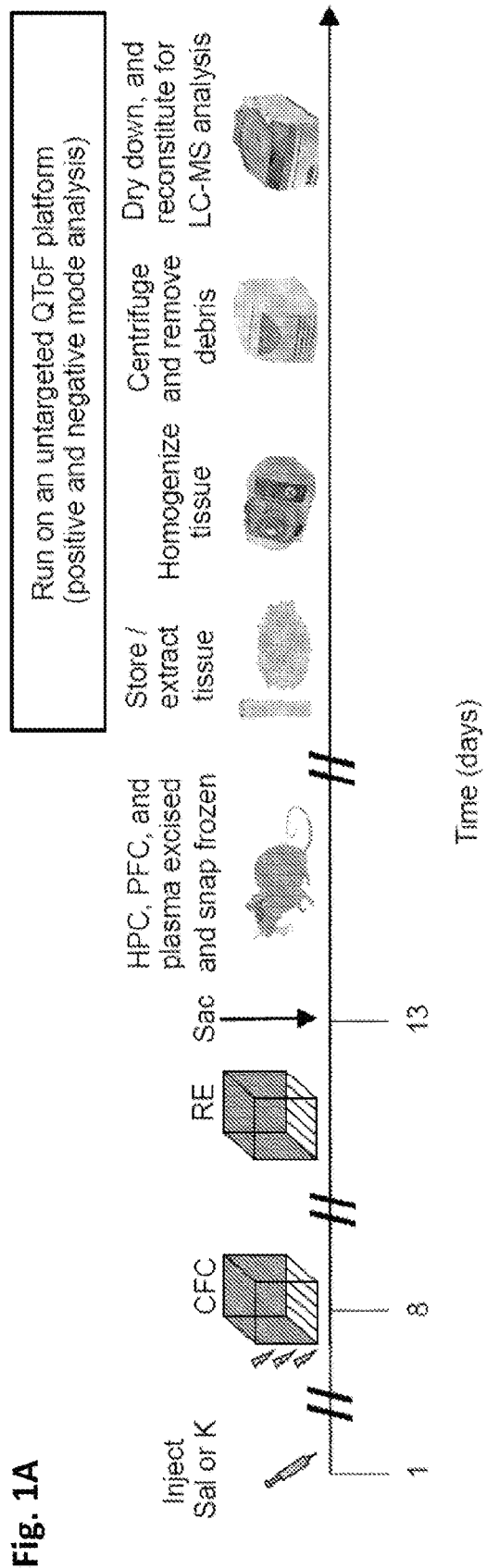
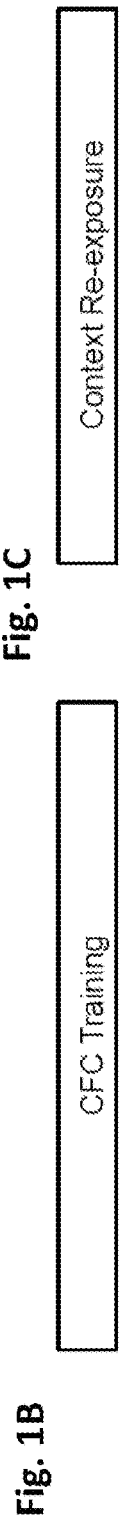
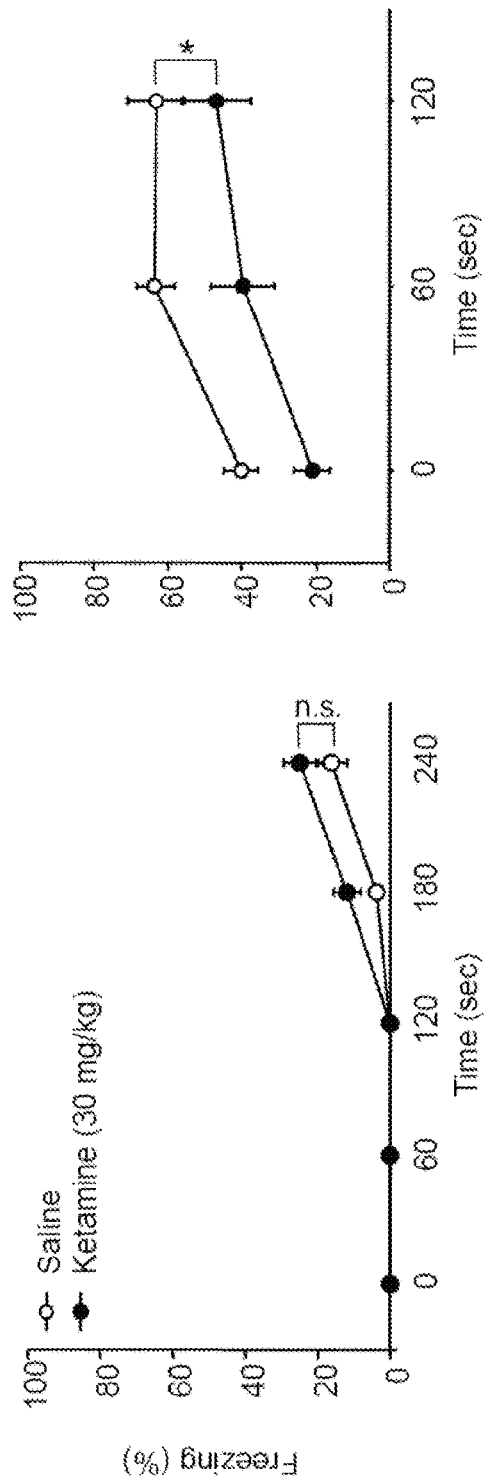
Fig. 1A
Fig. 1B
Fig. 1C

PFC: ☐ Sal, Left ■ K (30 mg/kg), Left ▨ Sal, Right ▨ K (30 mg/kg), Right
HPC: ☐ Sal, Left ■ K (30 mg/kg), Left ▨ Sal, Right ▨ K (30 mg/kg), Right

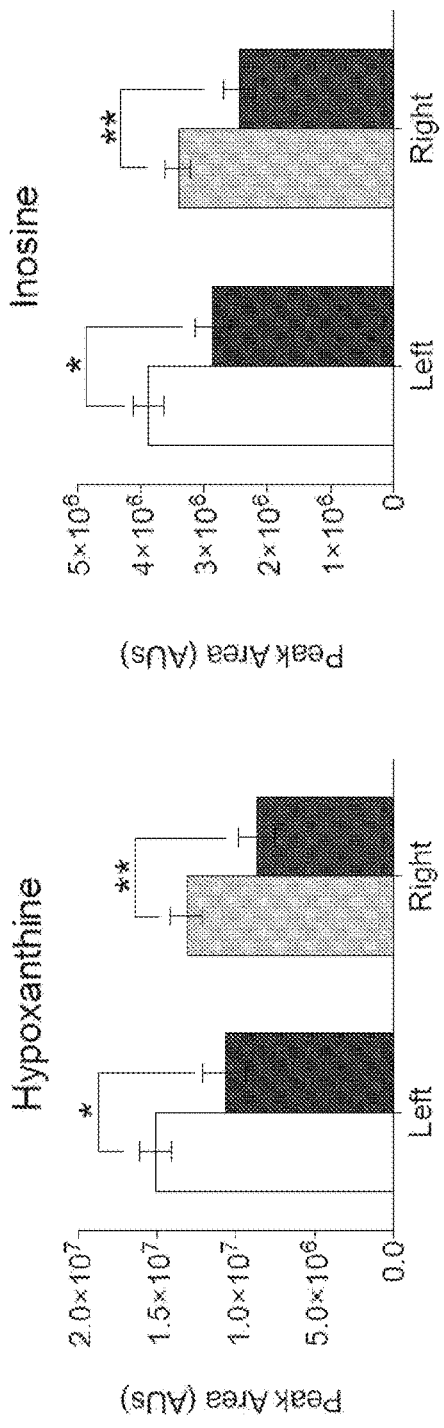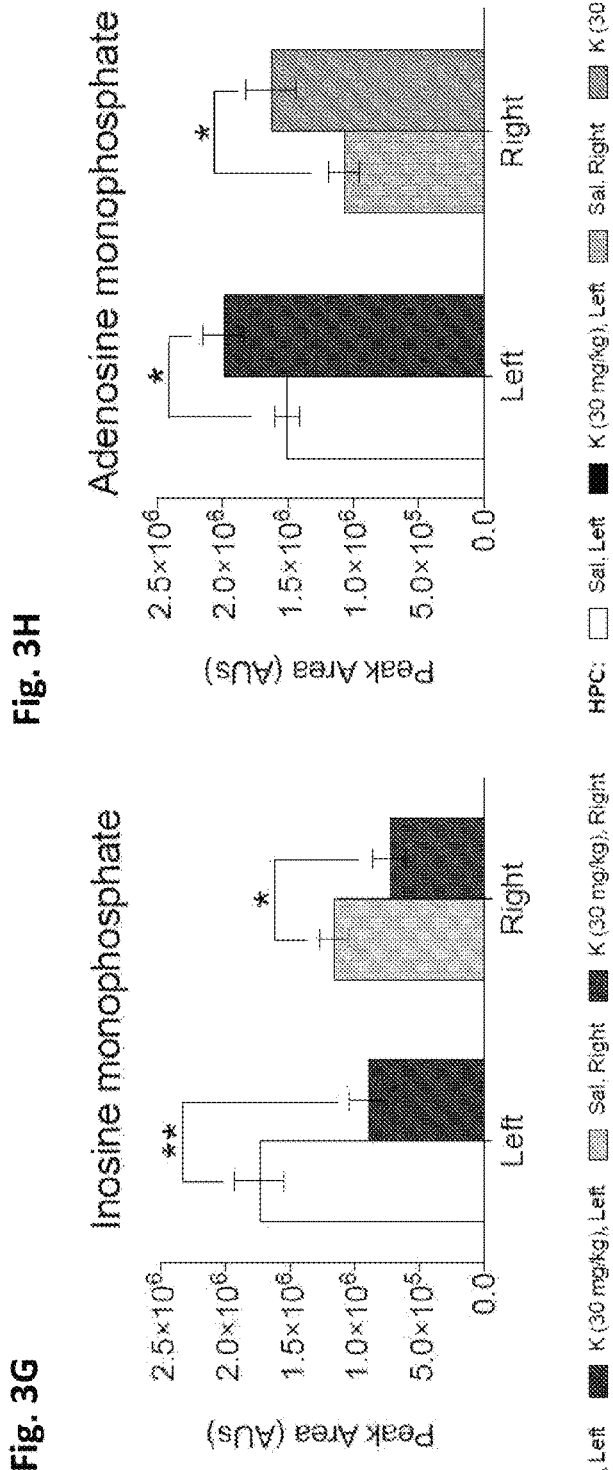
Fig. 3E Hypoxanthine
Fig. 3F Inosine
Fig. 3G Inosine monophosphate
Fig. 3H Adenosine monophosphate PFC: ☐ Sal, Left ■ K (30 mg/kg), Left ☒ Sal, Right ▨ K (30 mg/kg), Right HPC: ☐ Sal, Left ■ K (30 mg/kg), Left ☒ Sal, Right ▨ K (30 mg/kg), Right

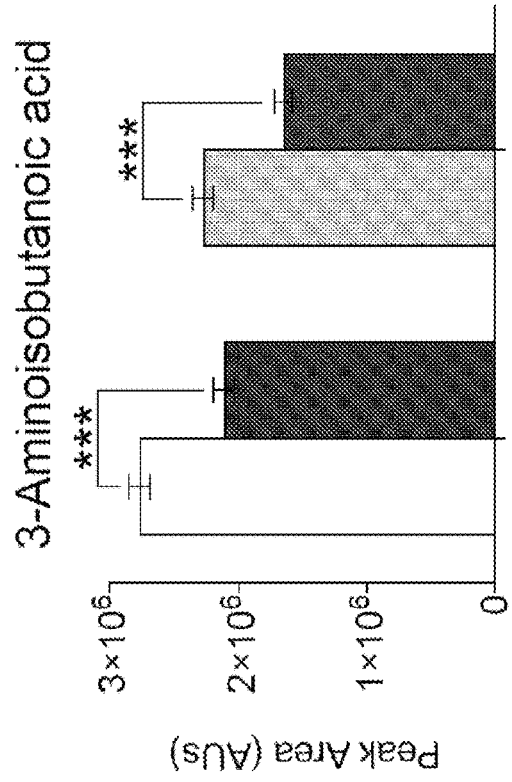
Fig. 4A
Fig. 4B
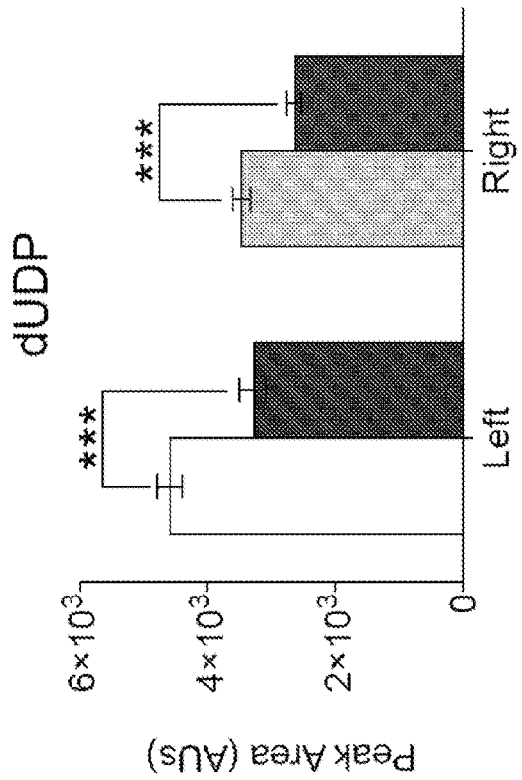
Fig. 4C
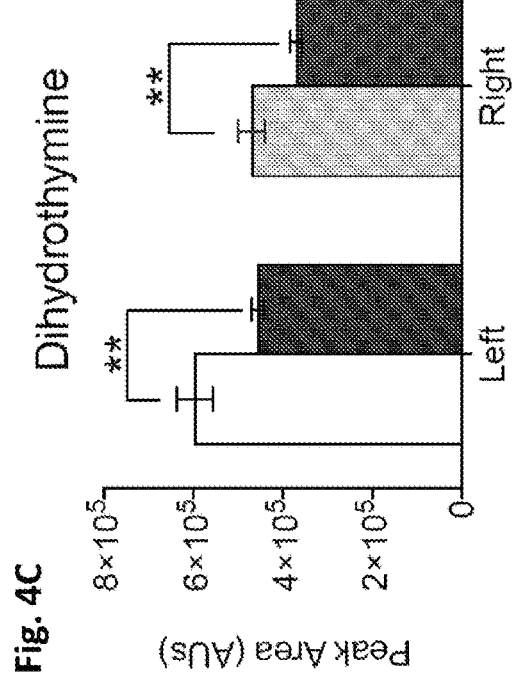
Fig. 4D

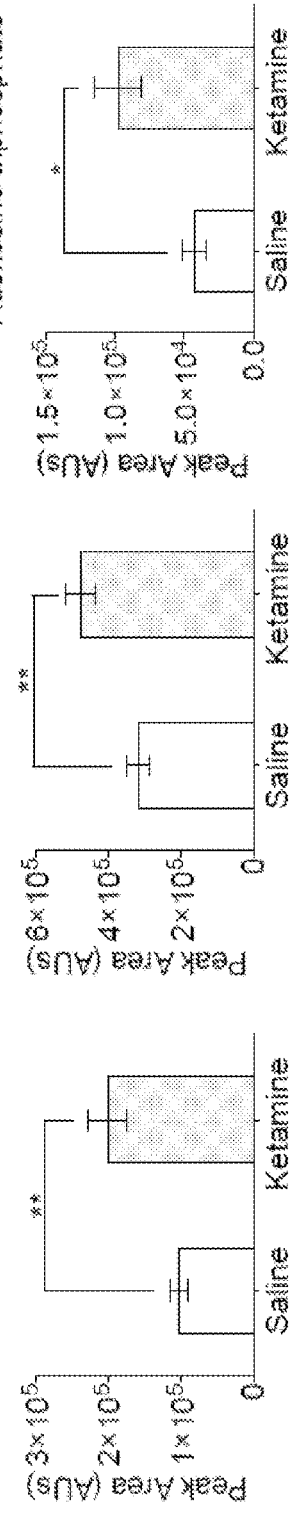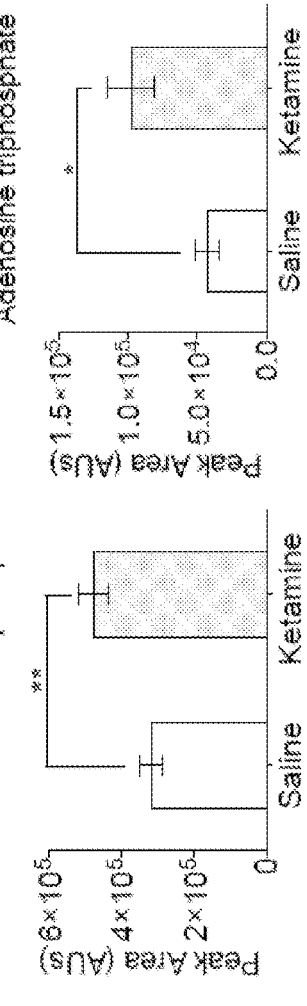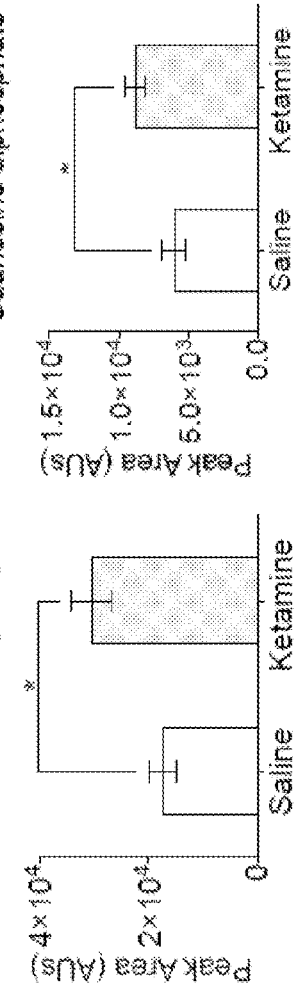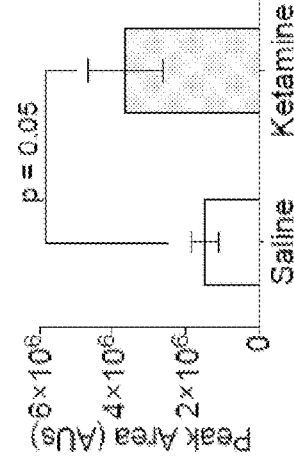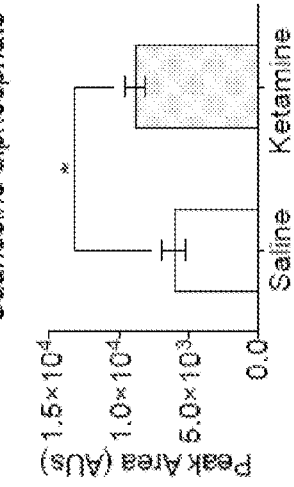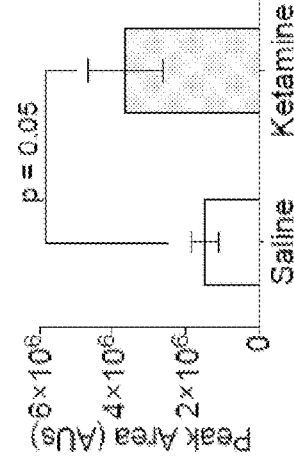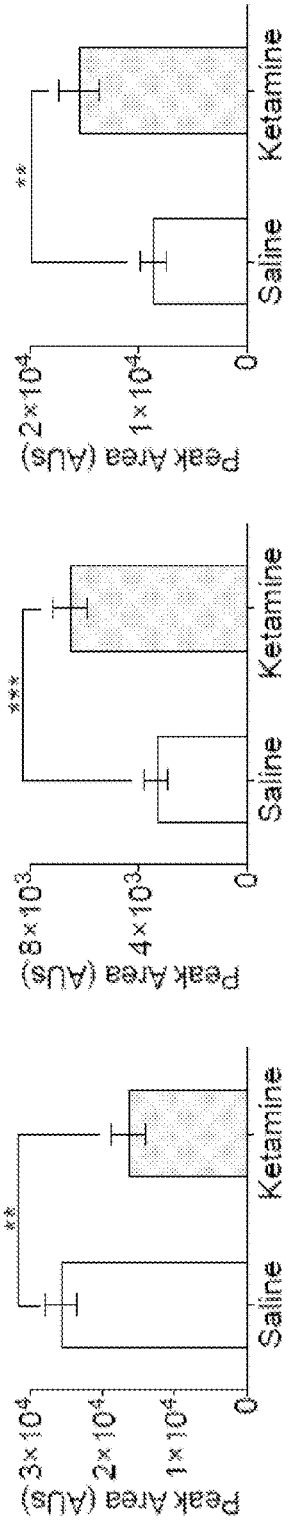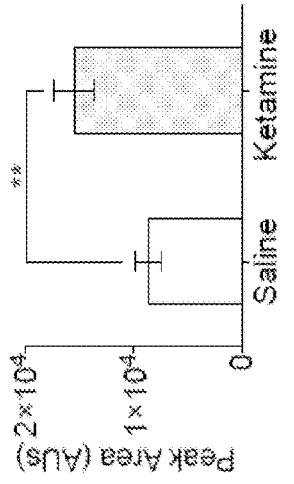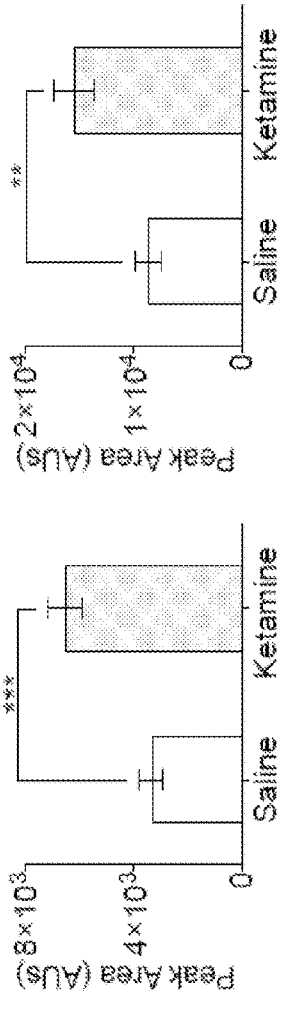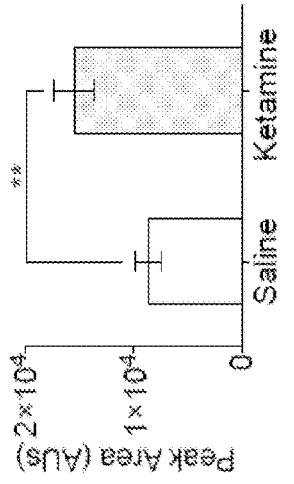

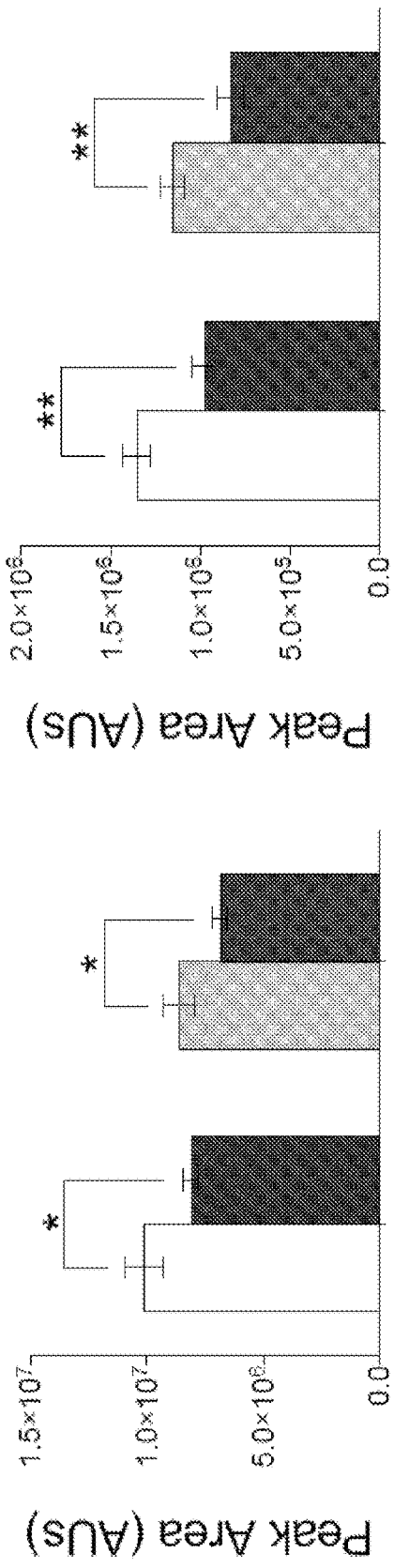
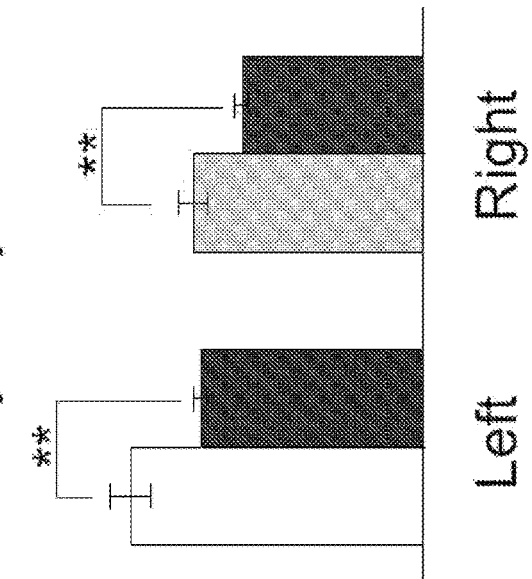
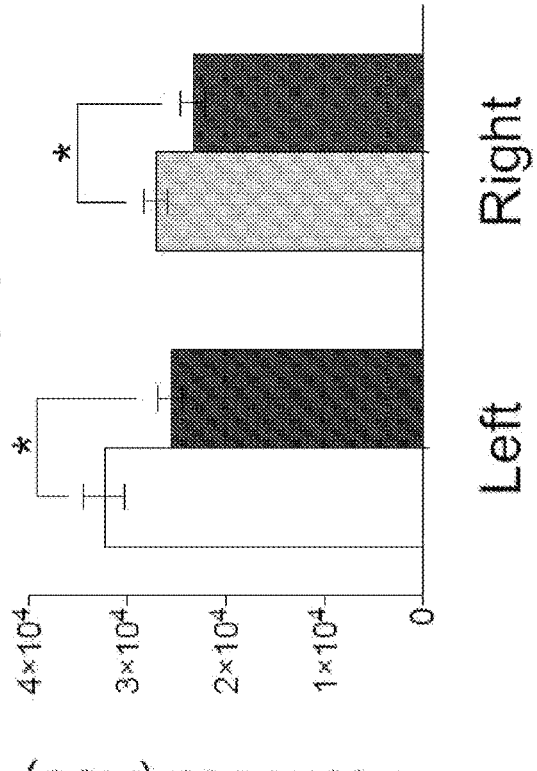
Fig. 6I, Fig. 6J, Fig. 6K, Fig. 6L

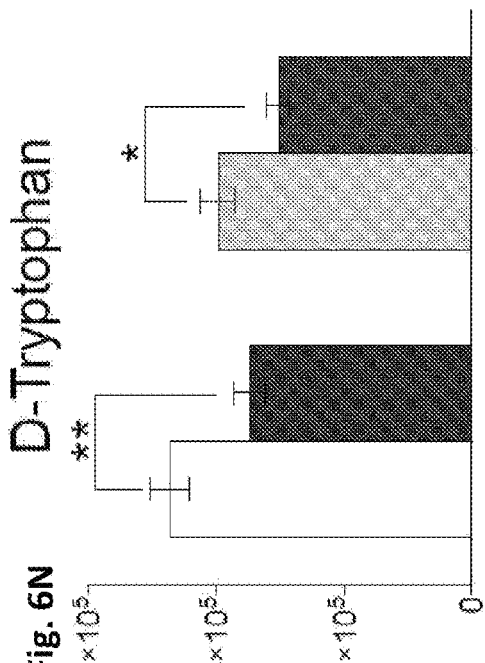
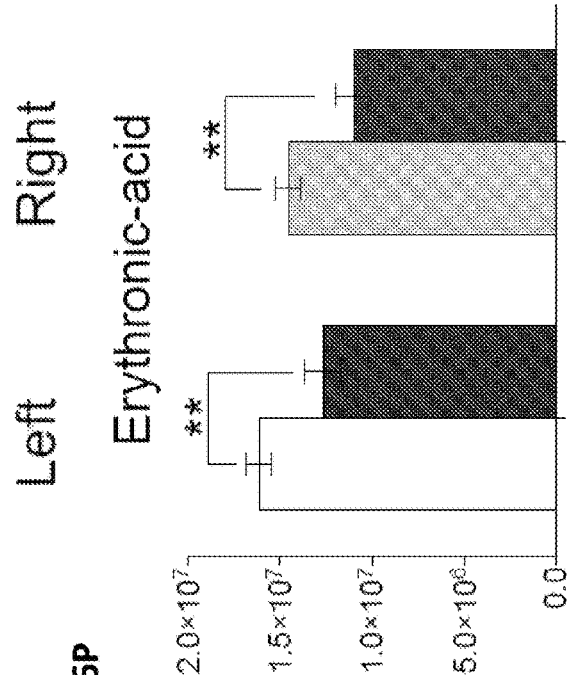
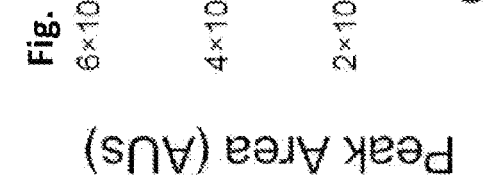
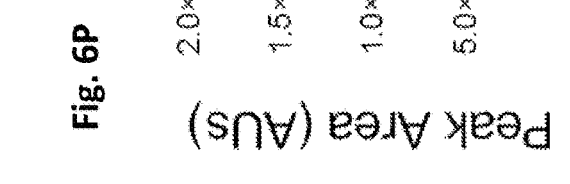
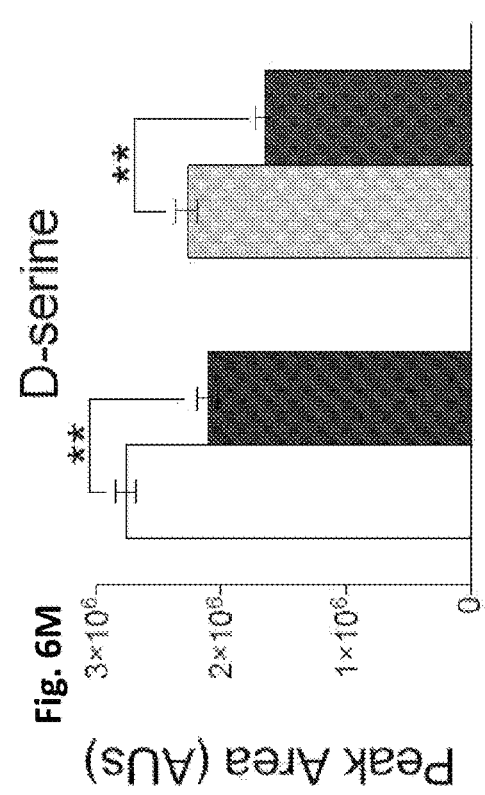

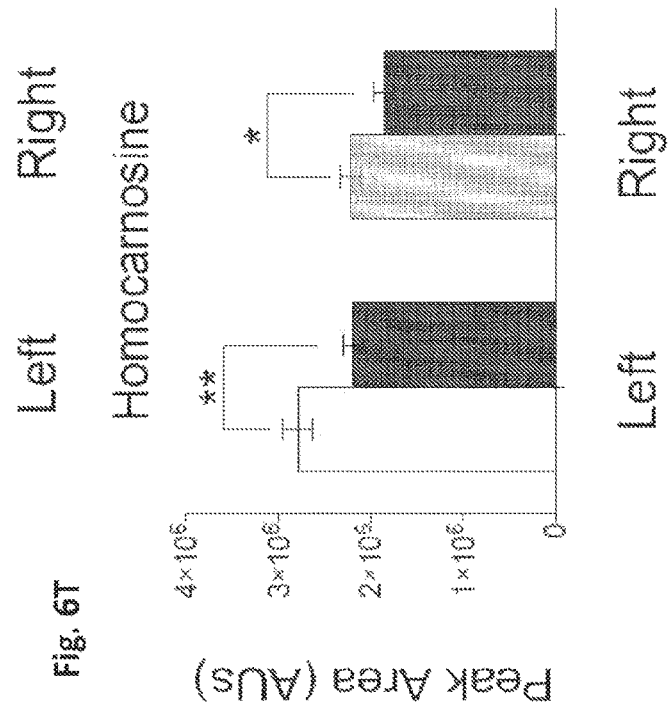
Fig. 6Q Glucosylgalactosyl-hydroxylysine
Fig. 6R Glycine
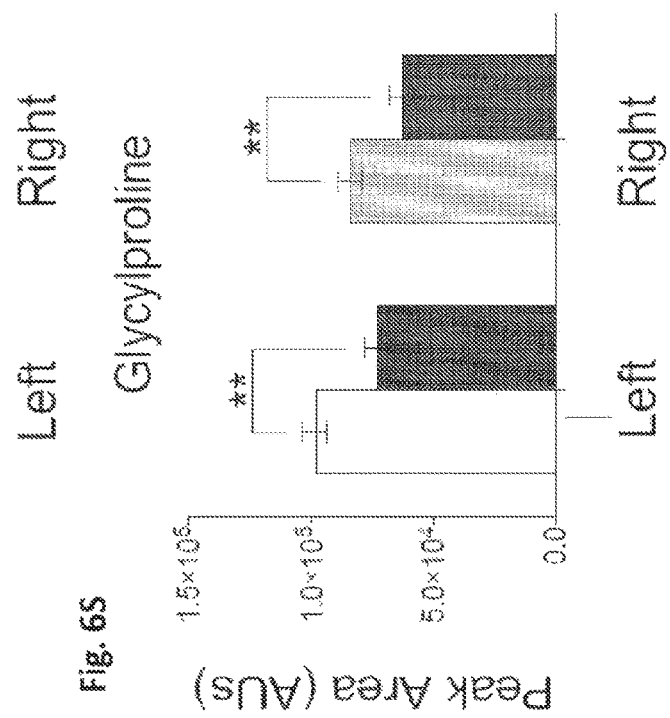
Fig. 6S Glycylproline
Fig. 6T Homocarnosine

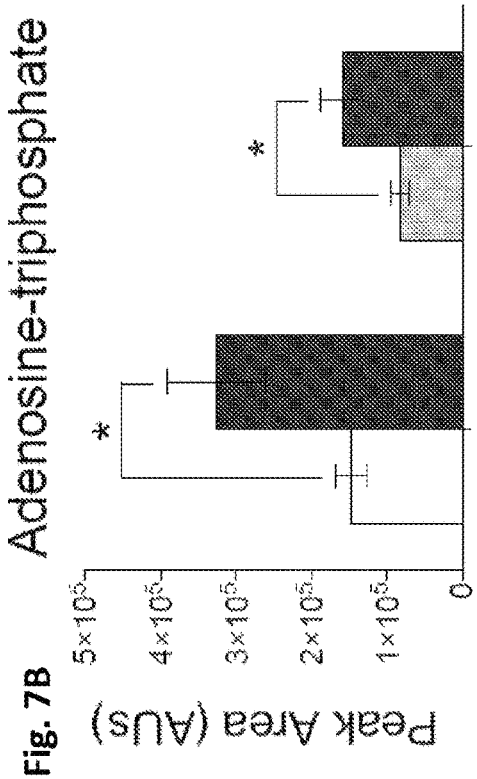
Fig. 7A Adenosine-monophosphate
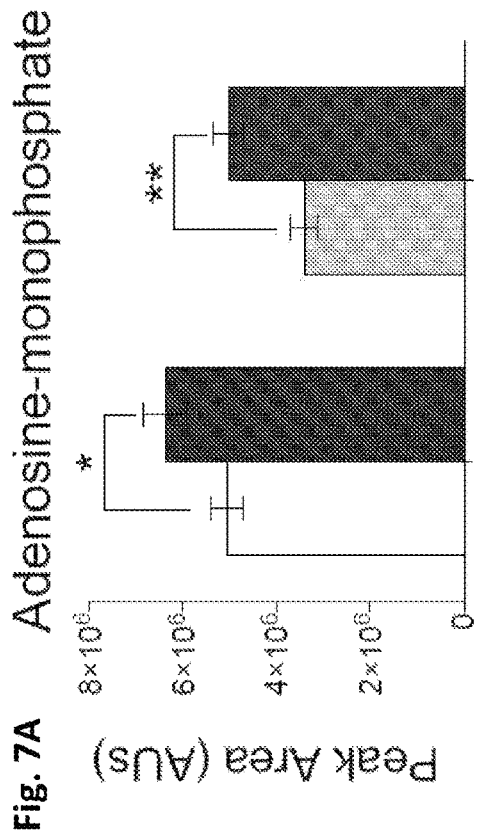
Fig. 7B Adenosine-triphosphate
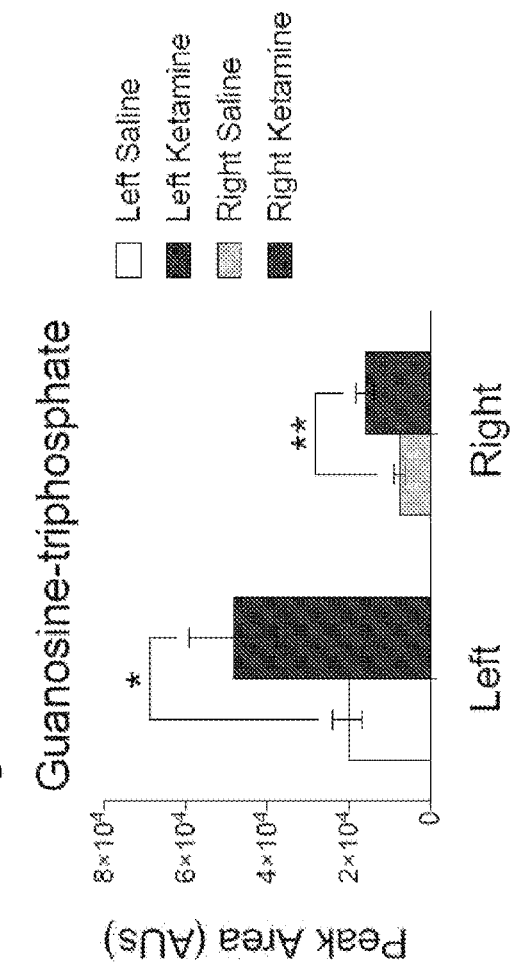
Fig. 7C Guanosine-diphosphate
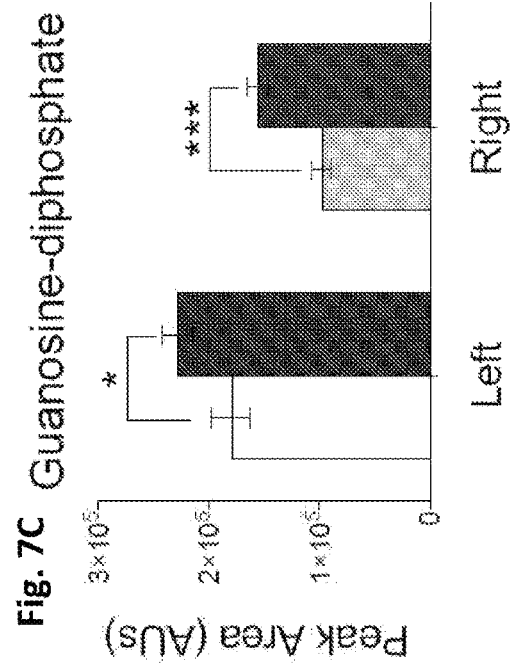
Fig. 7D Guanosine-triphosphate

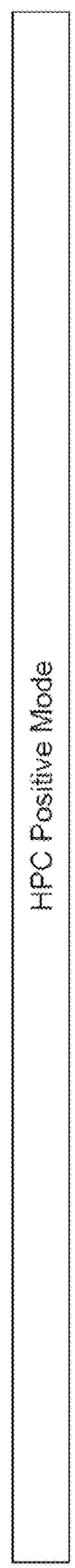
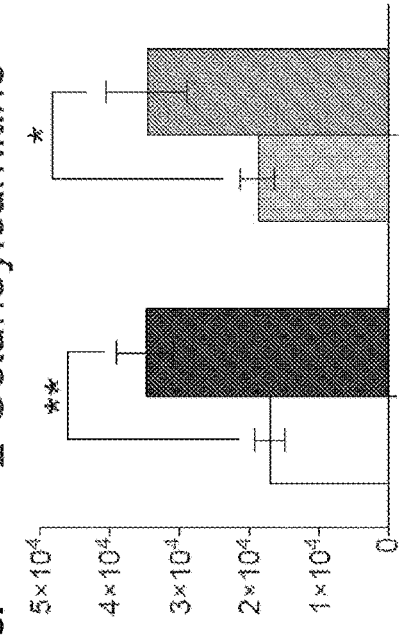
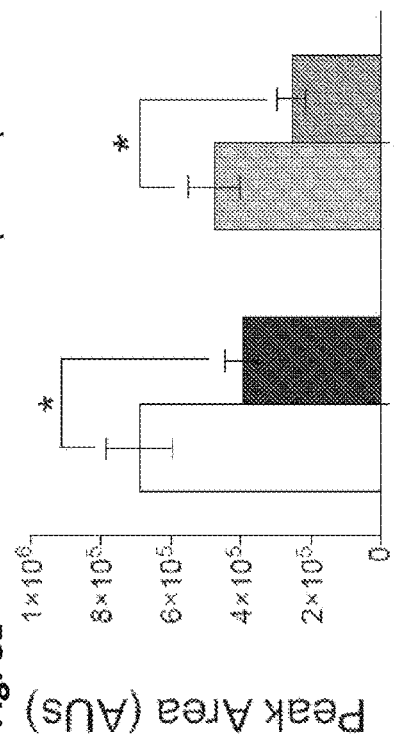
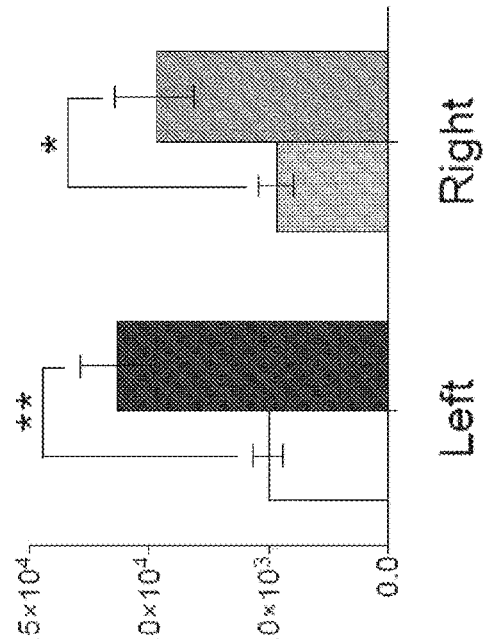
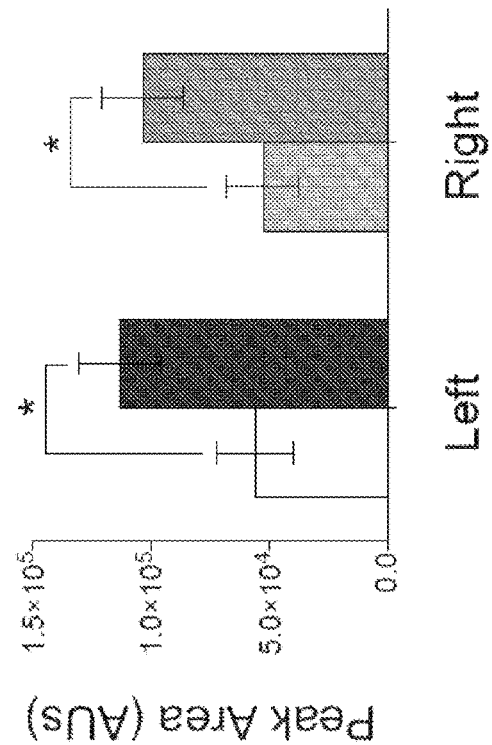

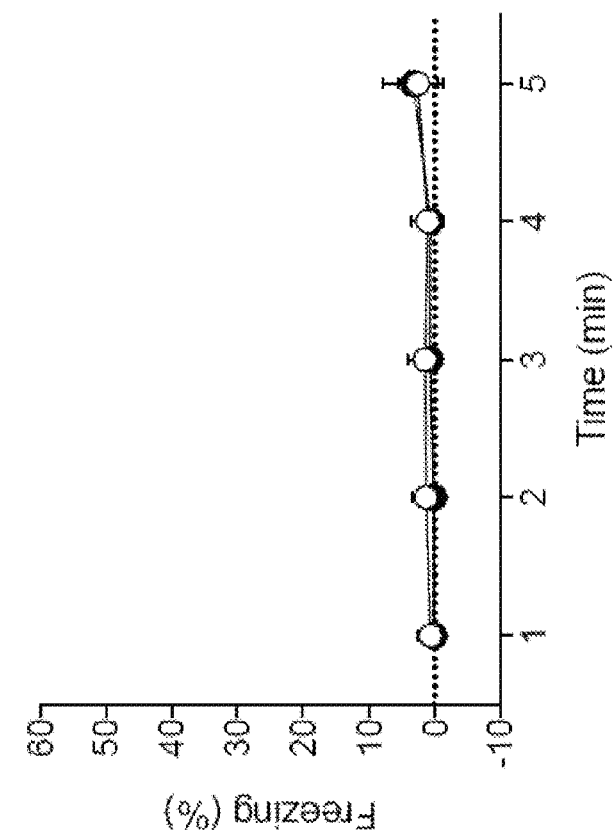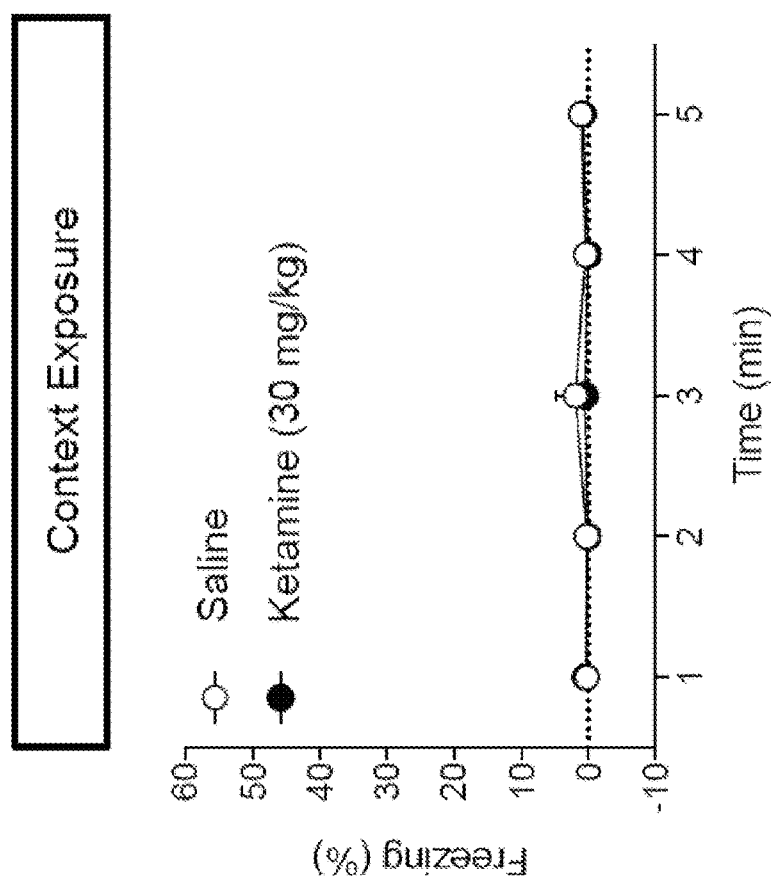

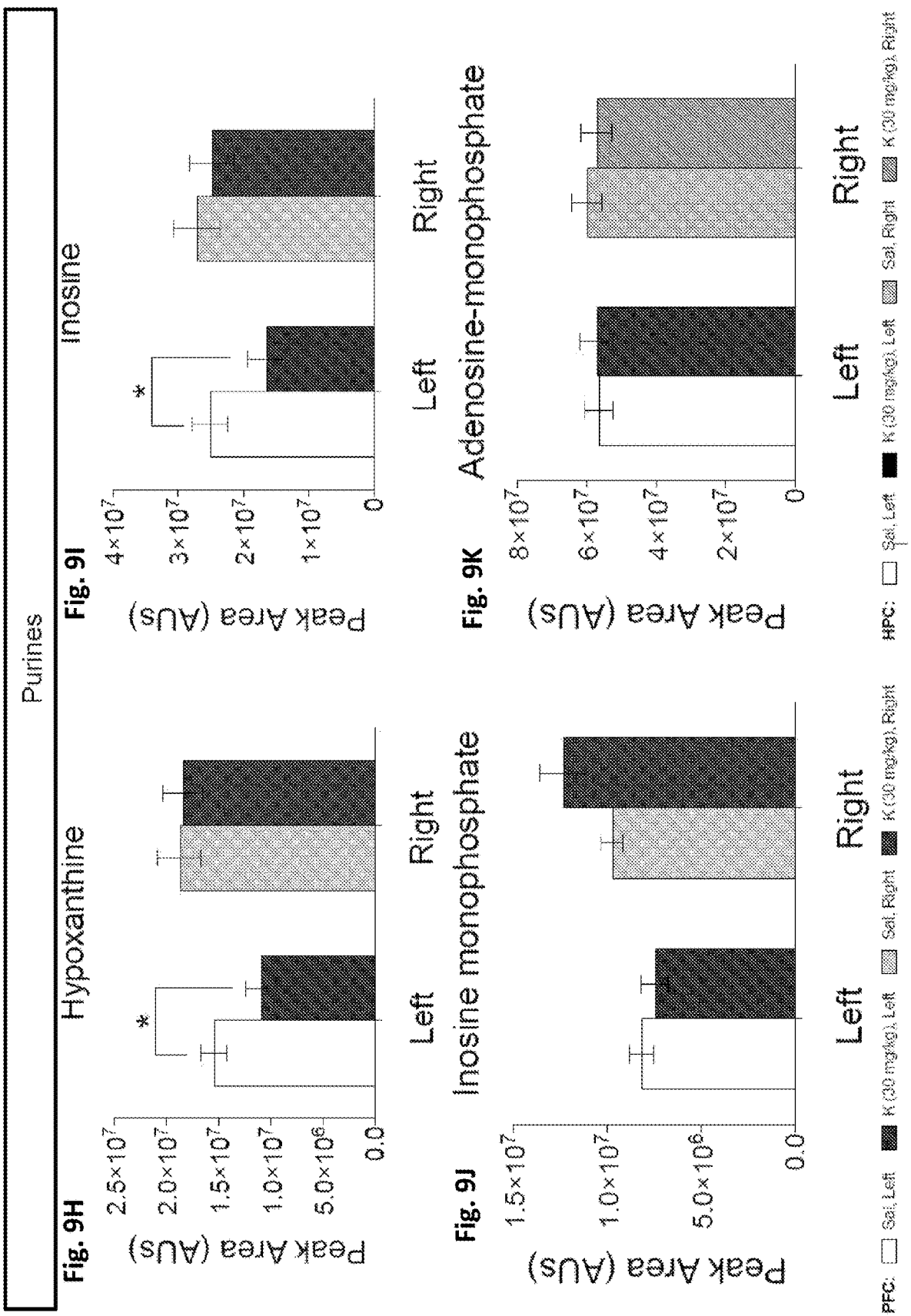

Purine

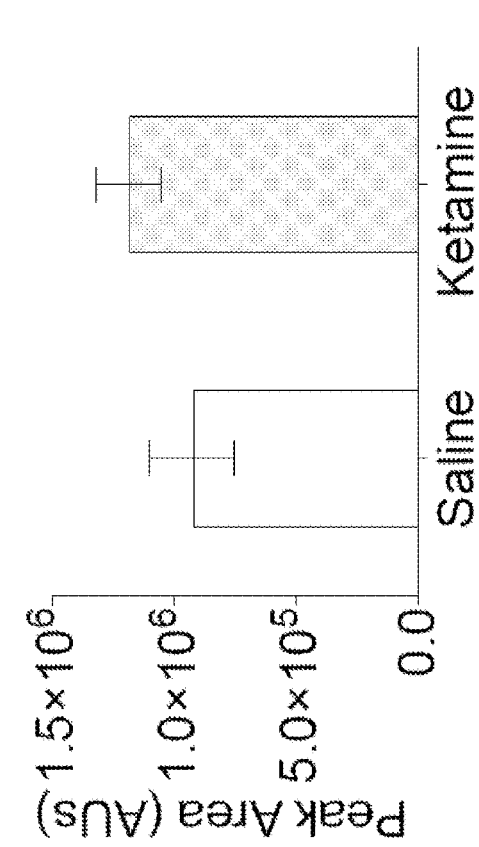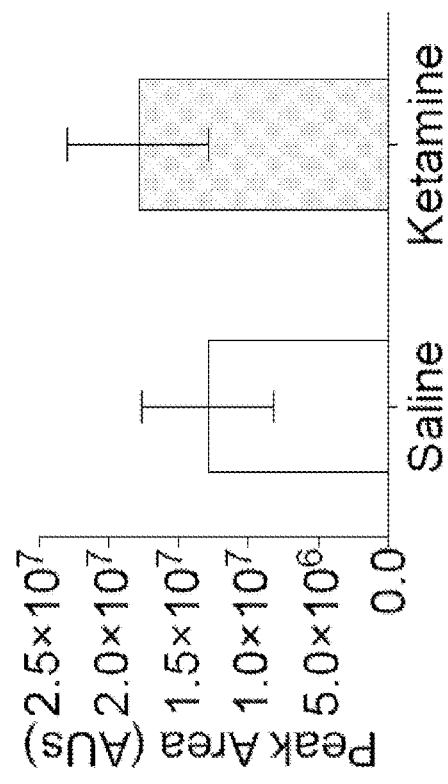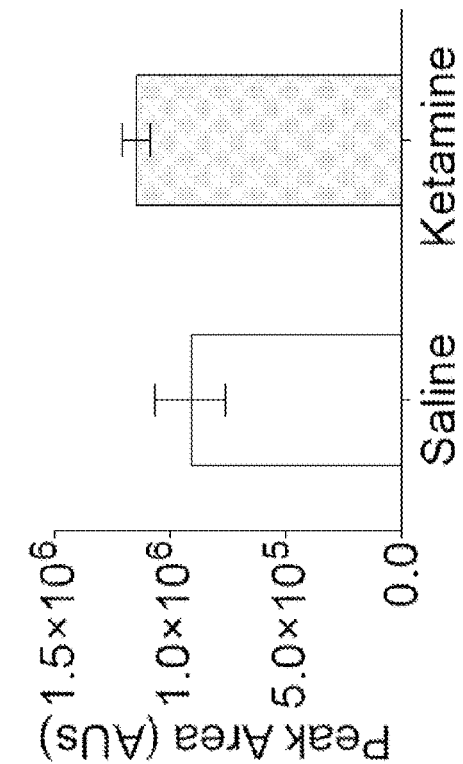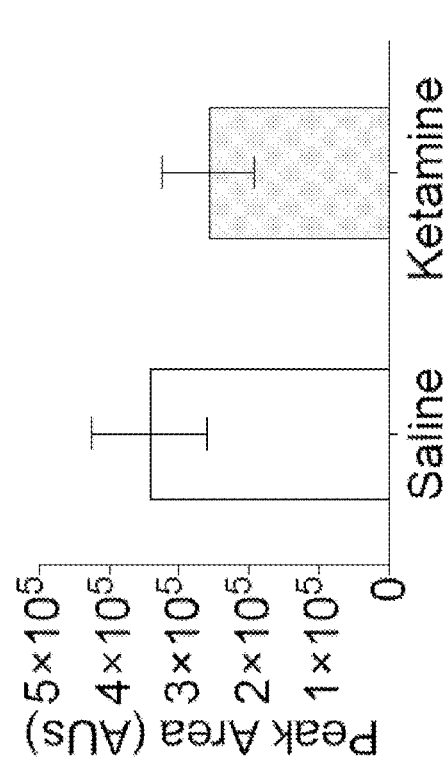
Fig. 10E  D-Ribulose 5-phosphate
Fig. 10F  Guanosine monophosphate
Fig. 10G  Guanosine diphosphate
Fig. 10H  Hypoxanthine
Purine

Pyrimidine

BIOMARKERS FOR EFFICACY OF PROPHYLACTIC TREATMENTS AGAINST STRESS-INDUCED AFFECTIVE DISORDERS

CROSS-REFERENCE TO RELATED APPLICATIONS

The present application claims priority to U.S. Provisional Patent Application No. 62/583,734 filed on Nov. 9, 2017, which is incorporated herein by reference in its entirety.

PARTIES TO A JOINT RESEARCH AGREEMENT

The presently claimed invention was made by or on behalf of the below listed parties to a joint research agreement. The joint research agreement was in effect on or before the effective filing date of the claimed invention, and the claimed invention was made as a result of activities undertaken within the scope of the joint research agreement. The parties to the joint research agreement are THE TRUSTEES OF COLUMBIA UNIVERSITY IN THE CITY OF NEW YORK, the RESEARCH FOUNDATION FOR MENTAL HYGIENE, INC., and BERG LLC.

STATEMENT OF GOVERNMENT SUPPORT

This invention was made with government support under grant numbers OD017908 and HD007430 awarded by the National Institutes of Health. The government has certain rights in the invention.

FIELD OF THE INVENTION

The present invention relates to biomarkers for assessing the efficacy of prophylactic treatments of stress-induced affective disorders such as post-traumatic stress disorder (PTSD).

BACKGROUND OF THE INVENTION

Stress is a common risk factor for psychiatric disorders such as major depressive disorder (MDD), posttraumatic stress disorder (PTSD), bipolar depression, and anxiety disorders. PTSD is an illness characterized by persistent, vivid re-experiencing of a traumatic event, hyperarousal, and avoidance of stimuli associated with the trauma (Charney et al., 1993, Psychobiologic mechanisms of posttraumatic stress disorder. *Arch Gen Psychiatry* 50:295-305). The National Center for PTSD reports that 7-8% of the United States population will experience PTSD at some point in their lives, and about 8 million adults suffer from the disorder each year (National Center for PTSD, 2015). PTSD is often comorbid with other prevalent psychiatric illnesses such as major depressive disorder (MDD) (28%) and substance use (73%) (Brady et al., 2000, Comorbidity of psychiatric disorders and posttraumatic stress disorder. *J Clin Psychiatry* 61: 22-32).

Ketamine, a non-selective glutamate N-methyl-D-aspartate (NMDA) antagonist, has been shown to have rapid acting antidepressant effects in treatment-resistant MDD (TRD) patients (Berman et al, 2000). The antidepressant onset is typically within 2 hours and these effects persist for 1-2 weeks following a single infusion (Price et al, 2009; Zarate et al, 2006). In addition to having efficacy in MDD, ketamine has therapeutic effects for PTSD (Feder et al, 2014), suicide ideation (Murrough et al, 2015), bipolar depression (Diazgranados et al, 2010; Zarate et al, 2012), and anxious bipolar depression (Ionescu et al, 2015).

Rather than treating symptomatology in psychiatric disorders, a novel approach has recently been suggested to prevent the induction of psychiatric disorders before they develop by administering prophylactic pharmaceuticals. It has been proposed that it may be possible to take prevention approaches, including pharmacological ones, for PTSD (Howlett and Stein, 2016). One study administered the kappa-opioid receptor (KOR) antagonist nor-binaltorphimine (norBNI) before the fear-potentiated startle (FPS) test and found that it attenuated conditioned fear (Knoll et al, 2007; Van't Veer and Carlezon, 2013). More recently, we found that a single injection of ketamine (30 mg kg$^{-1}$) 1 week before a stressor prevented stress-induced depressive-like behavior and social avoidance behavior for up to 4 weeks after injection (Brachman et al, 2016). Ketamine was efficacious as a prophylactic in 3 mouse models of stress, including learned helplessness (LH), social defeat (SD), and chronic corticosterone (CORT) administration. This efficacy was confirmed using a LH model in rats (Amat et al, 2016) and a chronic CORT model in mice (Soumier et al, 2016). Interestingly, the time window for prophylactic efficacy was limited to approximately 1 week before a stressor, but not 1 month or 1 hour before (McGowan et al, 2017).

To date, the mechanisms underlying prophylactic efficacy have yet to be identified. One potential area of interest is metabolomics, the study of chemical processes involving metabolites. The metabolome represents a collection of all metabolites, the end products of cellular processes, and therefore, the end results of potential disease or drug treatment; as such, metabolomics has been applied as a tool for biomarker discovery (Johnson et al, 2016). Analyzing metabolite profiles has already contributed to our understanding of depression and antidepressant treatment in mice, macaques, and humans (Pan et al, 2016; Park et al, 2016; Rotroff et al, 2016; Weckmann et al, 2014; Wen et al, 2016). Altered metabolites (e.g. decreased levels of 5-hydroxindoleacitc hydroxyindoleacetic acid (5-HIAA)) have been identified in cerebral spinal fluid (Asberg et al, 1976; Pan et al, 2011), urine, and plasma samples in depressed patients with a markedly elevated risk of suicide (Pan et al, 2017). However, uncovering metabolites that are implicated in prophylactic efficacy has yet to be explored. Elucidating metabolic changes in the brain and plasma that are changed with prophylactic treatment may lend insight into the biological mechanisms of long-lasting resilience enhancement.

Prophylactic pharmacological treatment with ketamine may be able to preempt the induction of stress-induced psychiatric disorders. However, given that up to a third of depression patients do not respond to pharmacological therapies, there remains a need for a method to identify individuals who are likely to benefit from such interventions.

SUMMARY

The present disclosure provides for a method for treating a subject for a stress-induced affective disorder or stress-induced psychopathology. The method may comprise the following steps: (a) administering or having administered a prophylactic treatment to the subject prior to a stressor; (b) determining the level of one or more biomarkers in a biological sample obtained from the subject after step (a) and after the stressor; and (c) comparing the level obtained in step (b) with the level of the one or more biomarkers in a control sample.

The present disclosure provides for a method for assessing a prophylactic treatment of a subject for a stress-induced affective disorder or stress-induced psychopathology. The method may comprise the following steps: (a) determining the level of one or more biomarkers in a biological sample obtained from the subject after a prophylactic treatment and after a stressor; and (b) comparing the level obtained in step (a) with the level of the one or more biomarkers in a control sample.

The present method may further comprise maintaining a treatment regime or determining the prophylactic treatment as being effective, when/if the level of one or more biomarkers increases or decreases by at least about 10%, at least about 15%, at least about 20%, at least about 30%, at least about 40%, at least about 50%, at least about 60%, at least about 70%, at least about 80%, at least about 90%, at least about 100%, at least 1.1-fold, at least 1.2-fold, at least 1.3-fold, at least 1.4-fold, at least 1.5-fold, at least 1.6-fold, at least 1.8-fold, at least 2-fold, at least 2.5-fold, at least 3-fold, at least 3.5-fold, at least 4-fold, at least 4.5-fold, at least 5-fold, from about 30% to about 3-fold, from about 40% to about 2.5-fold, from about 50% to about 2-fold, or from about 60% to about 1.5-fold, compared to its level in the control sample.

The present method may further comprise adjusting a treatment regime, when/if the level of one or more biomarkers is unchanged, or increases or decreases by less than about 10%, less than about 15%, less than about 20%, less than about 30%, less than about 40%, less than about 50%, less than about 60%, less than about 70%, less than about 80%, less than about 90%, less than about 100%, less than 1.1-fold, less than 1.2-fold, less than 1.3-fold, less than 1.4-fold, less than 1.5-fold, less than 1.6-fold, less than 1.8-fold, less than 2-fold, less than 2.5-fold, less than 3-fold, less than 3.5-fold, less than 4-fold, less than 4.5-fold, or less than 5-fold, compared to its level in the control sample.

The biomarkers may be purines, purine metabolites, purine precursors, purine derivatives, pyrimidines, pyrimidine metabolites, pyrimidine precursors, pyrimidine derivatives, nucleotides, nucleotide metabolites, nucleotide precursors, nucleotide derivatives, neurotransmitters, neurotransmitter metabolites, neurotransmitter precursors, neurotransmitter derivatives, and combinations thereof.

The neurotransmitters may be inhibitory neurotransmitters or excitatory neurotransmitters. The neurotransmitters may be amino acid-derived neurotransmitters.

In certain embodiments, the biomarkers are selected from those listed in FIGS. 5C-5Q. In certain embodiments, the biomarkers are selected from the group consisting of adenine, adenosine monophosphate (AMP), adenosine triphosphate (ATP), D-ribose 5-phosphate, D-ribulose 5-phosphate, guanosine monophosphate, guanosine diphosphate, hypoxanthine, inosine, phosphoribosyl pyrophosphate, and combinations thereof. In certain embodiments, the biomarkers are selected from the group consisting of cytidine monophosphate, dihydrothymine, uridine 5-monophosphate, and uridine 5-diphosphate, 5,6-dihydrouridine, and combinations thereof. In certain embodiments, the biomarkers are selected from those listed in Table 3. In certain embodiments, the biomarkers are selected from the group consisting of serine, glutamic acid, gamma-aminobuytric acid (GABA), 5-hydroxy-L-tryptophan (5-HTP), O-phosphoethanolamine (PE), N-acetyl-L-tyrosine, and combinations thereof.

The prophylactic treatment may comprise administering an effective amount of a pharmaceutic composition comprising ketamine, a ketamine analog, or a pharmaceutically acceptable salt, derivative, or metabolite thereof, to the subject prior to the stressor.

The prophylactic treatment may comprise administering an effective amount of a pharmaceutic composition comprising an antagonist of the glutamate N-methyl-D-aspartate (NMDA) receptor to a subject prior to a stressor. The antagonist of the NMDA receptor may comprise ketamine, a ketamine analog, or a pharmaceutically acceptable salt, derivative, or metabolite thereof.

The prophylactic treatment may comprise administering an effective amount of a pharmaceutic composition comprising an α-amino-3-hydroxy-5-methyl-4-isoxazolepropionic acid (AMPA) receptor agonist, to a subject prior to a stressor. The AMPA receptor agonist may be selected from the group consisting of glutamate, AMPA, 5-fluorowillardiine, domoic acid, quisqualic acid, and (2R,6R)-hydroxynorketamine, CX546, or a pharmaceutically acceptable salt, derivative, or metabolite thereof.

The pharmaceutic composition may be administered to the subject about 48 hours to about 3 weeks, about 72 hours to about 2 weeks, about 1 week, about 13 days, about 12 days, about 11 days, about 10 days, about 9 days, about 8 days, about 7 days, about 6 days, about 5 days, about 4 days, about 3 days, about 2 days, or about 1 day, prior to a stressor.

The pharmaceutic composition may be administered to the subject once prior to a stressor. The pharmaceutical composition may be administered in a booster series.

The pharmaceutic composition may be administered orally, intravenously, intranasally, or via injection to the subject.

The pharmaceutic composition may comprise norketamine, hydroxyketamines, dehydronorketamine, and/or hydroxynorketamine (HNK). The pharmaceutic composition may comprise (2R,6R)-HNK and/or (2S,6S)-HNK.

The biological sample may be a plasma, serum, blood and/or urine sample.

The control sample may be from a healthy subject or a plurality of healthy subjects. The control sample may be from a subject who has had a prophylactic treatment without experiencing a stressor, or a plurality of patients who have had a prophylactic treatment without experiencing a stressor. The control sample may be from a subject who has experienced a stressor without a prophylactic treatment, or from a plurality of patients who have experienced a stressor without a prophylactic treatment.

In one embodiment, the level of the one or more biomarkers is determined by mass spectrometry (MS). In one embodiment, the level of the one or more biomarkers is determined by chromatography coupled with MS.

The stress-induced affective disorder may comprise major depressive disorder (MDD) and/or posttraumatic stress disorder (PTSD).

The stress-induced affective disorder may be selected from the group consisting of: depressive-like behavior and associated affective disorders, anhedonic behavior and associated affective disorders, anxiety and associated affective disorders, cognitive impairments and deficits and associated disorders, and combinations thereof.

The stress-induced affective disorder may comprise stress-induced psychopathology. The the stress-induced psychopathology may comprise depressive and/or anxious behavior.

The subject may be a mammal, such as a human.

BRIEF DESCRIPTION OF THE DRAWINGS

FIGS. 1A-1C. Prophylactic ketamine buffers the fear response and alters a significant number of metabolites in the brain. (A) Experimental design. (B) Prophylactic ketamine does not alter CFC training behavior as measured by freezing. (C) Prophylactic ketamine administration decreases freezing behavior upon context re-exposure when compared with prophylactic saline administration. (n=9-10 male mice per group). Error bars represent±SEM. *p<0.05. Sal, saline; K, ketamine; CFC, contextual fear conditioning; RE, re-exposure; HPC, hippocampus; PFC, prefrontal cortex; Sac, sacrifice; QToF, quadrupole time-of-flight; LCMS, liquid chromatography mass spectrometry.

FIGS. 3A-3L. Prophylactic ketamine significantly alters purine metabolism in the PFC and HPC following stress. Purine precursors are significantly decreased and nucleotides are significantly increased in both hemispheres of the (A-G) PFC and (H-L) HPC following prophylactic ketamine administration. (n=9-10 male mice per group). Error bars represent ±SEM. *p<0.05, p<0.01, *p<0.001. Sal, saline; K, ketamine. (A-G) Left/white: Sal; left/black: K (30 mg/kg). Right/gray: Sal; right/black: K (30 mg/kg). (H-L) Left/white: Sal; left/black: K (30 mg/kg). Right/light gray (on the left of "Right"): Sal; right/dark gray (on the right of "Right"): K (30 mg/kg).

FIGS. 4A-4J. Prophylactic ketamine significantly alters pyrimidine metabolism in the PFC and HPC following stress. (A-E) Pyrimidine metabolites are significantly altered in both hemispheres of the PFC following prophylactic ketamine administration. (F-H) Pyrimidine metabolites are significantly altered in both hemispheres of the HPC following prophylactic ketamine administration. (I-J) The amount of dUDP in both hemispheres of the PFC, but not the HPC, is positively correlated with freezing levels upon context re-exposure in CFC in mice administered prophylactic ketamine and stress. (n=9-10 male mice per group). Error bars represent±SEM. *p<0.05, p<0.01, *p<0.001. Sal, saline; K, ketamine; PFC, prefrontal cortex; HPC, hippocampus; dUDP, deoxyuridine-diphosphate. (A-E) Left/white: Sal; left/black: K (30 mg/kg). Right/gray: Sal; right/black: K (30 mg/kg). (F-H) Left/white: Sal; left/black: K (30 mg/kg). Right/light gray (on the left of "Right"): Sal; right/dark gray (on the right of "Right"): K (30 mg/kg).

FIGS. 7A-7K. Negative mode metabolites changed in the PFC following prophylactic ketamine administration and CFC stress. (n=9-10 male mice per group). Error bars represent ±SEM. *p<0.05, p<0.01, *p<0.001. Left/white: Saline; left/black: Ketamine. Right/gray: Saline; right/black: Ketamine.

DETAILED DESCRIPTION OF THE INVENTION

Figure 2B:
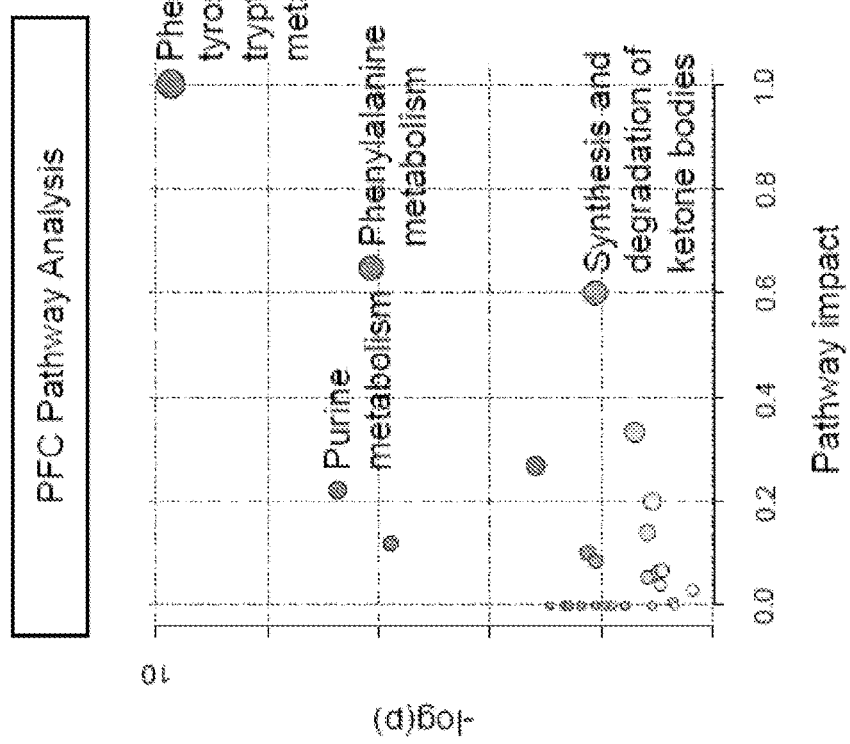
FIGS. 2A-2E. Prophylactic ketamine significantly alters metabolites in the PFC and HPC following stress. (A) A significant number of metabolites were changed in both brain regions and in both hemispheres. A total number of 8 metabolites were changed in both brain regions and in both hemispheres. (B) A pathway analysis of changed metabolites in the PFC. Purine metabolism; phenylalanine, tyrosine, and tryptophan metabolism; and phenylalanine metabolism are most significantly changed in the PFC following prophylactic ketamine administration. (C) A pathway analysis of changed metabolites in the HPC. Purine metabolism; alanine, aspartate, and glutamate metabolism; and glutamine and glutamate metabolism are most significantly changed in the HPC following prophylactic ketamine administration. (D) A heat map of metabolites changed in the PFC. (E) A heat map of metabolites changed in the HPC. (n=9-10 male mice per group). HPC, hippocampus; PFC, prefrontal cortex; ATP, adenosine triphosphate; NADH, nicotinamide adenine dinucleotide; UTP, uridine triphosphate; GDP, guanosine diphosphate; GTP, guanosine triphosphate; AMP, adenosine monophosphate; IMP, inosine monophosphate; dUDP, deoxyuridine-diphosphate; 13-HOTE, 13-OH-9Z,11E,15Z-octadecatrienoic acid; NAD, nicotinamide adenine dinucleotide; CDP, cytidine diphosphate; ADP, adenosine diphosphate.

Certain individuals are particularly vulnerable to developing stress-induced psychiatric disorders. Prophylactic treatments may be able to prevent the development of such psychiatric disorders, but there is currently no method to predict which patients are likely to benefit from such interventions. The present method uses therapeutic targets and biomarkers for the development of prophylactic treatments against stress-induced psychiatric disorders. The biomarkers can be used to develop targeted prophylactic treatments as well as blood tests to predict patient responsiveness to treatments (including pharmacological treatments) for informed treatment decisions.

Up to 30% of depression patients do not respond to pharmacological treatment. Khalid S A, Treatment-resistant depression: therapeutic trends, challenges, and future directions, Patient Preference and Adherence, 2012: 369-388. The present biomarkers may be used for a blood test to identify individuals who would be responsive to a prophylactic treatment against a stress-induced affective disorder or stress-induced psychopathology.

The present biomarkers may be used in drug discovery, e.g., identifying new targets for prophylactic treatments against stress-induced psychiatric disorders. This technology can enable the development of more targeted and effective therapies for stress-induced psychiatric disorders.

The biomarkers may help identify individuals at risk of developing stress-related psychiatric disorders. The biomarkers may be used for a diagnostic test to discriminate between different etiologies of a psychiatric disease.

The present disclosure provides for a method for treating a subject for a stress-induced affective disorder or stress-induced psychopathology. The method may comprise the following steps: (a) administering or having administered a prophylactic treatment to the subject prior to a stressor; (b) determining the level of one or more biomarkers in a biological sample obtained from the subject after step (a) and after the stressor; and (c) comparing the level obtained in step (b) with the level of the one or more biomarkers in a control sample.

The present disclosure also provides for a method for assessing a prophylactic treatment of a subject for a stress-induced affective disorder or stress-induced psychopathology. The method may comprise the following steps: (a) determining the level of one or more biomarkers in a biological sample obtained from the subject after a prophylactic treatment and after a stressor; and (b) comparing the level obtained in step (a) with the level of the one or more biomarkers in a control sample.

The method may further comprise maintaining a treatment regime or determining the prophylactic treatment as being effective, when the level of one or more biomarkers increases or decreases by at least 10% compared to its level in the control sample.

An additional step of the present method may alternatively be adjusting a treatment regime, when the level of one or more biomarkers is unchanged, or increases or decreases by less than 10%, compared to its level in the control sample.

In certain embodiments, the present method determines/detects the level of one or more biomarkers selected from those listed in FIGS. 2B-2E, 3A-3L, 4A-4J, 5A-5Q, 6A-6Z, 6AA-6HH, 7A-7K, 8A-8V, 9A-9W, 10A-10O, and Tables 1-3, and combinations thereof. In certain embodiments, the present method determines/detects the level of one or more biomarkers selected from those listed in any of FIGS. 1A-1C, 2A-2E, 3A-3L, 4A-4J, 5A-5Q, 6A-6Z, 6AA-6HH, 7A-7K, 8A-8V, 9A-9W, 10A-10O, and Tables 1-3, and combinations thereof.

If the level of at least one, or at least 2 (at least 3, at least 4, at least 5, at least 6, at least 7, at least 8, at least 9, at least 10, at least 20, at least 30, at least 40, at least 50, between 5 and 30, between 5 and 10, between 10 and 20, between 30 and 50, or between 50 and 100) biomarkers increases or decreases by about 1% to about 100%, about 5% to about 90%, about 10% to about 80%, about 5% to about 70%, about 5% to about 60%, about 10% to about 50%, about 15% to about 40%, about 5% to about 20%, about 1% to about 20%, about 10% to about 30%, about 5%, about 10%, about 20%, about 30%, about 40%, about 50%, about 60%, about 70%, about 80%, about 90%, about 100%, about 10% to about 90%, about 12.5% to about 80%, about 20% to about 70%, about 25% to about 60%, or about 25% to about 50%, about 2-fold, about 3-fold, about 4-fold, about 5-fold, about 6-fold, about 7-fold, about 8-fold, about 9-fold, about 10-fold, at least 1.1-fold, at least 1.2-fold, at least 1.3-fold, at least 1.4-fold, at least 1.5-fold, at least 1.6-fold, at least 1.8-fold, at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 50-fold, at least 100-fold, at least 120-fold, from about 2-fold to about 500-fold, from about 1.1-fold to about 10-fold, from about 1.1-fold to about 5-fold, from about 1.5-fold to about 5-fold, from about 2-fold to about 5-fold, from about 3-fold to about 4-fold, from about 5-fold to about 10-fold, from about 5-fold to about 200-fold, from about 10-fold to about 150-fold, from about 10-fold to about 20-fold, from about 20-fold to about 150-fold, from about 20-fold to about 50-fold, from about 30-fold to about 150-fold, from about 50-fold to about 100-fold, from about 70-fold to about-150 fold, from about 100-fold to about 150-fold, from about 10-fold to about 100-fold, from about 100-fold to about 200-fold, compared to its (or their) level in a control sample, the therapy is considered to be effective. An effective therapy may be maintained/continued, or discontinued if the patient's condition has improved and is no longer in need of treatment. An ineffective treatment may be altered or modified, or replaced with other treatment.

The present methods can include the steps of measuring the level of at least one biomarker in a sample from a patient having received, or receiving, a therapeutic intervention, and comparing the measured level to a reference level or the level of at least one biomarker in a control sample. The measured level of the at least one biomarker is indicative of the therapeutic efficacy of the therapeutic intervention.

Based on the measured biomarker levels, therapy may be continued or altered, e.g., by change of dose or dosing frequency, or by addition of other active agents, or change of therapeutic regimen altogether.

The present invention also encompasses a method of predicting or assessing the level of severity of the disorder/condition in a patient. In one embodiment, the method comprises measuring the level of at least one biomarker in a biological sample from a patient; and comparing the measured level to a reference level or the level of the at least one biomarker in a control sample, wherein the measured level of the at least one biomarker is indicative of the level of severity of the disorder/condition in the patient. In other embodiments, an increase or decrease (as described herein) in the level of the biomarker is indicative of the level of severity of the disorder/condition in the patient.

The level/amount of the biomarker(s) in a patient may be determined/detected. The level/amount of the biomarker(s) of the patient may be compared with a reference value, where the reference value is based on the level/amount of a set of biomarkers in a control sample, and/or based on a set of biomarkers in an unaffected individual or unaffected individuals, and/or based on a set of biomarkers in the patient before, after and/or during therapy. The changes in biomarker level may be used to alter or direct therapy, including, but not limited to, initiating, altering or stopping therapy.

Another aspect of the disclosure is a kit containing a reagent for measuring at least one biomarker in a biological sample, instructions for measuring at least one biomarker, and instructions for evaluating or monitoring therapeutic efficacy in a patient based on the level of the at least one biomarker. In some embodiments, the kit contains reagents for measuring from 1 to about 20 biomarkers, including 1, 2, 3, 4, 5, 6, 7, 8, 9, 10, 11, 12, 13, 14, 15, 16, 17, 18, 19, 20 up to n biomarkers. Also encompassed by the disclosure are kits for assessing or predicting the severity or progression of the disorder/condition in a subject. The kit may comprise a reagent for measuring at least one biomarker in a biological sample, and instructions for assessing severity or progression of the disorder/condition based on the level of the at least one biomarker. The kit may comprise one or biochips to assay the levels of a plurality biomarkers.

The level of at least one, or at least 2 (or at least 3, at least 4, at least 5, at least 6, at least 7, at least 8, at least 9, at least 10, at least 20, at least 30, at least 40, between 5 and 30, between 5 and 10, between 2 and 6, between 3 and 5, between 10 and 20, or between 20 and 45) biomarkers in the sample may increase or decrease by about 1% to about 100%, about 5% to about 90%, about 10% to about 80%, about 5% to about 70%, about 5% to about 60%, about 10% to about 50%, about 15% to about 40%, about 5% to about 20%, about 1% to about 20%, about 10% to about 30%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, about 10% to about 90%, about 12.5% to about 80%, about 20% to about 70%, about 25% to about 60%, or about 25% to about 50%, about 2-fold, about 3-fold, about 4-fold, about 5-fold, about 6-fold, about 7-fold, about 8-fold, about 9-fold, about 10-fold, at least 1.1-fold, at least 1.2-fold, at least 1.3-fold, at least 1.4-fold, at least 1.5-fold, at least 1.6-fold, at least 1.8-fold, at least 2-fold, at least 2.5-fold, at least 3-fold, at least 3.5-fold, at least 4-fold, at least 4.5-fold, at least 5-fold, at least 5.5-fold, at least 6-fold, at least 7-fold, at least 8-fold, at least 9-fold, at least 10-fold, at least 15-fold, at least 20-fold, at least 50-fold, at least 100-fold, at least 120-fold, from about 2-fold to about 500-fold, from about 1.1-fold to about 10-fold, from about 1.1-fold to about 5-fold, from about 1.5-fold to about 5-fold, from about 2-fold to about 5-fold, from about 3-fold to about 4-fold, from about 5-fold to about 10-fold, from about 5-fold to about 200-fold, from about 10-fold to about 150-fold, from about 10-fold to about 20-fold, from about 20-fold to about 150-fold, from about 20-fold to about 50-fold, from about 30-fold to about 150-fold, from about 50-fold to about 100-fold, from about 70-fold to about 150-fold, from about 100-fold to about 150-fold, from about 10-fold to about 100-fold, from about 100-fold to about 200-fold, compared to the level(s) in the control sample.

In certain embodiments, the levels of a plurality of biomarkers in the sample may be assayed, which comprises 2 or more, 3 or more, 4 or more, 5 or more, 6 or more, 7 or more, 8 or more, 9 or more, 10 or more, 15 or more, 20 or more, 25 or more, 30 or more, 35 or more, 3-50, 5-50, 10-50, 15-50, 20-50, 30-50, or 50-100, biomarkers.

The samples may include, but are not limited to, serum, plasma, blood, whole blood and derivatives thereof, cardiac tissue, bone marrow, urine, cerebrospinal fluid (CSF), myocardium, endothelium, skin, hair, hair follicles, saliva, oral mucus, vaginal mucus, sweat, tears, epithelial tissues, semen, seminal plasma, prostatic fluid, excreta, ascites, lymph, bile, as well as other samples or biopsies. In one embodiment, the biological sample is plasma or serum.

The level or amount of a biomarker in a patient sample can be compared to a reference level or amount of the biomarker present in a control sample. The control sample may be from a patient who has experienced a stressor without a prophylactic treatment, or from a plurality of patients who have experienced a stressor without a prophylactic treatment.

The control sample may be from a patient who has had a prophylactic treatment without experiencing a stressor, or a plurality of patients who have had a prophylactic treatment without experiencing a stressor. The control sample may be from a healthy subject or a plurality of healthy subjects. In other embodiments, a control sample is taken from a patient prior to a stressor or prior to a prophylactic treatment (from an untreated patient). In certain embodiments, a control sample is from a patient or a plurality of patients unresponsive to a prophylactic treatment. Reference levels for a biomarker can be determined by determining the level of a biomarker in a sufficiently large number of samples obtained from normal, healthy control subjects to obtain a predetermined reference or threshold value. A reference level can also be determined by determining the level of the biomarker in a sample from a patient prior to a stressor or prior to a prophylactic treatment (from an untreated patient). Reference (or calibrator) level information and methods for determining reference levels can be obtained from publicly available databases, as well as other sources.

The present methods may comprise prophylactically treating a stress-induced affective disorder or stress-induced psychopathology in a subject. Also encompassed by the present methods are inducing and/or enhancing stress resilience in a subject. In certain embodiments, an effective amount of an antagonist of the glutamate N-methyl-D-aspartate (NMDA) receptor, such as ketamine or a pharmaceutically acceptable salt or derivative thereof, is administered to a subject prior to a stressor.

The present agent/composition may be administered therapeutically to achieve a therapeutic benefit or prophylactically to achieve a prophylactic benefit. By therapeutic benefit is meant eradication or amelioration of the underlying stress-induced affective disorder being treated, and/or eradication or amelioration of one or more of the symptoms associated with the underlying disorder. By prophylactic benefit is meant prevention or delay of the onset of a stress-induced affective disorder, and/or prevention or delay of the onset of one or more of the symptoms associated with a stress-induced affective disorder. In certain embodiments, an effective amount of the present agent/composition to be administered prevents stress-related disorders from developing or being exacerbated into more serious conditions.

In certain embodiments, for prophylactic administration, the present agent/composition may be administered to a patient at risk of developing a stress-induced affective disorder, or to a patient reporting one or more of the physiological symptoms of a stress-induced affective disorder, even though a diagnosis of a stress-induced affective disorder may not have yet been made. In certain embodiments, prophylactic administration is applied to avoid the onset of the physiological symptoms of the underlying disorder, before the symptom manifests cyclically. In this latter embodiment, the therapy is prophylactic with respect to the associated physiological symptoms instead of the underlying indication. In certain embodiments, the present agent/composition is administered prior to recurrence of a stressor. In certain embodiments, the present agent/composition is administered prior to the onset of a particular symptom.

In a further embodiment, the present invention provides for the use of the present agent or a pharmaceutically acceptable salt or solvate thereof, or a physiologically functional derivative thereof, in the preparation of a medicament for the treatment of a stress-induced affective disorder.

"Treating" or "treatment" of a state, disorder or condition includes:
(1) preventing or delaying the appearance of clinical symptoms of the state, disorder, or condition developing in a person who may be afflicted with or predisposed to the state, disorder or condition but does not yet experience or display clinical symptoms of the state, disorder or condition; or
(2) inhibiting the state, disorder or condition, i.e., arresting, reducing or delaying the development of the disease or a relapse thereof (in case of maintenance treatment) or at least one clinical symptom, sign, or test, thereof; or
(3) relieving the disease, i.e., causing regression of the state, disorder or condition or at least one of its clinical or sub-clinical symptoms or signs.

The benefit to a subject to be treated is either statistically significant or at least perceptible to the patient or to the physician.

A "prophylactically effective amount" refers to an amount effective, at dosages and for periods of time necessary, to achieve the desired prophylactic result. In certain embodiments, since a prophylactic dose is used in subjects prior to or at an earlier stage of a disorder, the prophylactically effective amount is less than the therapeutically effective amount. In certain embodiments, the prophylactically effective amount is similar to, identical to, or more than, the therapeutically effective amount.

A therapeutically effective amount, or an effective amount, of a drug is an amount effective to demonstrate a desired activity of the drug. A "therapeutically effective amount" will vary depending on the compound, the disorder and its severity and the age, weight, physical condition and responsiveness of the subject to be treated. In certain embodiments, a effective amount of ketamine, or a pharmaceutically acceptable salt or solvate thereof, or a physiologically functional derivative thereof, is an amount effective to prevent or delay the onset of a stress-induced affective disorder, and/or effective to alleviate, one or more of the symptoms of a stress-induced affective disorder.

In certain embodiments, an effective amount of the present agent is a sub-anesthetic amount of ketamine, or a pharmaceutically acceptable salt or solvate thereof, or a physiologically functional derivative thereof. In certain embodiments, an effective amount of the present agent is a sub-analgesic amount of ketamine, or a pharmaceutically acceptable salt or solvate thereof, or a physiologically functional derivative thereof.

A subject may be treated with ketamine, or a pharmaceutically acceptable salt or solvate thereof, or a physiologically functional derivative thereof, via intravenous, oral, transdermal or intranasal administration. In certain embodiments, a subject is injected with ketamine, or a pharmaceutically acceptable salt or solvate thereof, or a physiologically functional derivative thereof.

A subject may be treated with a single dose of an effective amount of ketamine, or a pharmaceutically acceptable salt or solvate thereof, or a physiologically functional derivative thereof, prior to and/or after a stressor. In some aspects, a subject is treated with multiple doses of an effective amount of ketamine, or a pharmaceutically acceptable salt or solvate thereof, or a physiologically functional derivative thereof, prior to, during, and/or after, a stressor.

In certain embodiments, the present agent, such as ketamine, or a pharmaceutically acceptable salt or solvate thereof, or a physiologically functional derivative thereof, is administered in a composition comprising a pharmaceutically acceptable carrier, excipient or diluent. Also provided herein is a pharmaceutical composition that comprises ketamine, or a pharmaceutically acceptable salt or solvate thereof, or a physiologically functional derivative thereof, and a pharmaceutically acceptable carrier, excipient or diluent, for use in the prophylactic treatment of a stress-induced affective disorder.

"Patient" or "subject" refers to mammals and includes human and veterinary subjects. In certain embodiments, the subject is a mammal.

Biomarkers

The present method measures the level of at least one biomarker in a biological sample.

The biomarkers may be purines, purine metabolites, purine precursors, purine derivatives, pyrimidines, pyrimidine metabolites, pyrimidine precursors, pyrimidine derivatives, nucleotides, nucleotide metabolites, nucleotide precursors, nucleotide derivatives, neurotransmitters, neurotransmitter metabolites, neurotransmitter precursors, and neurotransmitter derivatives. Neurotransmitters may be inhibitory neurotransmitters or excitatory neurotransmitters. Neurotransmitters may be amino acid-derived neurotransmitters. Neurotransmitter precursors may be precursors to inhibitory neurotransmitters or precursors to excitatory neurotransmitters.

In one embodiment, the biomarkers include purine metabolites. The biomarkers may be selected from those listed in FIGS. 5C-5L. In one embodiment, the biomarkers include pyrimidine metabolites. The biomarkers may be selected from those listed in FIGS. 5M-5Q.

Biomarkers may include purine metabolites, such as adenine, adenosine monophosphate (AMP), adenosine triphosphate (ATP), D-ribose 5-phosphate, D-ribulose 5-phosphate, guanosine monophosphate, guanosine diphosphate, hypoxanthine, inosine, and phosphoribosyl pyrophosphate.

The level of the biomarker in the biological sample may increase or decrease compared to the level of the biomarker in the control sample.

Biomarkers may include pyrimidine metabolites, such as cytidine monophosphate, dihydrothymine, uridine 5-monophosphate, and uridine 5-diphosphate. Biomarkers may include pyrimidine metabolites, such as 5,6-dihydrouridine.

In one embodiment, the level of the biomarker in the biological sample increases compared to the level of the biomarker in the control sample. Non-limiting examples of such biomarkers include adenine, adenosine monophosphate (AMP), adenosine triphosphate (ATP), D-ribose 5-phosphate, D-ribulose 5-phosphate, guanosine monophosphate, guanosine diphosphate, hypoxanthine, inosine, and phosphoribosyl pyrophosphate. Non-limiting examples of such biomarkers also include cytidine monophosphate, dihydrothymine, uridine 5-monophosphate, and uridine 5-diphosphate.

In one embodiment, the level of the biomarker in the biological sample decreases compared to the level of the biomarker in the control sample. Non-limiting examples of such biomarkers include 5,6-dihydrouridine.

In one embodiment, the biomarkers include amino acid-derived neurotransmitters and precursors. The biomarkers may be selected from those listed in Table 3.

Biomarkers may include excitatory neurotransmitters such as serine (e.g., D-serine), glutamic acid (e.g., L-glutamic acid), and glutamate. Biomarkers may include inhibitory neurotransmitters such as gamma-aminobuytric acid (GABA), 5-hydroxy-L-tryptophan (5-HTP), O-phosphoethanolamine (PE), and N-acetyl-L-tyrosine.

In one embodiment, the level of the biomarker in the biological sample increases compared to the level of the biomarker in the control sample. Non-limiting examples of such biomarkers include 5-hydroxy-L-tryptophan (5-HTP), and O-phosphoethanolamine (PE).

In another embodiment, the level of the biomarker in the biological sample decreases compared to the level of the biomarker in the control sample. Non-limiting examples of such biomarkers include serine (e.g., D-Serine), glutamic acid (e.g., L-glutamic acid), glutamate, gamma-aminobuytric acid (GABA), and N-acetyl-L-tyrosine.

In certain embodiments, the sample is a body fluid. For example, the body fluid can include, but are not limited to, serum, plasma, blood, whole blood and derivatives thereof, urine, tears, saliva, sweat, cerebrospinal fluid (CSF), oral mucus, vaginal mucus, seminal plasma, semen, prostatic fluid, excreta, ascites, lymph, bile, and amniotic fluid. In certain embodiments, the biological sample is plasma or serum. In certain embodiment, samples can include, but are not limited to, skin, hair, hair follicles, epithelial tissues, bone marrow, endothelium, brain tissue, as well as other samples or biopsies.

The sample may be obtained at any time point after, during, and/or before, the prophylactic treatment and/or after a stressor, such as about 10 minutes, about 30 minutes, about 1 hour, about 2 hours, about 3 hours, about 4 hours, about 5 hours, about 6 hours, about 7 hours, about 8 hours, about 10 hours, about 12 hours, about 15 hours, about 18 hours, about 20 hours, about 22 hours, about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 3 years, about 5 years or longer after, during, and/or before, the prophylactic treatment and/or after the stressor. The time point may also be earlier or later. In one embodiment, the sample is obtained about 4 weeks after the prophylactic treatment and/or after the stressor.

In certain embodiments, 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or all, biomarkers selected from the biomarkers in FIGS. 2B-2E, 3A-3L, 4A-4J, 5A-5Q, 6A-6Z, 6AA-6HH, 7A-7K, 8A-8V, 9A-9W, 10A-10O, and Tables 1-3, and combinations thereof, are measured. In certain embodiments, 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or all, biomarkers selected from the biomarkers in FIGS. 1A-1C, 2A-2E, 3A-3L, 4A-4J, 5A-5Q, 6A-6Z, 6AA-6HH, 7A-7K, 8A-8V, 9A-9W, 10A-10O, and Tables 1-3, and combinations thereof, are measured. In some embodiments, a panel of no greater than 20, no greater than 15, no greater than 10, or no greater than 5 biomarkers is tested, the panel including 1, 2, 3, 4, 5, 6, 7, 8, 9, 10, 11, 12, 13, 14, 15, 16, 17, 18, 19, 20 or more of the biomarkers as described herein.

The level or amount of biomarkers in a patient sample can be compared to a reference level or amount of the biomarkers present in a control sample.

The level of a biomarker (or a plurality of biomarkers) can be detected and/or quantified by any of a number of methods well known to those of skill in the art. The biomarkers may be detected by, for example, mass spectrometry (MS). Also included are analytic biochemical methods such as electrophoresis, capillary electrophoresis, liquid chromatography, nuclear magnetic resonance (NMR), spectrophotometry, high-performance liquid chromatography (HPLC), thin layer chromatography (TLC), hyper-diffusion chromatography, liquid chromatography-tandem mass spectrometry, electrochemical analysis, and the like. Other techniques include refractive index spectroscopy (RI), ultra-violet spectroscopy (UV), fluorescent analysis, radiochemical analysis, near-infrared spectroscopy (Near-IR), light scattering analysis (LS), gas-chromatography-mass spectroscopy (GC-MS), gas chromatography, mass spectrometry, and liquid-chromatography-mass spectroscopy (LC-MS, LC-MS/MS) and other methods known in the art, alone or in combination. U.S. Pat. Nos. 4,366,241; 4,376,110; 4,517,288; and 4,837,168. Methods in Cell Biology Volume 37: Antibodies in Cell Biology, Asai, ed. Academic Press, Inc. New York (1993); Basic and Clinical Immunology 7th Edition, Stites & Terr, eds. (1991).

Levels of biomarkers can be detected using methods well known in the art as a reflection of metabolic activity, such as liquid chromatography. Liquid chromatography coupled with tandem mass spectrometric detection (LC/MS/MS) can be used as an analytical method. Using automated sample-processing techniques, such as on-line column switching, combined with high-sample-density microtiter plates, can further maximize analytical throughput. Selectivity can be further enhanced by the quadrupole ion trap, a device that "traps" ions in a space bounded by a series of electrodes. The unique feature of the ion trap is that an MS/MS experiment (or, multi-step MS experiments) can be performed sequentially in time within a single mass analyzer, yielding a wealth of structural information. Hybrid quadrupole-time-of-flight (Q-TOF) LC/MS/MS systems can also be used for the characterization of metabolite profiles. The configuration of Q-TOF results in high sensitivity in mass resolution and mass accuracy in a variety of scan modes.

Liquid chromatography coupled with nuclear magnetic resonance spectroscopy (LC-NMR) provides a way of confirming absolute molecular configurations. A linear ion-trap mass spectrometer possesses significantly enhanced production-scanning capabilities, while retaining all of the scan functions of a triple quadrupole MS. The ultra-high resolution and sensitivity of Fourier transform ion-cyclotron resonance MS (FI-ICRMS) can be useful for the analysis and characterization of biological mixtures.

HPLC columns equipped with coulometric array technology can be used to analyze the samples.

The compounds may be mapped to biochemical pathways and the pathways that are affected are determined.

The present method may comprise studying metabolites in the sample, conducting metabolomics analysis (including targeted or untargeted metabolomic profiling), and/or analyzing metabolite profiles of the sample.

The disclosure further includes arrays, microarrays, chips, biochips etc. for the analysis of levels of a plurality of biomarkers.

In one embodiment, a difference (increase or decrease) in the measured level of the biomarker(s) relative to the level of the biomarker(s) in the control sample or a pre-determined reference value is indicative of the therapeutic efficacy of the therapeutic intervention (e.g., a prophylactic treatment). In another embodiment, an increase (or decrease) in the measured level of the biomarker(s) relative to the level of the biomarker(s) in the control sample or pre-determined reference value is indicative of the therapeutic efficacy of the therapeutic intervention. For instance, in such embodiments, when the level of one or more biomarkers is increased (or decreased) when compared to the level in a control sample or pre-determined reference value in response to a therapeutic intervention, the increase (or decrease) is indicative of therapeutic efficacy of the therapeutic intervention.

In certain embodiments, a reduction or decrease in the measured level of the biomarker(s) relative to the level of the biomarker(s) in the control sample or pre-determined reference value can be indicative of the therapeutic efficacy of the therapeutic intervention. For instance, in such embodiments, when the level of one or more biomarkers is decreased (or increased) when compared to the level in a control sample or pre-determined reference value in response to a therapeutic intervention, the decrease (or increase) is indicative of therapeutic efficacy of the therapeutic intervention.

Patients showing different (elevated or reduced) levels of one or more biomarkers can be identified. The expression profile of these biomarkers may be used to calculate a score for the combined or individual biomarker expression. The scores of these patients will be compared to the score of individuals as a control. The clinical condition of these patients with respect to their psychiatric status may be correlated with the biomarker profiles. The scores may be used to identify groups of patients responsive to the prophylactic treatment.

Samples Sampling methods are well known by those skilled in the art and any applicable techniques for obtaining biological samples of any type are contemplated and can be employed with the methods of the present invention. (See, e.g., Clinical Proteomics: Methods and Protocols, Vol. 428 in Methods in Molecular Biology, Ed. Antonia Vlahou (2008).) The samples may be drawn before, during or after a prophylactic treatment and/or a stressor. The samples may be drawn at different time points before, during or after a prophylactic treatment and/or a stressor.

The sample may be obtained from the subject at any point before, during or after a prophylactic treatment and/or a stressor. In some embodiments, the sample is obtained about 1 week, about 2 weeks, about 3 weeks, about 1 month, about 2 months, about 3 months, about 4 months, about 5 months, about 6 months, at least 1, 2, 3, or 6 months, before, during or after a prophylactic treatment and/or a stressor. In some embodiments, the sample is obtained least 1, 2, 3, 4, 6 or 8 weeks before, during or after a prophylactic treatment and/or a stressor. In some embodiments, the sample is obtained at least 1, 2, 3, 4, 5, 6, or 7 days before, during or after a prophylactic treatment and/or a stressor. In some embodiments, the sample is obtained at least 10 minutes, 30 minutes, 1 hour, 6 hours, 12 hours, 18 hours or 24 hours before, during or after a prophylactic treatment and/or a stressor. In other embodiments, the sample is obtained at least one week before, during or after a prophylactic treatment and/or a stressor. In some embodiments, one or more biomarkers are measured between 1 and 8 weeks, between 2 and 7 weeks, at 1, 2, 3, 4, 5, 6, 7 or 8 weeks before, during or after a prophylactic treatment and/or a stressor.

Ketamine

Ketamine ((RS)-2-(2-chlorophenyl)-2-(methylamino)cyclohexanone) is an antagonist of the glutamate N-methyl-D-aspartate (NMDA) receptor (NMDAR). Ketamine also acts on opioid receptors, sigma receptors, muscarinic receptors, monoamine transporters, etc.

Ketamine is a chiral compound. As used herein, the term "ketamine" may refer to (S)-ketamine (also referred to as S(+)-ketamine or esketamine), (R)-ketamine (R(−)-ketamine), or a racemic mixture of (S)-ketamine and (R)-ketamine. In certain embodiments, the ketamine compositions contain different proportions of the S(+) and R(−) stereoisomers. In certain embodiments, the ketamine compositions contain only (S)-ketamine or (R)-ketamine, or are enantiomerically enriched for a ketamine enantiomer. In certain embodiments, the ketamine composition is enriched to contain, for example, greater than 60%, greater than 70%, greater than 80%, greater than 90%, greater than 95%, greater than 99%, or greater than 99.9 of (S)-ketamine or (R)-ketamine. Paul et al., "Comparison of racemic ketamine and S-ketamine in treatment-resistant major depression: report of two cases", World J. of Bio. Psych., 2009, pp 241-244, Vol. 10(3); Paskalis et al., Oral Administration of the NMDA Receptor Antagonist S-Ketamine as Add-on Therapy of Depression: A Case Series, Pharmacopsychiatry, 2010, pp 33-35, Vol. 40; Noppers et al., Absence of long-term analgesic effect from a short-term S-ketamine infusion on fibromyalgia pain: A randomized, prospective, double blind, active placebo-controlled trial", Eur. J. of Pain., 2011, 15(9):942-9; Matthews et al., Ketamine for Treatment-Resistant Unipolar Depression, CNS Drugs, 2012, 1-16; and International Patent Publication No. WO2013138322.

The term "pharmaceutically acceptable derivative" refers to any pharmaceutically acceptable salt, solvate or prodrug, e.g. ester, of a compound which upon administration to the recipient is capable of providing (directly or indirectly) a compound or an active metabolite or residue thereof. Such derivatives are recognizable to those skilled in the art, without undue experimentation. Derivatives are described, for example, in Burger's Medicinal Chemistry and Drug Discovery, 5th Edition, Vol 1: Principles and Practice, which is incorporated herein by reference. In certain embodiments, pharmaceutically acceptable derivatives include salts, solvates, esters, carbamates, and phosphate esters. In one embodiment, the present composition contains a hydrochloride salt of ketamine.

The present agent may be administered by various routes, including intravenous (i.v. or IV), intranasal (i.n. or IN), intramuscular (i.m. or IM), caudal, intrathecal, and subcutaneous (s.c.) routes.

NMDA Receptor Antagonists—Ketamine and Other Compounds

NMDA receptor antagonists are compounds that antagonize, or inhibit, the action of the NMDA receptor. An NMDA receptor antagonist may be a competitive antagonist, an uncompetitive antagonist, a noncompetitive antagonist, and/or a glycine antagonist.

Non-limiting examples of NMDA receptor antagonists include, ketamine, dextromethorphan (DXM), histogranin, memantine, meperidine, methadone, methoxetamine (MXE), phencyclidine (PCP), nitrous oxide ($N_2O$), AP5 (APV, R-2-amino-5-phosphonopentanoate), AP7 (2-amino-7-phosphonoheptanoic acid), CPPene ((3-[(R)-2-carboxypiperazin-4-yl]-prop-2-enyl-1-phosphonic acid), Selfotel, Amantadine, Atomoxetine, AZD6765, Agmatine, chloroform, dextrallorphan, dextromethorphan, dextrorphan, diphenidine, dizocilpine (MK-801), ethanol, eticyclidine, gacyclidine, ibogaine, magnesium, memantine, nitromemantine, rolicyclidine, tenocyclidine, methoxydine, tiletamine, neramexane, eliprodil, dexoxadrol, etoxadrol, remacemide, delucemine, WMS-2539, NEFA, 8A-PDHQ, HU-211, Aptiganel (Cerestat, CNS-1102), rhynchophylline, kynurenic acid, Rapastinel (GLYX-13), NRX-1074, 7-Chlorokynurenic acid, 4-Chlorokynurenine (AV-101), TK-40, 1-Aminocyclopropanecarboxylic acid (ACPC), L-Phenylalanine, Xenon, or analogs or derivatives thereof. Ketamine derivatives such as Rapastinel or Glyx-13 are also included. Rapastinel is an NMDA receptor glycine site partial agonist. It is an amidated tetrapeptide (Thr-Pro-Pro-Thr-$NH_2$) which rapidly crosses the blood brain barrier, but is not active orally.

Compounds that are mechanistically similar to ketamine are expected to be protective against stress-induced de novo psychopathology. Such compounds include:
- Ro 25-6981, a GluN2B-selective antagonist (Miller Ohio, et al. (2014), eLife 3:e03581), which has been shown to have rapid antidepressant actions in rodent models of depression.
- CP-101,606, a GluN2B-selective antagonist (Preskorn S, et al. (2007): A placebo-controlled trial of the NR2B specific NMDA antagonist CP-101, 606 plus paroxetine for treatment resistant depression (TRD). *American Psychological Association meeting*), which has been shown to be protective in animal models of brain injury and stroke.
- GLYX-13, a novel N-methyl-D-aspartate receptor (NMDAR) glycine-site functional partial agonist and rapid-acting antidepressant (Burgdorf J, et al. (2013), *Neuropsychopharmacology* 38:729-42). GLYX-13 received Breakthrough Therapy designation from the U.S. Food and Drug Administration (FDA) for adjunctive treatment of MDD in January, 2016, and
- CX546 (Tocris), an ampakine (an AMPA receptor agonist) (Zhou W, et al. (2014), *Eur. Psychiatry* 29:419-23), which relieves the respiratory depression induced by fentanyl.

Non-limiting examples of the NMDA receptor antagonists also include anti-receptor antibodies, anti-ligand antibodies, etc.

Several synthetic opioids function as NMDA receptor-antagonists, such as pethidine, methadone, meperidine, dextropropoxyphene, tramadol, levorphanol, and ketobemidone.

AMPA Receptor Agonists

AMPA receptor agonists are compounds that activate the action of the a-amino-3-hydroxy-5-methyl-4-isoxazolepropionic acid (AMPA) receptor. It is expected that compounds that activate the AMPA receptor, including metabolites, will have a similar effect as the present effects shown with ketamine, in view of recent findings that a ketamine metabolite's antidepressant activity in mice was due to sustained activation of the AMPA receptor, rather than inhibiting NMDAR. (See, Zanos et al., (2016). "NMDAR inhibition-independent antidepressant actions of ketamine metabolites. Nature, 533: 481-486.)

Thus, in certain embodiments, AMPA receptor agonists may be used in the methods described herein. Non-limiting examples of the AMPA receptor agonists include glutamate, AMPA, 5-fluorowillardiine, domoic acid, quisqualic acid, (2R,6R)-hydroxynorketamine, CX546, etc.

Ketamine Metabolites

Ketamine is a derivative of arylcyclohexylamine and contains a chiral center. Since the 1950s, a large number of arylcyclohexylamines have been synthesized: these compounds have shown a wide range of possible pharmacological activities. When administered orally, it undergoes first-pass metabolism, where it is stereo selectively metabolized into a broad array of metabolites, including norketamine, hydroxyketamines, dehydronorketamine and hydroxynorketamine (HNK). After ketamine administration, (2S,6S;2R,6R)-HNK are the two major HNK metabolites found in the plasma and brain. Interestingly, a recent study has shown that the (2R,6R)-HNK metabolite is: 1) essential for the antidepressant effects of ketamine, 2) dependent on a-amino-3-hydroxy-5-methyl-4-isoxazolepropionic acid (AMPA) receptor activation, and 3) non-hypnotic (Zanos et al., 2016). All of these compounds are expected to behave similarly in the presently described methods, including enantiomers and non-psychotomimetic metabolites of ketamine.

The present composition may also comprise ketamine's enantiomers and/or non-psychotomimetic metabolites. Such compounds include:
1. (2R,6R)-HNK, a metabolite of ketamine that may mediate the antidepressant effects of ketamine and lacks the ketamine-related side effects (Zanos et al., 2016)
2. (2S,6S)-HNK, a metabolite of ketamine (Zanos et al., 2016, synthesis of these compounds (2R,6R)-HNK and (2S,6S)-HNK are described in Zanos et al. 2016 and Wainer et al. WO 2013/056229 (2013), The use of (2R,6R)-hydroxynorketamine, (S)-dehydronorketamine and other stereoisomeric dehydro and hydroxylated metabolites of (R,S)-ketamine in the treatment of depression and neuropathic pain).
3. (R)-ketamine, the R-enantiomer of ketamine, which has rapid-onset and sustained antidepressant effects without psychotomimetic side effects (Yang et al., 2015), and
4. (S)-ketamine, the S-enantiomer of ketamine, which is being developed as an intranasal spray, currently in phase III clinical trials for treatment-resistant depression.

Other ketamine analogs may also be used. Such compounds include:
5. Fluorodeschloroketamine, an analog of ketamine where the chlorine (Cl) group has been replaced by fluorine (F), and
6. Tiletamine, an analog of ketamine commonly used as a veterinary anesthetic.

Pharmaceutical Compounds

The compounds used in the present methods include all hydrates, solvates, and complexes of the compounds. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

When the structure of the compounds used in this invention includes an asymmetric carbon atom such compound can occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "*Enantiomers, Racemates and Resolutions*" by J. Jacques, A. Collet and S. Wilen, Pub. John Wiley & Sons, N Y, 1981. For example, the resolution may be carried out by preparative chromatography on a chiral column.

The present disclosure is also intended to include use of all isotopes of atoms occurring on the compounds disclosed herein. Isotopes include those atoms having the same atomic number but different mass numbers. Isotopically-labeled compounds can generally be prepared by conventional techniques known to those skilled in the art or by processes analogous to those described in the Examples disclosed herein using an appropriate isotopically-labeled reagents in place of the non-labeled reagents employed.

The compounds of the instant invention may be in a salt form. As used herein, a "salt" is a salt of the instant compound which has been modified by making acid or base, salts of the compounds. In the case of compounds used for treatment of mammals, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately treating a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The present methods also encompass administering a physiologically functional derivative of the present compound. As used herein, the term "physiologically functional derivative" refers to a compound (e.g, a drug precursor) that is transformed in vivo to yield the present compound or its active metabolite, or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Dosages

In certain embodiments, the effective amount of the present compound is a dose of about 0.01 to about 3 mg of ketamine per kilogram of body weight of the subject (mg/kg), i.e., from about 0.01 mg/kg to about 3 mg/kg body weight. In certain embodiments, the effective amount of the present compound ranges 0.001 to approximately 3 mg/kg body weight, 0.001 to approximately 2 mg/kg body weight, from about 0.01 mg/kg to about 3 mg/kg body weight, from about 0.01 to about 2 mg/kg of body weight, about 0.01 to about 1.5 mg/kg of body weight, about 0.05 to about 1.4 mg/kg of body weight, about 0.05 to about 1.3 mg/kg of body weight, about 0.05 to about 1.2 mg/kg of body weight, about 0.05 to about 1.1 mg/kg of body weight, about 0.01 to about 1 mg/kg of body weight, or about 0.05 to about 0.7 mg/kg of body weight. In some aspects, the dose is about 0.05 to about 0.5 mg/kg. In some aspects, the dose is less than about 0.5 mg/kg, less that about 0.4 mg/kg, or less than about 0.3 mg/kg body weight. In some aspects, the effective amount of the present compound is a dose in the range of from about 0.01 mg/kg to about 1.5 mg/kg body weight. In some aspects, the effective amount of the present compound is a dose in the range of from about 0.01 mg/kg to about 1 mg/kg body weight. In some aspects, the effective amount of the present compound is a dose in the range of from about 0.01 mg/kg to about 0.75 mg/kg body weight. In some aspects, the effective amount of the present compound is a dose in the range of from about 0.75 mg/kg to about 1.5 mg/kg body weight. In some aspects, the effective amount of the present compound is a dose in the range of from about 0.5 mg/kg to about 1.2 mg/kg body weight. In some aspects, the effective amount of the present compound is a dose in the range of from about 0.05 mg/kg to about 0.5 mg/kg. In some aspects, the effective amount of the present compound is a dose of about 0.2 mg/kg or about 0.4 mg/kg body weight. In some aspects, the dose of the present compound is, about 0.01 to about 1 mg/kg, about 0.1 to about 0.5 mg/kg, about 0.8 to about 1.2 mg/kg, about 0.7 to about 1.1 mg/kg, about 0.05 to about 0.7 mg/kg, about 0.01 mg/kg, about 0.05 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg, or about 3 mg/kg body weight.

In certain embodiments, the dose of the present compound per administration is from about 1 to about 250 mg, from about 10 mg to about 300 mg, about 10 mg to about 250 mg, about 10 to about 200 mg, about 15 to about 175 mg, about 20 to about 175 mg, about 8 mg to about 32 mg, about 50 mg to about 75 mg, about 25 to about 150 mg, about 25 to about 125 mg, about 25 to about 100 mg, about 50 to about 100 mg, about 50 mg to about 75 mg, about 75 mg to about 100 mg, or about 75 mg to about 200 mg, about 1 mg, 2 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, and 250 mg. In some aspects, the dose of the present compound is about 50 mg. In some aspects, the dose of the present compound is about 75 mg. In some aspects, the total dose of the present compound is about 100 mg.

In some aspects, the therapeutically effective amount of the present compound is a sub-anesthetic dose. In some aspects, the therapeutically effective amount of the present compound is a sub-analgesic dose. In certain embodiments, the therapeutically effective amount of the present compound is below the level that results in one or more side effects of the compound. In certain embodiments, the therapeutically effective amount of the present compound is an anesthetic dose or analgesic dose. U.S. Patent Publication No. 20160067196.

In some aspects, the (therapeutically) effective amount of the present compound is about 0.01 mg to about 1000 mg, from about 0.01 mg to about 500 mg, from about 0.1 mg to about 250 mg, or any amount or range therein. In another aspect, the (therapeutically) effective amount of the present compound is, e.g., 0.01 mg, 0.025 mg, 0.05 mg, 0.1 mg, 0.5 mg, 1 mg, 5 mg, 10 mg, 25 mg, 50 mg, 55 mg, 60 mg, 65 mg, 70 mg, 75 mg, 80 mg, 90 mg, 95 mg, 100 mg, 150 mg, 200 mg, 250 mg, or 500 mg.

In certain embodiments, a therapeutically effective dose of the present compound may be adjusted depending on conditions of the disease/disorder to be treated or prophetically treated, the age, body weight, general health conditions, sex, and diet of the subject, dose intervals, administration routes, excretion rate, and combinations of drugs.

An initial dose of the present compound may be larger, followed by one or more smaller maintenance doses. Other ranges are possible, depending on the subject's response to the treatment. An initial dose may be the same as, or lower or higher than subsequently administered doses.

The dose may be administered daily, weekly, biweekly, several times daily, semi-weekly, every other day, bi-weekly, quarterly, several times per week, semi-weekly, monthly etc., to maintain an effective dosage level. The duration and frequency of treatment may depend upon the subject's response to treatment.

In certain embodiments, a subject may be administered 1 dose, 2 doses, 3 doses, 4 doses, 5 doses, 6 doses or more of the present composition. In certain embodiments, a single dose of the present agent/composition is administered in the present method. In certain embodiments, multiple doses of the present agent/composition (e.g., 2 doses, 3 doses, 4 doses, 5 doses, 6 doses, 7 doses, 8 doses, 9 doses, 10 doses or more) are administered in the present method.

In certain embodiments, when there are more than one doses of the present compound/composition administered to a subject, the second dose is lower than the first dose. In certain embodiments, the second dose is an amount that is at most one-half, one-quarter, or one-tenth the amount of the first dose.

The number and frequency of doses may be determined based on the subject's response to administration of the composition, e.g., if one or more of the patient's symptoms improve and/or if the subject tolerates administration of the composition without adverse reaction.

In certain embodiments, the present agent/composition is administered at least once a day, at least twice a day, at least three times per day, or more. In certain embodiments, the present agent/composition is administered at least once a week, at least twice a week, at least three times per week, or more frequently. In certain embodiments, the present agent/composition is administered at least twice per month, or at least once per month.

Treatment using the present method can continue as long as needed.

Dosing Time Frame

In certain embodiments, the present agent/composition is administered to a subject prior to a stressor. In certain embodiments, the present agent/composition is administered to a subject both prior to and after a stressor. In certain embodiments, the present agent/composition is administered to a subject after a stressor. In certain embodiments, the present agent/composition is administered to a subject prior to a stressor, and again prior to a recurrence of the stressor or a different stressor.

In certain embodiments, the present agent/composition is administered to the subject about 12 hours to about 4 weeks, about 18 hours to about 4 weeks, about 1 day to about 3.5 weeks, about 2 days to about 3 weeks, about 3 days to about 3 weeks, about 4 days to about 3 weeks, about 5 days to about 3 weeks, about 6 days to about 3 weeks, about 2 days to about 2.5 weeks, about 3 days to about 2.5 weeks, about 4 days to about 2.5 weeks, about 5 days to about 2.5 weeks, about 6 days to about 2.5 weeks, about 1 week to about 2.5 weeks, about 1 week to about 2.5 weeks, about 1 week to about 2 weeks, about 3 days, about 4 days, about 5 days, about 6 days, about 1 week, about 8 days, about 9 days, about 10 days, about 11 days, about 12 days, about 13 days, about 2 weeks, about 2.5 weeks, about 3 weeks, about 3.5 weeks, or about 4 weeks, prior to, and/or after a stressor.

In certain embodiments, the administration of the present agent/composition is continued over a period of up to 2 days, up to 3 days, up to 4 days, up to 5 days, up to 6 days, up to 1 week, up to 2 weeks, up to 3 weeks, up to 4 weeks, 2 weeks, 3 weeks, 4 weeks, 5 weeks, 6 weeks, 7 weeks, 8 weeks, 9 weeks, 10 weeks, or longer.

In certain embodiments, the present agent/composition is administered once, twice, at least twice, at least three times, at least four times, at least five time, at least six times, at least seven times, at least eight times, at least nine times, or more per treatment.

In certain embodiments, the present agent/composition is administered at least once a day, at least twice a day, at least three times per day, at least once a week, at least twice a week, at least three times a week, at least once per month, at least twice per month, or more frequently. Treatment can continue as long as needed.

Stressors

A stressor is a stimulus that causes stress. It can be an event or other factor that disrupts the body's homeostasis of temperature, blood pressure, and/or other functions. In certain embodiments, a stressor is a traumatic or stressful event. Because humans have sophisticated brains and thought processes, anticipating a disruption can also be a stressor. In certain embodiments, a stressor is injury, trauma, combat, warfare, surgery, an accident, a criminal assault, child abuse, natural or human-caused disasters, a crash, grief, hunger, heat, cold, chemical exposure, chemical withdrawal, auto-immune disease, infectious disease, viral infection, cancer, exhaustion, physical distress, neuropathy, hyperalgesia, allodynia, emotional distress, or depression. A traumatic event may be an event or something that threatens the person's life or the life of a close one or it could be something witnessed.

A stressor may be acute, or may be chronic.

There are numerous physiological processes that are altered in response to stress. Among these are altered cortisol, corticotropin, catecholamine and serotonin levels. These levels return to baseline after an acute stressor is removed (McEwen N Eng J Med 1998 338(3):171-179). These biochemical markers of stress in turn lead to ill health and psychosocial disorders. Consequently, stress plays a major role in physical and mental health. Stress can affect the onset of, or susceptibility to disease. It can also affect the progression or course of disease even when there is another underlying pathophysiology of the disease. Recovery from an existing disease can also be delayed due to stress. For example, stress is a contributing factor to high blood pressure, heart disease, headaches, colitis, irritable bowel syndrome, temporo-mandibular joint disorder, cancer, peptic ulcers, insomnia, skin disorders and asthma. Stress can also aggravate other conditions such as multiple sclerosis, diabetes, herpes, mental illness, substance abuse and psychiatric disorders characterized by the presence of violent or aggressive tendencies. Particularly, stress contributes to functional somatic disorders, affective disorders and major depressive disorder. These include disorders such as chronic fatigue syndrome (CFS), fibromyalgia (FMS), Gulf War Syndrome, anxiety and post-traumatic stress disorder (PTSD). Stressors that disrupt normal exercise or sleep patterns.

Additional examples of use include administration prior to military deployment to protect service members (active combat soldiers, battlefield surgeons, etc.) and even military working dogs against stress. Potential non-military use cases include, but are not limited to: police, firefighters, first responders, EMTs, ER doctors, prison guards (and prisoners), humanitarian aid workers, and refugees.

In certain embodiments, a subject may be administered the present agent or composition prior to a situation in which the subject (such as an early responder or military personnel) is likely to be exposed to traumatic stress, immediately after exposure to traumatic stress, and/or when the subject feels that his or her PTSD symptoms are likely to appear.

Resilience to Stress

Resilience to stress refers to the capacity of a subject to adapt or change successfully, and/or to maintain physiological, neurological, or psychological homeostasis, in the face of a stressor (e.g., adversity). As used herein, the term "enhancing resilience" refers to increasing the ability of a subject to experience a stressor (e.g., a traumatic event) without suffering a stress-induced affective disorder, and/or with less post-event symptomatology or disruption of homeostasis and/or normal activities of daily living. In certain embodiments, improving resilience can prevent a stress-induced affective disorder. In certain embodiments, improving resilience can reduce at least one of the signs, symptoms, or symptom clusters of a stress-induced affective disorder. In certain embodiments, the present method enhances a subject's resilience to stress, helps protect against developing stressor-related psychopathology, decrease the functional consequences of stressor-induced disorders (e.g., PTSD, etc.), and reduce medical morbidity and mortality.

The Connor-Davidson Resilience Scale (CD-RISC) is a 25-item self-report scale, each rated on a 5-point scale (0-4), with higher scores reflecting greater resilience (Connor K M & Davidson, J R T. Development of a new resilience scale: the Connor-Davidson Resilience Scale (CD-RISC). Depression and Anxiety, 2003: 18: 71-82).

Resilience, psychological growth and life satisfaction may be measured with the CD-RISC, the Purpose in Life Scale, the abbreviated MOS Social Support Survey, the PTGI, and the Q-LES-Q.

Combination Therapy

The present compound or composition may be administered to a subject alone, or may be administered to a subject in combination with one or more other treatments/agents.

In certain embodiments, the second agent is an antidepressant, an anxiolytic, or combinations thereof. In certain embodiments, the second agent is a serotonin reuptake inhibitor (SRI), or a selective serotonin reuptake inhibitor (SSRI). In certain embodiments, the second agent is fluoxetine, paroxetine, sertraline, lithium, riluzole, prazosin, lamotrigine, ifenprodil, or combinations thereof. In certain embodiments, the second agent is a dual serotonin norepinephrine reuptake inhibitor compound (DRI). In certain embodiments, the second agent is venlafaxine, duloxetine, milnacipran, or combinations thereof. In certain embodiments, the second agent is a non-tricyclic triple reuptake inhibitor (TRI).

In certain embodiments, the present compound or composition is administered to a subject in combination with one or more treatments/agents such as antidepressants, analgesics, muscle relaxants, anorectics, stimulants, antiepileptic drugs, and sedative/hypnotics. Non-limiting examples of compounds that can be administered in combination with the present compound or composition include, neurontin, pregabalin, pramipexole, L-DOPA, amphetamine, tizanidine, clonidine, tramadol, morphine, tricyclic antidepressants, codeine, carbamazepine, sibutramine, amphetamine, valium, trazodone and combinations thereof.

In certain embodiments, combination therapy means simultaneous administration of the compounds in the same dosage form, simultaneous administration in separate dosage forms, or separate administration of the compounds.

In certain embodiments, the second agent/treatment is used as adjunctive therapy to the present compound or composition. In certain embodiments, the treatment includes a phase wherein treatment with the second agent/treatment takes place after treatment with the present compound or composition has ceased. In certain embodiments, the treatment includes a phase where treatment with the present compound or composition and treatment with the second agent/treatment overlap.

Combination therapy can be sequential or can be administered simultaneously. In either case, these drugs and/or therapies are said to be "co-administered." It is to be understood that "co-administered" does not necessarily mean that the drugs and/or therapies are administered in a combined form (i.e., they may be administered separately (e.g., as separate compositions or formulations) or together (e.g., in the same formulation or composition) to the same or different sites at the same or different times).

In certain embodiments, a subject is treated concurrently (or concomitantly) with the present compound or composition and a second agent. In certain embodiments, a subject is treated initially with the present compound or composition, followed by cessation of the present compound or composition treatment and initiation of treatment with a second agent. In certain embodiments, the present compound or composition is used as an initial treatment, e.g., by administration of one, two or three doses, and a second agent is administered to prolong the effect of the present compound or composition, or alternatively, to boost the effect of the present compound or composition. A person of ordinary skill in the art will recognize that other variations of the presented schemes are possible, e.g., initiating treatment of a subject with the present compound or composition, followed by a period wherein the subject is treated with a second agent as adjunct therapy to the present compound or composition treatment, followed by cessation of the present compound or composition treatment.

The present compound and the other pharmaceutically active agent(s) may be administered together or separately and, when administered separately this may occur simultaneously or sequentially in any order. The amounts of the present compound and the other pharmaceutically active agent(s) and the relative timings of administration will be selected in order to achieve the desired combined therapeutic effect.

In various embodiments, the therapies (e.g., a composition provided herein and a second agent in a combination therapy) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In certain embodiments, the therapies are administered no more than 24 hours apart or no more than 48 hours apart. In certain embodiments, two or more therapies are administered within the same patient visit. In other embodiments, the composition provided herein and the second agent are administered concurrently. In other embodiments, the composition provided herein and the second agent are administered at about 2 to 4 days apart, at about 4 to 6 days apart, at about 1 week part, at about 1 to 2 weeks apart, or more than 2 weeks apart. In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months. In certain embodiments, a composition provided herein and a second agent are administered to a subject in a sequence and within a time interval such that the composition provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the composition provided herein and the second active agent exerts their effect at times which overlap. Each second active agent can be administered separately, in any appropriate form and by any suitable route. In other embodiments, the composition provided herein is administered before, concurrently or after administration of the second active agent. The term "about" refers to +10% of the referenced value. In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day. The second agent can act additively or synergistically with the compound provided herein. In one embodiment, the composition provided herein is administered concurrently with one or more second agents in the same pharmaceutical composition. In another embodiment, a composition provided herein is administered concurrently with one or more second agents in separate pharmaceutical compositions. In still another embodiment, a composition provided herein is administered prior to or subsequent to administration of a second agent. Also contemplated are administration of a composition provided herein and a second agent by the same or different routes of administration, e.g., oral and parenteral. In certain embodiments, when the composition provided herein is administered concurrently with a second agent that potentially produces adverse side effects including, but not limited to, toxicity, the second active agent can advantageously be administered at a dose that falls below the threshold that the adverse side effect is elicited.

Encompassed by the present disclosure are methods to prophylactically treat a subject prior to a stressor. In certain embodiments, the present method prevents or delays a stress-induced affective disorder or stress-induced psychopathology in a subject. In certain embodiments, stress-induced affective disorders include major depressive disorder and posttraumatic stress disorder.

Stress-Induced Affective Disorders

There are numerous disorders that are either caused by or exacerbated by stress. These include addictive disorders such as substance abuse, anorexia, bulimia, obesity, smoking addiction, and weight addiction; anxiety disorders such as agoraphobia, anxiety disorder, obsessive compulsive disorder, panic attacks, performance anxiety, phobias, and posttraumatic stress disorder; autoimmune diseases such as allergies, arthritis, fibromyalgia, fibromytosis, lupus, multiple sclerosis, rheumatoid arthritis, Sjogren's syndrome, and vitiligo; cancer such as bone cancer, brain cancer, breast cancer, cervical cancer, colon cancer, Hodgkin's disease, leukemia, liver cancer, lung cancer, lymphoma, multiple myeloma, ovarian cancer, pancreatic cancer, and prostate cancer; cardiovascular disorders such as arrhythmia, arteriosclerosis, Burger's disease, essential hypertension, fibrillation, mitral valve prolapse, palpitations, peripheral vascular disease, Raynaud's disease, stroke, tachycardia, and Wolff-Parkinson-White Syndrome; and developmental disorders such as attention deficit disorder, concentration problems, conduct disorder, dyslexia, hyperkinesis, language and speech disorders, and learning disabilities.

Anxiety Disorders

The five major types of anxiety disorders are: panic disorder, obsessive-compulsive disorder, post-traumatic stress disorder, generalized anxiety disorder and phobias (including social phobia, also called social anxiety disorder). Each anxiety disorder has its own distinct features, but they are all bound together by the common theme of excessive, irrational fear and dread. It is common for an anxiety disorder to accompany depression, eating disorders, substance abuse, or another anxiety disorder.

Panic disorder is characterized by repeated episodes of intense fear that strike often and without warning. Physical symptoms include chest pain, heart palpitations, shortness of breath, dizziness, abdominal distress, feelings of unreality, and fear of dying. Obsessive-compulsive disorder is characterized by repeated, unwanted thoughts or compulsive behaviors that seem impossible to stop or control. Generalized Anxiety Disorder is characterized by exaggerated worrisome thoughts and tension about everyday routine life events and activities, lasting at least six months. Almost always anticipating the worst even though there is little reason to expect it; accompanied by physical symptoms, such as fatigue, trembling, muscle tension, headache, or nausea. Phobias are characterized into two major types of phobias, social phobia and specific phobia. People with social phobia have an overwhelming and disabling fear of scrutiny, embarrassment, or humiliation in social situations, which leads to avoidance of many potentially pleasurable and meaningful activities. People with specific phobia experience extreme, disabling, and irrational fear of something that poses little or no actual danger; the fear leads to avoidance of objects or situations and can cause people to limit their lives unnecessarily.

Posttraumatic Stress Disorder (PTSD)

Typically, a subject suffering from PTSD was exposed to a traumatic event in which the person experienced, witnessed, or was confronted with an event or events that involved actual or threatened death or serious injury, or a threat to the physical integrity of self or others and the person's response involved intense fear, helplessness, or horror.

Having repeated intrusive memories of the trauma exposure is one of the core symptoms of PTSD. Patients with PTSD are known to display impairments in learning and memory during neuropsychological testing. Other core symptoms of PTSD include heightened stress sensitivity (startle), tension and anxiety, memory disturbances, and dissociation.

In certain embodiments, the present method prevents or inhibits the development of post-traumatic stress disorder (PTSD) in a subject. In certain embodiments, the present method prevents or inhibits the development of one or more PTSD-like symptoms. In certain embodiments, a subject may be administered the present agent or composition prior to a situation in which the subject (such as an early responder or military personnel) is likely to be exposed to traumatic stress, immediately after exposure to traumatic stress, and/or when the subject feels that his or her PTSD symptoms are likely to appear.

Typically, the traumatic event is persistently re-experienced in one or more of the following ways: recurrent and intrusive distressing recollections of the event, including images, thoughts, or perceptions, recurrent distressing dreams of the event, acting or feeling as if the traumatic event were recurring (includes a sense of reliving the experience, illusions, hallucinations, and dissociative flashback episodes, including those that occur on awakening or when intoxicated), intense psychological distress at exposure to internal or external cues that symbolize or resemble an aspect of the traumatic event, physiological reactivity on exposure to internal or external cues that symbolize or resemble an aspect of the traumatic event. An individual suffering from PTSD also has persistent avoidance of stimuli associated with the trauma and numbing of general responsiveness (not present before the trauma), as indicated by 3 or more of the following: efforts to avoid thoughts, feelings, or conversations associated with the trauma, efforts to avoid activities, places, or people that arouse recollections of the trauma, inability to recall an important aspect of the trauma, significantly diminished interest or participation in significant activities, feeling of detachment or estrangement from others, restricted range of affect (e.g., unable to have loving feelings), sense of a foreshortened future (e.g., does not expect to have a career, marriage, children, or a normal life span), persistent symptoms of increased arousal (not present before the trauma), as indicated by 2 or more of the following: difficulty falling or staying asleep, irritability or outbursts of anger, difficulty concentrating, hypervigilance, exaggerated startle response. The disturbance, which has lasted for at least a month, causes clinically significant distress or impairment in social, occupational, or other important areas of functioning.

In certain embodiments, the present compound or composition prevents, reduces, eliminates or delays one or more of the symptoms including, but not limited to, re-experiencing of the traumatic experience in the form of intrusive memories, nightmares, flashbacks; emotional and physical reactions triggered by reminders of the trauma; distancing from others; decreased interest in activities and other people; numbing of feelings; avoidance of trauma reminders; hyperarousal symptoms, including disrupted sleep, irritability, hypervigilance, decreased concentration; increased startle reflex; and combinations thereof.

Whatever the source of the problem, some people with PTSD repeatedly relive the trauma in the form of nightmares and disturbing recollections during the day. They may also experience other sleep problems, feel detached or numb, or be easily startled. They may lose interest in things they used to enjoy and have trouble feeling affectionate. They may feel irritable, more aggressive than before, or even violent. Things that remind them of the trauma may be very distressing, which could lead them to avoid certain places or situations that bring back those memories.

The disorder may be accompanied by depression, substance abuse, or one or more other anxiety disorders. In severe cases, the person may have trouble working or socializing.

Major Depressive Disorder

Major depressive disorder refers to a class of syndromes characterized by negative affect and repeated episodes of depression without any history of independent episodes of mood elevation and over-activity that fulfill the criteria of mania. Multiple subtypes of major depressive disorders are recognized, including these with atypical characteristics, psychotic components, etc. The age of onset and the severity, duration and frequency of the episodes of depression are all highly variable. The disorder may begin at any age. The symptoms of major depressive disorder typically develop over days to weeks. Prodromal symptoms include generalized anxiety, panic attacks, phobias or depressive symptoms and may occur during several months preceding the episode. Individual episodes also last between 3 and 12 months but recur less frequently. Most patients are asymptomatic between episodes, but a minority of patients may develop a persistent depression, mainly in old age. Individual episodes of any severity are often precipitated by stressful life events. Common symptoms of a depressive episode include reduced concentration and attention; reduced self-esteem and self-confidence; ideas of guilt and unworthiness, ideas or acts of self-harm or suicide; disturbed sleep; and diminished appetite. In certain embodiments, a major depressive episode follows a psychosocial stressor, e.g., death of a loved one, marital separation, childbirth or the end of an important relationship. The lowered mood varies little from day to day and is often unresponsive to circumstances, yet may show a characteristic diurnal variation as the day goes on. As with manic episodes, the clinical presentation shows marked individual variations, and atypical presentations are particularly common in adolescence. In some cases, anxiety, distress, and motor agitation may be more prominent at times that the depression, and the mood change may also be masked by added features such as irritability, excessive consumption of alcohol, histrionic behavior, and exacerbation of pre-existing phobic or obsessional symptoms, or by hypochondria.

Psychiatric Evaluations

The psychiatric conditions of the subject, and/or the effects or efficacy of treatment with the present agent/composition, may be evaluated by the subject and/or a medical professional, e.g., the subject's physician. In certain embodiments, the evaluation is conducted within about 10 minutes, within about 15 minutes, within about 20 minutes, within about 25 minutes, within about 0.5 hours, within about 1 hour, within about 2 hours, within about 2.5 hours, within about 3 hours, within about 3.5 hours, within about 4 hours, within about 4.5 hours, within about 5 hours, within about 5.5 hours, within about 6 hours, within about 6.5 hours, within about 7 hours, within about 7.5 hours, within about 8 hours, within about 8.5 hours, within about 9 hours, within about 9.5 hours, within about 10 hours, within about 10.5 hours, within about 11 hours, within about 11.5 hours, within about 12 hours, within about 18 hours, within about 1 day, within about 2 days, within about 3 days, within about 4 days, within about 5 days, within about 6 days, within about 1 week, within about 2 weeks, within about 3 weeks, within about 4 weeks, within about 1 month, within about 2 months, within about 3 months, within about 4 months, within about 5 months, within about 6 months, within about 1 year, within about 2 years, or longer, before, during, or after a stressor and/or administration of the present agent/composition.

Psychiatric evaluations of a patient being treated with the present method can be conducted to determine whether the method is effective. In certain embodiments, the psychiatric evaluation may be carried out before treatment, at the time of treatment, during treatment, and/or after treatment. When the psychiatric evaluation is carried out both before treatment and after (and/or during) treatment with the present method, the results of the evaluation before treatment can provide a baseline for comparison to the results of the evaluation during and/or after treatment. In certain embodiments, psychiatric evaluation is conducted only after treatment.

Psychophysiological stress tests can be performed to measure the amount of stress-induced anxiety present in the various systems of the body (i.e. muscular, cardiovascular, digestive, respiratory and neurological systems). These stress tests are routinely used in the art. Test results are compared to both local and national norms, to determine if the individual is exhibiting an excessive amount of physiological anxiety and whether or not they are able to recover from a standardized stressful stimuli in an appropriate length of time.

Psychiatric testing can be used to monitor a subject to determine the emotional and/or social etiology of the stress disorder. These tests are known in the art and include health-related assessments, mental health assessments, personality tests, and personality type assessment.

In certain embodiments, clinician-administered evaluation and/or self-report instruments are used, with the aim of measuring baseline symptomatology as well as drug actions on (1) the overall severity of the disorder, (2) the core symptoms, and (3) depressed mood.

Non-limiting examples of psychiatric evaluation tools and questionnaires include the following measures.

The Diagnostic and Statistical Manual of Mental Disorders (DSM-5) includes the revised diagnostic criteria for PTSD. See, American Psychiatric Association: Diagnostic and Statistical Manual of Mental Disorders, Fifth Edition. Arlington, Va., American Psychiatric Association, 2013. See also ptsd.va.gov/professional/PTSD-verview/dsm5_criteria_ptsd.asp.

The Structured Clinical Interview for DSM-IV Axis I Disorders, Patient Edition (SCID-P) is a semi-structured interview that provides probe questions as well as follow-up questions to be asked by the clinician to assist in diagnosis. First et al., Structured Clinical Interview for DSM-IV TR Axis I Disorders, Research Version, Patient Edition (SCID-I/P). New York: New York State Psychiatric Institute, Biometrics Research; 2001. It includes an overview to obtain information about demographics, work, chief complaint, history of present illness, past history, treatment history, and current functioning. The main body of SCID-P includes 9 modules that are designed to diagnose 51 mental illnesses in all.

The SCID-P for DSM-5 is the SCID—Patient version, and is the next edition of the SCID modified to incorporate the new DSM-5 criteria.

The Clinician-Administered PTSD Scale (CAPS) is a structured clinical interview designed to assess the essential features of PTSD as defined by the DSM-IV. Weathers et al., Clinician-administered PTSD scale: a review of the first ten years of research. Depress Anxiety. 2001; 13(3):132-156. The CAPS can be used to provide categorical ratings of diagnostic status as well as a quantitative index of symptom severity. Both frequency and intensity scores are derived for each individual symptom. The CAPS total score is based on an individual's response to the 17 items that assess the frequency and intensity of current PTSD symptoms. Subscales of the CAPS are utilized to assess specific symptom clusters. The total score can range from 0 to 136.

The Clinician-Administered PTSD Scale for DSM-5 (CAPS-5) is a 30-item structured interview that can be used to make current (past month) diagnosis of PTSD, make lifetime diagnosis of PTSD, and to assess PTSD symptoms over the past week. CAPS-5 is a 30-item questionnaire, corresponding to the DSM-5 diagnosis for PTSD. The language of the CAPS-5 reflects both changes to existing symptoms and the addition of new symptoms in DSM-5. Weathers, F. W., et al (2013). The Clinician-Administered PTSD Scale for DSM-5 (CAPS-5).

The Treatment Outcome PTSD Scale (TOP-8) is a brief interviewer-administered scale designed specifically for the assessment of commonly occurring signs and symptoms of PTSD that are subject to change in response to treatment (Davidson, J. R., & Colket, J. T. (1997). The eight-item treatment-outcome post-traumatic stress disorder scale: A brief measure to assess treatment outcome in post-traumatic stress disorder. International Clinical Psychopharmacology, 12(1), 41-45). The TOP-8 is comprised of eight items, each measured on a scale of 0-4, with defined anchors given for each item. The items are representative of the three core features of PTSD with a maximum possible score of 32.

The Hamilton Psychiatric Rating Scale for Anxiety (HAM-A) is a widely used observational rating measure of anxiety severity. The scale consists of 14 items. Each item is rated on a scale of 0 to 4. This scale is administered to assess the severity of anxiety and its improvement during the course of treatment. The HAM-A total score is the sum of the 14 items and the score ranges from 0 to 56. Hamilton M. The Assessment of Anxiety-States by Rating. Br J Med Psychol. 1959; 32(1):50-55.

The Montgomery-Asberg Depression Rating Scale (MADRS) is a 10-item instrument used for the evaluation of depressive symptoms in adults and for the assessment of any changes to those symptoms. Montgomery S. A., et al., A new depression scale designed to be sensitive to change. Br J Psychiatry. 1979 April; 134:382-389. Each of the 10 items is rated on a scale of 0 to 6, with differing descriptors for each item. These individual item scores are added together to form a total score, which can range between 0 and 60 points.

The Young Mania Rating Scale, item 1 (YMRS-1) used to assess mood elevation on the infusion days. Young R C, et al. Rating-Scale for Mania—Reliability, Validity and Sensitivity. Br J Psychiatry. 1978; 133(November):429-435.

The Brief Psychiatric Rating Scale (BPRS) is used to assess acute behavioral changes during the infusions. Overall J E et al., The Brief Psychiatric Rating-Scale. Psychol. Rep. 1962; 10(3):799-812 Four key BPRS items for the positive (+) symptoms of psychosis are used: conceptual disorganization, hallucinatory behavior, suspiciousness, and unusual thought content. Three items representing the negative (−) symptoms of psychosis will also be used: blunted affect, emotional withdrawal, and motor retardation.

The Clinician-Administered Dissociative States Scale (CADSS) is used to measure dissociative effects during the infusions. Bremner J D, et al., Measurement of Dissociative States with the Clinician-Administered Dissociative States Scale (CADSS). J Trauma Stress. 1998; 11(1):125-136 The scale includes 19 questions and 8 observer ratings scored from 0 (not at all) to 4 (extremely). The CADSS measures impairment in body perception, environmental perception, time perception, memory impairment, and feelings of unreality.

The Patient Rating Inventory of Side Effects (PRISE) is a patient self-report used to qualify side effects by identifying and evaluating the tolerability of each symptom. Levine J, Schooler N R. SAFTEE: A technique for the systematic assessment of side effects in clinical trials. Psychopharmacol Bull. 1986; 22(2):343-381.

The Clinical Global Impression (CGI) scale assesses treatment response in psychiatric patients. The administration time is 2 minutes. This scale consists of three items: Severity of Illness (item 1); Global Improvement (item 2); and Efficacy Index (item 3). Item 1 is rated on a seven-point scale (1=normal, 7=among the most extremely ill patients) as is item 2 (1=very much improved, 7=very much worse). Each includes an additional response of "not assessed." Item 3 is rated on a four-point scale (from "none" to "outweighs therapeutic effect").

The Impact of Events Scale (IES) is one of the most widely used self-report measures of stress reactions to traumatic events. Horowitz et al., Impact of Event Scale: a measure of subjective stress. Psychosom Med. 1979 May; 41(3):209-218. See also, Weiss et al., The Impact of Event Scale—Revised In: Wilson J, Keane T M, eds. Assessing psychological trauma and PTSD. New York: Guilford; 1996: 399-411. It measures both intrusion and avoidance. Sundin et al., Impact of Event Scale: psychometric properties. Br J Psychiatry. 2002 March; 180:205-209. Joseph S. Psychometric evaluation of Horowitz's Impact of Event Scale: a review. J Trauma Stress. 2000 January; 13(1):101-113. The total score can range from 0 to 75.

The Posttraumatic Stress Disorder Checklist (PCL-5) is a 17-item self-report measure reflecting DSM-5 symptoms of PTSD. The PCL-5 measures symptoms in response to stressful situations (Weathers, F., et al. (1993). The PTSD checklist (PCL): Reliability, validity, and diagnostic utility. Annual Convention of the International Society for Traumatic Stress Studies, San Antonio, Tex.).

The Quick Inventory of Depressive Symptomatology, Self Report (QIDS-SR) is a 16-item self-rated instrument designed to assess the severity of depressive symptoms present in the past seven days. Rush A J, Trivedi M H, Ibrahim H M et al. The 16-Item quick inventory of depressive symptomatology (QIDS), clinician rating (QIDS-C), and self-report (QIDS-SR): a psychometric evaluation in patients with chronic major depression. Biol. Psychiatry. 2003; 54(5):573-583. The 16 items cover the nine symptom domains of major depression, and are rated on a scale of 0-3. Total score ranges from 0 to 27, with ranges of 0-5 (normal), 6-10 (mild), 11-15 (moderate), 16-20 (moderate to severe), and 21+(severe).

The Childhood Trauma Questionnaire (CTQ) is a 28-item self-report instrument that assesses childhood trauma in the following areas: physical, sexual and emotional abuse and physical and emotional neglect. Bernstein D P, Stein J A, Newcomb M D et al. Development and validation of a brief screening version of the Childhood Trauma Questionnaire. Child Abuse Negl. 2003 February; 27(2): 169-190. Each item is rated on a scale of 1 (never true) to 5 (very often true). The 5 subscales are then totaled, with scores ranging from 5-25 for each traumatic category.

Visual Analogue Scales (VAS) are used to assess subjective state changes. Bond A, Lader M. The use of analogue scales in rating subjective feelings. Br J Med Psychol. 1974; 47(3):211-218. They are 100-mm horizontal lines marked proportionately to the perceived intensity of the subjective experience (0=not at all, to 10=extremely) for the following states: anxious, depressed, drowsy, high, hungry, and nauseous.

The Sheehan Disability Scale (SDS) is a self-report disability measure. It has demonstrated sensitivity to impairment and changes as a result of treatment across a wide range of psychiatric disorders. The SDS asks only about current levels of impairment, providing no indication of whether the person has done better or worse in the past, thus making it a reasonable short-term outcome measure that is un-confounded by historical impressions. The dependent variable is the total score, which is based on the sum of three 10-point items (work, social life, and family life), with higher scores reflecting greater disability. Sheehan D. The Anxiety Disease. New York, N.Y.: Scribner; 1983.

The Wechsler Abbreviated Scale of Intelligence 2-Subtest (WASI-2) is a reliable brief measure of IQ for 6 to 89 year-olds that includes Vocabulary (an estimate of verbal fluid abilities) and Matrix Reasoning (an estimate of nonverbal fluid abilities). Wechsler D. Wechsler Abbreviated Scale of Intelligence San Antonio, Tex.: Psychological Corporation; 1999. It is extensively used in clinical, educational, and research settings. Average reliability coefficient is 0.96 and test-retest reliability is 0.88.

The Hopkins Verbal Learning Test (HVLT) is a repeatable test of memory acquisition and delayed recall of words. Subjects are presented with the same 12-item list for 3 learning trials and asked each time to repeat the items on each list. Delayed recall and recognition conditions are administered later. Dependent variables used in this study include total learning over the 3 trials (for the acquisition variable) and total delayed recall score (for the recall component). Brandt J, Benedict R. Hopkins Verbal Learning Test, Revised. Odessa, Fla.: Psychological Assessment Resources; 1997.

The Profile of Mood States-Bipolar (POMS-Bi) scale measures moods and feelings primarily in clinical rather than nonclinical settings. It can help to determine an individual's psychiatric status for therapy, or be used to compare mood profiles associated with various personality disorders. It is also a useful instrument in identifying the effects of drug treatments.

The Post-Traumatic Cognitions Inventory (PTCI) is a 33-item scale, which is rated on a Likert-type scale ranging from 1 (totally disagree) to 7 (totally agree). Scale scores are formed for the three subscales, which show a high degree of intercorrelation (rs=0.57-0.75).

The New Cognitions scale is a 6-item pilot scale, which is rated on a Likert-type scale ranging from 1 (not at all) to 4 (a lot). The scale is based on the Post Traumatic Growth Inventory (PTGI) from which items have been directly selected (new items were added to the scale as well), and on the Brief-COPE (see Carver, C. S. (1997) "You want to measure coping but your protocol's too long: Consider the brief COPE." International Journal of Behavioral Medicine 4; 92-100).

The Medical Outcomes Study (MOS) Social Support Survey is a 19-item self-report measure designed to assess levels of functional social support. The MOS-SS has two subscales (emotional and instrumental social support) to identify potential social support deficits (Sherbourne, C. D. & Stewart, A. L. (1991). "The MOS Social Support Survey." Soc Sci Med 32(6): 705-714).

The Purpose in Life test-Short Form (PIL-SF) is a brief, 4-item form of the 20-item Purpose in Life test. This scale asks respondents to report to what extent they have achieved their goals in life, and to what extent they perceive their life to be meaningful or purposeful. (Schulenberg et al 2010; Psychotherapy (Chic). 2008 December; 45(4):447-63).

Posttraumatic Growth Inventory (PTGI)-Short Version is a 10-item shortened version of the PTGI self-report questionnaire (ref). It asks respondents to rate the extent to which they have changed as the result of experiencing a highly stressful life event. Items span positive changes in five domains: relating to others, new possibilities, personal strength, spiritual change, and appreciation of life (Cann, A., et al. (2010). A short form of the Posttraumatic Growth Inventory. Anxiety, Stress & Coping, 23, 127-137).

The Quality of Life Enjoyment and Satisfaction Questionnaire (Q-LES-Q) is a self-report scale measuring the degree of enjoyment and satisfaction experienced by subjects in various areas of daily functioning. The summary scores are reliable and valid measures of these dimensions in a group of depressed subjects (Endicott J, et al. Quality of Life Enjoyment and Satisfaction Questionnaire: A New Measure. Psychopharmacology Bulletin; 1993; 29:321-326).

In certain embodiments, self-evaluation of the subject being treated is conducted.

Pharmaceutical Compositions

While it is possible that the present a compound, as well as salts, solvates and physiological functional derivatives thereof, may be administered as the raw chemical, it is possible to present the active ingredient as a pharmaceutical composition. Accordingly, the invention further provides a pharmaceutical composition, which comprises the present compound and/or salts, solvates and physiological functional derivatives thereof, and one or more pharmaceutically acceptable carriers, diluents, or excipients. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing the present compound, or salts, solvates and physiological functional derivatives thereof, with one or more pharmaceutically acceptable carriers, diluents or excipients.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing compound 20, and pharmaceutically acceptable excipients.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopeias for use in animals, and more particularly in humans.

Pharmaceutical compositions of the present invention may be presented in unit dose forms containing a predetermined amount of active ingredient per unit dose. Such a unit may contain, for example, 5 μg to 1 g, preferably 1 mg to 700 mg, more preferably 5 mg to 100 mg of the present compound, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), inhaled, nasal, ocular, or parenteral (including intravenous and intramuscular) route. The present composition may be injected. Such compositions may be prepared by any method known in the art of pharmacy, for example by bringing into association the active ingredient with the carrier(s) or excipient(s).

In a further embodiment, the present invention provides a pharmaceutical composition adapted for administration by the oral route, the treatment of stress-induced affective disorder.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

It should be understood that, in addition to the ingredients particularly mentioned above, the compositions may include other agents conventional in the art having regard to the type of formulation in question, for example those suitable for oral administration may include flavoring agents.

A therapeutically effective amount of a compound of the present invention will depend upon a number of factors including, for example, the age and weight of the subject, the precise condition requiring treatment and its severity, the nature of the formulation, and the route of administration, and will ultimately be at the discretion of the attendant physician or veterinarian.

Kits

Another aspect of the disclosure is a kit containing a reagent or reagents for measuring at least one biomarker in a biological sample, instructions for measuring the at least one biomarker, and/or instructions for evaluating or monitoring efficacy of a prophylactic treatment in a patient based on the level of the at least one biomarker, and/or instructions for assessing a prophylactic therapy in a patient. In some embodiments, the kit contains reagents for measuring from 1 to about 20 biomarkers, including at least 1, 2, 3, 4, 5, 6, 7, 8, 9, 10, 11, 12, 13, 14, 15, 16, 17, 18, 19, 20 or more biomarkers as described herein.

The invention may also encompass arrays, microarrays, chips, biochips, etc.

Any of the compositions described herein may be comprised in a kit. In one embodiment, the kit contains a reagent for measuring at least one biomarker in a biological sample, instructions for measuring the at least one biomarker, and instructions for evaluating or monitoring efficacy of a prophylactic treatment in a patient based on the level of the at least one biomarker. In some embodiments, the kit contains reagents for measuring the level of at least 2, 3, 4, 5, 6 or 10 (or more) biomarkers. The kit may also be customized for determining the efficacy of therapy for a stress-induced affective disorder or stress-induced psychopathology, and thus provides the reagents for determining 50 or fewer, 40 or fewer, 30 or fewer, or 25 or fewer biomarkers.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed (e.g., sterile, pharmaceutically acceptable buffer and/or other diluents). However, various combinations of components may be comprised in a vial. The kits also will typically include a means for containing the reagents, and any other reagent containers in close confinement for commercial sale. Such containers may include injection or blow molded plastic containers into which the desired vials are retained.

When the components of the kit are provided in one and/or more liquid solutions, the liquid solution may be an aqueous solution. The components of the kit may also be provided as dried powder(s). When reagents and/or components are provided as a dry powder, the powder can be reconstituted by the addition of a suitable solvent. It is envisioned that the solvent may also be provided in another container means.

Such kits may also include components that preserve or maintain the reagents or that protect against their degradation. Such components may be protease inhibitors or protect against proteases. Such kits generally will comprise, in suitable means, distinct containers for each individual reagent or solution.

A kit will also include instructions for employing the kit components as well the use of any other reagent not included in the kit. Instructions may include variations that can be implemented.

This invention will be better understood from the examples, which follow. However, one skilled in the art will readily appreciate that the specific methods and results discussed are merely illustrative of the invention as described more fully in the claims that follow thereafter.

Example 1 Prophylactic Ketamine Alters Nucleotide and Neurotransmitter Metabolism in Brain and Plasma Following Stress Recently, we have shown that ketamine given prior to stress exposure protects against the development of depressive-like behavior in mice. These data suggest that it may be possible to prevent the induction of affective disorders before they develop by administering prophylactic pharmaceuticals, a relatively nascent and unexplored strategy for psychiatry. Here, we performed metabolomics analysis of brain and plasma following prophylactic ketamine treatment in order to identify markers of stress resilience enhancement. We administered prophylactic ketamine in mice to buffer against fear expression. Following behavioral analyses, untargeted metabolomic profiling was performed on both hemispheres of the prefrontal cortex (PFC) and the hippocampus (HPC), and plasma. We found that prophylactic ketamine attenuated learned fear. Eight metabolites were changed in the PFC and HPC upon ketamine treatment. Purine and pyrimidine metabolism were most significantly changed in the HPC, PFC, and, interestingly, plasma of mice two weeks after prophylactic administration. Moreover, most precursors to inhibitory neurotransmitters were increased whereas precursors to excitatory neurotransmitters were decreased. Strikingly, these long-term metabolomic changes were not observed when no stressor was administered. Our results suggest that prophylactic treatment differentially affects purine and pyrimidine metabolism and neurotransmission in brain and plasma following stress, which may underlie the long-lasting resilience to stress induced by a single injection of ketamine. These data may provide novel targets for prophylactic development, and indicate an interaction effect of prophylactic ketamine and stress. To our knowledge, this is the first study that identifies metabolomic alterations and biomarker candidates for prophylactic ketamine efficacy in mice.

Here, in order to begin to address the mechanism behind the efficacy of prophylactic treatment, we administered saline or ketamine (30 mg $kg^{-1}$) 1 week before a 3-shock contextual fear-conditioning (CFC) paradigm or before context exposure without shocks, and subsequently profiled the metabolome of both hemispheres of the PFC and HPC, as well as plasma. As we previously reported (McGowan et al, 2017), prophylactic ketamine attenuated learned fear. Purine and pyrimidine metabolism was significantly altered in the HPC, PFC, and plasma following prophylactic ketamine treatment and stress as compared with saline-treated mice. Moreover, most precursors to inhibitory neurotransmitters were increased, while most precursors to excitatory neurotransmitters were decreased. Interestingly, these changes were not observed in non-stressed mice, indicating that ketamine interacts with a stressful experience to induce long-lasting changes in the metabolome and on behavior. These results point to potential metabolites as mediators in ketamine's resilience-enhancing effects, which may be easily identifiable in the clinic.

Materials and Methods

Mice

129S6/SvEvTac mice were purchased from Taconic (Hudson, N.Y.) at 7 weeks of age. Mice were housed 4-5 per cage in a 12-h (06:00-18:00) light-dark colony room at 22° C. Food and water were provided ad libitum. Behavioral testing was performed during the light phase. All experiments were approved by the Institutional Animal Care and Use Committee at New York State Psychiatric Institute (NYSPI).

Drugs

A single injection of saline (0.9% NaCl) or ketamine (30 mg $kg^{-1}$) (Ketaset III, Ketamine HCl injection, Fort Dodge Animal Health, Fort Dodge, Iowa) was administered once at 8 weeks of age as previously described (Brachman et al, 2016; McGowan et al, 2017). Ketamine was prepared in physiological saline and all injections were administered intraperitoneally (i.p.) in volumes of 0.1 cc per 10 mg body weight.

Contextual Fear Conditioning (CFC)

A 3-shock CFC paradigm was administered as previously described (Denny et al, 2014; Drew et al, 2010; McGowan et al, 2017). Mice were placed in the conditioning chamber and received 3 shocks 180, 240, and 300 s later (2 s, 0.75 mA) and were removed 15 s following the last shock. For context re-exposure, mice were placed back into the context for 180 s. The no-shock control group underwent the same protocol, but did not receive 3 shocks during the first exposure. All sessions were scored for freezing using FreezeView2 (http://actimetrics.com/downloads/freezeframe/). All behavioral statistical analyses are included in Table 1.

Brain Extraction

Mice were sacrificed via cervical dislocation 2 h following CFC re-exposure. Brains were extracted and frozen at –20° C. for 30 sec. Brains were cut using a brain matrix slicer (Cat. #BSMAS001-1, Zivic Instruments, Pittsburgh, Pa., USA). Bilateral punches were then excised from the PFC using a brain punch tissue set (Cat. #57401, Stoelting, Wood Dale, Ill.) according to the coordinates of Paxinos and Franklin (2001) in a glass dish containing ice. Left and right punches were stored separately. The HPC was manually dissected and left and right hemispheres were stored separately. Each sample was weighed. The weights of all samples are included in Table 1. All tissue samples were then stored at –80° C. until metabolomic analysis.

Blood Plasma Collection

Trunk blood was collected immediately following decapitation and spun down (10,000 rpm) in Eppendorf tubes pre-coated with 5 l 0.5 M EDTA to obtain plasma. Samples were transferred to new tubes and stored at –80° C. until analysis. All tissue samples were then stored at –80° C. until analysis.

Preparation of Brain Tissue

Frozen brain tissue was transferred to a homogenization tube containing ceramic beads (Omni International, Kennesaw, Ga.). A volume of ice-cold 80% MeOH was added to obtain a 20 mg/ml solution to each of the tubes. The tubes were snap frozen in liquid nitrogen during processing to ensure the tissue was kept cold. After a brief thawing period, the tubes were then transferred to a Bead Ruptor Homogenizer (Omni International, Kennesaw, Ga.). Tissue was homogenized for 2 cycles of 45 seconds, with a 15 second rest period in between. Samples were sonicated for 10 minutes at room temperature (RT) and then centrifuged at 14,000 rpm for 10 minutes at 4° C. All of the supernatant was removed, transferred to an Eppendorf tube, and evaporated to dryness overnight using a centrifugal evaporator. Once dry, the dried lysate was stored at −80° C. until analysis.

Preparation of Plasma

Plasma was stored at −80° C. until extraction. The samples were thawed at RT for 10 minutes. Thirty μl were removed and were added to 270 μl of ice-cold 80% MeOH. The lysate was then vortexed and spun in a centrifuge at 14,000 rpm for 10 minutes at 4° C. One hundred μl of supernatant were taken and transferred to a fresh Eppendorf tube and evaporated to dryness overnight using a centrifugal evaporator. Once dry, the lysate was stored at −80° C. until analysis.

Metabolomics Analysis

For untargeted metabolomics analysis, brain samples were reconstituted in 2:1:1 acetonitrile:MeOH:$H_2O$, to yield a concentration of 200 mg/ml. Plasma samples were reconstituted in the same solvent, at a 30 μl resuspension volume. Both were spun at 14,000 rpm for 10 minutes at 4° C. to remove excess debris before analysis. Chromatography was performed using an Agilent 1290 Infinity UPLC. Ten μl of each sample were injected onto a ZIC-pHILIC column (EMD Millipore, Billerica, Mass.) with dimensions of 150× 4.6 mm, 5 μm. Metabolites were separated using an acetonitrile/$H_2O$ with 20 mM ammonium carbonate (pH 9.2) gradient over a 29-minute period. A 10-minute re-equilibration time was carried out in between injections. Detection was performed using an Agilent 6550 Quadrupole-time-of-flight (QToF) mass spectrometer, operated in both negative and positive modes. Full scan MS data was collected from m/z 70-1000 and metabolites were identified in an untargeted manner by looking within 10 ppm of the expected m/z values. Real-time mass calibration was performed throughout the duration of sample analysis.

Figure 6A:
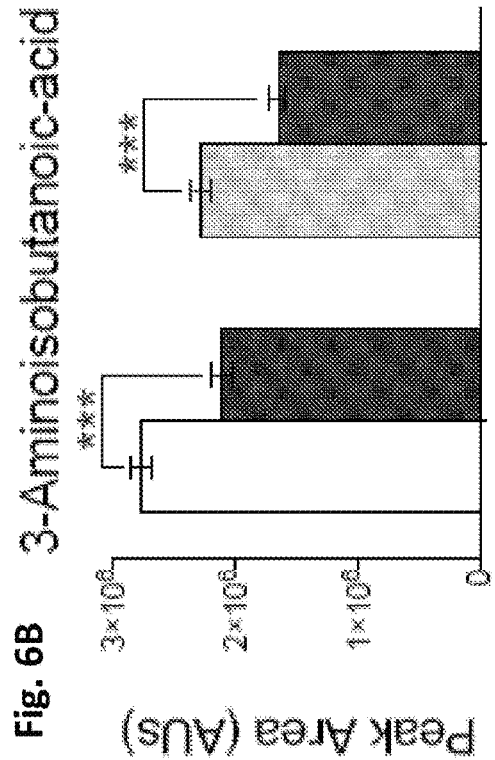
FIGS. 6A-6Z, 6AA-6HH. Positive mode metabolites changed in the PFC following prophylactic ketamine administration and CFC stress. (n=9-10 male mice per group). Error bars represent ±SEM. *p<0.05, p<0.01, *p<0.001. Left/white: Saline; left/black: Ketamine. Right/gray: Saline; right/black: Ketamine.
Figure 6B:
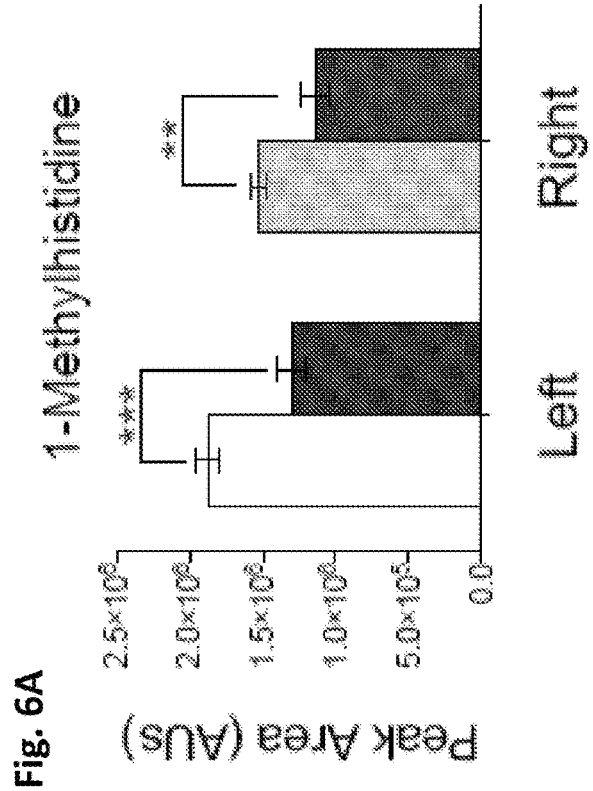
Figure 6C:
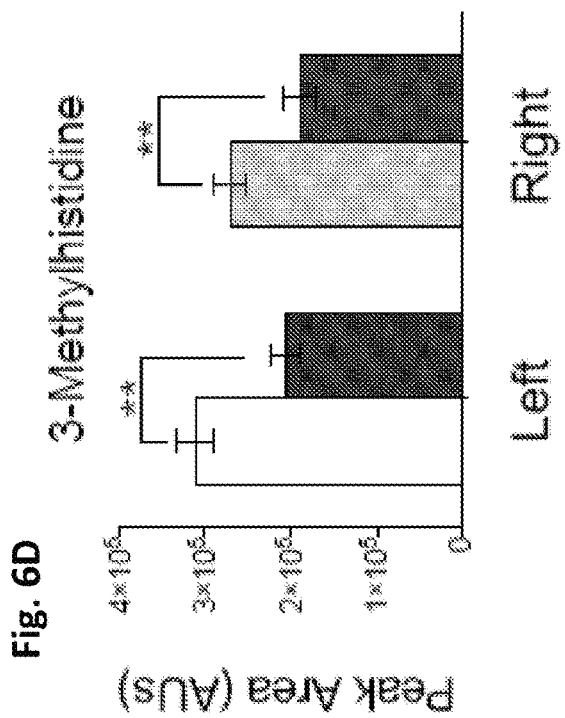
Figure 6D:
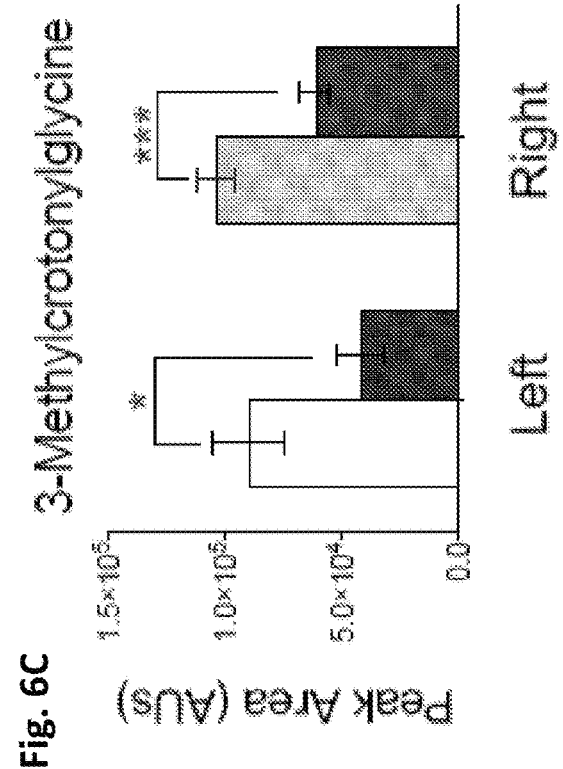
Figure 6E:
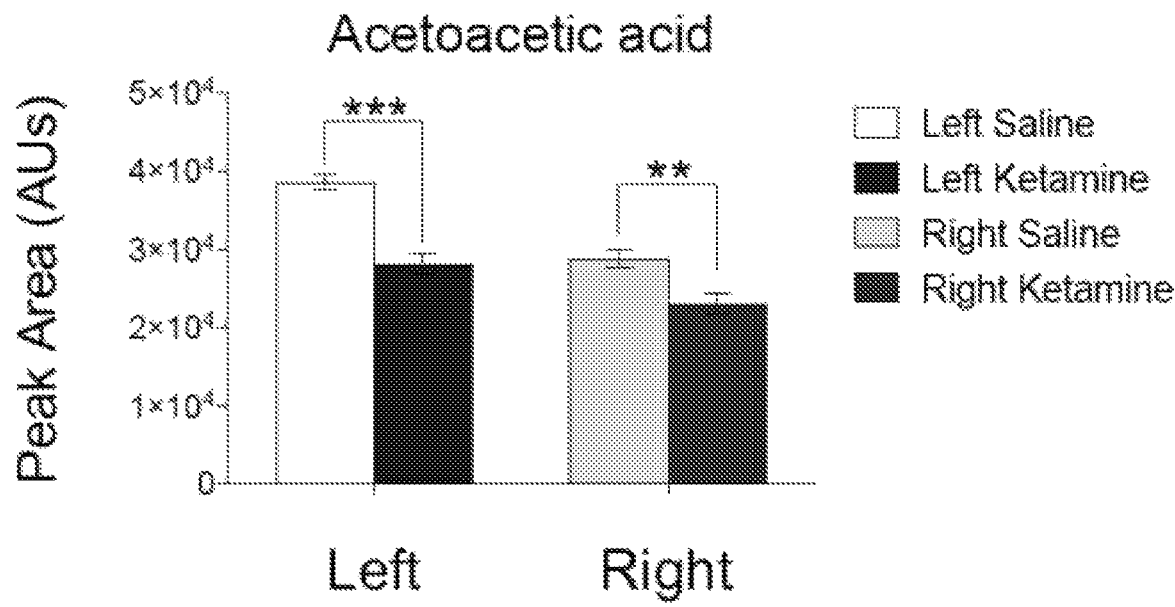
Figure 6F:
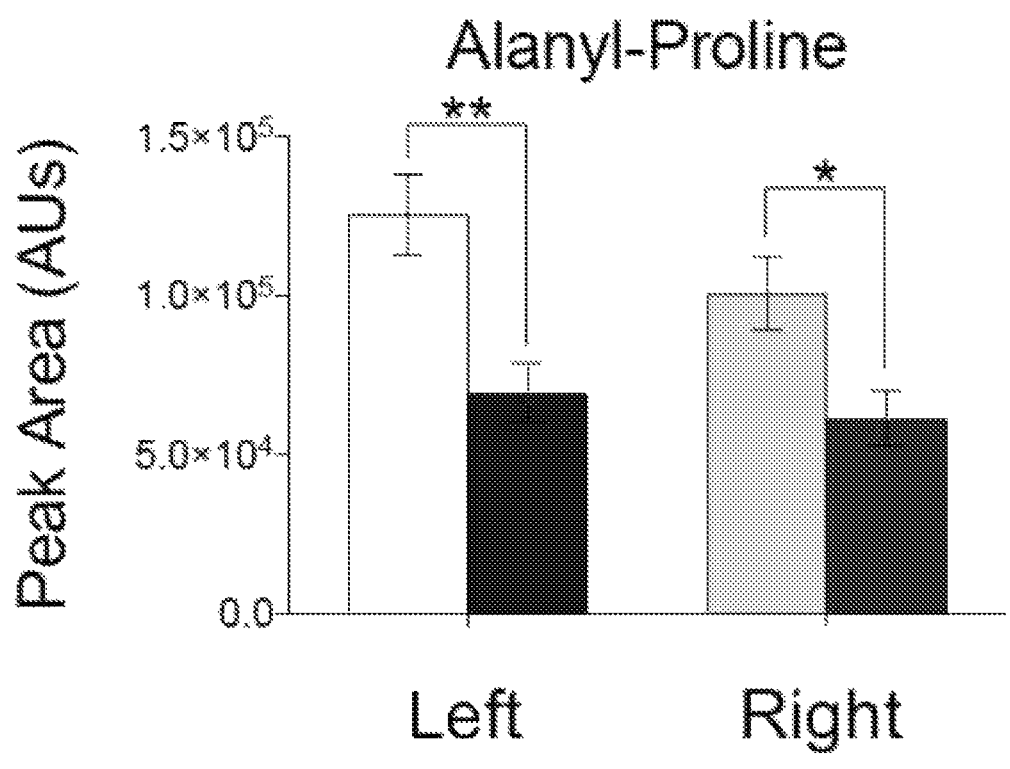
Figure 6G:
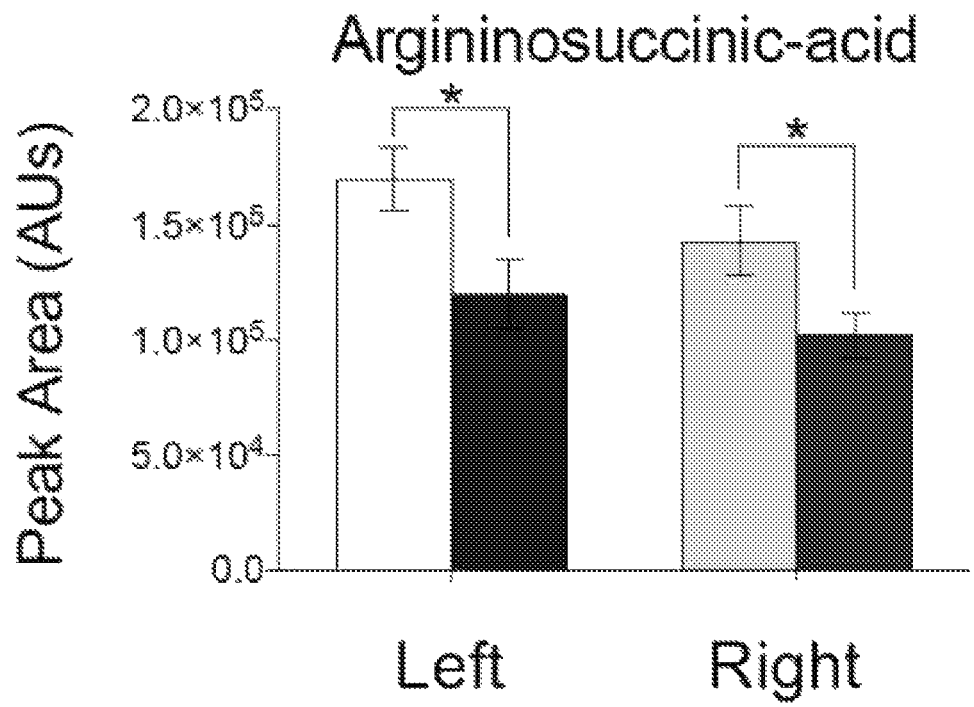
Figure 6H:
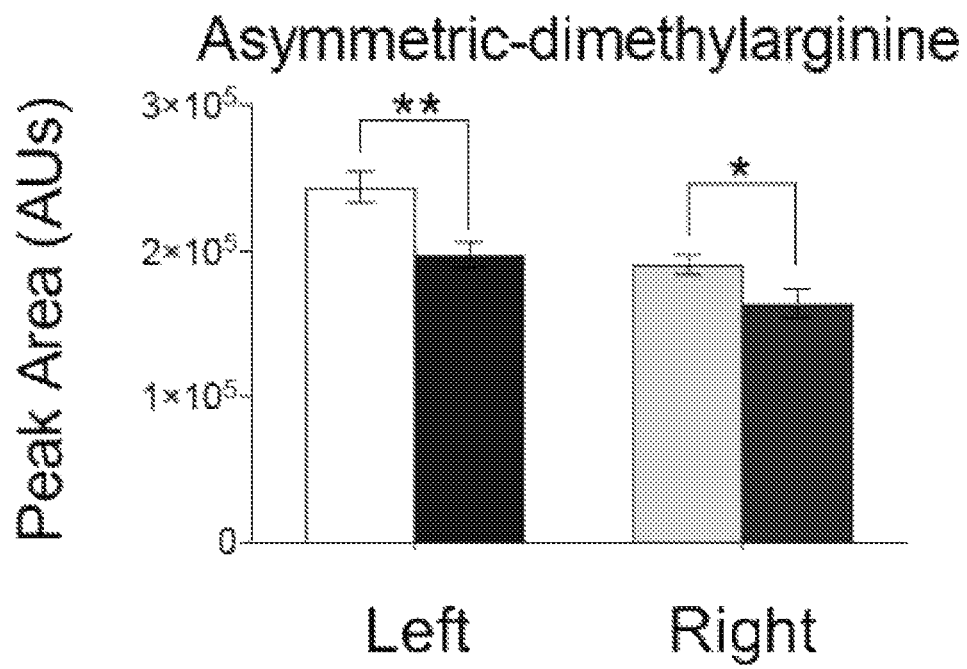
Figure 6U:
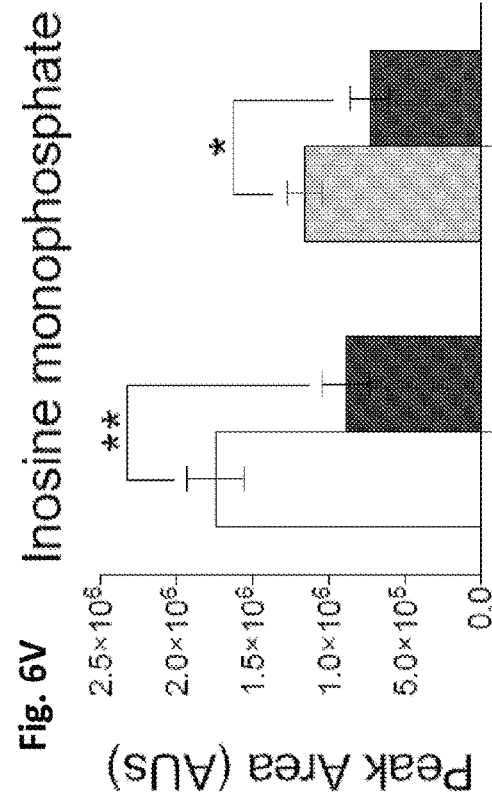
Figure 6V:
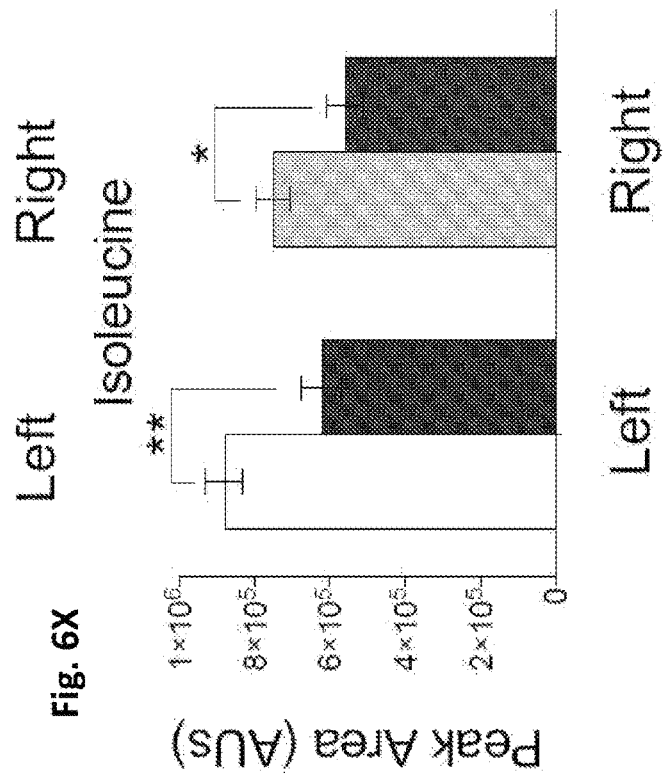
Figure 6W:
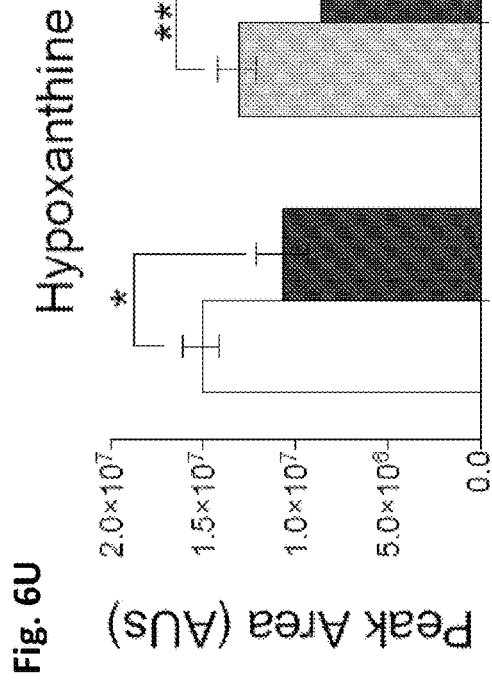
Figure 6X:
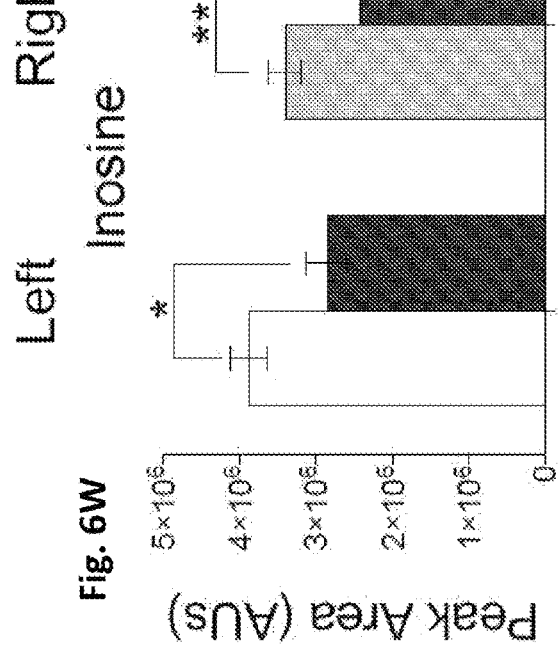
Figure 6Y:
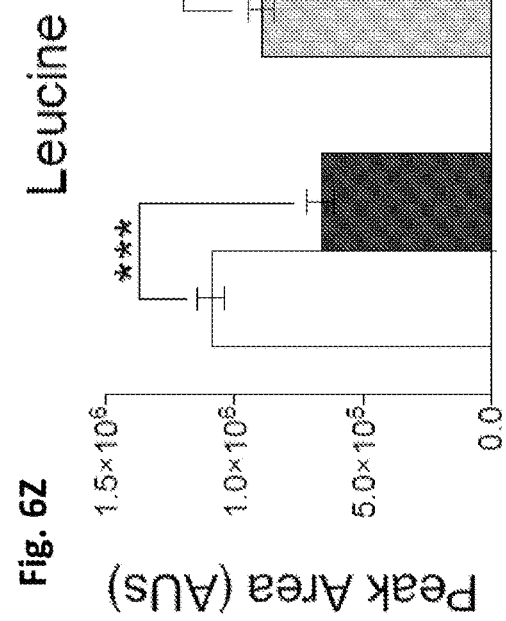
Figure 6A:
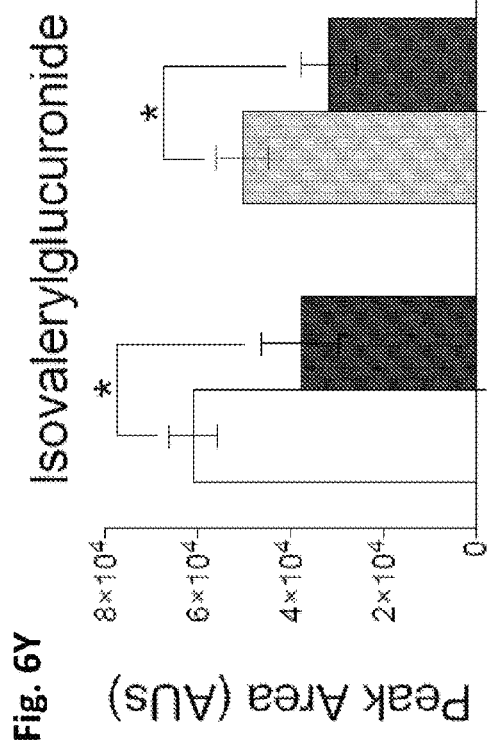
Figure 6Z:
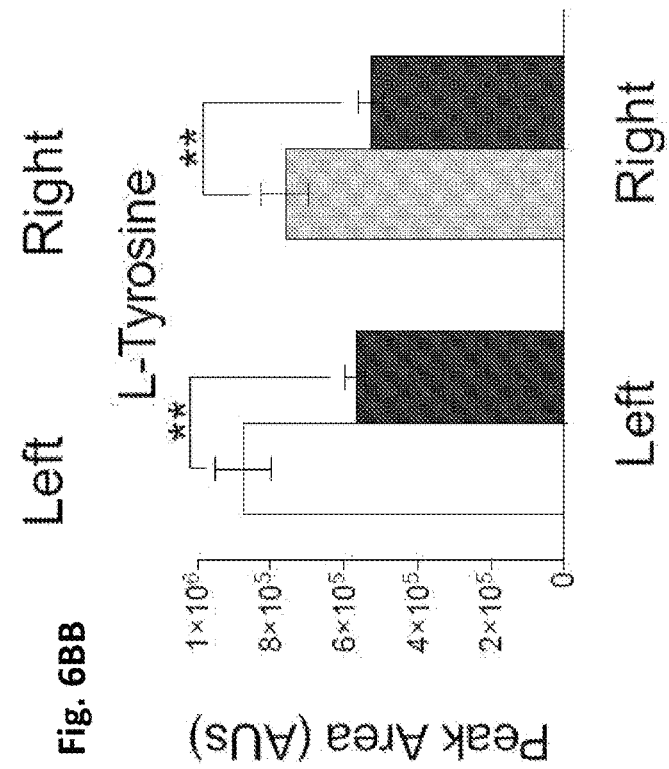
Figure 6B:
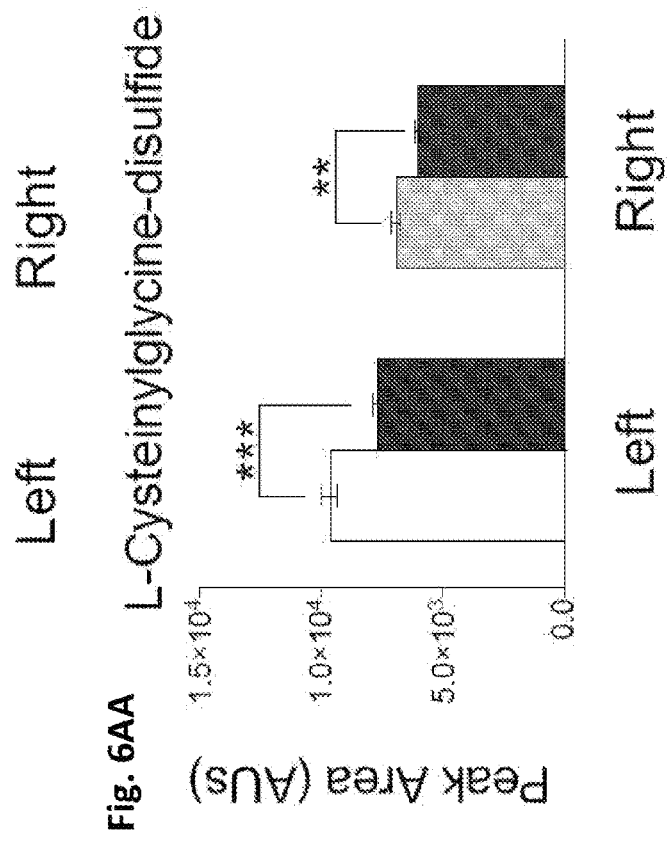
Figure 6C:
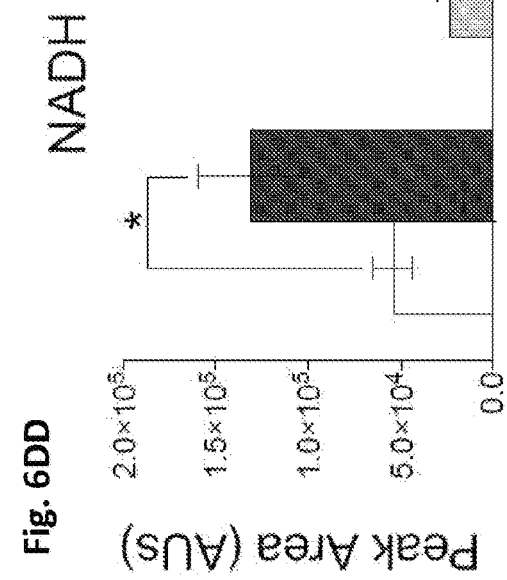
Figure 6D:
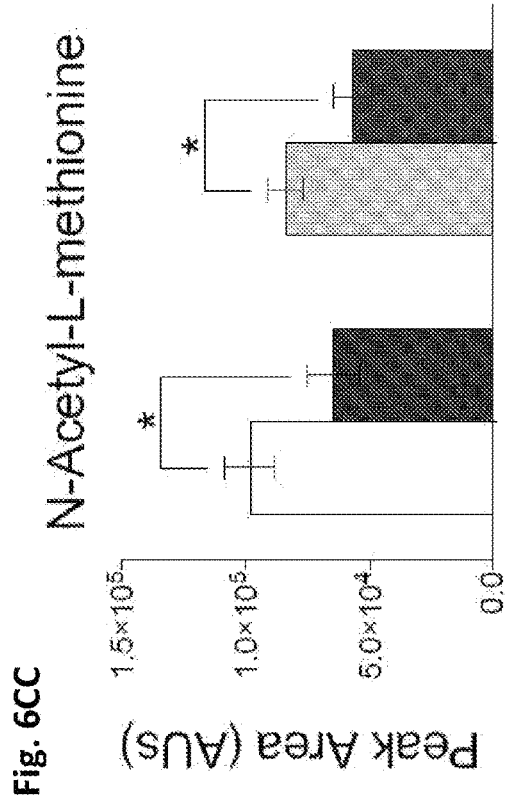
Figure 6E:
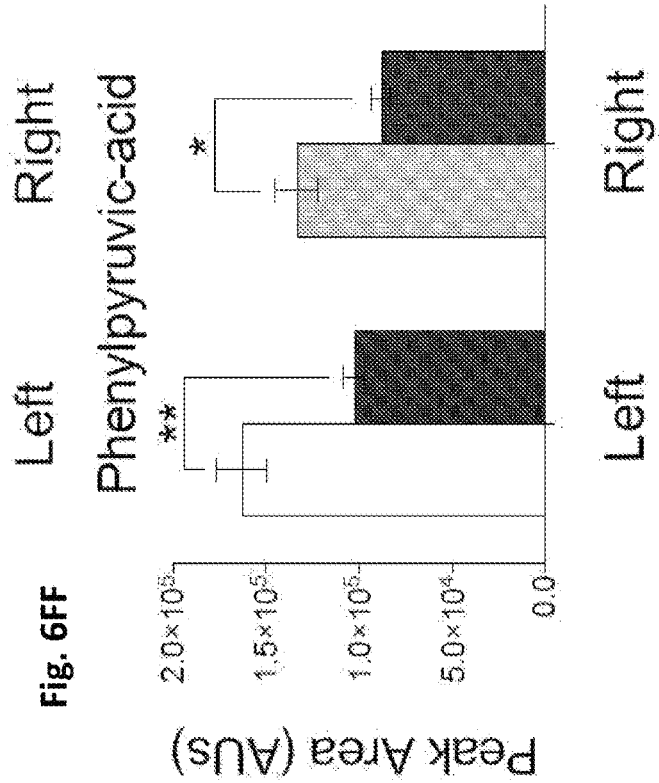
Figure 6F:
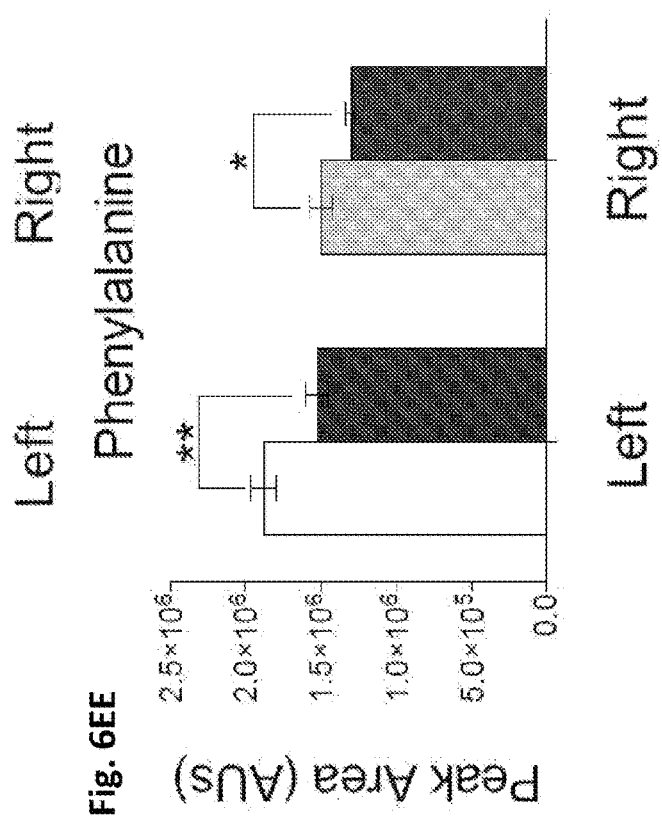
Figure 6H:
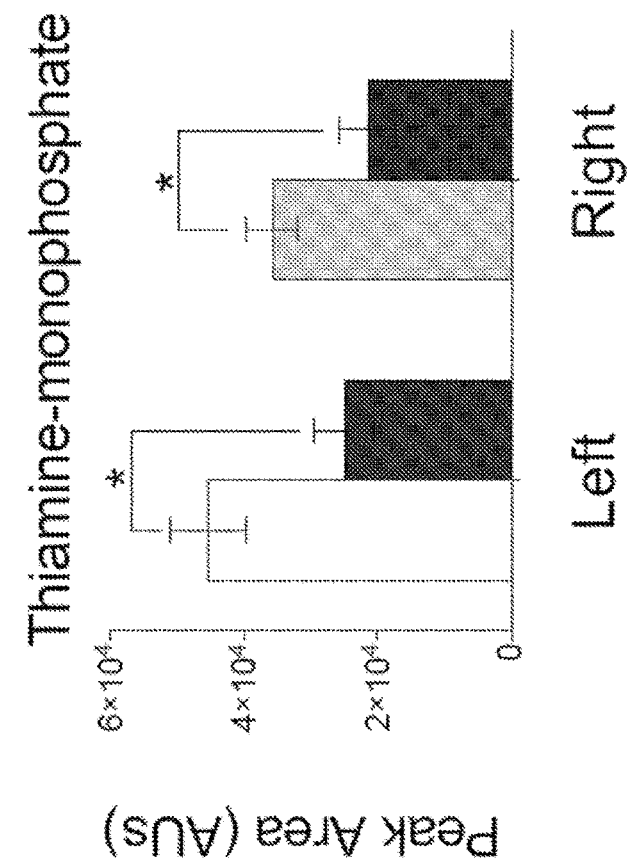
Figure 6G:
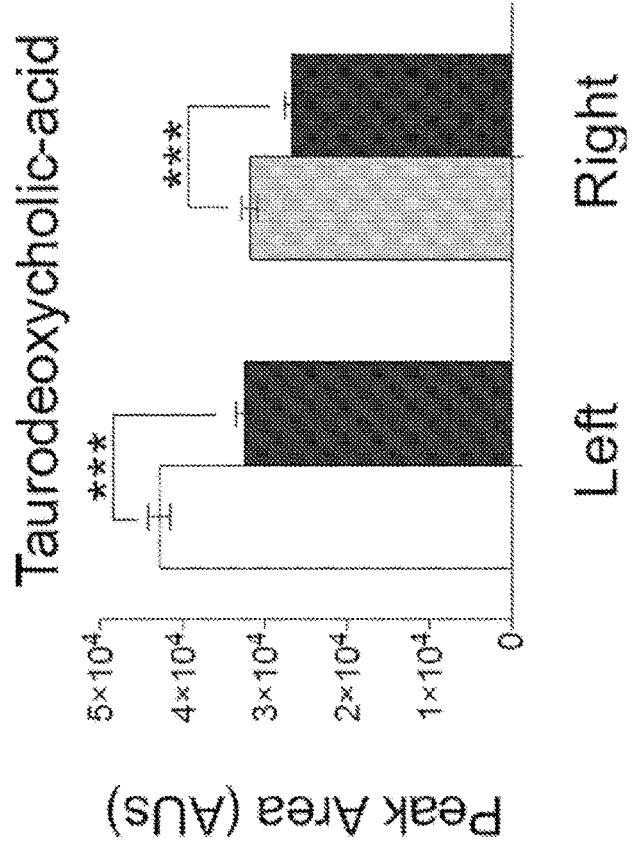
Figure 7E:
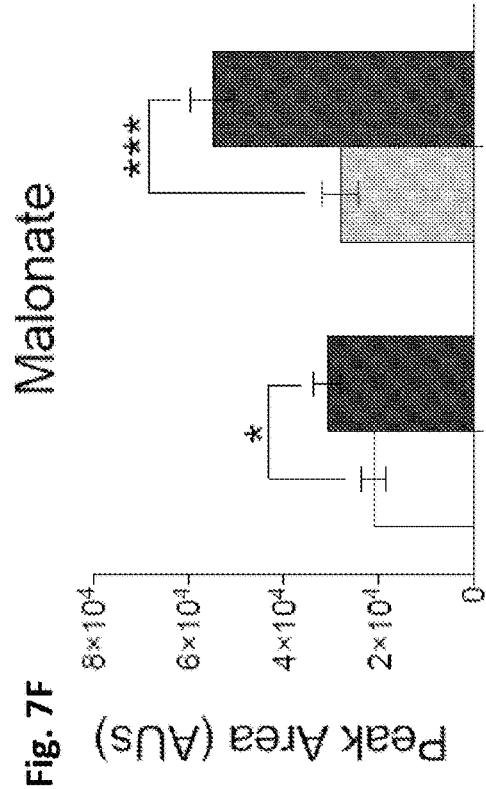
Figure 7F:
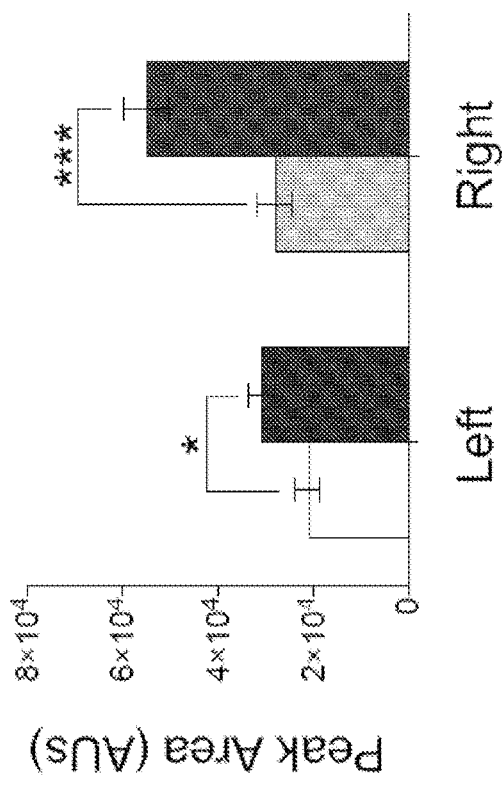
Figure 7G:
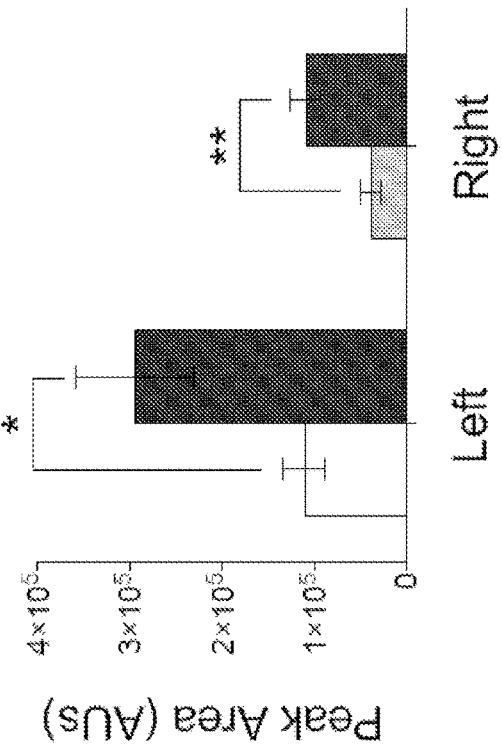
Figure 7H:
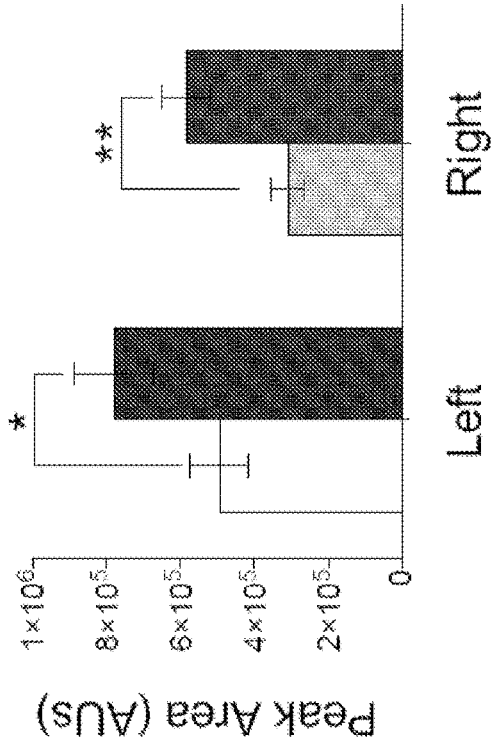
Figure 7I:
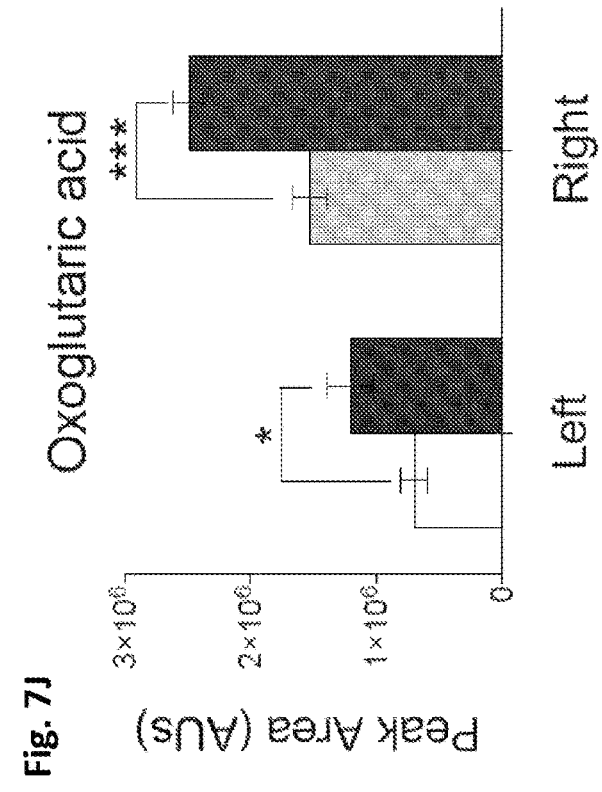
Figure 7J:
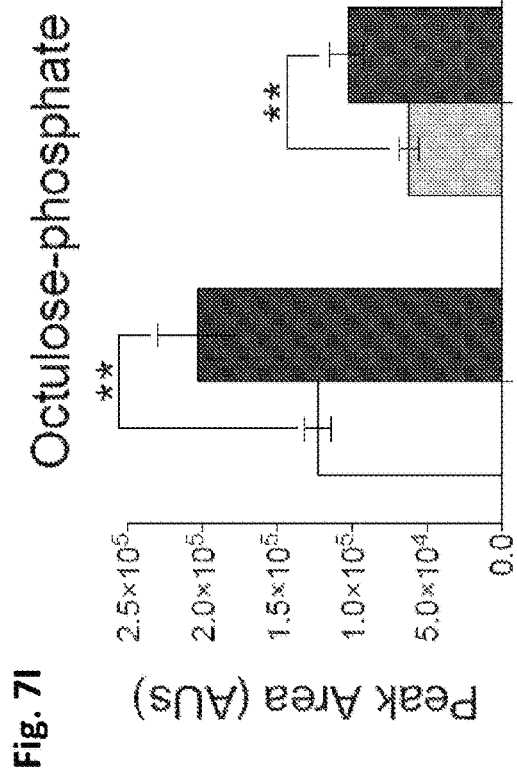
Figure 7K:
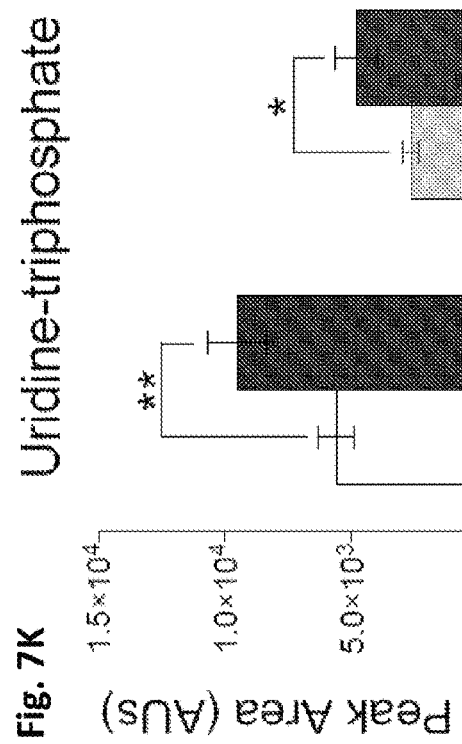

Plasma samples were also subjected to a separate analysis of metabolites involved in neurotransmission. The dried plasma samples were reconstituted in 30 μl of $H_2O$. Five μl of each sample were injected onto a Kinetix F5 column (Phenomenex, Torrance, Calif.) with dimensions of 100×3 mm, 2.6 am. Metabolites were separated using water with 0.2% formic acid and MeOH gradient over a 12-minute period. A re-equilibration time of 3 minutes was carried out in between injections. Similarly, detection was performed using an Agilent 6550 QToF mass spectrometer, operated in both negative and positive modes (FIGS. 6A-6Z, 6AA-6HH, 7A-7K, 8A-8V). Full scan MS data was collected and metabolites were identified using expected m/z values, as well as confirmation against purified chemical standards. Data was processed using a publically available software package, MAVEN (https://www.ncbi.nlm.nih.gov/pubmed/22389014). Area under the chromatographic peak for each metabolite was calculated and exported to assess for differences in metabolite abundances.

Pathway Analysis

For each pathway analysis, the metabolites that were changed in both hemispheres or in the plasma were entered into MetaboAnalyst 3.0 using their HMDB IDs (http://www.metaboanalyst.ca/faces/Secure/upload/PathUploadView.xhtml).

Heat Map

MATLAB (https://www.mathworks.com/, Mathworks, Natick, Mass.) was used to transform metabolomics data for the heat maps. The function NormalizeforHeatMap takes a data input that is in the form of a matrix (size X by Y) and normalizes each row to values between 0 and 1. This function loops through each row, and at each iteration, the function first takes the minimum of each row and subtracts that from all of the values in that row. It then divides each value in that row by the maximum value of that row. The data are accumulated into a new matrix that contains all of the normalized values.

Statistical Analysis

All data were analyzed using StatView 5.0 software (SAS Institute, Cary, N.C.) or Prism 7.0 (Graphpad Software, Inc., La Jolla, Calif.). Alpha was set to 0.05 for all analyses. In general, the effect of Drug was analyzed using an analysis of variance (ANOVA), using repeated measures where appropriate. Unpaired t-tests were performed on each metabolite analyzed. All statistical tests and p values for metabolomic analyses are listed in Table 1.

Results

Prophylactic Ketamine Buffers Conditioned Fear Responses

Figure 9A:
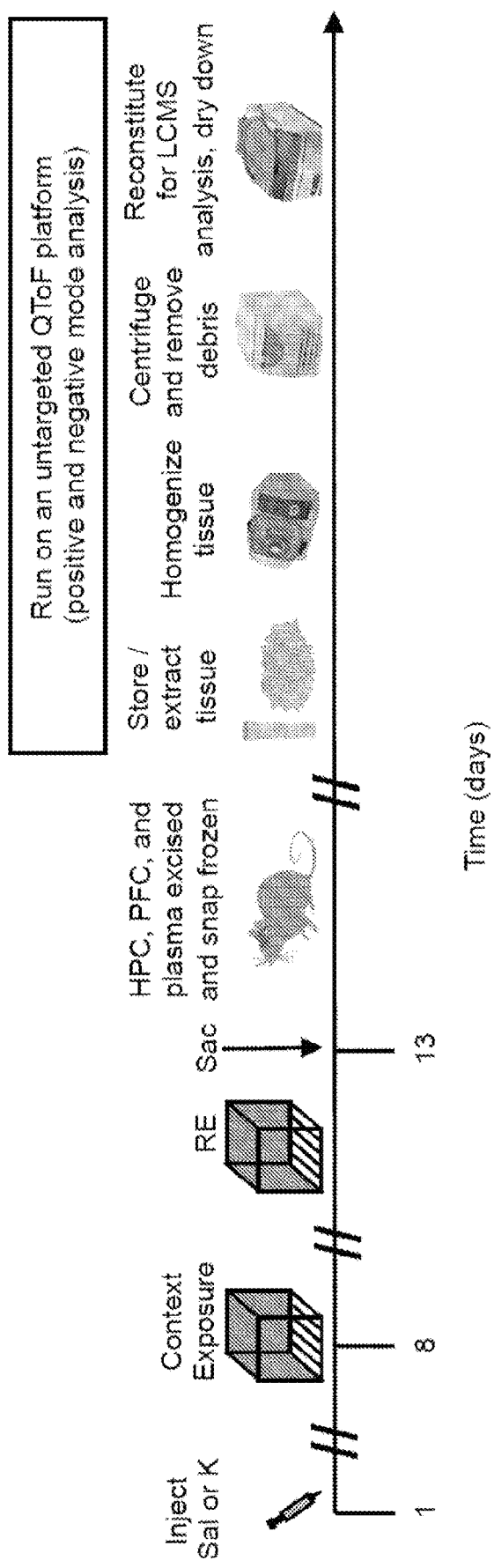
FIGS. 9A-9W. Prophylactic ketamine does not impact freezing behavior, and does not significantly alter purine or pyrimidine metabolism in the PFC and HPC. (A) Experimental design. (B-C) Prophylactic ketamine does not alter context exposure or context re-exposure as measured by freezing when compared with prophylactic saline administration. Only 3 purine metabolites are significantly altered by ketamine administration in one hemisphere of the (D-J) PFC or (K-O) HPC. Only 2 pyrimidines are significantly altered by ketamine administration in one hemisphere of the (P-T) PFC, or (U-W) HPC. (n=8-9 male mice per group). Error bars represent ±SEM. *p<0.05, **p<0.01. Sal, saline; K, ketamine; RE, re-exposure; HPC, hippocampus; PFC, prefrontal cortex; Sac, sacrifice; QToF, quadrupole time-of-flight; LCMS, liquid chromatography mass spectrometry; min, minutes; dUDP, deoxyuridine-diphosphate. (D-J), (P-T): Left/white: Saline; left/black: Ketamine (30 mg/kg). Right/gray: Saline; right/black: Ketamine (30 mg/kg). (K-O), (U-W): Left/white: Saline; left/black: Ketamine (30 mg/kg). Right/light gray (on the left of "Right"): Saline; right/dark gray (on the right of "Right"): Ketamine (30 mg/kg).
Figure 9D:
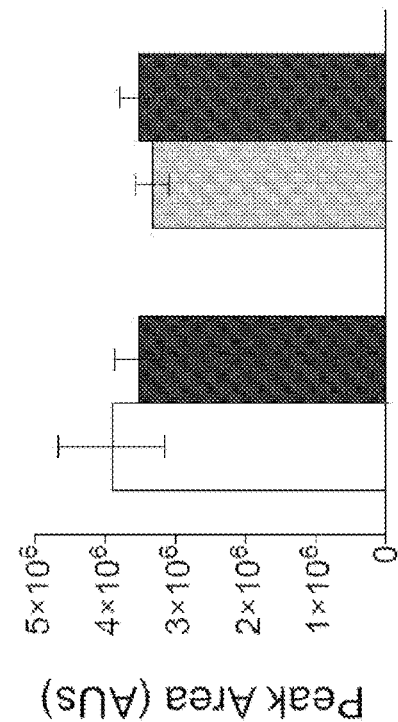
Figure 9E:
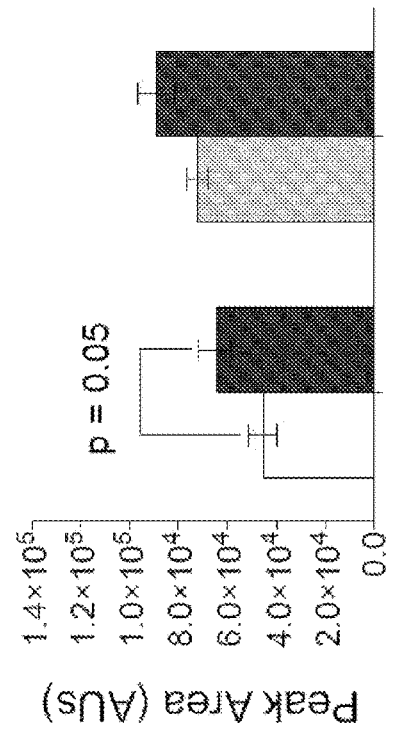
Figure 9F:
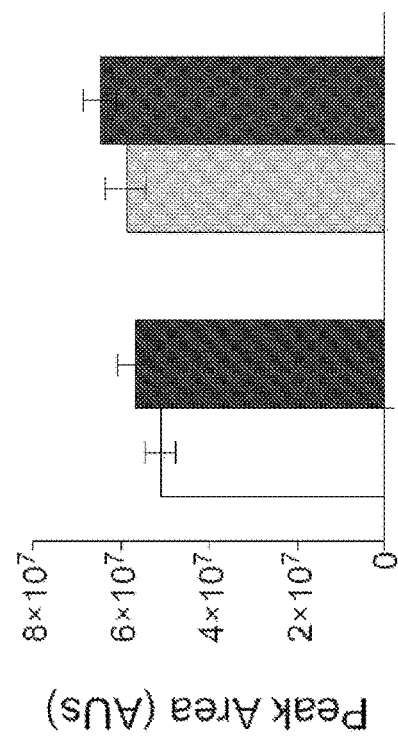
Figure 9G:
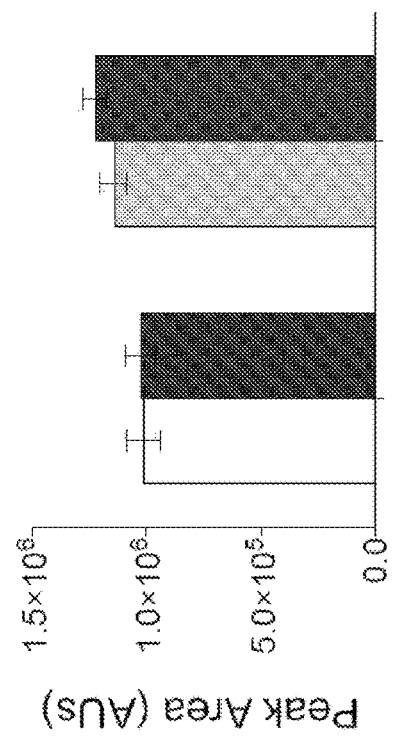
Figure 9L:
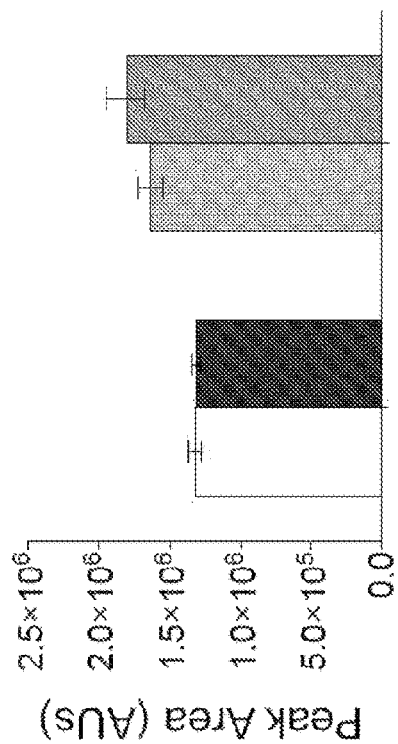
Figure 9M:
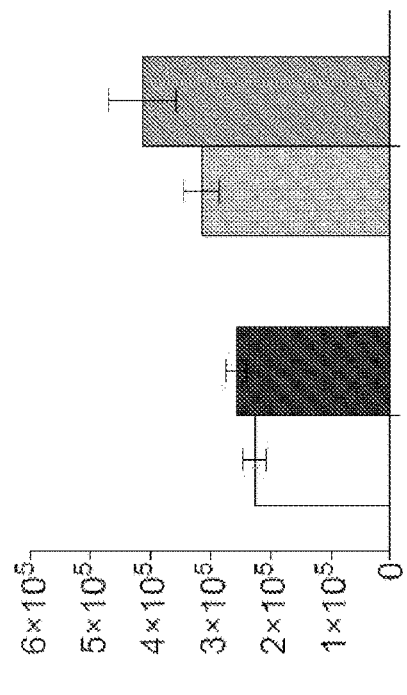
Figure 9N:
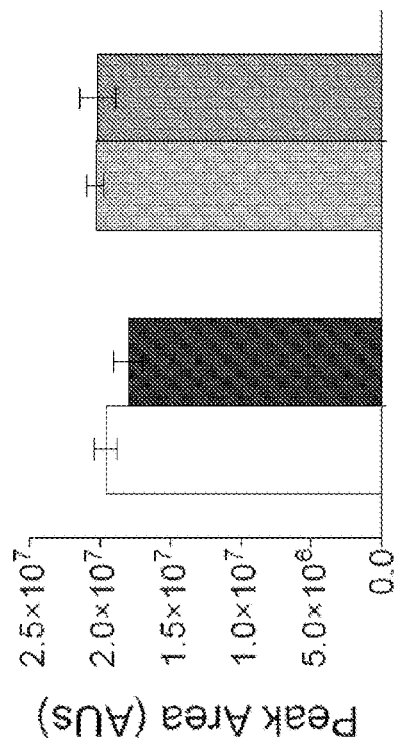
Figure 9O:
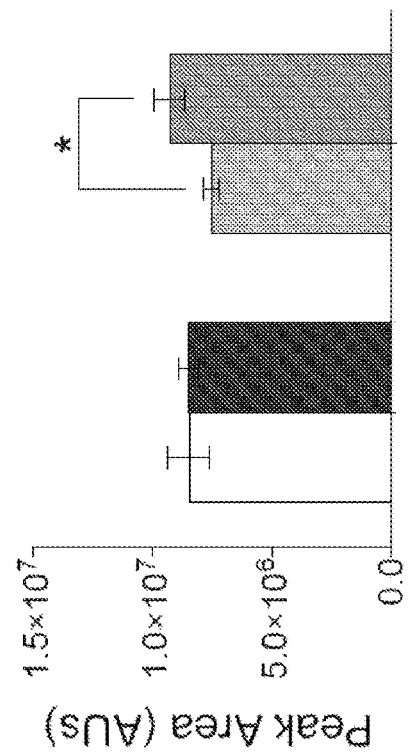
Figure 9P:
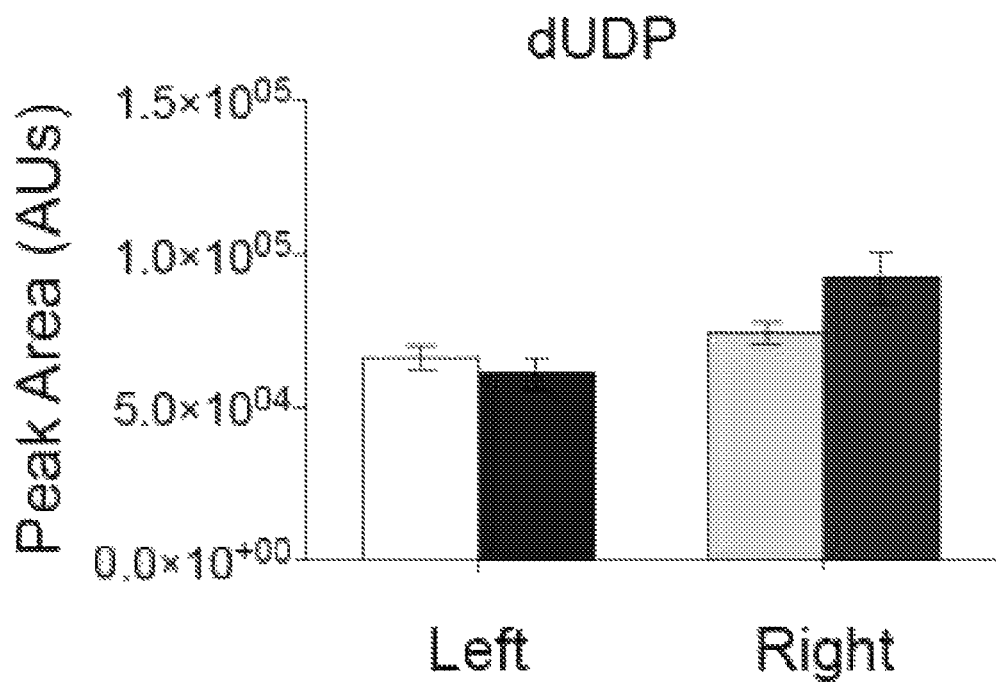
Figure 9Q:
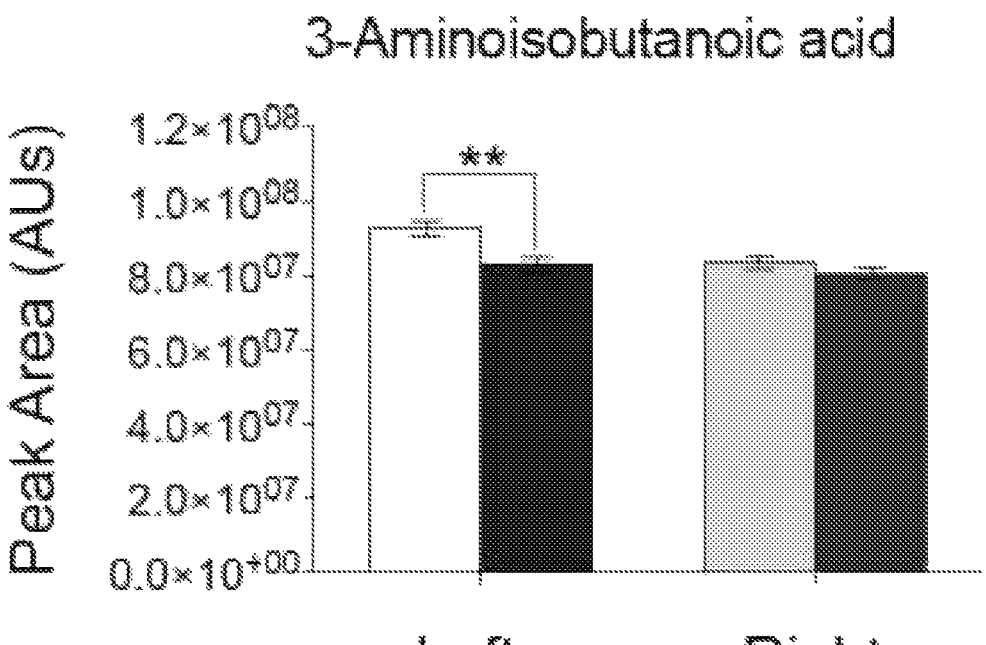
Figure 9R:
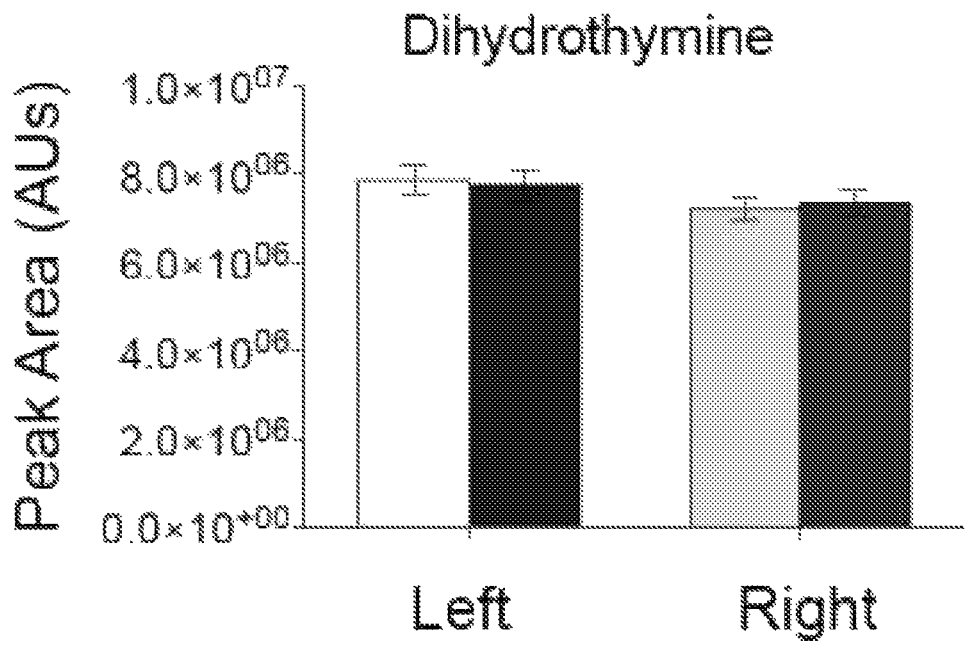
Figure 9S:
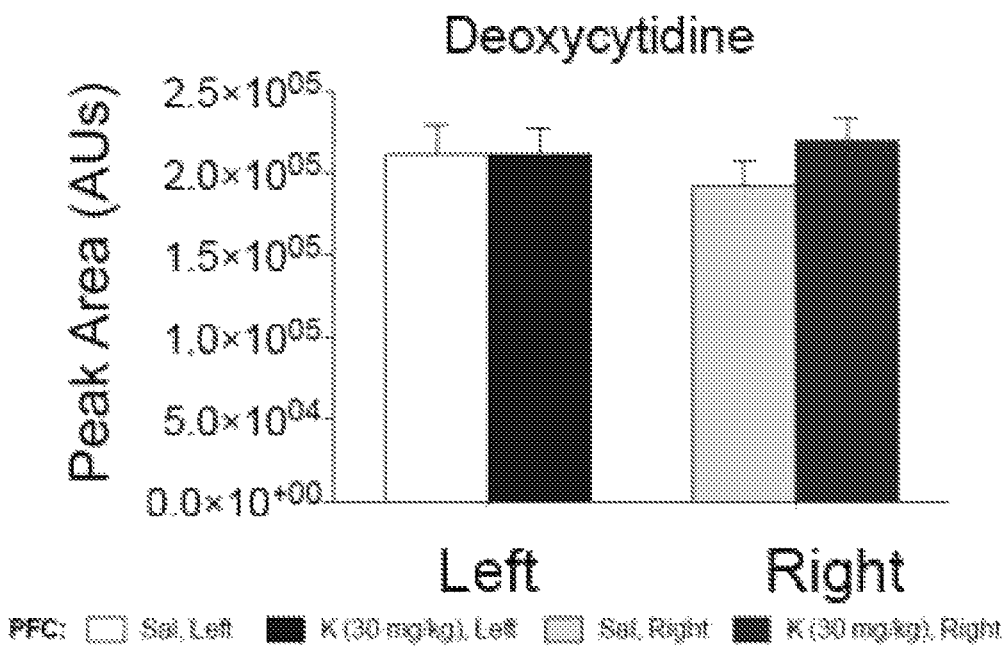
Figure 9T:
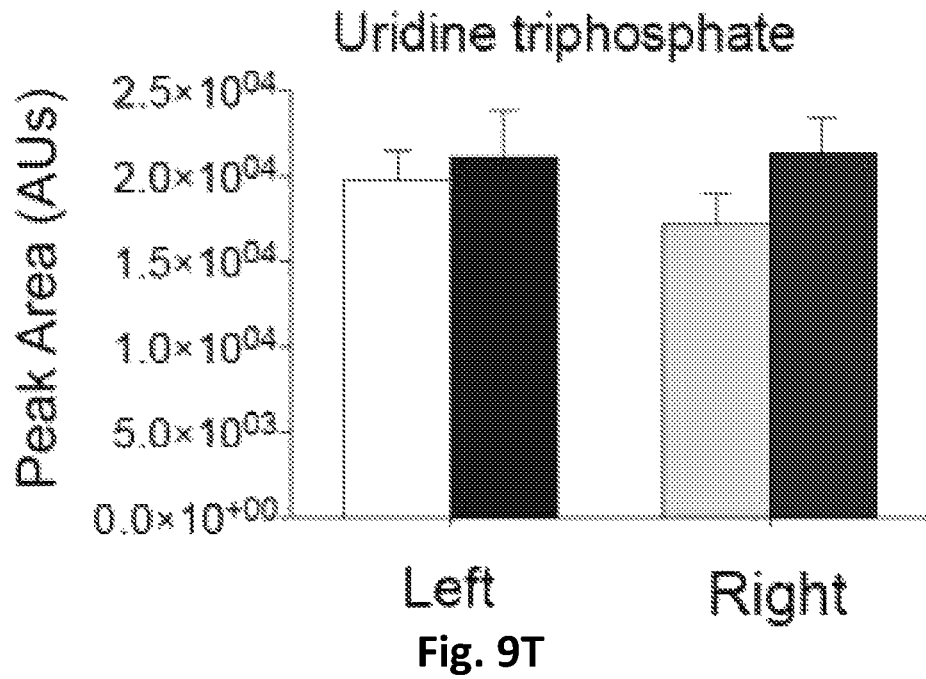
Figure 9U:
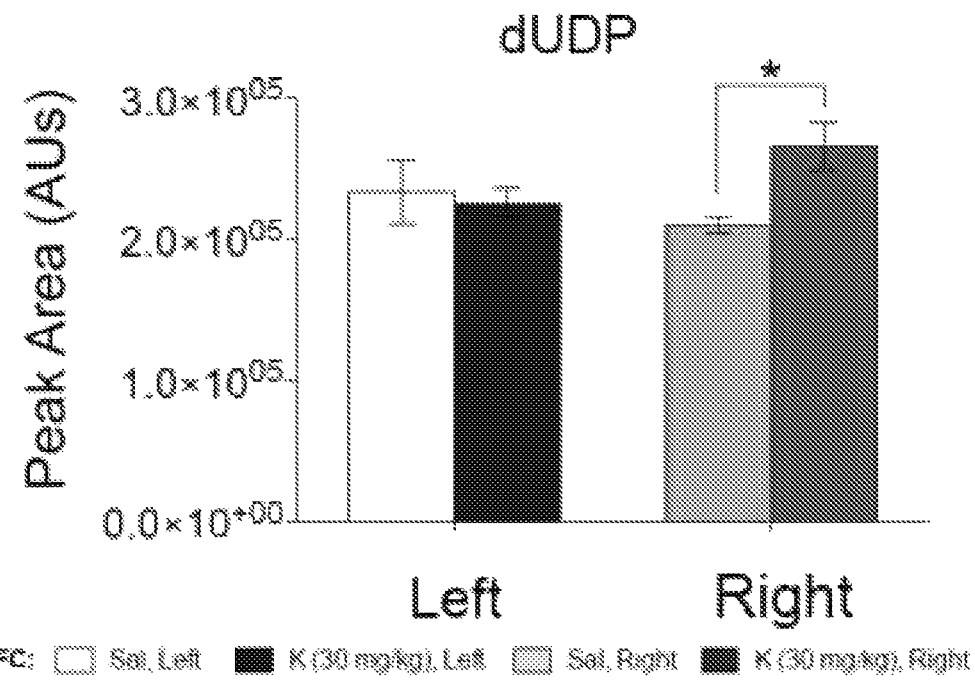
Figure 9V:
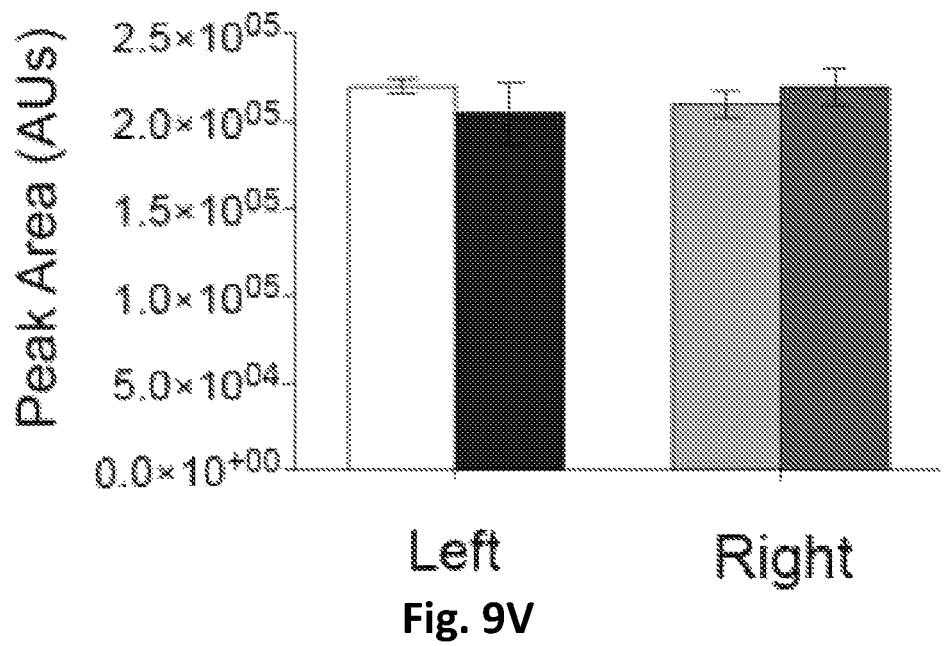

First, to validate our previously reported effect of prophylactic ketamine on CFC, we administered a single dose of saline or ketamine (30 mg $kg^{-1}$) to mice 1 week before a 3-shock CFC paradigm (FIG. 1A). Prophylactic ketamine did not alter freezing behavior during CFC encoding (FIG. 1B). As we previously reported (McGowan et al., 2017), during context re-exposure, prophylactic ketamine attenuated the fear response (FIG. 1C). In another group of mice, we administered a single dose of saline or ketamine (30 mg $kg^{-1}$) to mice 1 week before being exposed to the CFC context, with no shocks (FIG. 9A). Prophylactic ketamine did not alter freezing behavior during context exposure or re-exposure (FIG. 9B-9C).

Figure 2A:
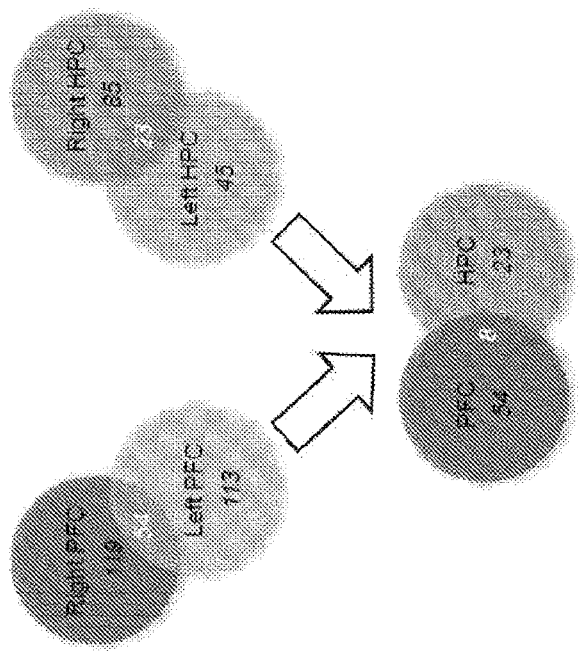
Figure 2C:
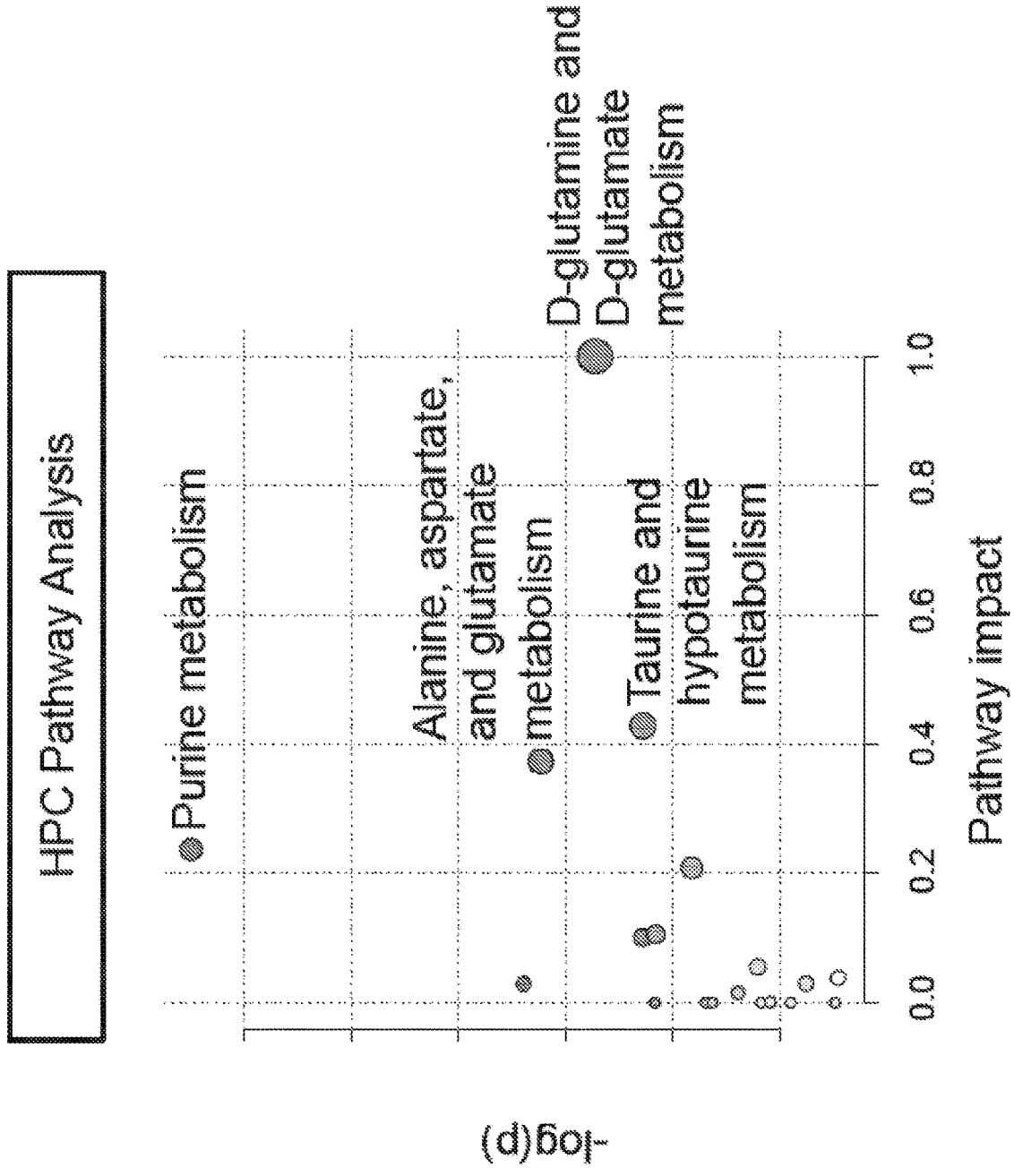
Figure 8A:
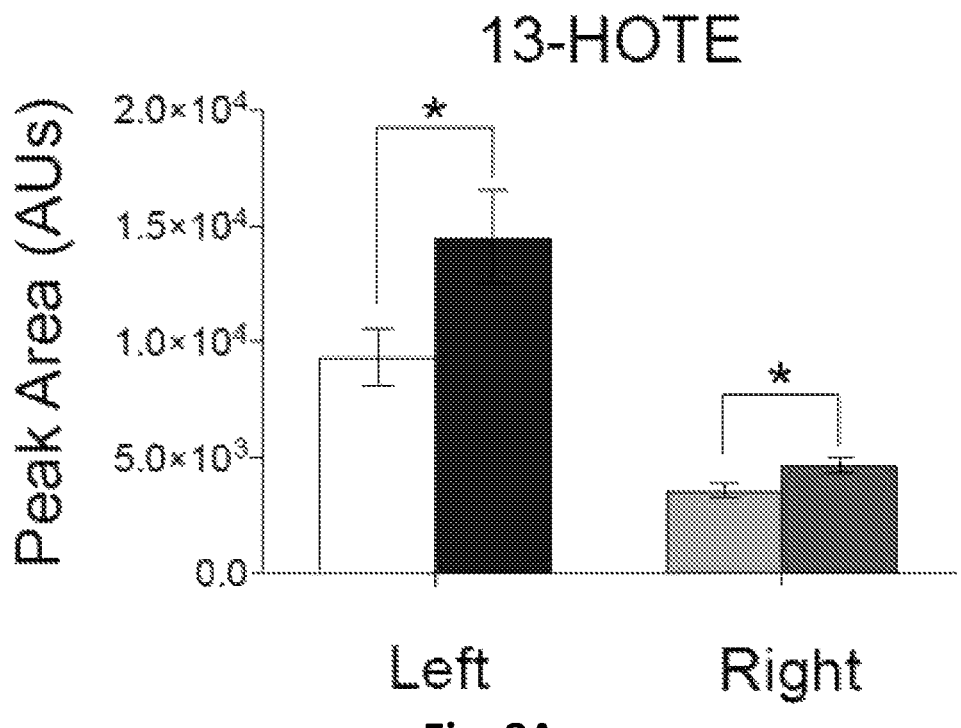
FIGS. 8A-8V. Positive and negative mode metabolites changed in the HPC following prophylactic ketamine administration and CFC stress. (n=9-10 male mice per group). Error bars represent ±SEM. *p<0.05, p<0.01, *p<0.001. Left/white: Saline; left/black: Ketamine. Right/light gray (on the left of "Right"): Saline; right/dark gray (on the right of "Right"): Ketamine.
Figure 8B:
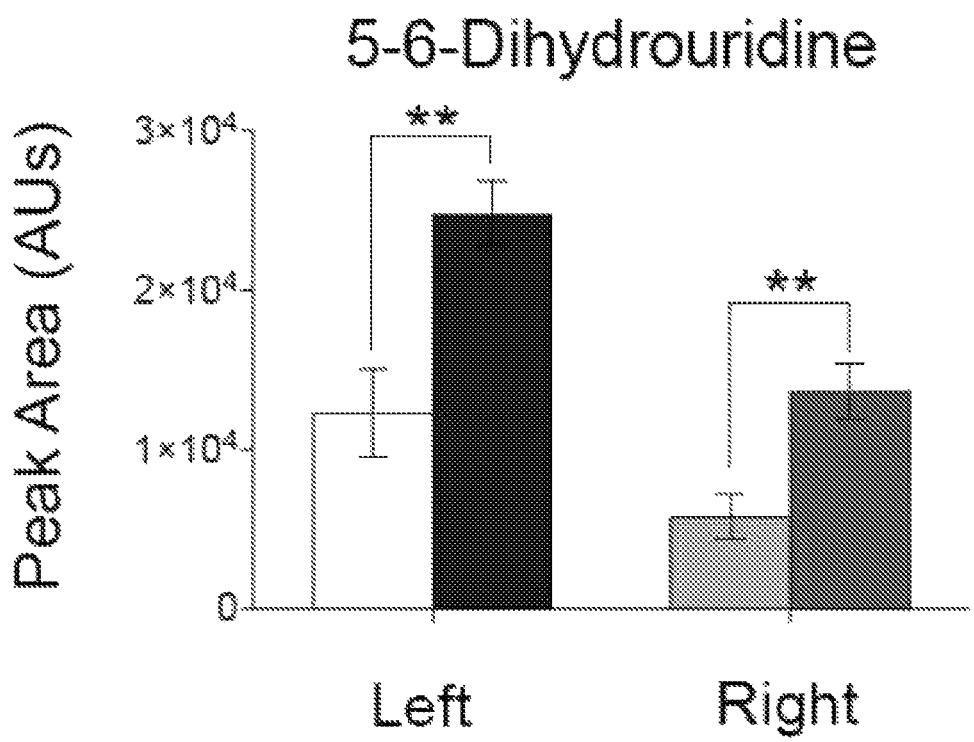
Figure 8C:
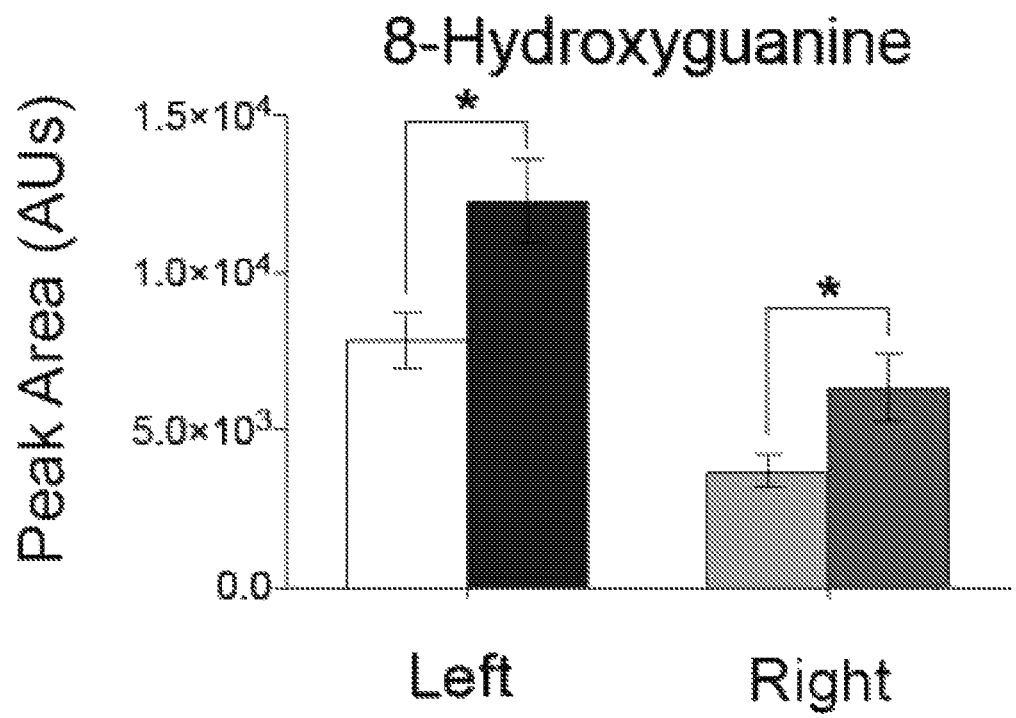
Figure 8D:
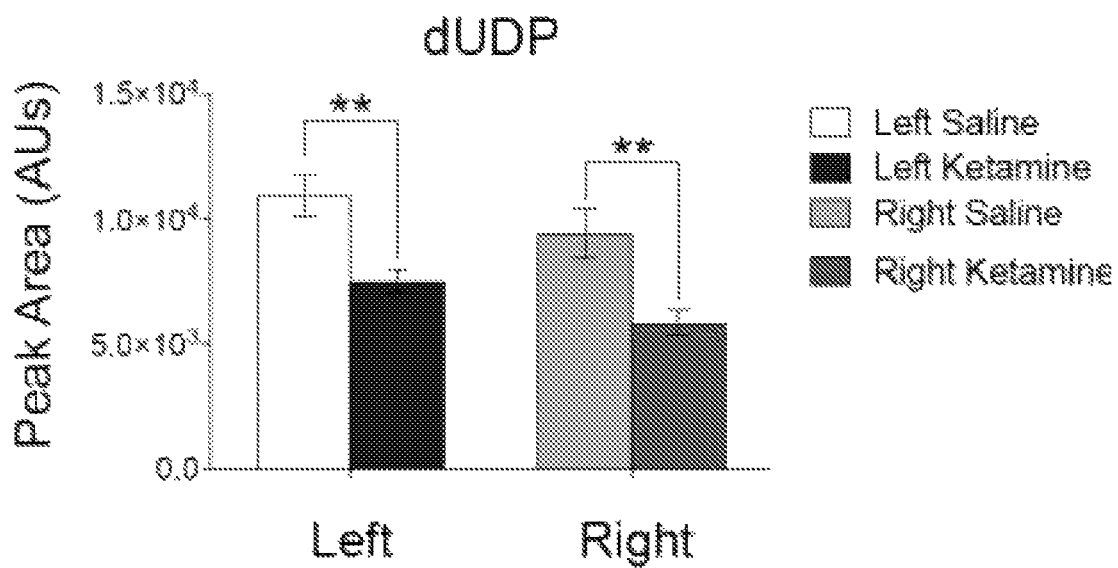
Figure 8I:
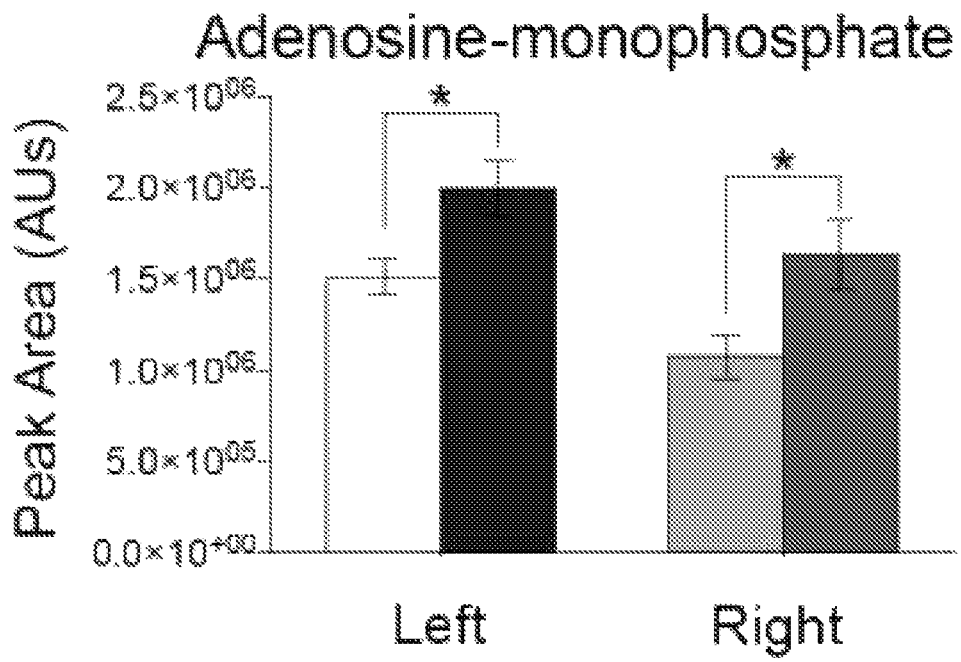
Figure 8J:
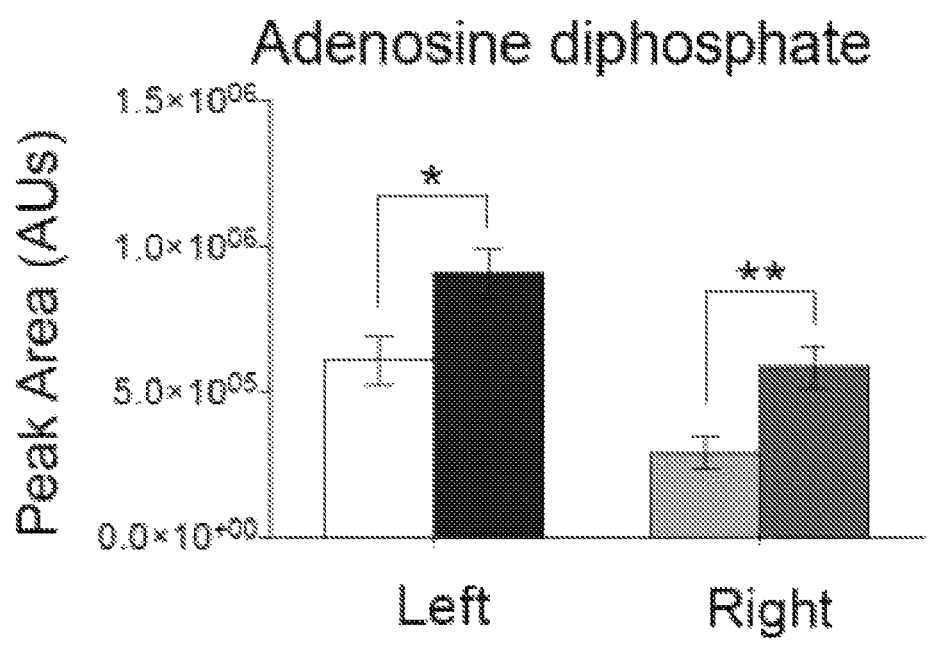
Figure 8K:
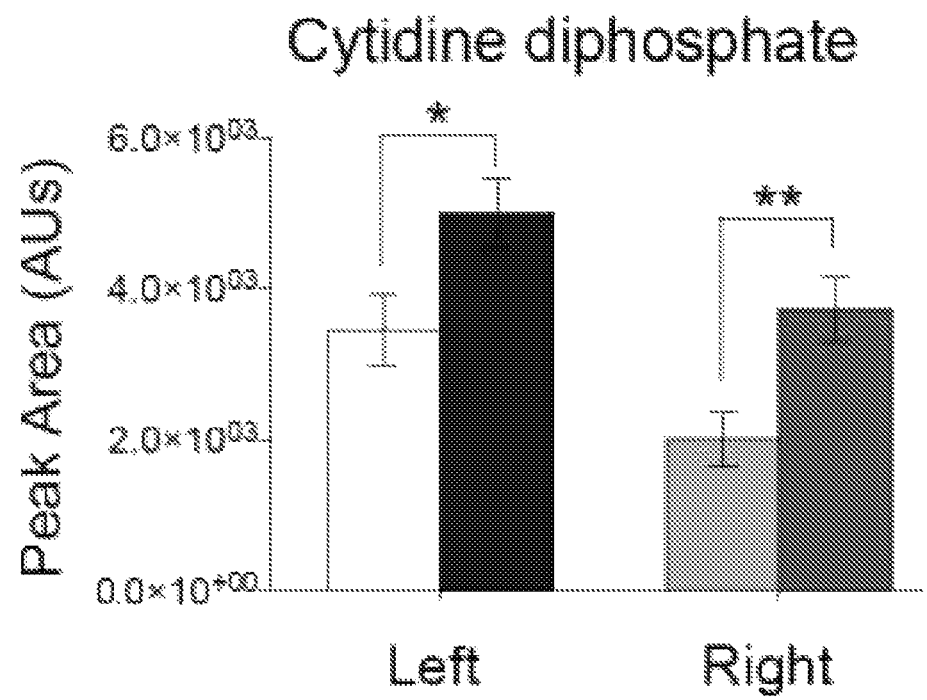
Figure 8L:
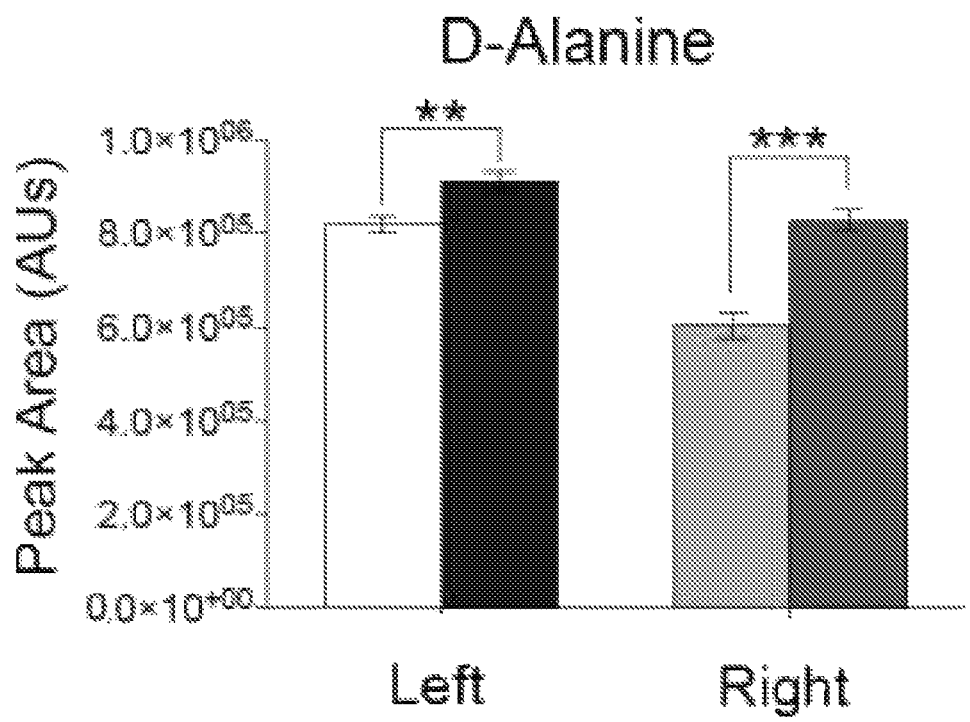
Figure 8M:
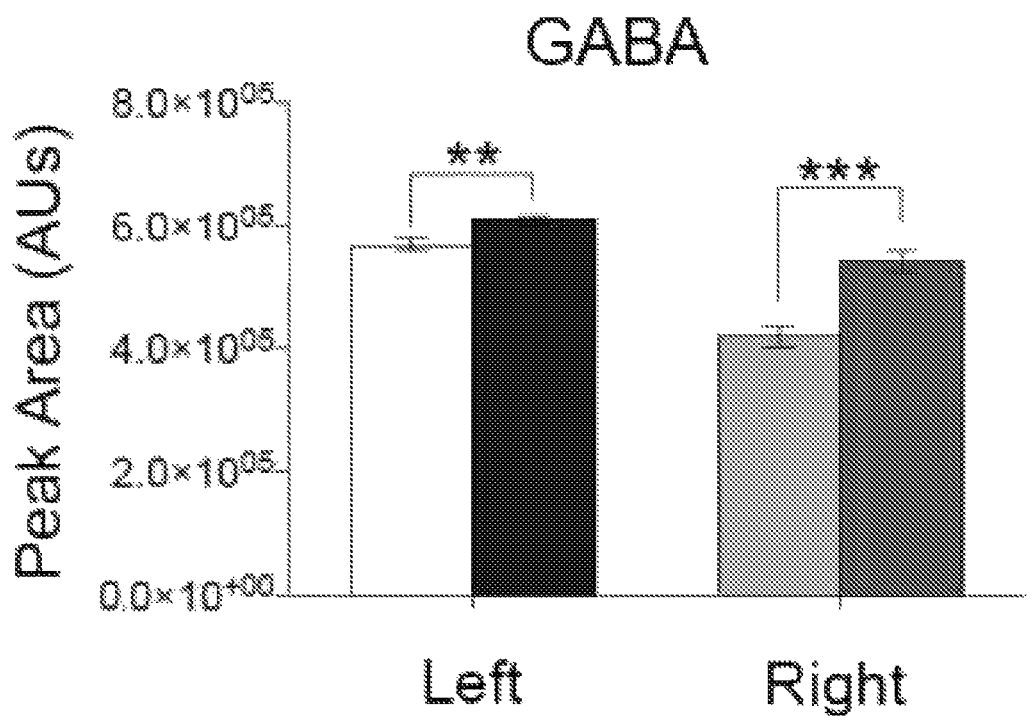
Figure 8N:
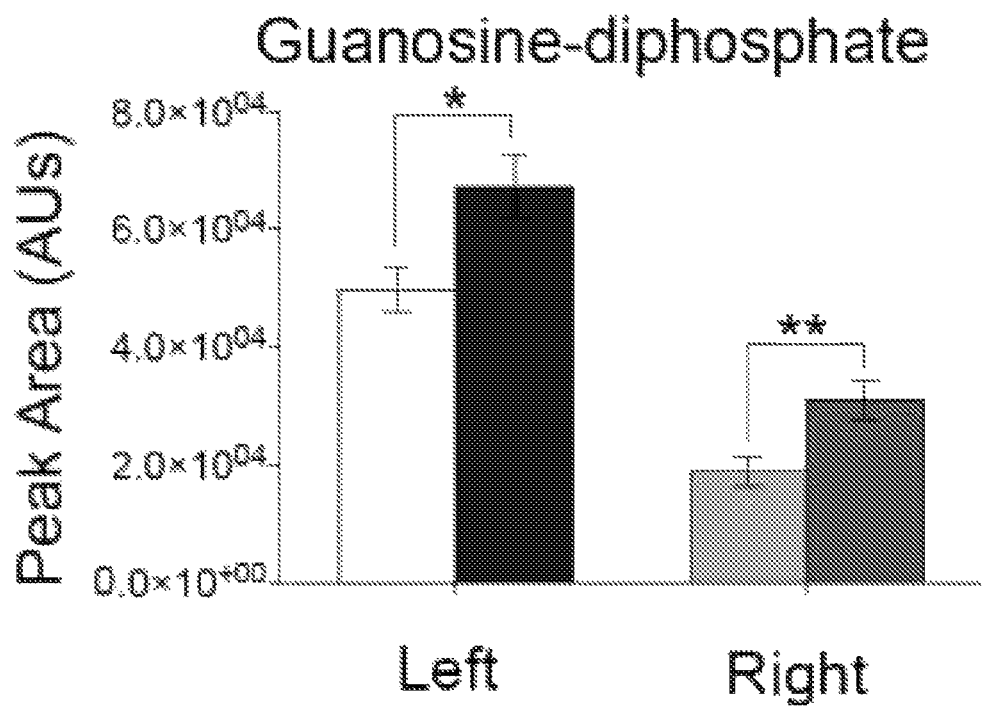
Figure 8O:
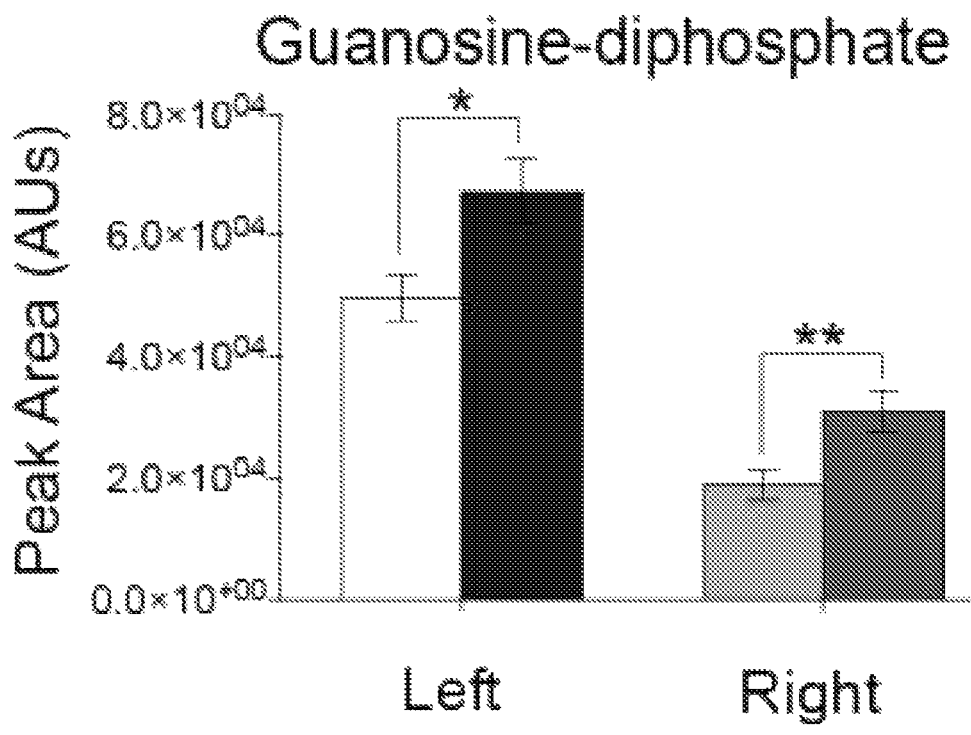
Figure 8P:
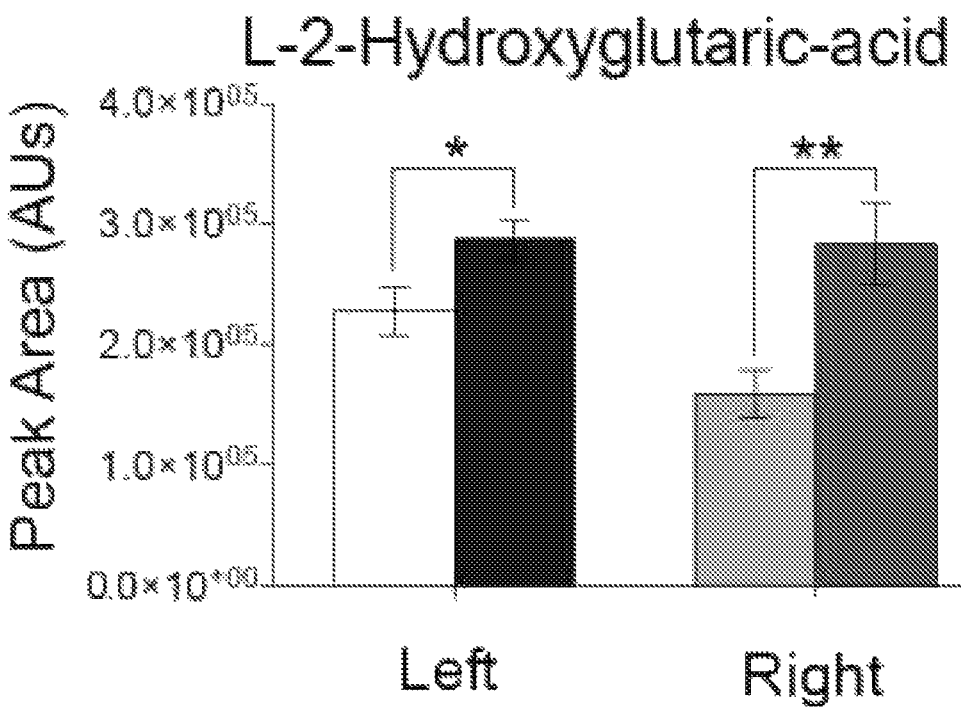
Figure 8Q:
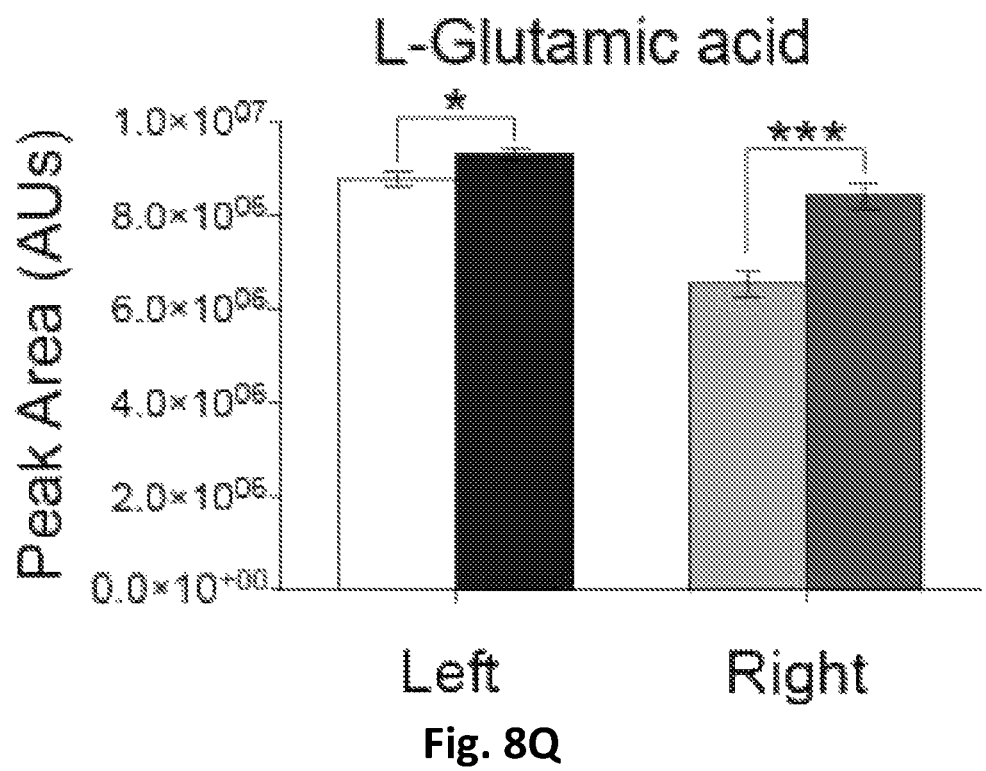
Figure 8R:
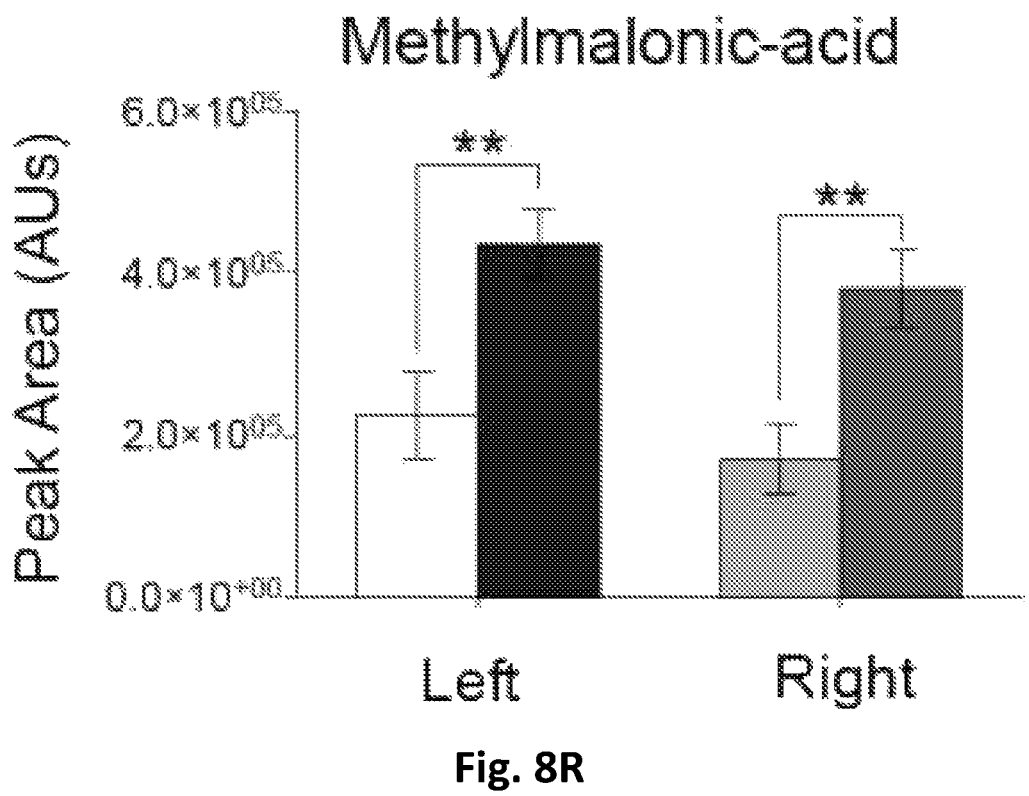
Figure 8S:
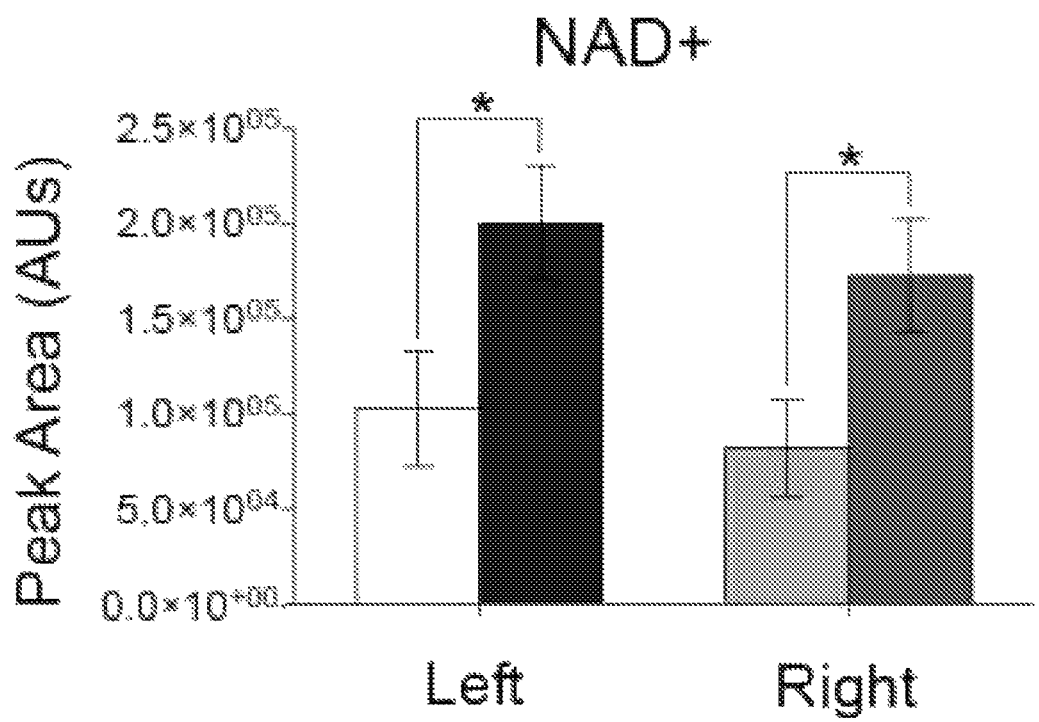
Figure 8T:
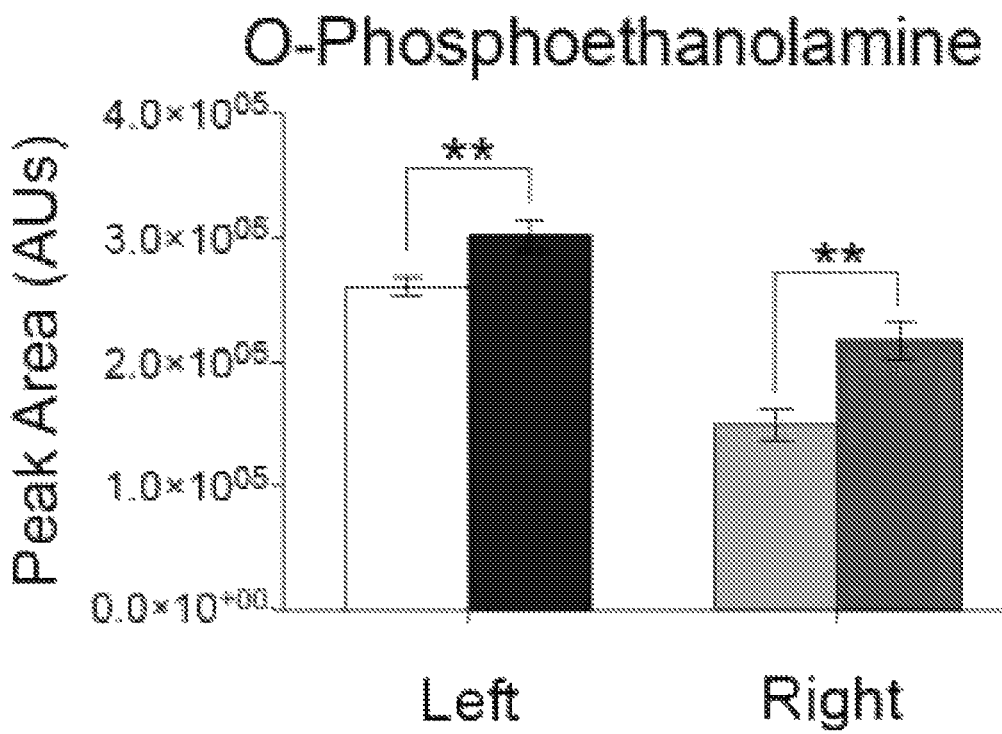
Figure 8U:
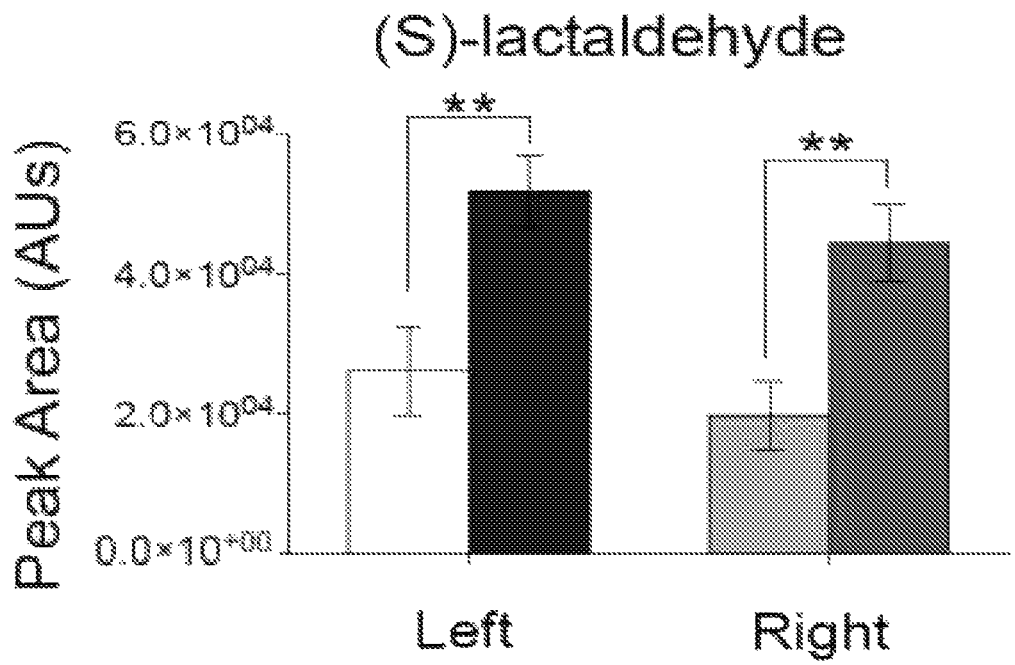
Figure 8V:
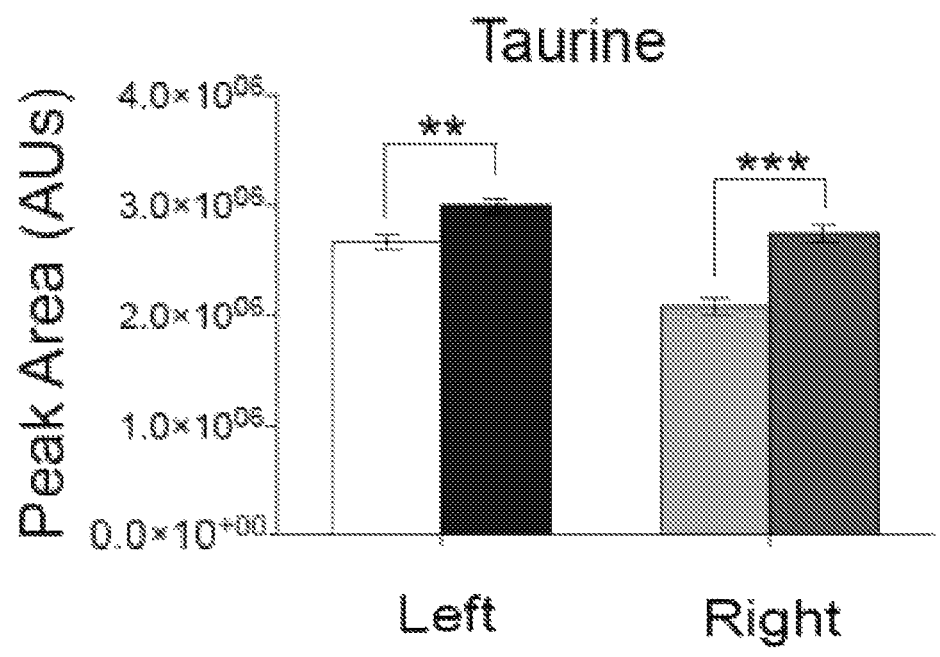

Prophylactic Ketamine Significantly Alters Metabolites in the PFC and HPC Following Stress A number of positive and negative mode metabolites were changed in the PFC (FIGS. 6A-6Z, 6AA-6HH, 7A-7K) and HPC (FIGS. 8A-8V) following prophylactic ketamine administration and a CFC stressor. Notably, 8 metabolites were changed in both hemispheres of the PFC and HPC (FIG. 2A, Table 2). A pathway analysis of changed metabolites in the PFC indicated that purine metabolism; phenylalanine, tyrosine, and tryptophan metabolism; and phenylalanine metabolism are most significantly changed in the PFC following prophylactic ketamine administration and stress (FIG. 2B). A pathway analysis of changed metabolites in the HPC indicated that as in the PFC, purine metabolism was also significantly altered (FIG. 2C). However, prophylactic ketamine treatment before stress also altered alanine, aspartate, and glutamate metabolism; glutamine and glutamate metabolism; and taurine and hypotaurine metabolism in the HPC (FIG. 2C).

Figure 2D:
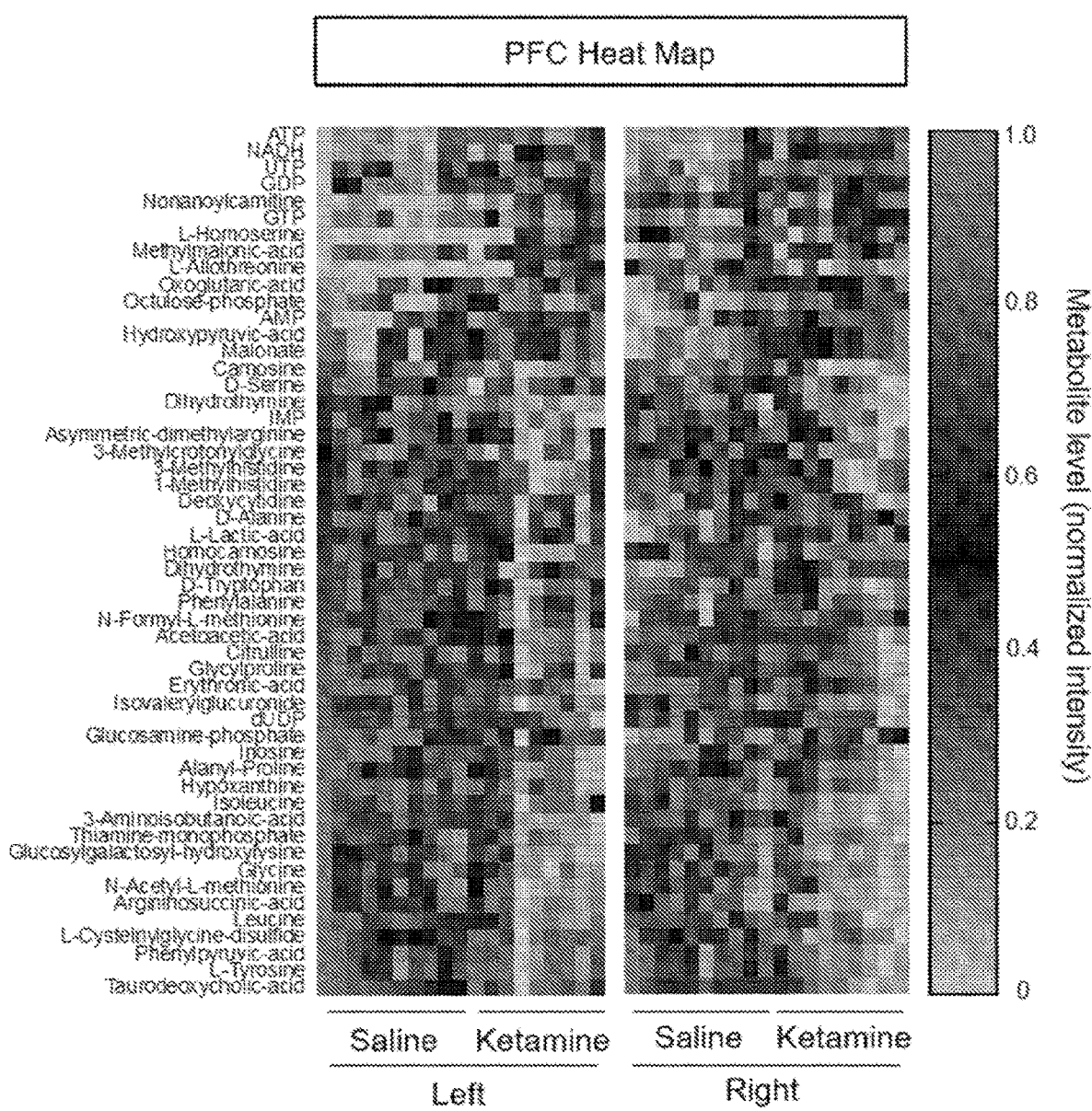
Figure 2E:
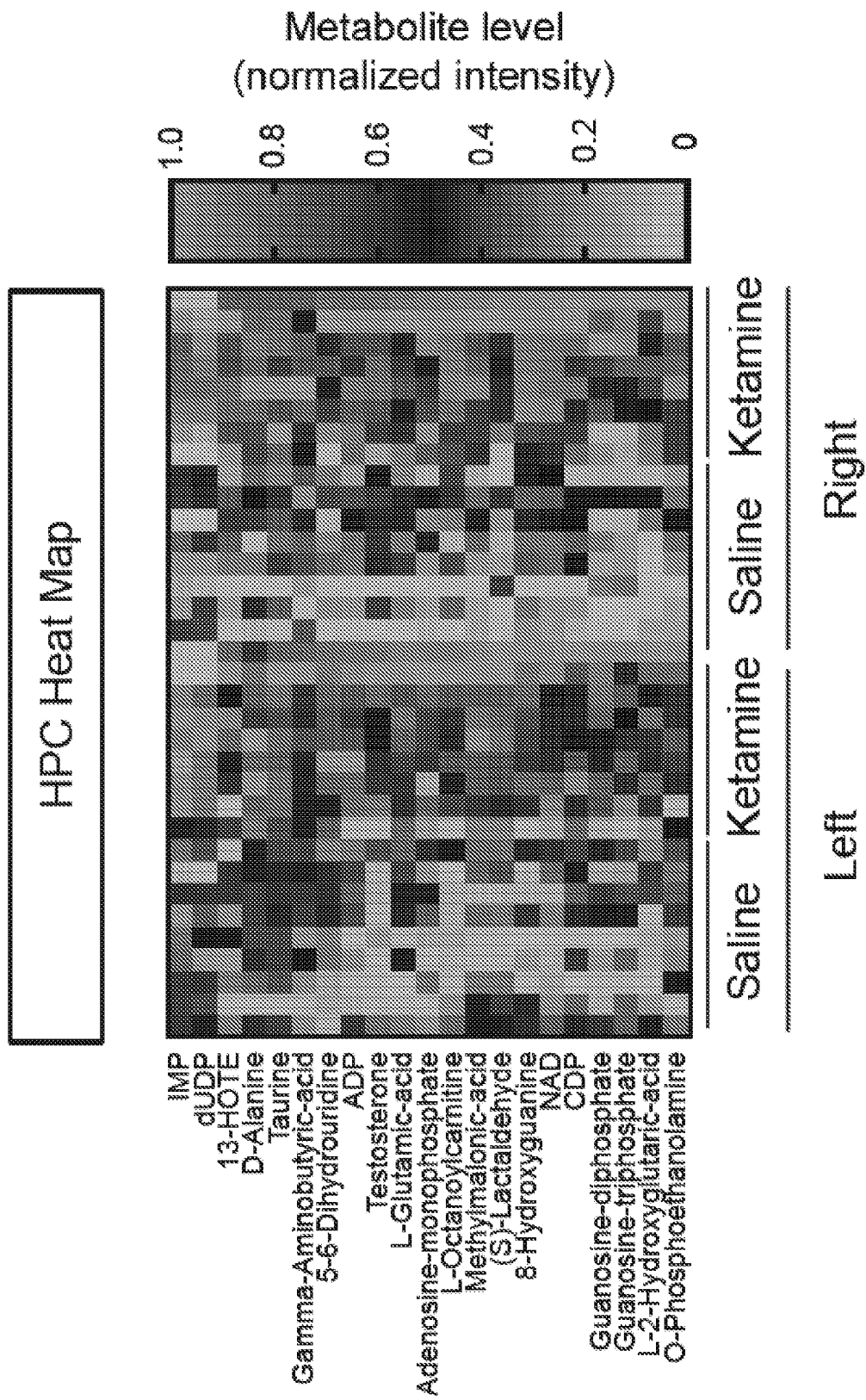
Figure 3B:
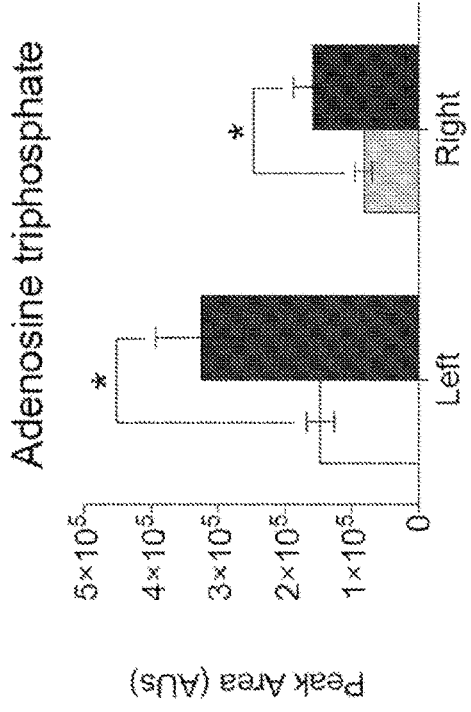
Figure 3D:
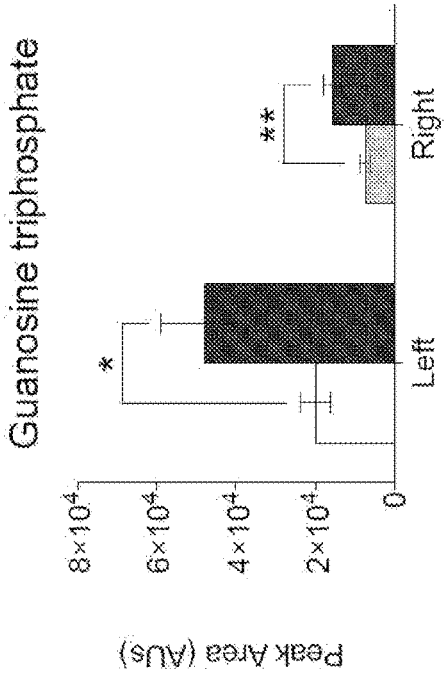
Figure 3A:
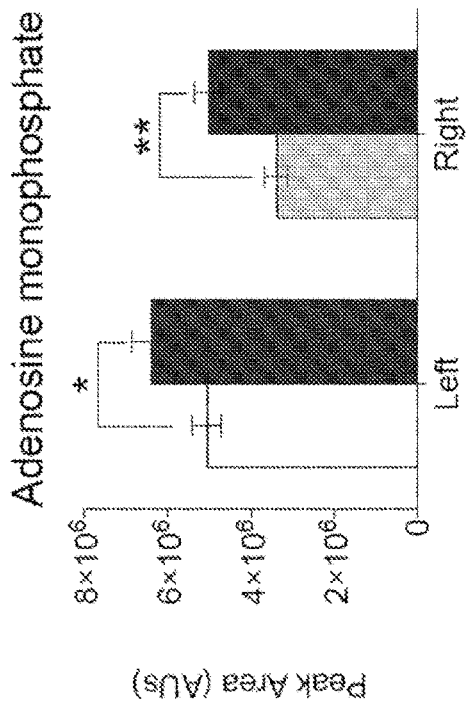
Figure 3C:
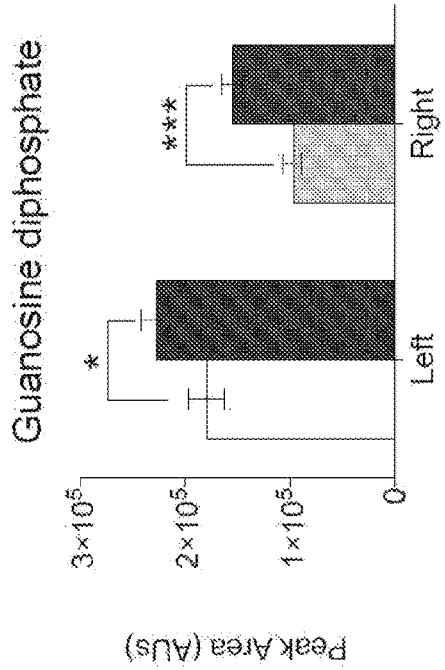
Figure 3I:
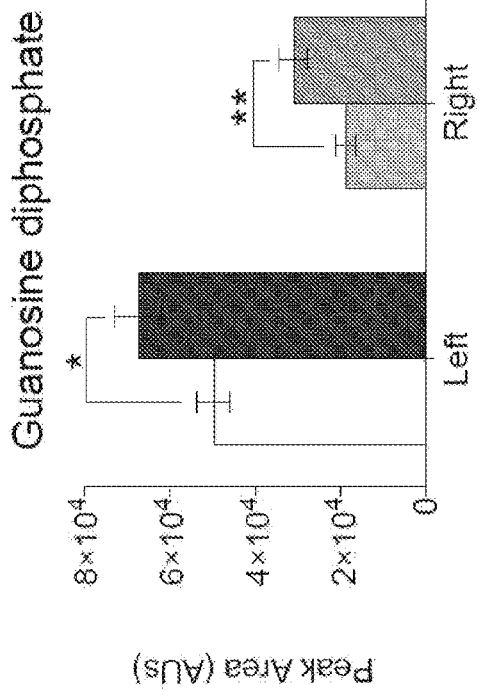
Figure 3J:
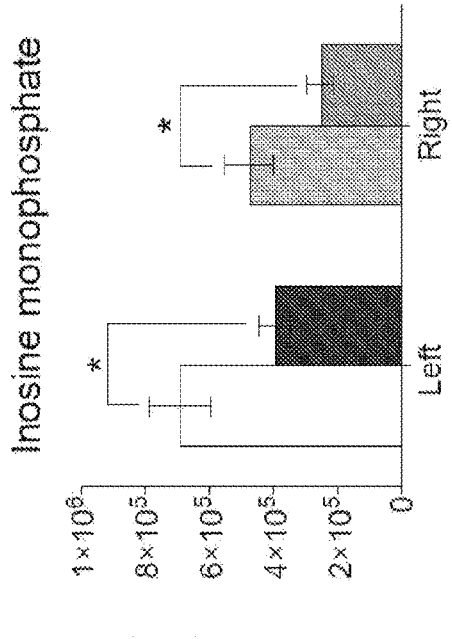
Figure 3K:
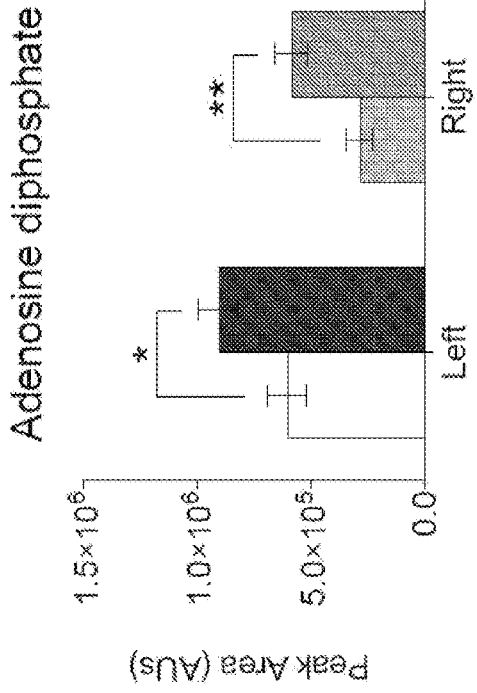
Figure 3L:
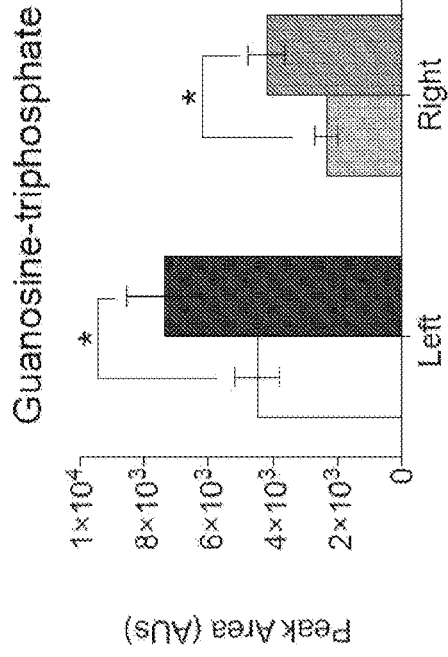

Next, heat maps of the changed metabolites in the PFC and HPC were created for the stressed mice (FIGS. 2D-2E). Heat maps were used to visualize changes following ketamine treatment in the left versus right hemispheres of each brain region. A number of metabolites had altered expression following prophylactic ketamine administration when compared with prophylactic saline expression.

Prophylactic Ketamine Significantly Alters Purine Metabolism Following Stress

Figure 9W:
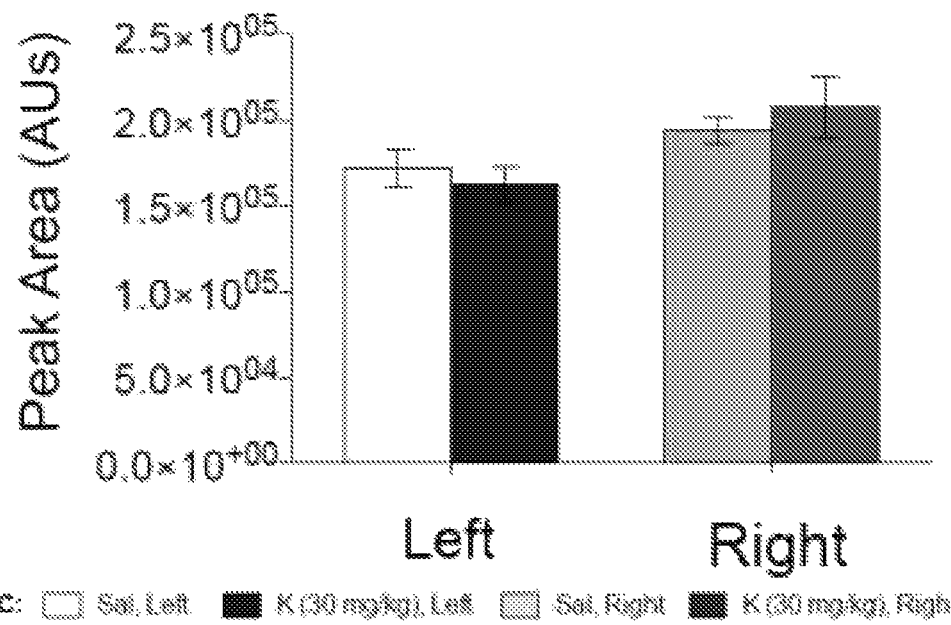
Figure 10B:
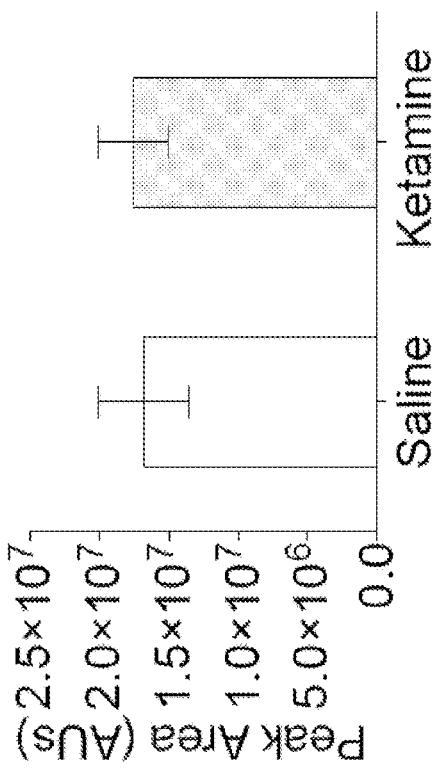
FIGS. 10A-10O. Prophylactic ketamine without CFC stress does not significantly alter purine or pyrimidine metabolism in plasma. (A-J) Purine metabolites were not significantly changed following prophylactic ketamine administration. (K-O) Pyrimidine metabolites were not significantly changed following prophylactic ketamine administration. (n=8-9 male mice per group). Error bars represent ±SEM.
Figure 10D:
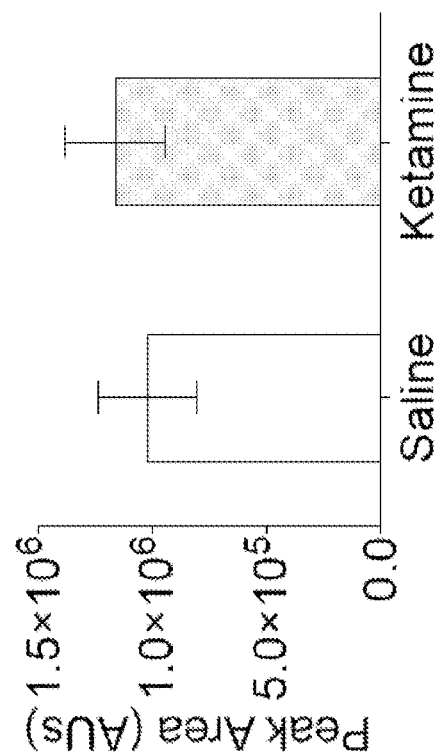
Figure 10A:
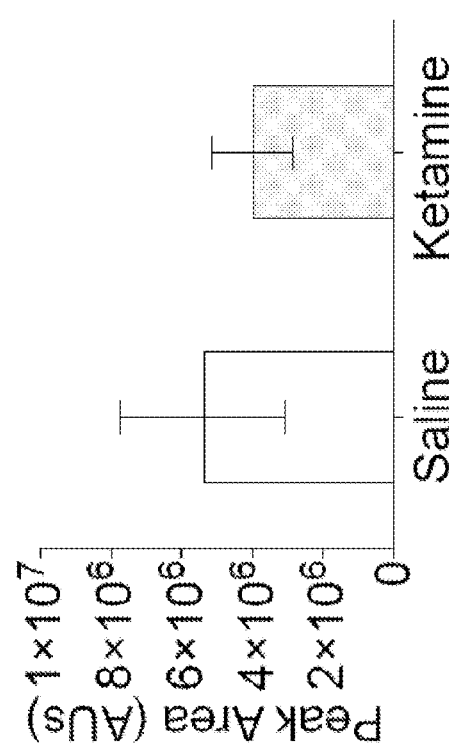
Figure 10C:
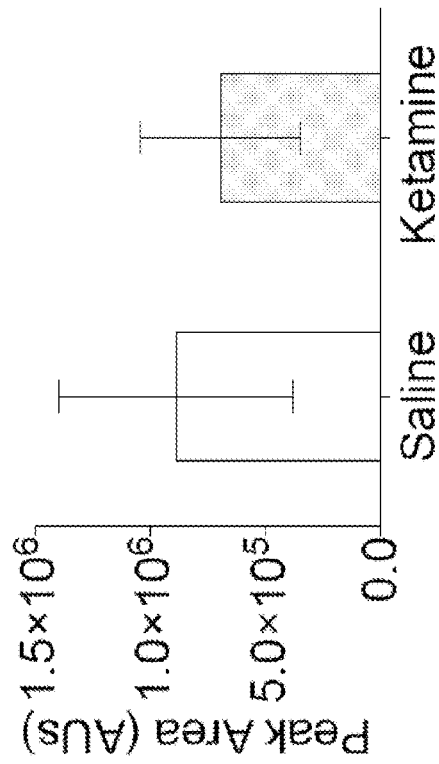
Figure 10I:
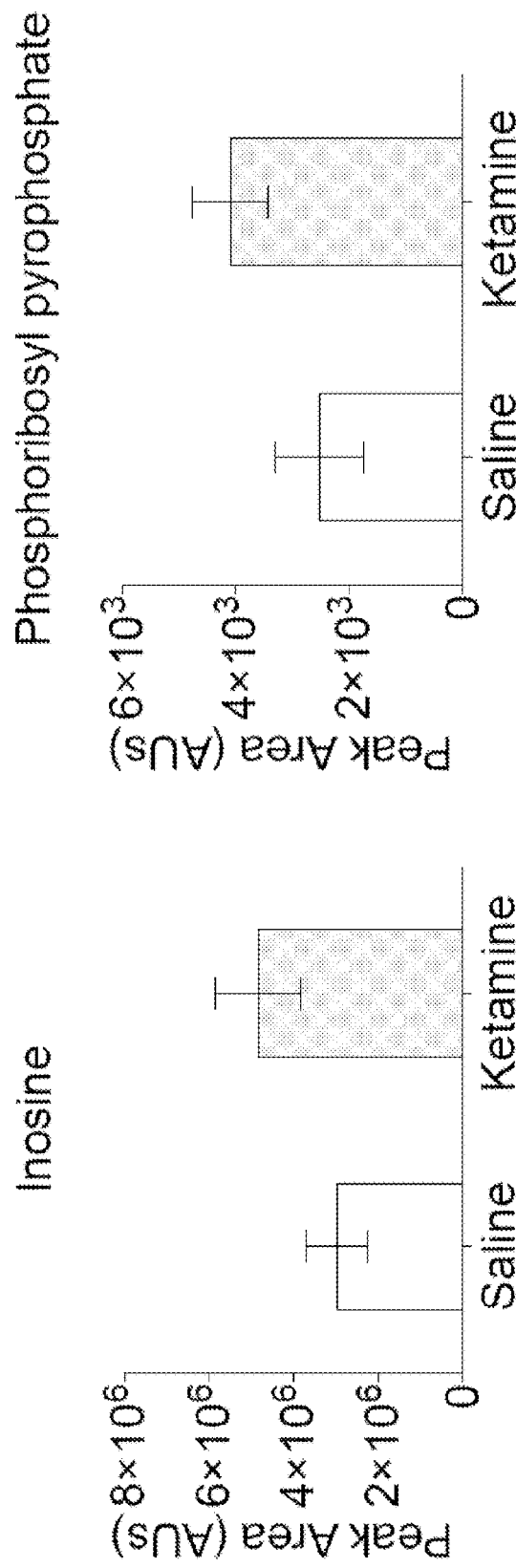
Figure 10J:
Figure 10K:
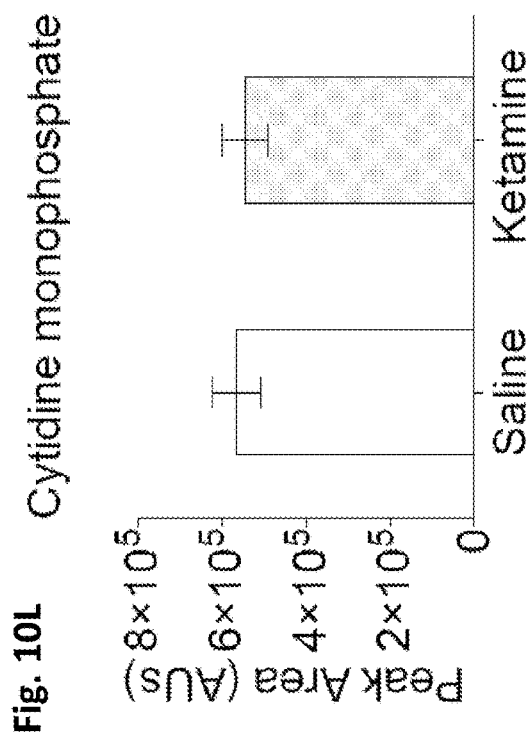
Figure 10L:
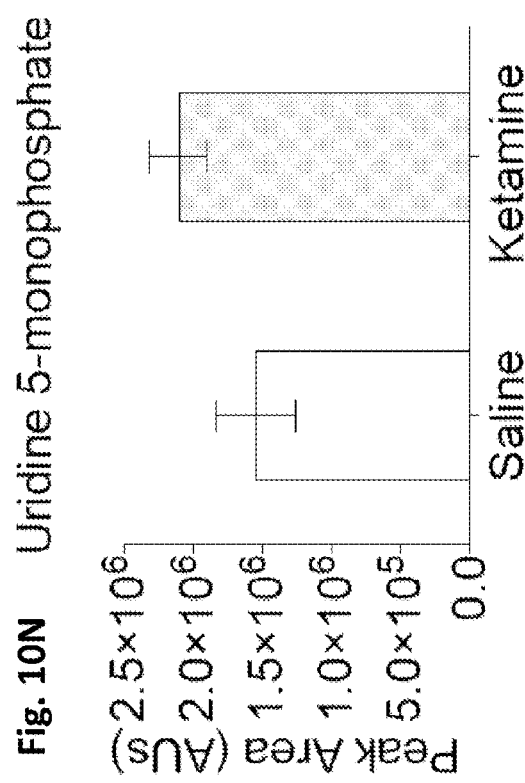
Figure 10M:
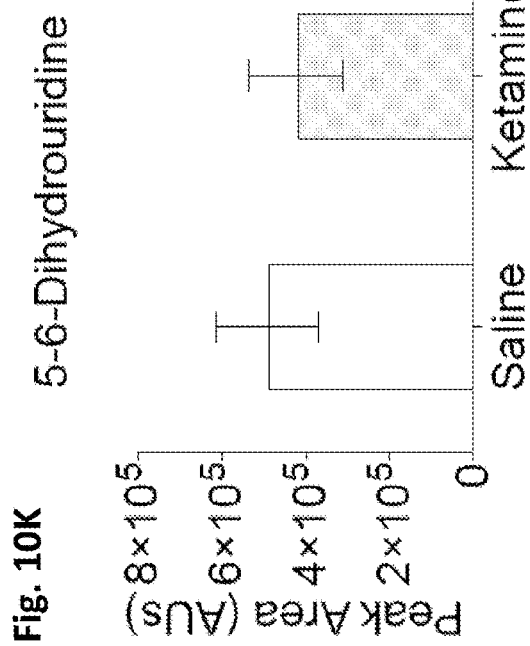
Figure 10N:
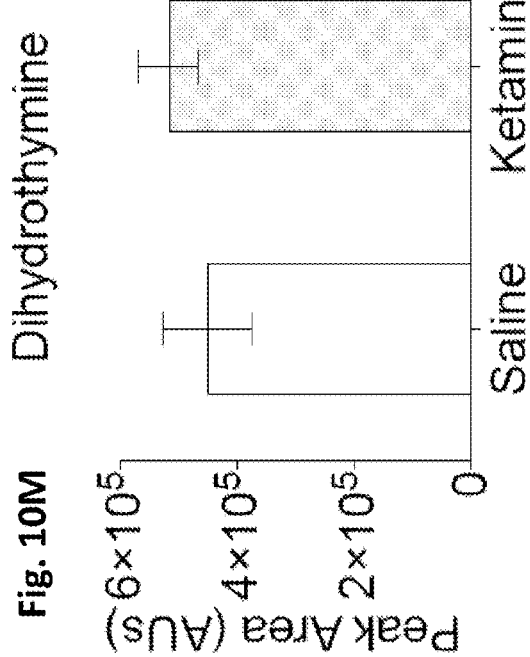
Figure 10O:
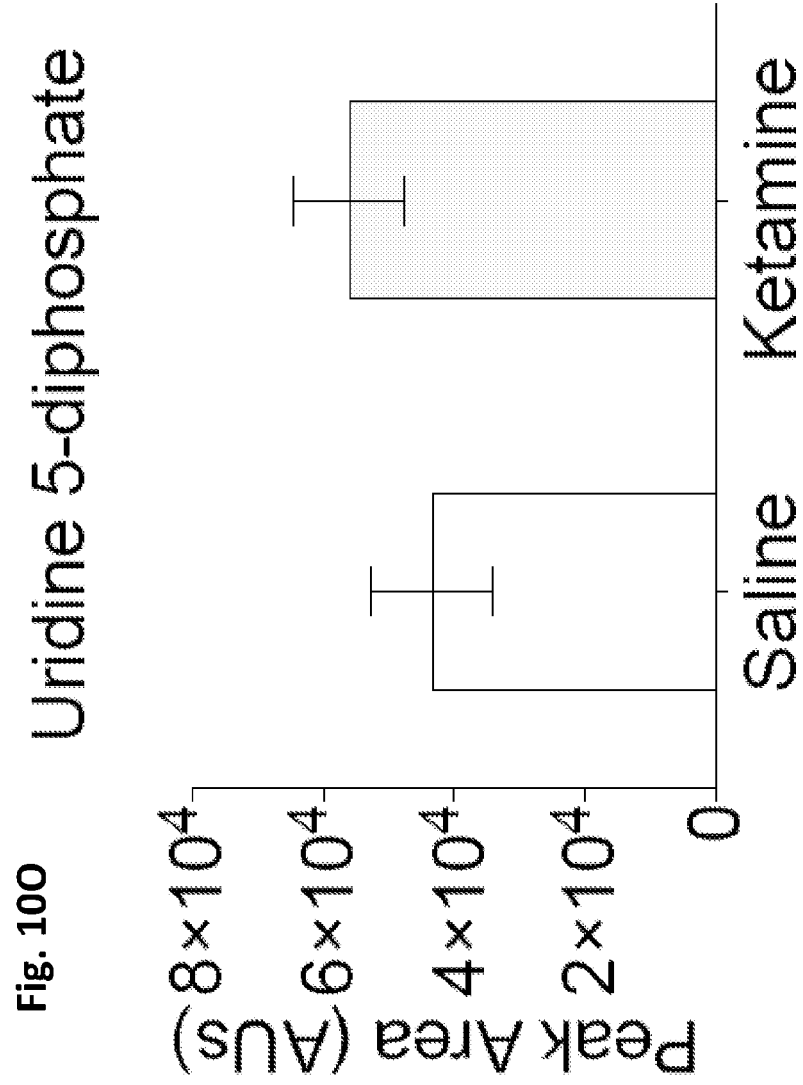

Of the 8 metabolites changed, 6 metabolites were changed in the same direction in both hemispheres of the PFC and HPC of prophylactic ketamine-treated mice that had undergone stress, and these metabolites were involved in purine and pyrimidine biosynthesis (Table 2). We first analyzed individual purine metabolites in the PFC and HPC. Purine precursors and nucleotides were significantly altered in both hemispheres of the PFC (FIGS. 3A-3G) and HPC (FIGS. 3H-3L). Specifically, inosine metabolites were decreased following prophylactic ketamine administration, and the downstream metabolites adenosine and guanosine metabolites were increased. However, these changes were not observed in a group of mice that received prophylactic ketamine without stress (FIGS. 9A-9W).

Figure 4E:
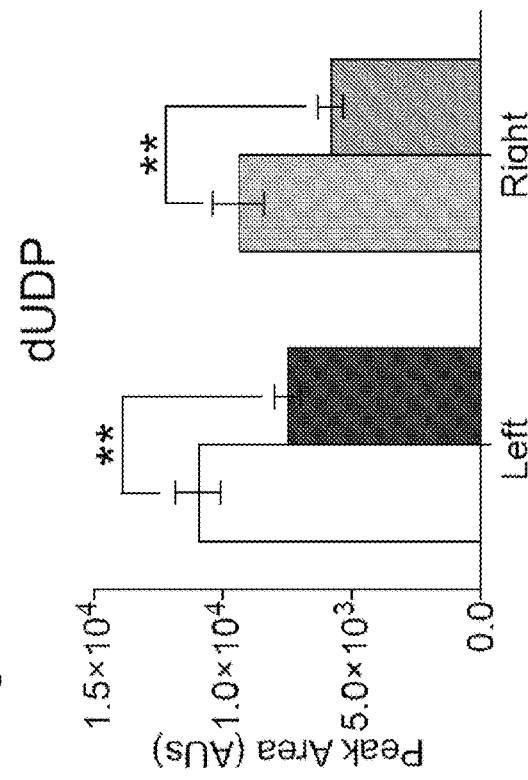
Figure 4F:
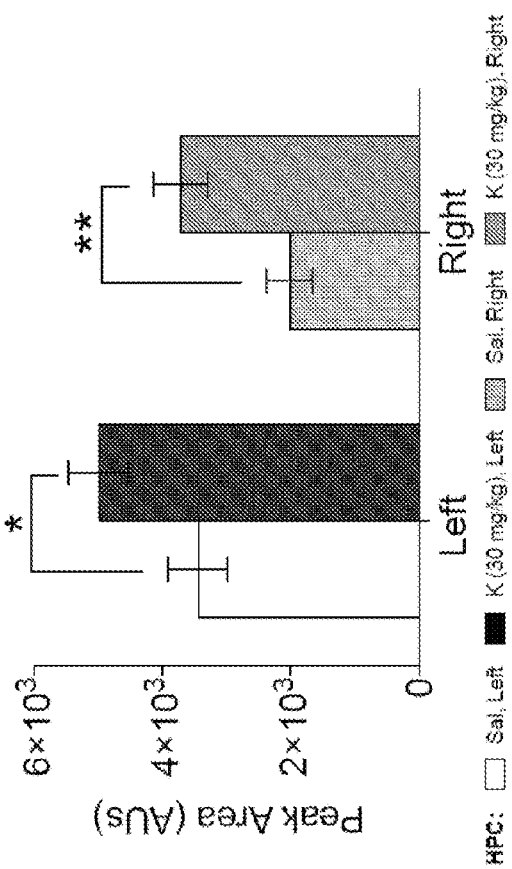
Figure 4G:
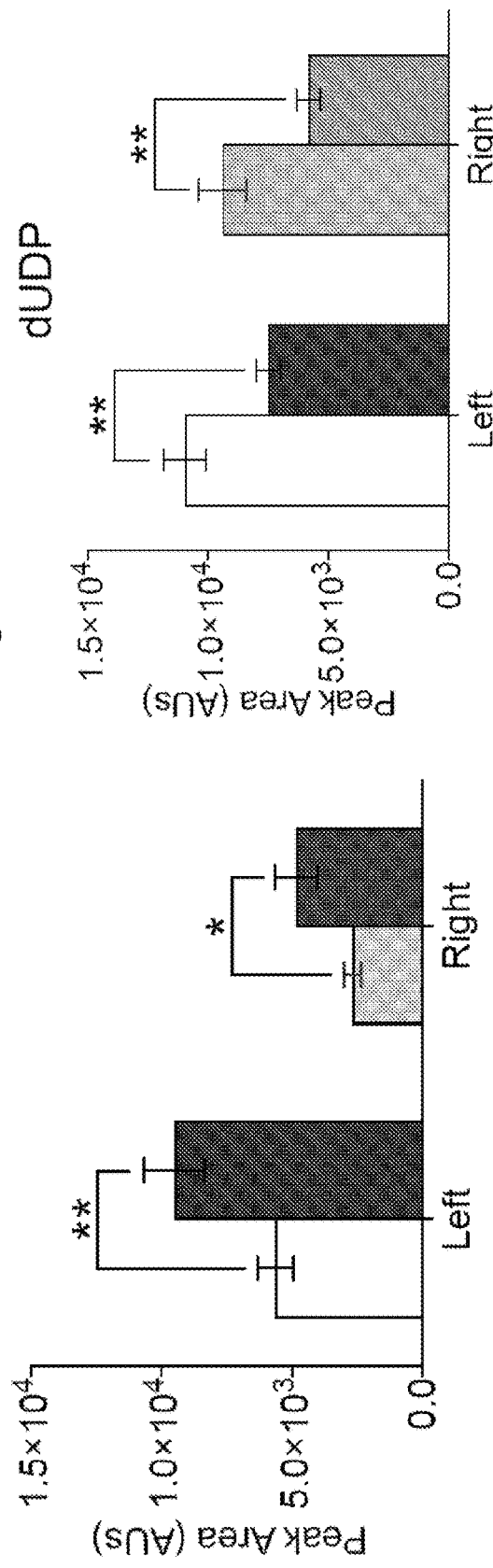
Figure 4H:
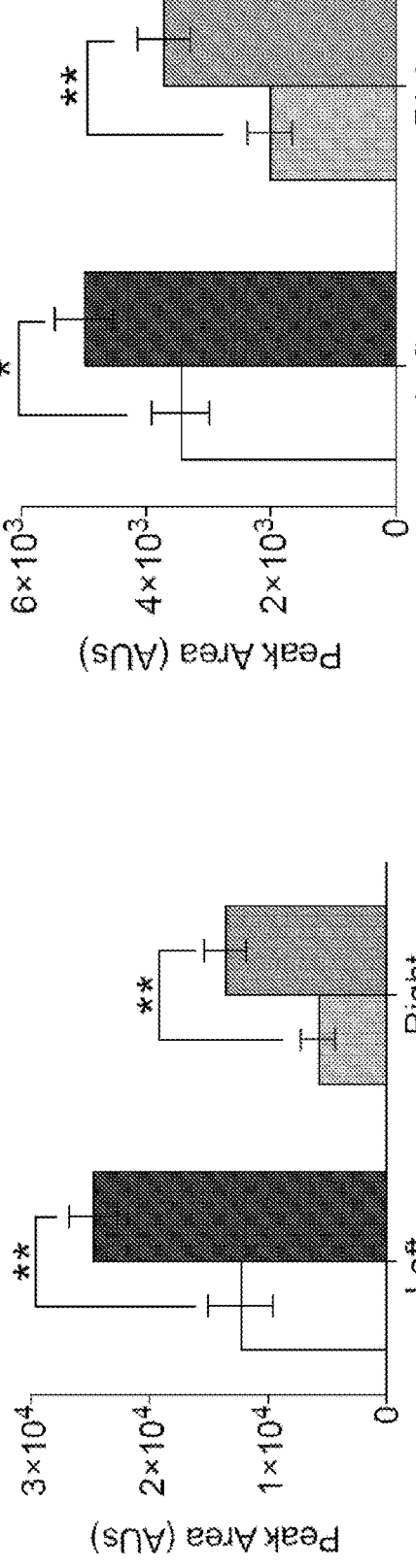
Figure 4I:
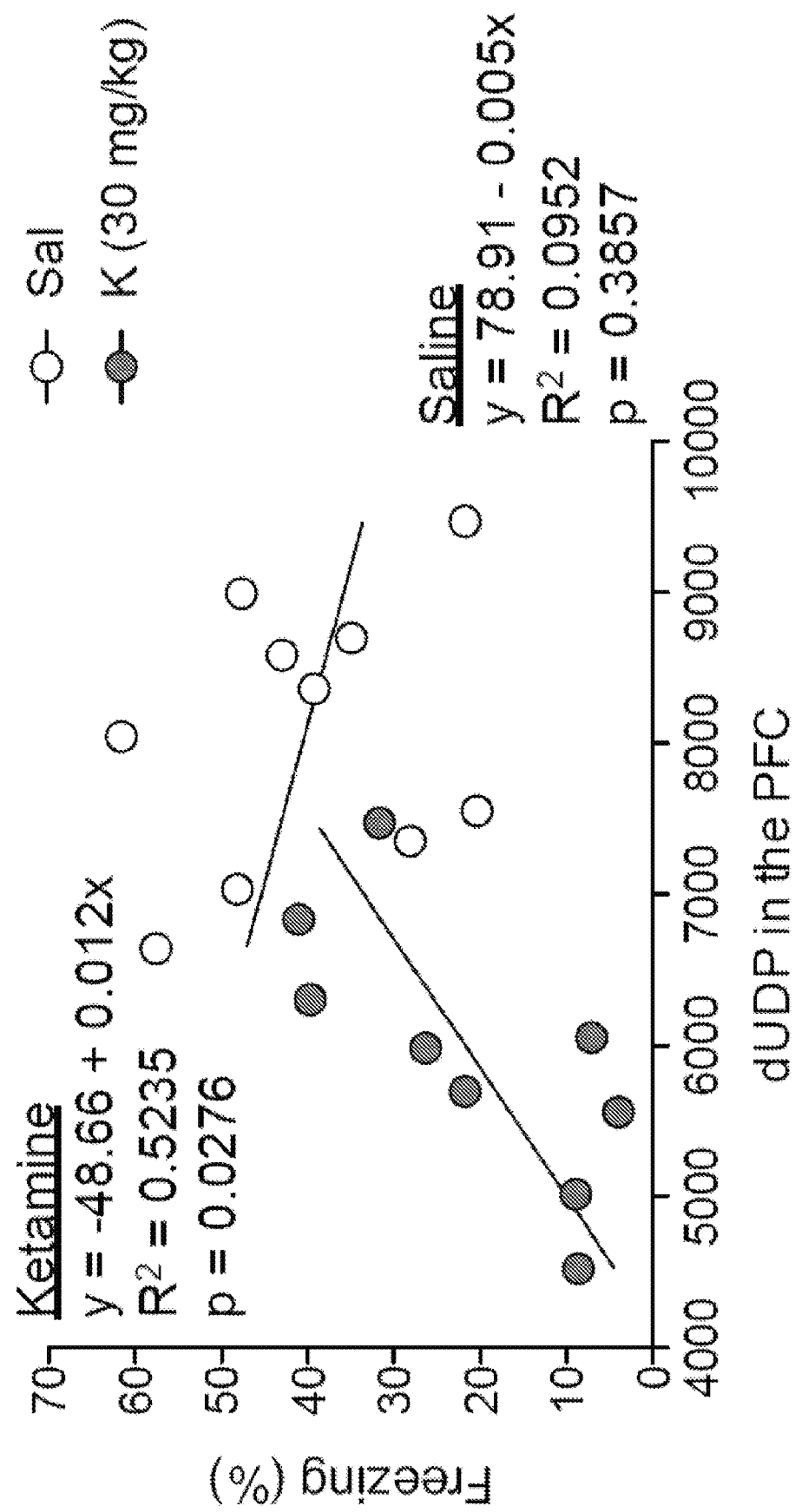
Figure 4J:
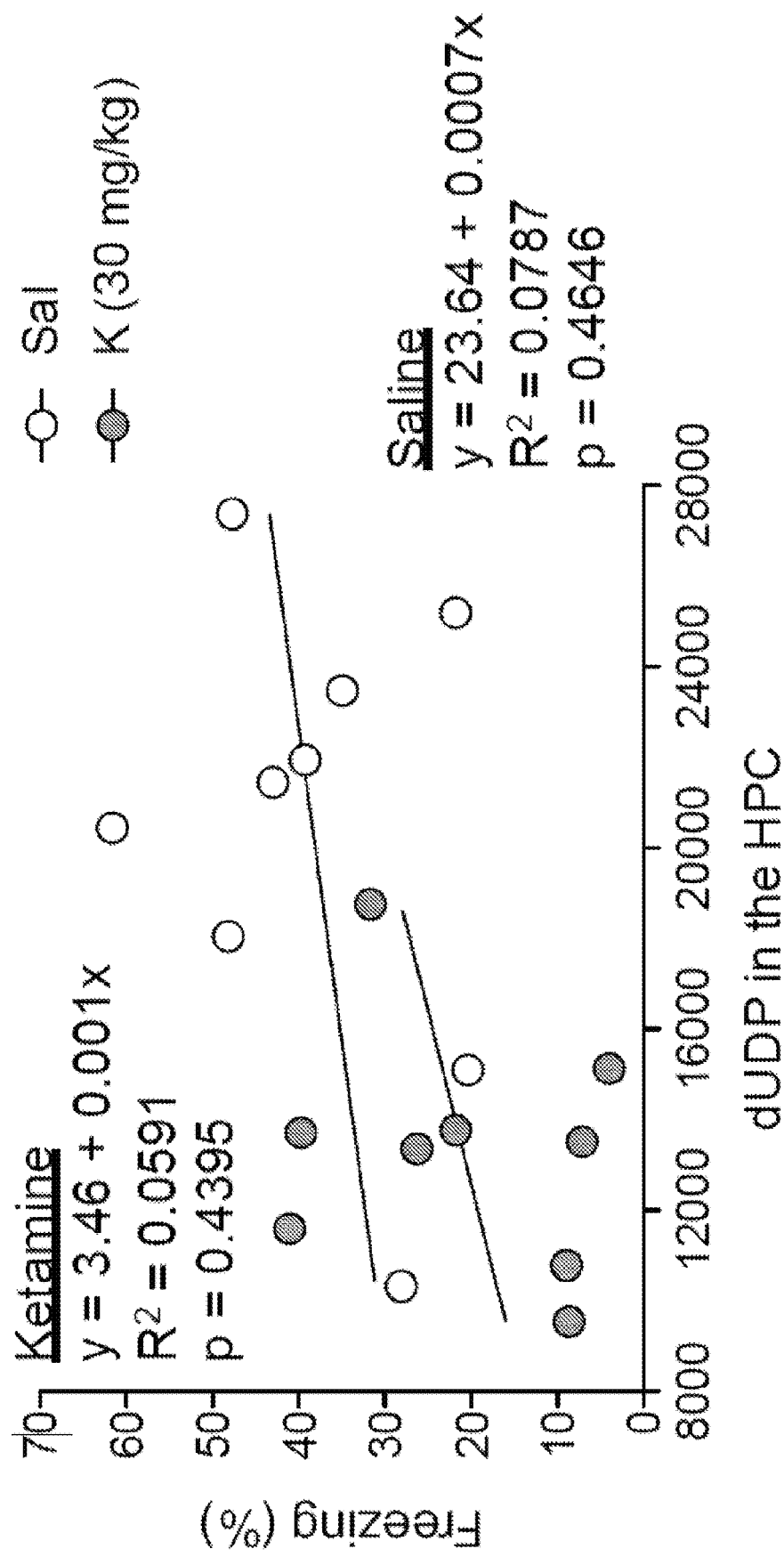

Prophylactic Ketamine Significantly Alters Pyrimidine Metabolism Following Stress Pyrimidine metabolites were next analyzed in both the PFC (FIGS. 4A-4E) and HPC (FIGS. 4F-4H). Since both the PFC and HPC showed alterations in deoxyuridine diphosphate (dUDP), we performed a regression analysis on dUDP expression and freezing behavior in both the PFC (FIG. 4I) and in the HPC (FIG. 4J). In the PFC, dUDP expression is positively correlated with freezing levels upon context re-exposure in mice administered prophylactic ketamine prior to stress. These alterations in pyrimidine metabolism were not observed in mice that received prophylactic ketamine without stress (FIGS. 9A-9W).

Figure 5A:
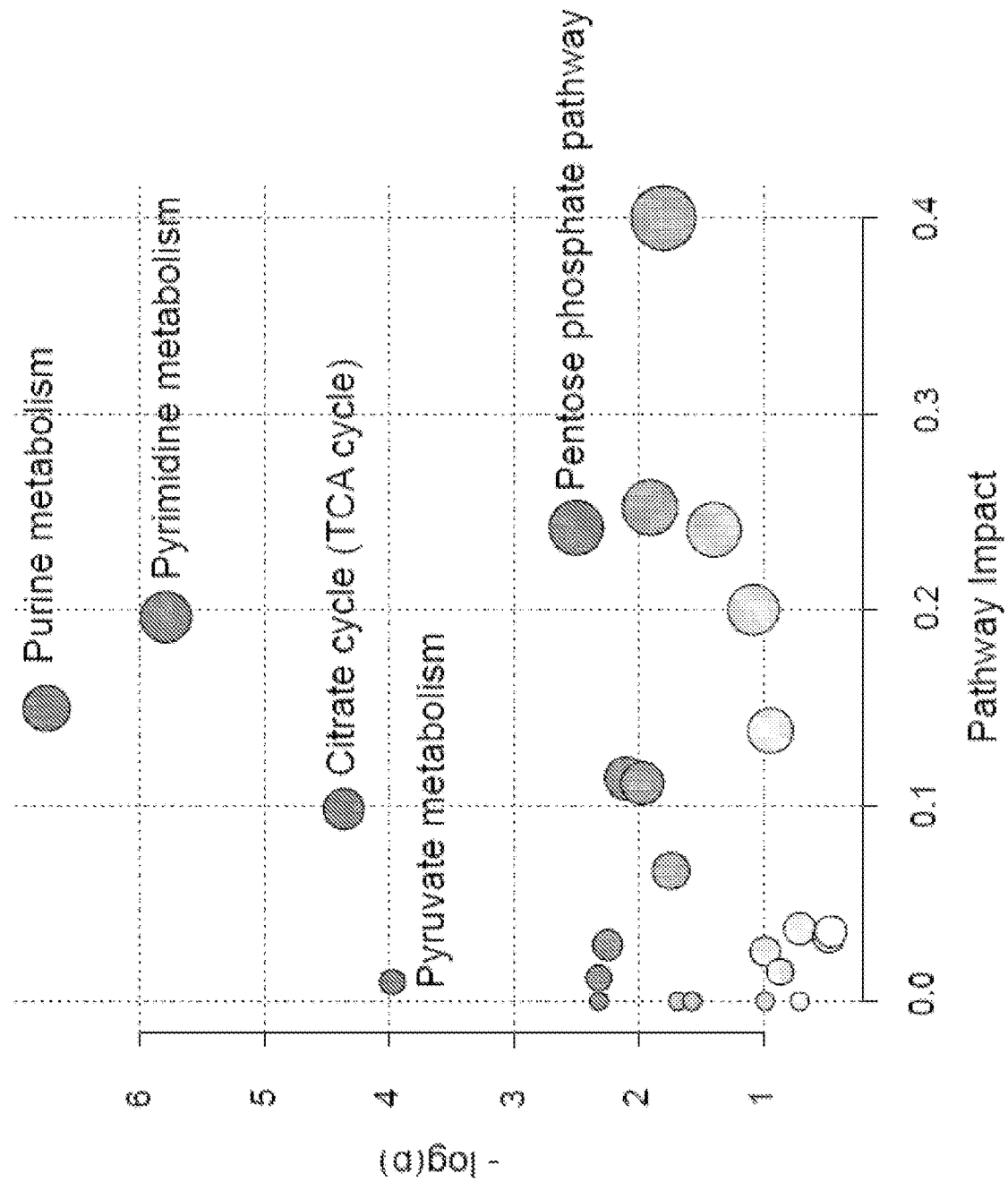
FIGS. 5A-5Q. Prophylactic ketamine significantly alters purine and pyrimidine metabolism in plasma following stress. (A) A pathway analysis of changed metabolites in the plasma. Purine metabolism; pyrimidine metabolism; and the TCA cycle were most significantly changed following prophylactic ketamine administration. (B) A heat map of changed metabolites in the plasma. (C-L) Purine metabolites significantly increased in the plasma following prophylactic ketamine administration. (M-Q) Pyrimidine metabolites significantly increased in the plasma following prophylactic ketamine administration. (n=9-10 male mice per group). Error bars represent ±SEM. *p<0.05, p<0.01, *p<0.001. TCA, tricarboxylic acid; Glu, glutamate; Asp, aspartate; GABA, gamma-aminobutyric acid; Ser, serine; 5-HTP, 5-hydroxytryptophan; PEP, phosphoenolpyruvic acid; TPP, thiamine pyrophosphate; AMP, adenosine monophosphate; Ade, adenosine; MCA, monochloroacetic acid; CMP, cytidine monophosphate; GSSG, glutathione disulfide; PE, phosphatidylethanolamine; 5'-UMP, 5'-uridine monophosphate; RLA, R-(+)-enantiomer lipoic acid; Ino, inosine; GMP, guanosine monophosphate; 3-PGA, 3-phosphoglyceric acid; ATP, adenosine triphosphate; NANA, N-acetylneuraminic acid; SAMe, S-adenosyl methionine; GDP, guanosine diphosphate; PRPP, 5-phospho-alpha-D-ribosyl 1-pyrophosphate; TRA, tiaramide; 5'-UDP, 5'-uridine diphosphate; CYSSG, cysteine-glutatione disulfide.
Figure 5B:
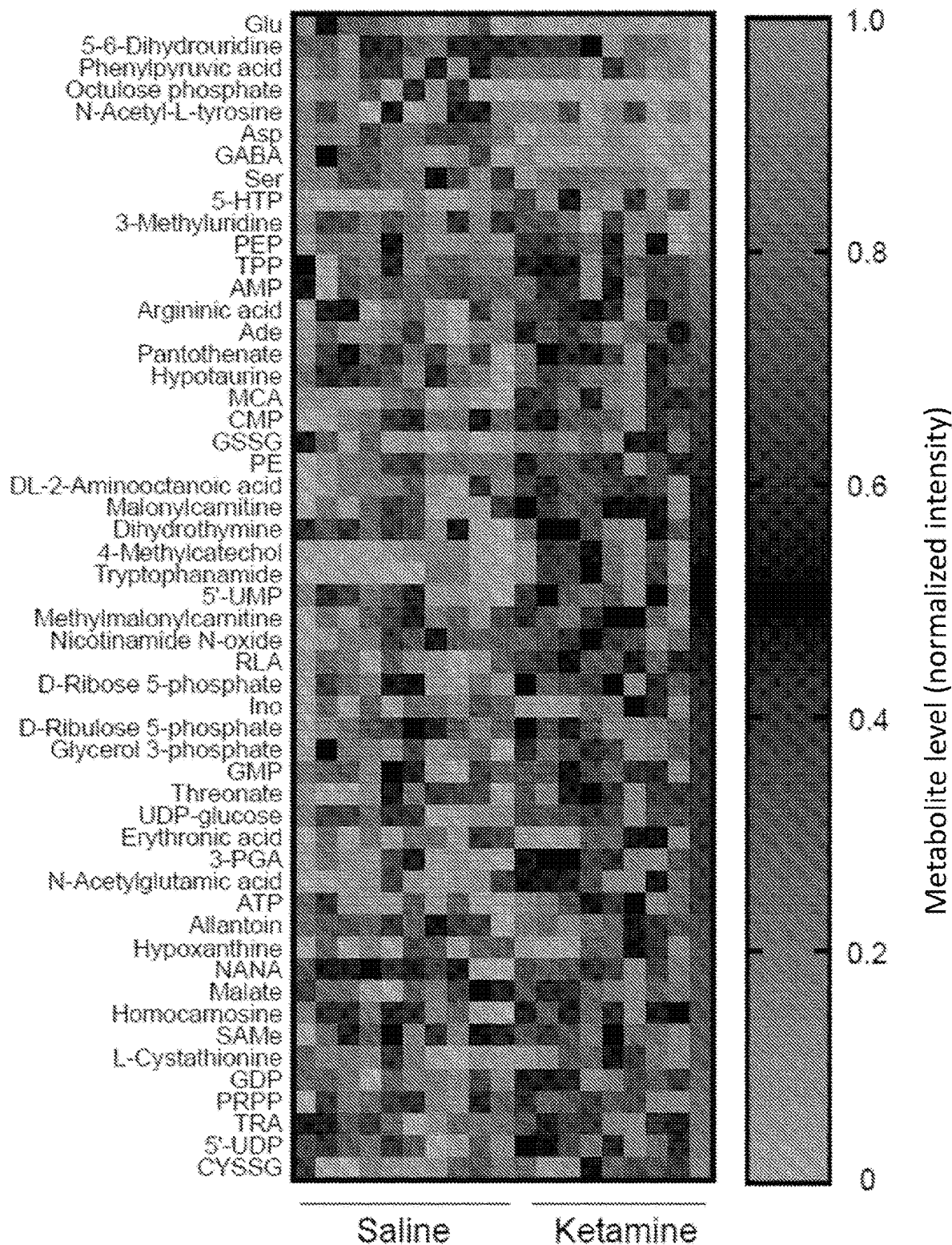
Figure 5F:
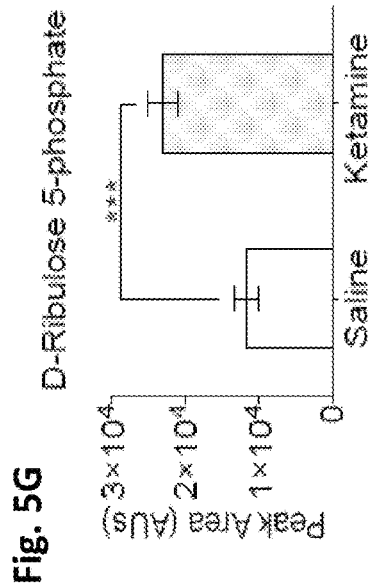
Figure 5K:
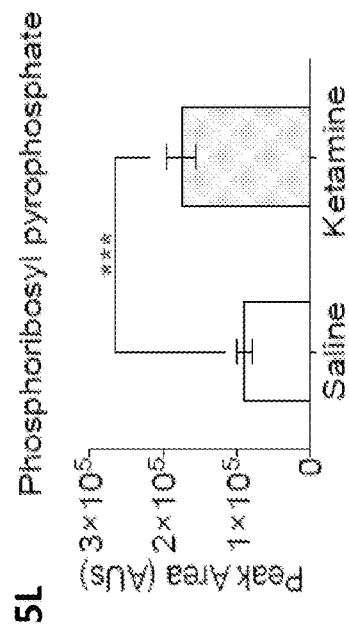
Figure 5P:
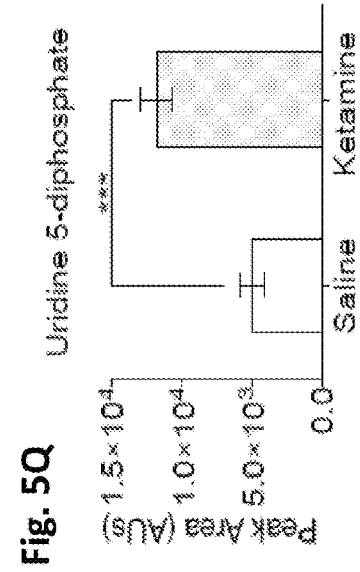
Figure 5G:
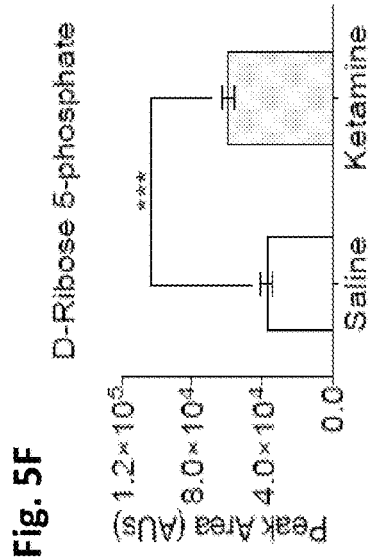
Figure 5L:
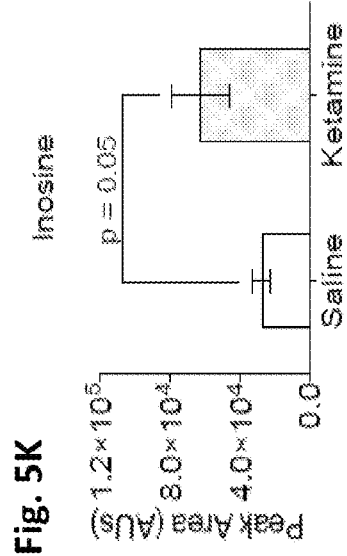
Figure 5Q:
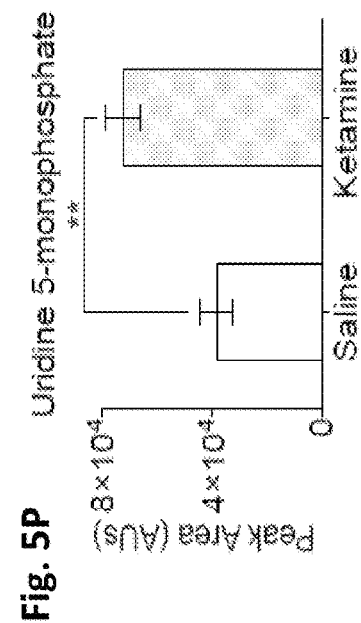

Prophylactic Ketamine Significantly Alters Purine and Pyrimidine Metabolism in Plasma After Stress We next predicted that the effects of prophylactic ketamine might be apparent in the periphery as well as in the brain. Therefore, metabolomics analysis was next performed on plasma samples of stressed and non-stressed mice. A pathway analysis was first performed of changed metabolites indicating that purine metabolism, pyrimidine metabolism, the citrate cycle (TCA cycle), and the pentose phosphate pathway were most significantly changed following prophylactic ketamine administration and stress (FIG. 5A). A heat map was created of all metabolites changed in the plasma between the two groups (FIG. 5B). Prophylactic ketamine administration significantly increased purine metabolites in the plasma (FIGS. 5C-5L). Moreover, with the exception of 5,6-dihydrouridine, prophylactic ketamine administration increased expression of pyrimidine metabolites in the plasma (FIG. 5M-5Q). Interestingly, when the mice were not administered shocks, no changes in purines or pyrimidine metabolites were observed, suggesting that prophylactic ketamine interacts with stress to produce long-term peripheral changes in purine and pyrimidine metabolism (FIGS. 9A-9W).

Amino Acid-Derived Neurotransmitters and Precursors are Significantly Changed Following Prophylactic Ketamine and Stress in the PFC and HPC All amino-acid derived neurotransmitters and their precursors were next analyzed for alterations following prophylactic ketamine administration (Table 3). Interestingly, following stress, almost all inhibitory neurotransmitter metabolites were increased (e.g., alanine, gamma-aminobutyric acid (GABA), taurine) and nearly all excitatory neurotransmitter metabolites were decreased (e.g., serine, tyrosine, and phenylalanine). The main exception to this observation was glutamic acid, a precursor to GABA. Therefore, it is possible that the increase in glutamic acid is directly related to the increase in GABA. In contrast, in non-stressed mice, only the inhibitory neurotransmitter metabolite taurine was changed. These data suggest that prophylactic ketamine and stress may increase inhibitory tone in the brain following administration, resulting in long-lasting protection.

Amino Acid-Derived Neurotransmitters and Precursors are Significantly Changed Following Prophylactic Ketamine and Stress in Plasma As performed on brain tissue, amino-acid derived neurotransmitters and their precursors in plasma were next analyzed for alterations following prophylactic ketamine administration (Table 3). A number of amino acid-derived neurotransmitters and precursors were altered, but only in stressed mice. Interestingly, as in the brain tissue, two excitatory neurotransmitters serine and glutamic acid were decreased. However, unlike in the brain tissue, GABA, an inhibitory neurotransmitter, was decreased. These data suggest that metabolite profiling of plasma samples may indicate effectiveness of prophylactic treatment.

Discussion

Here, we have shown that a single injection of ketamine before a 3-shock CFC protocol attenuated learned fear and produced long-lasting changes in the metabolite profile of PFC and HPC tissues, as well as of plasma. Interestingly, a single injection of ketamine without stress did not produce similar long-lasting changes in the PFC, HPC, or plasma, suggesting that prophylactic ketamine may interact with stress to induce long-lasting metabolic changes, especially in the periphery, that affect behavior. To our knowledge, this is the first study that identifies metabolite alterations and biomarker candidates for prophylactic ketamine efficacy in mice.

Purine and pyrimidine metabolism was affected not only in the PFC and in the HPC, but also in plasma of prophylactic ketamine-treated stressed mice. Genetically determined aberrations in purine and pyrimidine metabolism have been associated with neurological dysfunction (Jinnah et al, 2013; Kelley and Andersson, 2014; Micheli et al, 2011) and psychiatric disorders (Astakhova and Asanova, 1985; Cieslak et al, 2016). Purine and pyrimidine metabolism has also recently been implicated in antidepressant treatment response in mice and humans (Park et al, 2016). In this study, a commonly used selective serotonin reuptake inhibitor (SSRI), paroxetine, was administered to DBA/2J mice for 28 days. Drug non-responder and responder mice were identified, and the metabolomic profile was assessed in the HPC and plasma. Their results suggest that chronic SSRI treatment differentially affects purine and pyrimidine metabolism, which may explain the heterogeneous antidepressant treatment response, and represents a potential biosignature of the disease. Specifically, the authors observed decreased purine and pyrimidine metabolism in antidepressant non-responders, and increased metabolism in responders. Here, we have similarly assessed efficacy of the rapid-acting antidepressant ketamine, but when administered prior to stress. The effect of prophylactic ketamine on purine and pyrimidine metabolism after stress suggests that several mechanisms of successful antidepressant treatment may overlap with prophylactic responsiveness. Additionally, to further assess how changes in the metabolome relate to behavioral output, we correlated the freezing levels of stressed mice with the amount of the pyrimidine dUDP in both hemispheres of the PFC and HPC. We found that dUDP levels positively correlated with freezing levels upon context re-exposure, but only in the PFC of mice administered ketamine, suggesting that the alterations in the metabolome induced by ketamine and stress may directly influence pathological states.

Prophylactic ketamine increased precursors to inhibitory neurotransmitters, while decreasing most precursors to excitatory neurotransmitters in stressed mice. Increasing evidence demonstrates that MDD is associated with an imbalance of excitatory and inhibitory neurotransmitters glutamate and GABA (Hasler et al, 2007). Specifically, glutamic acid and GABA dysregulation is a hallmark of MDD pathology (Abdallah et al, 2014; Pehrson and Sanchez, 2015), as well as of PTSD and other panic and social anxiety disorders (Averill et al, 2016; Meyerhoff et al, 2014). Interestingly, in a model of chronic social defeat stress (CSDS), mice that exhibited depressive-like behavior showed a reduction in glutamate in the GABAergic pathway, suggesting that glutamatergic disorders may be implicated in susceptibility to stress (Wang et al, 2016). Collectively, these data suggest that prophylactic ketamine may be increasing stress resilience by regulating GABA and glutamate neurotransmission and therefore, preventing stress-induced phenotypes.

No previous studies have identified the alterations in the metabolome that occur upon administering a resilience-enhancing pharmaceutical, as the current study sought to assess. However, previous studies have been conducted in regards to ketamine's rapid-acting antidepressant effects and the resultant metabolomic and proteomic changes. Specifically, adenosine has been shown to mediate antidepressant action of ketamine, and that enhancement of the adenosine $A_1$ receptors (AIRs) in forebrain neurons of mice produced resilience-enhancing effects (Serchov et al, 2015). In general, adenosine has been known to act as an anti-inflammatory agent involved in neuroprotection, and it is hypothesized that imbalanced levels of adenosine-5'-triphosphate (ATP) and adenosine in the extracellular space may lead to neuropsychiatric diseases (Cieslak et al, 2016). These data are in agreement with our results demonstrating that prophylactic ketamine administration increases levels of adenosine monophosphate (AMP) and ATP in both hemispheres of the PFC and HPC, and in the plasma.

Thyrotropin-releasing hormone (TRH) and TRH-like peptides, which are potential therapeutic targets for MDD, are also increased in various brain regions, including the PFC and HPC, upon ketamine administration (Pekary et al, 2015). It has also been demonstrated that in as rapidly as 2 hours post-ketamine injection, hippocampal pathways including glycolysis, pentose phosphate pathway, and citrate cycle are impacted (Weckmann et al, 2014). Importantly, the pentose phosphate pathway is known to be important for purine formation. Here, we show that ribose and ribulose phosphate, pentose phosphate pathway intermediates, are significantly changed in plasma, which is in agreement with Weckmann et al.'s study demonstrating the role of ketamine on the pentose phosphate pathway and purine formation. Thus, there may be a cascade of changes occurring after ketamine administration that are activated during stress, which could explain its long-lasting resilience-enhancing effects, such as changes in the pentose phosphate pathway that lead to changes in purine formation.

The use of metabolite supplements in the treatment of depression has been attempted, as metabolic syndromes have been associated with MDD (Marazziti et al, 2014; Martinac et al, 2014) and PTSD (Bartoli et al, 2013). Interestingly, one clinical study found that up to two-thirds of TRD patients may demonstrate at least one metabolic abnormality (Pan et al, 2017). Systemic folate deficiency has been of particular relevance to this study, as cerebral folate deficiency (CFD) was the most common in the TRD patients. Typically, CFD syndromes present as developmental and psychiatric disorders (Ramaekers et al, 2013; Serchov et al, 2015). Folate, a water-soluble B-vitamin, is involved in nearly 100 metabolic reactions including the purine synthetic pathway (Pan and Vockley, 2013), and is necessary for the biosynthesis of monoamine neurotransmitters serotonin, epinephrine, and dopamine (Serchov et al, 2015). Low folate levels have been associated with reduced response to antidepressants, and have been correlated with MDD symptomology; thus, folate supplements such as folic acid or methylfolate have been prescribed to MDD patients (Nelson, 2012). The influence of folate on monoamine neurotransmitters is reflected in our data, as folate changes may have influenced changes we observed in neurotransmitters such as tyrosine and phenylalanine in the brain, which are precursors to dopamine, norepinephrine, and epinephrine.

The identification of specific metabolite markers associated with psychiatric disease using metabolomics platforms has only been recently pursued. There are an emerging series of studies assessing urinary and peripheral blood metabolite biomarkers to aid in diagnosis of MDD (Lee et al, 2016; Redei and Mehta, 2015; Zheng et al, 2013a; Zheng et al, 2016; Zheng et al, 2013b). Prior to metabolomics studies, research focused on identifying genomic markers of MDD, but efforts have not yet yielded diagnostic and treatment biomarkers in the genome (Miller and O'Callaghan, 2013). Interestingly, we found that prophylactic ketamine significantly altered metabolites in both the brain and the plasma after stress. Importantly, prophylactic ketamine alone does not induce the same changes in metabolites, but rather, these changes are triggered only after the experience of a stressor. This is noteworthy, as it suggests that there are peripheral changes with prophylactic treatment and stress that may be identified in the clinic.

Overall, the present study may lead to novel insights on how ketamine treatment prior to a stressor may alter metabolic pathways that are involved in neurotransmission, and how these pathways are implicated in mood disorders. These data suggest that a single dose of ketamine induces a cascade of effects following a stressor that may underlie its long-lasting resilience against stress-induced disorders. These results may elucidate potential biological processes in the brain and plasma that are critical for maintaining resilience against stressors.

Table 1. Statistical analysis summary for CFC data, weights of HPC and PFC samples used for analyses, and statistical analysis summary for metabolomics data.

Table 2. Prophylactic ketamine prior to CFC stress results in altered purine and pyrimidine metabolism. Of the 8 metabolites changed following prophylactic ketamine and CFC stress, 6 metabolites were changed in the same direction in both hemispheres of the PFC and HPC and these metabolites were primarily involved in purine and pyrimidine biosynthesis.

Table 3. Amino acid-derived neurotransmitters and precursors are significantly changed following prophylactic ketamine and CFC stress in the PFC, HPC, and plasma. Amino-acid derived neurotransmitters and their precursors were next analyzed for alterations following prophylactic ketamine administration and CFC stress. Interestingly, in the PFC and HPC almost all inhibitory neurotransmitter metabolites were increased (e.g. alanine, gamma-aminobutyric acid (GABA), taurine) and nearly all excitatory neurotransmitter metabolites were decreased (e.g. serine, tryosine, and phenylalanine). The main exception to this observation was glutamic acid, a precursor to GABA. Therefore, it is possible that the increase in glutamic acid is directly related to the increase in GABA. These data suggest that prophylactic ketamine may increase inhibitory tone in the brain following administration, resulting in long-lasting protection. As performed on brain tissue, metabolomic profiling was performed on plasma samples. A number of amino acid-derived neurotransmitters and precursors were altered following prophylactic ketamine and CFC stress. Interestingly, as in the brain tissue, two excitatory neurotransmitters serine and glutamic acid were decreased. However, unlike in the brain tissue, GABA, an inhibitory neurotransmitter, was decreased. These data suggest that metabolite profiles of plasma samples may indicate effectiveness of prophylactic treatment.

REFERENCES

Abdallah C G, Jiang L, De Feyter H M, Fasula M, Krystal J H, Rothman D L, et al (2014). Glutamate metabolism in major depressive disorder. *The American journal of psychiatry* 171(12): 1320-1327.

Amat J, Dolzani S D, Tilden S, Christianson J P, Kubala K H, Bartholomay K, et al (2016). Previous Ketamine Produces an Enduring Blockade of Neurochemical and Behavioral Effects of Uncontrollable Stress. *The Journal of neuroscience: the official journal of the Society for Neuroscience* 36(1): 153-161.

Asberg M, Traskman L, Thoren P (1976). 5-HIAA in the cerebrospinal fluid. A biochemical suicide predictor? *Archives of general psychiatry* 33(10): 1193-1197.

Astakhova L N, Asanova N K (1985). [Borderline neuropsychiatric disorders in purine metabolism disorders in children]. *Zhurnal nevropatologii i psikhiatrii imeni SS Korsakova* (Moscow, Russia: 1952) 85(3): 421-426.

Averill L A, Purohit P, Averill C L, Boesl M A, Krystal J H, Abdallah C G (2016). Glutamate dysregulation and glutamatergic therapeutics for PTSD: Evidence from human studies. *Neuroscience letters*.

Bartoli F, Carra G, Crocamo C, Carretta D, Clerici M (2013). Metabolic syndrome in people suffering from posttraumatic stress disorder: a systematic review and meta-analysis. *Metabolic syndrome and related disorders* 11(5): 301-308.

Berman R M, Cappiello A, Anand A, Oren D A, Heninger G R, Charney D S, et al (2000). Antidepressant effects of ketamine in depressed patients. *Biological psychiatry* 47(4): 351-354.

Brachman R A, McGowan J C, Perusini J N, Lim S C, Pham T H, Faye C, et al (2016). Ketamine as a Prophylactic Against Stress-Induced Depressive-like Behavior. *Biological psychiatry* 79(9): 776-786.

Cieslak M, Czarnecka J, Roszek K (2016). The roles of purinergic signaling in psychiatric disorders. *Acta biochimica Polonica* 63(1): 1-9.

Denny C A, Kheirbek M A, Alba E L, Tanaka K F, Brachman R A, Laughman K B, et al (2014). Hippocampal memory traces are differentially modulated by experience, time, and adult neurogenesis. *Neuron* 83(1): 189-201.

Diazgranados N, Ibrahim L, Brutsche N E, Newberg A, Kronstein P, Khalife S, et al (2010). A randomized add-on trial of an N-methyl-D-aspartate antagonist in treatment-resistant bipolar depression. *Archives of general psychiatry* 67(8): 793-802.

Drew M R, Denny C A, Hen R (2010). Arrest of adult hippocampal neurogenesis in mice impairs single—but not multiple-trial contextual fear conditioning. *Behavioral neuroscience* 124(4): 446-454.

Feder A, Parides M K, Murrough J W, Perez A M, Morgan J E, Saxena S, et al (2014). Efficacy of intravenous ketamine for treatment of chronic posttraumatic stress disorder: a randomized clinical trial. *JAMA psychiatry* 71(6): 681-688.

Hasler G, van der Veen J W, Tumonis T, Meyers N, Shen J, Drevets W C (2007). Reduced prefrontal glutamate/glutamine and gamma-aminobutyric acid levels in major depression determined using proton magnetic resonance spectroscopy. *Archives of general psychiatry* 64(2): 193-200.

Howlett J R, Stein M B (2016). Prevention of Trauma and Stressor-Related Disorders: A Review. *Neuropsychopharmacology: official publication of the American College of Neuropsychopharmacology* 41(1): 357-369.

Ionescu D F, Luckenbaugh D A, Niciu M J, Richards E M, Zarate C A, Jr. (2015). A single infusion of ketamine improves depression scores in patients with anxious bipolar depression. *Bipolar disorders* 17(4): 438-443.

Jinnah H A, Sabina R L, Van Den Berghe G (2013). Metabolic disorders of purine metabolism affecting the nervous system. *Handbook of clinical neurology* 113: 1827-1836.

Johnson C H, Ivanisevic J, Siuzdak G (2016). Metabolomics: beyond biomarkers and towards mechanisms. *Nature reviews Molecular cell biology* 17(7): 451-459.

Kelley R E, Andersson H C (2014). Disorders of purines and pyrimidines. *Handbook of clinical neurology* 120: 827-838.

Knoll A T, Meloni E G, Thomas J B, Carroll F I, Carlezon W A, Jr. (2007). Anxiolytic-like effects of kappa-opioid receptor antagonists in models of unlearned and learned fear in rats. *The Journal of pharmacology and experimental therapeutics* 323(3): 838-845.

Lee M Y, Kim E Y, Kim S H, Cho K C, Ha K, Kim K P, et al (2016). Discovery of serum protein biomarkers in drug-free patients with major depressive disorder. *Progress in neuro-psychopharmacology & biological psychiatry* 69: 60-68.

Marazziti D, Rutigliano G, Baroni S, Landi P, Dell'Osso L (2014). Metabolic syndrome and major depression. *CNS spectrums* 19(4): 293-304.

Martinac M, Pehar D, Karlovic D, Babic D, Marcinko D, Jakovljevic M (2014). Metabolic syndrome, activity of the hypothalamic-pituitary-adrenal axis and inflammatory mediators in depressive disorder. *Acta clinica Croatica* 53(1): 55-71.

McGowan J C, LaGamma C T, Lim S C, Tsitsiklis M, Neria Y, Brachman R A, et al (2017). Prophylactic Ketamine Attenuates Learned Fear. *Neuropsychopharmacology: official publication of the American College of Neuropsychopharmacology*.

Meyerhoff D J, Mon A, Metzler T, Neylan T C (2014). Cortical gamma-aminobutyric acid and glutamate in posttraumatic stress disorder and their relationships to self-reported sleep quality. *Sleep* 37(5): 893-900.

Micheli V, Camici M, Tozzi M G, Ipata P L, Sestini S, Bertelli M, et al (2011). Neurological disorders of purine and pyrimidine metabolism. *Current topics in medicinal chemistry* 11(8): 923-947.

Miller D B, O'Callaghan J P (2013). Personalized medicine in major depressive disorder—opportunities and pitfalls. *Metabolism: clinical and experimental* 62 Suppl 1: S34-39.

Murrough J W, Soleimani L, DeWilde K E, Collins K A, Lapidus K A, Iacoviello B M, et al (2015). Ketamine for rapid reduction of suicidal ideation: a randomized controlled trial. *Psychological medicine* 45(16): 3571-3580.

Nelson J C (2012). The evolving story of folate in depression and the therapeutic potential of 1-methylfolate. *The American journal of psychiatry* 169(12): 1223-1225.

Pan L, McKain B W, Madan-Khetarpal S, McGuire M, Diler R S, Perel J M, et al (2011). GTP-cyclohydrolase deficiency responsive to sapropterin and 5-HTP supplementation: relief of treatment-refractory depression and suicidal behaviour. *BMJ case reports* 2011.

Pan L, Vockley J (2013). Neuropsychiatric Symptoms in Inborn Errors of Metabolism: Incorporation of Genomic and Metabolomic Analysis into Therapeutics and Prevention. *Current genetic medicine reports* 1(1): 65-70.

Pan L A, Martin P, Zimmer T, Segreti A M, Kassiff S, McKain B W, et al (2017). Neurometabolic Disorders: Potentially Treatable Abnormalities in Patients With Treatment-Refractory Depression and Suicidal Behavior. *The American journal of psychiatry* 174(1): 42-50.

Pan X, Zeng X, Hong J, Yuan C, Cui L, Ma J, et al (2016). Effects of Ketamine on Metabolomics of Serum and Urine in Cynomolgus Macaques (*Macaca fascicularis*). *Journal of the American Association for Laboratory Animal Science: JAALAS* 55(5): 558-564.

Park D I, Dournes C, Sillaber I, Uhr M, Asara J M, Gassen N C, et al (2016). Purine and pyrimidine metabolism: Convergent evidence on chronic antidepressant treatment response in mice and humans. *Scientific reports* 6: 35317.

Pehrson A L, Sanchez C (2015). Altered gamma-aminobutyric acid neurotransmission in major depressive disorder: a critical review of the supporting evidence and the influence of serotonergic antidepressants. *Drug design, development and therapy* 9: 603-624.

Pekary A E, Sattin A, Lloyd R L (2015). Ketamine modulates TRH and TRH-like peptide turnover in brain and peripheral tissues of male rats. *Peptides* 69: 66-76.

Price R B, Nock M K, Charney D S, Mathew S J (2009). Effects of intravenous ketamine on explicit and implicit measures of suicidality in treatment-resistant depression. *Biological psychiatry* 66(5): 522-526.

Ramaekers V, Sequeira J M, Quadros E V (2013). Clinical recognition and aspects of the cerebral folate deficiency syndromes. *Clinical chemistry and laboratory medicine* 51(3): 497-511.

Redei E E, Mehta N S (2015). The promise of biomarkers in diagnosing major depression in primary care: the present and future. *Current psychiatry reports* 17(8): 601.

Rotroff D M, Corum D G, Motsinger-Reif A, Fiehn O, Bottrel N, Drevets W C, et al (2016). Metabolomic signatures of drug response phenotypes for ketamine and esketamine in subjects with refractory major depressive disorder: new mechanistic insights for rapid acting antidepressants. *Translational psychiatry* 6(9): e894.

Serchov T, Clement H W, Schwarz M K, Iasevoli F, Tosh D K, Idzko M, et al (2015). Increased Signaling via Adenosine A1 Receptors, Sleep Deprivation, Imipramine, and Ketamine Inhibit Depressive-like Behavior via Induction of Homer1a. *Neuron* 87(3): 549-562.

Soumier A, Carter R M, Schoenfeld T J, Cameron H A (2016). New Hippocampal Neurons Mature Rapidly in Response to Ketamine But Are Not Required for Its Acute Antidepressant Effects on Neophagia in Rats. *eNeuro* 3(2).

Van't Veer A, Carlezon W A, Jr. (2013). Role of kappa-opioid receptors in stress and anxiety-related behavior. *Psychopharmacology* 229(3): 435-452.

Wang W, Guo H, Zhang S X, Li J, Cheng K, Bai S J, et al (2016). Targeted Metabolomic Pathway Analysis and Validation Revealed Glutamatergic Disorder in the Prefrontal Cortex among the Chronic Social Defeat Stress Mice Model of Depression. *Journal of proteome research* 15(10): 3784-3792.

Weckmann K, Labermaier C, Asara J M, Muller M B, Turck C W (2014). Time-dependent metabolomic profiling of Ketamine drug action reveals hippocampal pathway alterations and biomarker candidates. *Translational psychiatry* 4: e481.

Wen C, Zhang M, Zhang Y, Sun F, Ma J, Hu L, et al (2016). Brain metabolomics in rats after administration of ketamine. *Biomedical chromatography: BMC* 30(1): 81-84.

Zarate C A, Jr., Brutsche N E, Ibrahim L, Franco-Chaves J, Diazgranados N, Cravchik A, et al (2012). Replication of ketamine's antidepressant efficacy in bipolar depression: a randomized controlled add-on trial. *Biological psychiatry* 71(11): 939-946.

Zarate C A, Jr., Singh J B, Carlson P J, Brutsche N E, Ameli R, Luckenbaugh D A, et al (2006). A randomized trial of an N-methyl-D-aspartate antagonist in treatment-resistant major depression. *Archives of general psychiatry* 63(8): 856-864.

Zheng P, Chen J J, Huang T, Wang M J, Wang Y, Dong M X, et al (2013a). A novel urinary metabolite signature for diagnosing major depressive disorder. *Journal of proteome research* 12(12): 5904-5911.

Zheng P, Fang Z, Xu X J, Liu M L, Du X, Zhang X, et al (2016). Metabolite signature for diagnosing major depressive disorder in peripheral blood mononuclear cells. *Journal of affective disorders* 195: 75-81.

Zheng P, Wang Y, Chen L, Yang D, Meng H, Zhou D, et al (2013b). Identification and validation of urinary metabolite biomarkers for major depressive disorder. *Molecular & cellular proteomics: MCP* 12(1): 207-214.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, and publications are cited throughout this application, the disclosures of which, particularly, including all disclosed chemical structures, are incorporated herein by reference. Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

TABLE 1

| Behavioral Paradigm | Abbrev | Measurement | Comparison | F | ° of freedom | p | * | FIG. |
|---|---|---|---|---|---|---|---|---|
| Contextual Fear Conditioning (3-shock) | CFC D1 | Freezing | Drug | 3.528 | 1.68 | 0.0776 | — | 1B |
| | | | Time | 33.644 | 4.68 | <0.0001 | *** | |
| | | | Drug × Time | 2.275 | 4.68 | 0.0701 | — | |
| | CFC D2 | Freezing | Drug | 5.191 | 1.68 | 0.0359 | * | 1C |
| | | | Time | 27.495 | 4.68 | <0.0001 | *** | |
| | | | Drug × Time | 0.519 | 4.68 | 0.5996 | — | |

TABLE 1-continued

| | | | | | | | | |
|---|---|---|---|---|---|---|---|---|
| Contextual Fear Conditioning (No shock) | CFC D1 | Freezing | Drug | 0.679 | 1.64 | 0.0422 | — | S5B |
| | | | Time | 3.402 | 4.64 | 0.0138 | * | |
| | | | Drug × Time | 1.579 | 4.64 | 0.2621 | — | |
| | CFC D2 | Freezing | Drug | 0.402 | 1.64 | 0.5353 | — | S5C |
| | | | Time | 4.3 | 4.64 | 0.0038 | ** | |
| | | | Drug × Time | 0.528 | 4.64 | 0.7159 | — | |

| Mouse ID | CFC | Drug | Left PFC Weight (g) | Right PFC Weight (g) | Total PFC Weight (g) | Left HPC Weight (g) | Right HPC Weight (g) | Total HPC Weight (g) |
|---|---|---|---|---|---|---|---|---|
| 1 | 3-shock | Sal | 0.0156 | 0.0132 | 0.0288 | 0.0156 | 0.0146 | 0.0302 |
| 2 | 3-shock | Sal | 0.0151 | 0.0160 | 0.0311 | 0.0209 | 0.0190 | 0.0399 |
| 3 | 3-shock | Sal | 0.0200 | 0.0200 | 0.0400 | 0.0107 | 0.0254 | 0.0361 |
| 4 | 3-shock | Sal | 0.0284 | 0.0223 | 0.0507 | 0.0141 | 0.0168 | 0.0309 |
| 5 | 3-shock | Sal | 0.0221 | 0.0210 | 0.0431 | 0.0162 | 0.0191 | 0.0353 |
| 6 | 3-shock | Sal | 0.0122 | 0.0100 | 0.0222 | 0.0160 | 0.0150 | 0.0310 |
| 7 | 3-shock | Sal | 0.0150 | 0.0110 | 0.0260 | 0.0128 | 0.0170 | 0.0298 |
| 8 | 3-shock | Sal | 0.0140 | 0.0134 | 0.0274 | 0.0125 | 0.0145 | 0.0270 |
| 9 | 3-shock | Sal | 0.0140 | 0.0150 | 0.0290 | 0.0157 | 0.0124 | 0.0281 |
| 10 | 3-shock | Sal | 0.0130 | 0.0120 | 0.0250 | 0.0132 | 0.0115 | 0.0247 |
| 11 | 3-shock | K | 0.0195 | 0.0205 | 0.0400 | 0.0150 | 0.0155 | 0.0305 |
| 12 | 3-shock | K | 0.0270 | 0.0272 | 0.0542 | 0.0219 | 0.0207 | 0.0426 |
| 13 | 3-shock | K | 0.0170 | 0.0130 | 0.0300 | 0.0140 | 0.0140 | 0.0280 |
| 14 | 3-shock | K | 0.0248 | 0.0223 | 0.0471 | 0.0155 | 0.0144 | 0.0299 |
| 15 | 3-shock | K | 0.0195 | 0.0174 | 0.0369 | 0.0139 | 0.0123 | 0.0262 |
| 16 | 3-shock | K | 0.0137 | 0.0110 | 0.0247 | 0.0160 | 0.0147 | 0.0307 |
| 17 | 3-shock | K | 0.0130 | 0.0150 | 0.0280 | 0.0124 | 0.0135 | 0.0259 |
| 18 | 3-shock | K | 0.0200 | 0.0200 | 0.0490 | 0.0143 | 0.0130 | 0.0273 |
| 19 | 3-shock | K | 0.0150 | 0.0150 | 0.0300 | 0.0190 | 0.0159 | 0.0349 |
| 20 | No shock | Sal | 0.0150 | 0.0129 | 0.0279 | 0.0155 | 0.0177 | 0.0332 |
| 21 | No shock | K | 0.0183 | 0.0213 | 0.0396 | 0.0137 | 0.0133 | 0.027 |
| 22 | No shock | Sal | 0.0205 | 0.0181 | 0.0386 | 0.0221 | 0.0139 | 0.036 |
| 23 | No shock | Sal | 0.0152 | 0.0146 | 0.0298 | 0.017 | 0.0138 | 0.0308 |
| 24 | No shock | Sal | 0.0208 | 0.0200 | 0.0408 | 0.019 | 0.017 | 0.036 |
| 25 | No shock | K | 0.0180 | 0.0238 | 0.0418 | 0.019 | 0.015 | 0.034 |
| 26 | No shock | K | 0.0166 | 0.0183 | 0.0349 | 0.0178 | 0.015 | 0.0328 |
| 27 | No shock | K | 0.0250 | 0.0193 | 0.0443 | 0.01 | 0.0133 | 0.0233 |
| 28 | No shock | Sal | 0.0197 | 0.0238 | 0.0435 | 0.0144 | 0.0153 | 0.0297 |
| 29 | No shock | Sal | 0.0278 | 0.0227 | 0.0595 | 0.0176 | 0.017 | 0.0346 |
| 30 | No shock | Sal | 0.0190 | 0.0242 | 0.0432 | 0.0159 | 0.0134 | 0.0293 |
| 31 | Ng shock | Sal | 0.0200 | 0.0219 | 0.0419 | 0.0158 | 0.0132 | 0.029 |
| 32 | No shock | Sal | 0.0143 | 0.0161 | 0.0304 | 0.0157 | 0.0142 | 0.0299 |
| 33 | No shock | K | 0.0236 | 0.0213 | 0.0449 | 0.0175 | 0.0157 | 0.0332 |
| 34 | No shock | K | 0.0136 | 0.0168 | 0.0394 | 0.0148 | 0.0123 | 0.0271 |
| 35 | No shock | K | 0.0211 | 0.0167 | 0.0378 | 0.0145 | 0.0137 | 0.0282 |
| 36 | No shock | K | 0.0137 | 0.0150 | 0.0287 | 0.0157 | 0.0102 | 0.0259 |
| 37 | No shock | K | 0.1690 | 0.0166 | 0.1856 | 0.0183 | 0.0122 | 0.0305 |

Stressed Mice

| Region | Mode | Metabolite | Left PFC p value | Right PFC p value |
|---|---|---|---|---|
| PFC | Positive | 1-Methylhistidine | 0.0004 | 0.0032 |
| | | 11-Hydroxyandrosterone | 0.0387 | 0.6853 |
| | | 13-HOTE | 0.0021 | 0.2243 |
| | | 19-Norandrosterone | 0.0377 | 0.3451 |
| | | 2-Hexenoylcarnitine | 0.9272 | 0.3088 |
| | | 2-Methoxyestradiol | 0.2216 | 0.4853 |
| | | 3--5-Tetradecadiencarnitine | 0.9217 | 0.0457 |
| | | 3-5-Diiodothyronine | 0.5416 | 0.1165 |
| | | 3-Aminoisobutanoic-acid | 0.0000 | 0.0000 |
| | | 3-Methylcrotonylglycine | 0.0212 | 0.0007 |
| | | 3-Methylhistidine | 0.0023 | 0.0091 |
| | | 3-Methyluridine | 0.1794 | 0.2124 |
| | | 5--Methylthioadenosine | 0.0084 | 0.1503 |
| | | 5-6-Dihydrouridine | 0.6656 | 0.0929 |
| | | 5-Methylcytidine | 0.6431 | 0.3072 |
| | | 8-Hydroxyguanine | 0.1223 | 0.0251 |
| | | 9-12-Hexadecadienoylcarnitine | 0.2105 | 0.0618 |
| | | 9-Decenoylcarnitine | 0.4361 | 0.4361 |
| | | Acetoacetic-acid | 0.0000 | 0.0038 |
| | | Adenosine-triphosphate | 0.0291 | 0.1557 |
| | | Alanyl-Proline | 0.0025 | 0.0180 |
| | | Aminoadipic-acid | 0.4701 | 0.5719 |
| | | Argininosuccinic-acid | 0.0274 | 0.0424 |
| | | Asymmetric-dimethylarginine | 0.0050 | 0.0363 |
| | | Carnosine | 0.0406 | 0.0337 |

TABLE 1-continued

|  | | | |
|---|---|---|---|
|  | Citrulline | 0.0019 | 0.0050 |
|  | Cyclic-AMP | 0.3953 | 0.4846 |
|  | Cystathionine-ketimine | 0.0310 | 0.2109 |
|  | Cytidine | 0.6916 | 0.6714 |
|  | D-Serine | 0.0011 | 0.0092 |
|  | D-Tryptophan | 0.0056 | 0.0129 |
|  | Deoxycytidine | 0.0165 | 0.0477 |
|  | Deoxyuridine | 0.0017 | 0.5072 |
|  | Dihydrothymine | 0.0054 | 0.0095 |
|  | Dodecanoylcarnitine | 0.1678 | 0.0547 |
|  | dUDP | 0.0002 | 0.0003 |
|  | Erythronic-acid | 0.0096 | 0.0077 |
|  | Estradiol | 0.0027 | 0.1554 |
|  | Glucosylgalactosyl-hydroxylysine | 0.0050 | 0.0123 |
|  | Glycine | 0.0136 | 0.0061 |
|  | Glycylproline | 0.0028 | 0.0100 |
|  | Guanosine-diphosphate | 0.6691 | 0.3997 |
|  | Guanosine-monophosphate | 0.3745 | 0.0330 |
|  | Guanosine-triphosphate | 0.0433 | 0.0544 |
|  | Hexanoylcarnitine | 0.6060 | 0.0104 |
|  | Homo-L-arginine | 0.0485 | 0.0871 |
|  | Homocarnosine | 0.0069 | 0.0309 |
|  | Hypoxanthine | 0.0188 | 0.0096 |
|  | IMP | 0.0031 | 0.0218 |
|  | Inosine | 0.0127 | 0.0086 |
|  | Isobutyryl-L-carnitine | 0.1272 | 0.0332 |
|  | Isoleucine | 0.0027 | 0.0105 |
|  | Isovalerylcarnitine | 0.5210 | 0.2595 |
|  | Isovalerylglucuronide | 0.0302 | 0.0336 |
|  | Ketoprofen-glucuronide | 0.0018 | 0.0019 |
|  | L-Allothreonine | 0.0023 | 0.0024 |
|  | L-Cystathionine | 0.2210 | 0.6509 |
|  | L-Cysteinylglycine-disulfide | 0.0001 | 0.0010 |
|  | L-Homoserine | 0.0021 | 0.0289 |
|  | L-Octanoylcarnitine | 0.5390 | 0.0150 |
|  | L-Tyrosine | 0.0022 | 0.0059 |
|  | Leucine | 0.0000 | 0.0046 |
|  | Malonylcarnitine | 0.0091 | 0.2928 |
|  | MET-ENKEPHELIN | 0.1336 | 0.0035 |
|  | methionine | 0.0153 | 0.0830 |
|  | N--Phosphoguanidinoethyl methyl phosphate | 0.2092 | 0.1060 |
|  | N-Acetyl-L-methionine | 0.0325 | 0.0206 |
|  | N-Acetylcystathionine | 0.0758 | 0.0198 |
|  | N-Acetylglutamine | 0.0154 | 0.1573 |
|  | N-Acetylneuraminic-acid | 0.0045 | 0.2486 |
|  | N-acetyltryptophan | 0.0206 | 0.1415 |
|  | N-Acetylvanilalanine | 0.1695 | 0.1871 |
|  | N-Formyl-L-methionine | 0.7312 | 0.0085 |
|  | N4-Acetylaminobutanal | 0.0045 | 0.0518 |
|  | NAD | 0.2233 | 0.0431 |
|  | NAD+ | 0.2640 | 0.0482 |
|  | NADH | 0.0171 | 0.0150 |
|  | Nicotinamide | 0.0018 | 0.0597 |
|  | Nonanoylcarnitine | 0.0013 | 0.0198 |
|  | p-Cresol-glucuronide | 0.1964 | 0.1862 |
|  | Phenylalanine | 0.0064 | 0.0337 |
|  | Phenylpyruvic-acid | 0.0011 | 0.0031 |
|  | Pipecolic-acid | 0.0143 | 0.0630 |
|  | Progesterone | 0.1866 | 0.6845 |
|  | Proline-betaine | 0.1691 | 0.4450 |
|  | Prolylhydroxyproline | 0.0577 | 0.0509 |
|  | S-adenosyl-L-homoCysteine | 0.0246 | 0.1132 |
|  | S-Adenosylmethionine | 0.1136 | 0.0061 |
|  | Suberylglycine | 0.1818 | 0.1991 |
|  | Succinyladenosine | 0.0941 | 0.0405 |
|  | Taurocholic-acid | 0.0033 | 0.0510 |
|  | Taurodeoxycholic-acid | 0.0000 | 0.0006 |
|  | Testosterone | 0.0698 | 0.0089 |
|  | Thiamine-monophosphate | 0.0128 | 0.0223 |
|  | Thyroxine | 0.1623 | 0.1869 |
|  | trans-2-Dodecenoylcarnitine | 0.4636 | 0.0027 |
|  | Trimethylamine-N-oxide | 0.4867 | 0.3878 |
|  | Uracil | 0.0840 | 0.0423 |
|  | Urolithin-C | 0.0410 | 0.7105 |
|  | Xanthine | 0.0392 | 0.0515 |
|  | Xanthurenic-acid | 0.6185 | 0.0141 |
| Negative | (S)-Lactaldehyde | 0.0553 | 0.0019 |
|  | 11b-Hydroxyprogesterone | 0.0083 | 0.3228 |
|  | 12-13-DHOME | 0.0068 | 0.4807 |
|  | 1-Methylxanthine | 0.6021 | 0.0000 |

TABLE 1-continued

| | | |
|---|---|---|
| 2-Arachidonylglycerol | 0.0127 | 0.3843 |
| 2-Hexenoylcarnitine | 0.0308 | 0.5644 |
| 2-Hydroxyadipic-acid | 0.2927 | 0.0028 |
| 2-Phenylpropionate | 0.0569 | 0.6244 |
| 3-Chlorotyrosine | 0.0009 | 0.2610 |
| 3-Dehydrocarnitine | 0.0834 | 0.9597 |
| 3-Hydroxydodecanoic-acid | 0.0022 | 0.6950 |
| 3-Hydroxytetradecanedioic-acid | 0.0037 | 0.9384 |
| 3-Sulfinoalanine | 0.5418 | 0.6465 |
| 5-6-Dihydrouridine | 0.6066 | 0.0001 |
| 5-Methylcytidine | 0.1470 | 0.0123 |
| 5-Tetradecenoic-acid | 0.0467 | 0.8897 |
| 6-Hydroxydaidzein | 0.0013 | 0.7263 |
| Adenine | 0.3341 | 0.0044 |
| Adenosine | 0.3086 | 0.0045 |
| Adenosine-monophosphate | 0.0318 | 0.0011 |
| Adenosine-triphosphate | 0.0142 | 0.0164 |
| ADP | 0.5191 | 0.0143 |
| ADP-Glucose | 0.8177 | 0.0002 |
| Aminoadipic-acid | 0.1931 | 0.0000 |
| Butyrylcarnitine | 0.0027 | 0.8076 |
| CDP | 0.7795 | 0.0271 |
| Cyclic-AMP | 0.7048 | 0.0044 |
| Cytidine | 0.1892 | 0.0205 |
| Cytidine-monophosphate | 0.9227 | 0.0051 |
| Cytosine | 0.2507 | 0.0030 |
| D-Alanine | 0.0178 | 0.0000 |
| Dihydrothymine | 0.0200 | 0.0001 |
| Dihydroxyacetone-phosphate | 0.4940 | 0.0052 |
| D-Lysine | 0.6999 | 0.0077 |
| Dodecanedioic-acid | 0.0021 | 0.9179 |
| Dodecanoic-acid | 0.0447 | 0.8702 |
| D-Serine | 0.1125 | 0.0000 |
| D-Tryptophan | 0.0220 | 0.2810 |
| Enkephalin-L | 0.1345 | 0.0007 |
| FAD | 0.3991 | 0.0503 |
| Fructose-1-6-bisphosphate | 0.1661 | 0.0415 |
| Gamma-Aminobutyric-acid | 0.5252 | 0.0000 |
| Gamma-Glutamyl-Glutamine | 0.0651 | 0.3903 |
| Glucosamine-phosphate | 0.0037 | 0.0044 |
| glutathione | 0.4697 | 0.0422 |
| Glyceric-acid | 0.6690 | 0.0000 |
| Glycerol-3-phosphate | 0.4140 | 0.0071 |
| GMP | 0.2672 | 0.0225 |
| Guanosine-diphosphate | 0.0445 | 0.0004 |
| Guanosine-triphosphate | 0.0194 | 0.0041 |
| Hexanoylcarnitine | 0.0339 | 0.8636 |
| Homocarnosine | 0.8750 | 0.0000 |
| Homocitrulline | 0.0019 | 0.3921 |
| Hydroxyhexanoycarnitine | 0.0037 | 0.2976 |
| Hydroxyoctanoic-acid | 0.0048 | 0.6490 |
| Hydroxypyruvic-acid | 0.0214 | 0.0003 |
| IMP | 0.0168 | 0.6032 |
| Inosine | 0.0416 | 0.4426 |
| Isovaleric-acid | 0.5087 | 0.0045 |
| L-2-Hydroxyglutaric-acid | 0.3218 | 0.0096 |
| L-3-Phenyllactic-acid | 0.8600 | 0.0032 |
| L-Acetylcarnitine | 0.0060 | 0.7490 |
| L-Carnitine | 0.2011 | 0.0038 |
| L-Glutamic-acid | 0.3732 | 0.0000 |
| Linoleic-acid | 0.0115 | 0.5766 |
| L-Lactic-acid | 0.0348 | 0.0081 |
| L-Malic-acid | 0.0373 | 0.3364 |
| L-Tyrosine | 0.0077 | 0.7414 |
| Malonate | 0.0214 | 0.0003 |
| Methionine | 0.2286 | 0.0330 |
| Methylmalonic-acid | 0.0426 | 0.0032 |
| N-Acetylglutamine | 0.0694 | 0.6250 |
| NAD+ | 0.0739 | 0.0043 |
| NADH | 0.0125 | 0.0021 |
| N-Formyl-L-methionine | 0.0092 | 0.0496 |
| Nicotinamide-ribotide | 0.1333 | 0.0083 |
| Octulose-phosphate | 0.0093 | 0.0043 |
| Oleic-acid | 0.0317 | 0.1234 |
| O-Phosphoethanolamine | 0.3872 | 0.0000 |
| Oxidized-glutathione | 0.1284 | 0.0001 |
| Oxoadipic-acid | 0.0041 | 0.1049 |
| Oxoglutaric-acid | 0.0274 | 0.0001 |
| Palmitic-acid | 0.0261 | 0.5972 |
| Palmitoleic-acid | 0.0024 | 0.6231 |

TABLE 1-continued

|  |  | Metabolite | | |
| --- | --- | --- | --- | --- |
|  |  | p-Cresol-sulfate | 0.0018 | 0.4236 |
|  |  | Phenylalanine | 0.1502 | 0.0007 |
|  |  | Phenylpropionylglycine | 0.0071 | 0.3014 |
|  |  | Phosphoenolpyruvic-acid | 0.0404 | 0.1528 |
|  |  | Propionylcarnitine | 0.0018 | 0.2549 |
|  |  | Propionylglycine | 0.2466 | 0.0000 |
|  |  | Ribothymidine | 0.0000 | 0.1674 |
|  |  | Sarcosine | 0.1092 | 0.0251 |
|  |  | Sphingosine-1-phosphate | 0.9527 | 0.0042 |
|  |  | Stearic-acid | 0.0727 | 0.2743 |
|  |  | Taurine | 0.8738 | 0.0000 |
|  |  | Testosterone-sulfate | 0.0009 | 0.9284 |
|  |  | Tetradecanedioic-acid | 0.0035 | 0.7318 |
|  |  | Thiamine-pyrophosphate | 0.2380 | 0.0001 |
|  |  | Thymine | 0.0016 | 0.0733 |
|  |  | Uracil | 0.2300 | 0.5986 |
|  |  | Uric-acid | 0.5679 | 0.0024 |
|  |  | Uridine | 0.1539 | 0.0332 |
|  |  | Uridine-diphosphate-glucose | 0.3417 | 0.0100 |
|  |  | Uridine-diphosphate-N-acetylglucosamine | 0.0536 | 0.0170 |
|  |  | Uridine-triphosphate | 0.0085 | 0.0202 |
|  |  | Urolithin-C | 0.0011 | 0.2275 |
|  |  | Valeric-acid | 0.2847 | 0.0003 |
|  |  | Valerylcarnitine | 0.0133 | 0.9297 |
|  |  | Xanthine | 0.0661 | 0.6403 |
|  |  | Xanthosine-5-phosphate | 0.3232 | 0.0042 |

| Region | Mode | Metabolite | Left HPC p value | Right HPC p value |
| --- | --- | --- | --- | --- |
| HPC | Positive | 1-Methylhistidine | 0.0416 | 0.1744 |
|  |  | 11-Hydroxyandrosterone | 0.5556 | 0.5952 |
|  |  | 13-HOTE | 0.0421 | 0.0242 |
|  |  | 19-Norandrosterone | 0.8228 | 0.6511 |
|  |  | 2-Hexenoylcarnitine | 0.6606 | 0.9663 |
|  |  | 2-Methoxyestradiol | 0.4757 | 0.9931 |
|  |  | 3--5-Tetradecadiencarnitine | 0.0588 | 0.1658 |
|  |  | 3-5-Diiodothyronine | 0.3726 | 0.6775 |
|  |  | 3-Aminoisobutanoic-acid | 0.0345 | 0.0605 |
|  |  | 3-Methylcrotonylglycine | 0.0648 | 0.7030 |
|  |  | 3-Methylhistidine | 0.0127 | 0.0598 |
|  |  | 3-Methyluridine | 0.2461 | 0.8378 |
|  |  | 5--Methylthioadenosine | 0.6837 | 0.0074 |
|  |  | 5-6-Dihydrouridine | 0.0022 | 0.0030 |
|  |  | 5-Methylcytidine | 0.0540 | 0.3678 |
|  |  | 8-Hydroxyguanine | 0.0152 | 0.0405 |
|  |  | 9-12-Hexadecadienoylcarnitine | 0.0984 | 0.7821 |
|  |  | 9-Decenoylcarnitine | 0.0880 | 0.1751 |
|  |  | Acetoacetic-acid | 0.7095 | 0.8305 |
|  |  | Adenosine-triphosphate | 0.0704 | 0.1266 |
|  |  | Alanyl-Proline | 0.0296 | 0.1327 |
|  |  | Aminoadipic-acid | 0.0690 | 0.2016 |
|  |  | Argininosuccinic-acid | 0.3259 | 0.4922 |
|  |  | Asymmetric-dimethylarginine | 0.8378 | 0.6567 |
|  |  | Carnosine | 0.6346 | 0.8656 |
|  |  | Citrulline | 0.1826 | 0.5655 |
|  |  | Cyclic-AMP | 0.0875 | 0.1405 |
|  |  | Cystathionine-ketimine | 0.0443 | 0.8138 |
|  |  | Cytidine | 0.1426 | 0.2717 |
|  |  | D-Serine | 0.1869 | 0.8959 |
|  |  | D-Tryptophan | 0.2462 | 0.4534 |
|  |  | Deoxycytidine | 0.4804 | 0.3590 |
|  |  | Deoxyuridine | 0.2250 | 0.6074 |
|  |  | Dihydrothymine | 0.0808 | 0.1165 |
|  |  | Dodecanoylcarnitine | 0.4180 | 0.8433 |
|  |  | dUDP | 0.0029 | 0.0051 |
|  |  | Erythronic-acid | 0.0185 | 0.1153 |
|  |  | Estradiol | 0.4064 | 0.9947 |
|  |  | Glucosylgalactosyl-hydroxylysine | 0.2679 | 0.1711 |
|  |  | Glycine | 0.2668 | 0.8485 |
|  |  | Glycylproline | 0.0892 | 0.2478 |
|  |  | Guanosine-diphosphate | 0.0363 | 0.0685 |
|  |  | Guanosine-monophosphate | 0.6696 | 0.2641 |
|  |  | Guanosine-triphosphate | 0.0319 | 0.0736 |
|  |  | Hexanoylcarnitine | 0.0342 | 0.0942 |
|  |  | Homo-L-arginine | 0.1317 | 0.4405 |
|  |  | Homocarnosine | 0.9057 | 0.3667 |
|  |  | Hypoxanthine | 0.0287 | 0.1542 |
|  |  | IMP | 0.0134 | 0.0204 |
|  |  | Inosine | 0.0146 | 0.0621 |

TABLE 1-continued

|  | | | |
|---|---|---|---|
|  | Isobutyryl-L-carnitine | 0.1058 | 0.0577 |
|  | Isoleucine | 0.1750 | 0.4787 |
|  | Isovalerylcarnitine | 0.1611 | 0.3156 |
|  | Isovalerylglucuronide | 0.2864 | 0.8821 |
|  | Ketoprofen-glucuronide | 0.0010 | 0.0564 |
|  | L-Allothreonine | 0.1602 | 0.8601 |
|  | L-Cystathionine | 0.0878 | 0.0344 |
|  | L-Cysteinylglycine-disulfide | 0.3245 | 0.4862 |
|  | L-Homoserine | 0.8507 | 0.1369 |
|  | L-Octanoylcarnitine | 0.0014 | 0.0234 |
|  | L-Tyrosine | 0.0522 | 0.2079 |
|  | Leucine | 0.1488 | 0.2082 |
|  | Malonylcarnitine | 0.9241 | 0.8249 |
|  | MET-ENKEPHELIN | 0.0795 | 0.7499 |
|  | Methionine | 0.7775 | 0.8700 |
|  | N--Phosphoguanidinoethyl methyl phosphate | 0.2701 | 0.4484 |
|  | N-Acetyl-L-methionine | 0.3115 | 0.9274 |
|  | N-Acetylcystathionine | 0.2693 | 0.1513 |
|  | N-Acetylglutamine | 0.5036 | 0.9774 |
|  | N-Acetylneuraminic-acid | 0.6110 | 0.5381 |
|  | N-acetyltryptophan | 0.0594 | 0.1616 |
|  | N-Acetylvanilalanine | 0.3890 | 0.4706 |
|  | N-Formyl-L-methionine | 0.0885 | 0.7685 |
|  | N4-Acetylaminobutanal | 0.6462 | 0.6132 |
|  | NAD | 0.0278 | 0.0430 |
|  | NAD+ | 0.0301 | 0.0461 |
|  | NADH | 0.0075 | 0.0877 |
|  | Nicotinamide | 0.0743 | 0.0159 |
|  | Nonanylcarnitine | 0.1313 | 0.0383 |
|  | p-Cresol-glucuronide | 0.6377 | 0.8879 |
|  | Phenylalanine | 0.7497 | 0.8954 |
|  | Phenylpyruvic-acid | 0.0685 | 0.2399 |
|  | Pipecolic-acid | 0.9596 | 0.7845 |
|  | Progesterone | 0.2279 | 0.3776 |
|  | Proline-betaine | 0.2189 | 0.4441 |
|  | Prolylhydroxyproline | 0.2644 | 0.6170 |
|  | S-adenosyl-L-homoCysteine | 0.2590 | 0.5549 |
|  | S-Adenosylmethionine | 0.1013 | 0.0063 |
|  | Suberylglycine | 0.8441 | 0.1883 |
|  | Succinyladenosine | 0.1831 | 0.4121 |
|  | Taurocholic-acid | 0.7990 | 0.7520 |
|  | Taurodeoxycholic-acid | 0.5248 | 0.1932 |
|  | Testosterone | 0.0018 | 0.0128 |
|  | Thiamine-monophosphate | 0.0608 | 0.0215 |
|  | Thyroxine | 0.5634 | 0.4695 |
|  | trans-2-Dodecenoylcarnitine | 0.0218 | 0.1847 |
|  | Trimethylamine-N-oxide | 0.4533 | 0.0275 |
|  | Uracil | 0.0917 | 0.4630 |
|  | Urolithin-C | 0.5196 | 0.2006 |
|  | Xanthine | 0.0628 | 0.3702 |
|  | Xanthurenic-acid | 0.3880 | 0.9391 |
| Negative | (S)-Lactaldehyde | 0.0064 | 0.0042 |
|  | 11b-Hydroxyprogesterone | 0.3488 | 0.5851 |
|  | 12-13-DHOME | 0.4395 | 0.0008 |
|  | 1-Methylxanthine | 0.3016 | 0.2375 |
|  | 2-Arachidonylglycerol | 0.2195 | 0.0671 |
|  | 2-Hexenoylcarnitine | 0.2634 | 0.0004 |
|  | 2-Hydroxyadipic-acid | 0.8925 | 0.0000 |
|  | 2-Phenylpropionate | 0.7219 | 0.3278 |
|  | 3-Chlorotyrosine | 0.7517 | 0.0182 |
|  | 3-Dehydrocarnitine | 0.6270 | 0.0066 |
|  | 3-Hydroxydodecanoic-acid | 0.7606 | 0.0327 |
|  | 3-Hydroxytetradecanedioic-acid | 0.2857 | 0.0021 |
|  | 3-Sulfinoalanine | 0.0589 | 0.0003 |
|  | 5-6-Dihydrouridine | 0.1574 | 0.0085 |
|  | 5-Methylcytidine | 0.0284 | 0.1033 |
|  | 5-Tetradecenoic-acid | 0.1464 | 0.3673 |
|  | 6-Hydroxydaidzein | 0.9145 | 0.0097 |
|  | Adenine | 0.0130 | 0.0550 |
|  | Adenosine | 0.0128 | 0.0612 |
|  | Adenosine-monophosphate | 0.0150 | 0.0258 |
|  | Adenosine-triphosphate | 0.0747 | 0.0670 |
|  | ADP | 0.0247 | 0.0051 |
|  | ADP-Glucose | 0.2876 | 0.0094 |
|  | Aminoadipic-acid | 0.1148 | 0.0009 |
|  | Butyrylcarnitine | 0.4150 | 0.0148 |
|  | CDP | 0.0327 | 0.0073 |
|  | Cyclic-AMP | 0.0554 | 0.0227 |
|  | Cytidine | 0.0969 | 0.0899 |
|  | Cytidine-monophosphate | 0.7747 | 0.1819 |

TABLE 1-continued

| | | |
|---|---|---|
| Cytosine | 0.0670 | 0.0331 |
| D-Alanine | 0.0025 | 0.0000 |
| Dihydrothymine | 0.4422 | 0.0076 |
| Dihydroxyacetone-phosphate | 0.3423 | 0.0431 |
| D-Lysine | 0.1333 | 0.0004 |
| Dodecanedioic-acid | 0.3113 | 0.0040 |
| Dodecanoic-acid | 0.4542 | 0.9220 |
| D-Serine | 0.2479 | 0.0008 |
| D-Tryptophan | 0.4039 | 0.1403 |
| Enkephalin-L | 0.0776 | 0.0319 |
| FAD | 0.6285 | 0.0449 |
| Fructose-1-6-bisphosphate | 0.5368 | 0.1262 |
| Gamma-Aminobutyric-acid | 0.0042 | 0.0001 |
| Gamma-Glutamyl-Glutamine | 0.1732 | 0.3545 |
| Glucosamine-phosphate | 0.9447 | 0.0011 |
| glutathione | 0.4302 | 0.2151 |
| Glyceric-acid | 0.9877 | 0.0015 |
| Glycerol-3-phosphate | 0.0328 | 0.0855 |
| GMP | 0.5653 | 0.2310 |
| Guanosine-diphosphate | 0.0169 | 0.0099 |
| Guanosine-triphosphate | 0.0475 | 0.0131 |
| Hexanoylcarnitine | 0.7981 | 0.0055 |
| Homocarnosine | 0.2542 | 0.2154 |
| Homocitrulline | 0.0975 | 0.0036 |
| Hydroxyhexanoycarnitine | 0.5054 | 0.9992 |
| Hydroxyoctanoic-acid | 0.1974 | 0.0429 |
| Hydroxypyruvic-acid | 0.8104 | 0.0068 |
| IMP | 0.0172 | 0.1582 |
| Inosine | 0.0899 | 0.9878 |
| Isovaleric-acid | 0.2710 | 0.2508 |
| L-2-Hydroxyglutaric-acid | 0.0346 | 0.0060 |
| L-3-Phenyllactic-acid | 0.2768 | 0.0227 |
| L-Acetylcarnitine | 0.4143 | 0.5135 |
| L-Carnitine | 0.4812 | 0.1800 |
| L-Glutamic-acid | 0.0100 | 0.0001 |
| Linoleic-acid | 0.1818 | 0.8592 |
| L-Lactic-acid | 0.1026 | 0.0003 |
| L-Malic-acid | 0.6960 | 0.0005 |
| L-Tyrosine | 0.0993 | 0.5132 |
| Malonate | 0.8104 | 0.0068 |
| Methionine | 0.8526 | 0.0036 |
| Methylmalonic-acid | 0.0070 | 0.0051 |
| N-Acetylglutamine | 0.1734 | 0.0489 |
| NAD+ | 0.0360 | 0.0356 |
| NADH | 0.0092 | 0.0830 |
| N-Formyl-L-methionine | 0.4225 | 0.0019 |
| Nicotinamide-ribotide | 0.3209 | 0.0089 |
| Octulose-phosphate | 0.0722 | 0.0685 |
| Oleic-acid | 0.3155 | 0.0284 |
| O-Phosphoethanolamine | 0.0097 | 0.0043 |
| Oxidized-glutathione | 0.1527 | 0.0094 |
| Oxoadipic-acid | 0.7109 | 0.0104 |
| Oxoglutaric-acid | 0.4281 | 0.0126 |
| Palmitic-acid | 0.2218 | 0.0018 |
| Palmitoleic-acid | 0.2921 | 0.9979 |
| p-Cresol-sulfate | 0.6283 | 0.1339 |
| Phenylalanine | 0.9799 | 0.0041 |
| Phenylpropionylglycine | 0.5040 | 0.0057 |
| Phosphoenolpyruvic-acid | 0.0974 | 0.0335 |
| Propionylcarnitine | 0.4493 | 0.0091 |
| Propionylglycine | 0.2793 | 0.0001 |
| Ribothymidine | 0.0099 | 0.9998 |
| Sarcosine | 0.4234 | 0.0000 |
| Sphingosine-1-phosphate | 0.4054 | 0.0005 |
| Stearic-acid | 0.0657 | 0.0000 |
| Taurine | 0.0022 | 0.0000 |
| Testosterone-sulfate | 0.2940 | 0.0078 |
| Tetradecanedioic-acid | 0.1047 | 0.0024 |
| Thiamine-pyrophosphate | 0.2377 | 0.0688 |
| Thymine | 0.4149 | 0.9098 |
| Uracil | 0.2814 | 0.5391 |
| Uric-acid | 0.5572 | 0.0086 |
| Uridine | 0.7700 | 0.1794 |
| Uridine-diphosphate-glucose | 0.0561 | 0.0606 |
| Uridine-diphosphate-N-acetylglucosamine | 0.2481 | 0.3630 |
| Uridine-triphosphate | 0.1983 | 0.1072 |
| Urolithin-C | 0.8878 | 0.0469 |
| Valeric-acid | 0.1203 | 0.0099 |
| Valerylcarnitine | 0.2109 | 0.0014 |
| Xanthine | 0.0667 | 0.8798 |

TABLE 1-continued

| Region | Mode | Metabolite | | p value | |
|---|---|---|---|---|---|
| | | Xanthosine-5-phosphate | | 0.0218 | 0.0671 |
| Plasma | N/A | (R)-lipoic acid | | 0.0298 | — |
| | | 2-Methylcitric acid | | 0.0003 | — |
| | | 3-Methyluridine | | 0.0043 | — |
| | | 3-Phosphoglyceric acid | | 0.0001 | — |
| | | 4-Methylcatechol | | 0.0002 | — |
| | | 5-6-Dihydrouridine | | 0.0083 | — |
| | | 5-Hydroxy-L-tryptophan | | 0.0086 | — |
| | | Adenine | | 0.0031 | — |
| | | Adenosine monophosphate | | 0.0057 | — |
| | | Adenosine triphosphate | | 0.0103 | — |
| | | Allantoin | | 0.0301 | — |
| | | Argininic acid | | 0.0470 | — |
| | | Cysteineglutathione disulfide | | 0.0041 | — |
| | | Cytidine monophosphate | | 0.0007 | — |
| | | D-Aspartic acid | | 0.0032 | — |
| | | Dihydrothymine | | 0.0058 | — |
| | | DL-2-Aminooctanoic acid | | 0.0003 | — |
| | | D-Ribose 5-phosphate | | 0.0004 | — |
| | | D-Ribulose 5-phosphate | | 0.0005 | — |
| | | D-Serine | | 0.0178 | — |
| | | Erythronic acid | | 0.0469 | — |
| | | Gamma-Aminobutryic acid | | 0.0194 | — |
| | | Glycerol 3-phosphate | | 0.0213 | — |
| | | Guanosine diphosphate | | 0.0236 | — |
| | | Guanosine monophosphate | | 0.0103 | — |
| | | Homocarnosine | | 0.0072 | — |
| | | Hypotaurine | | 0.0527 | — |
| | | Hypoxanthine | | 0.0545 | — |
| | | Inosine | | 0.0511 | — |
| | | L-Cystathionine | | 0.0044 | — |
| | | L-Glutamic acid | | 0.0223 | — |
| | | L-Malic acid | | 0.0005 | — |
| | | Malonylcarnitine | | 0.0020 | — |
| | | Methylmalonylcarnitine | | 0.0045 | — |
| | | N-Acetylglutamic acid | | 0.0084 | — |
| | | N-Acetyl-L-tyrosine | | 0.0438 | — |
| | | N-Acetylneuraminic acid | | 0.0399 | — |
| | | Nicotinamide N-oxide | | 0.0084 | — |
| | | Octulose phosphate | | 0.0275 | — |
| | | O-Phosphoethanolamine | | 0.9012 | — |
| | | Oxidized glutathione | | 0.0260 | — |
| | | Pantothenate | | 0.0539 | — |
| | | Phenylpyruvic acid | | 0.0107 | — |
| | | Phosphoenolpyruvic acid | | 0.0390 | — |
| | | Phosphoribosyl pyrophosphate | | 0.0008 | — |
| | | S-Adenosylmethionine | | 0.0476 | — |
| | | Thiamine pyrophosphate | | 0.0039 | — |
| | | Threonic acid | | 0.0206 | — |
| | | trans-Aconitic acid | | 0.0081 | — |
| | | Tryptophanamide | | 0.0002 | — |
| | | Uridine 5--diphosphate | | 0.0002 | — |
| | | Uridine 5--monophosphate | | 0.0010 | — |
| | | Uridine diphosphate glucose | | 0.0017 | — |

Non-Stressed Mice

| Region | Purine or Pyrimidine | Metabolite | Left PFC p value | Right PFC p value |
|---|---|---|---|---|
| PFC | Purines | Adenosine monophosphate | 0.2928 | 0.4380 |
| | | Adenosine triphosphate | 0.6485 | 0.5829 |
| | | Guanosine diphosphate | 0.8918 | 0.3221 |
| | | Guanosine triphosphate | 0.0500 | 0.0689 |
| | | Hypoxanthine | 0.0339 | 0.9303 |
| | | Inosine | 0.0458 | 0.6518 |
| | | Inosine monophosphate | 0.4642 | 0.1102 |
| | Pyrimidines | dUDP | 0.4351 | 0.0853 |
| | | 3-Aminoisobutanoic acid | 0.0029 | 0.2381 |
| | | Dihydrothymine | 0.7843 | 0.7012 |
| | | Deoxycytidine | 0.9995 | 0.2264 |
| | | Uridine triphosphate | 0.6823 | 0.1330 |

TABLE 1-continued

| Region | Purine or Pyrimidine | Metabolite | Left HPC p value | Right HPC p value |
|---|---|---|---|---|
| HPC | Purines | Adenosine-diphosphate | 0.2328 | 0.9157 |
|  |  | Adenosine-monophosphate | 0.9061 | 0.6704 |
|  |  | Guanosine-diphosphate | 0.9460 | 0.2914 |
|  |  | Guanosine-triphosphate | 0.2320 | 0.1292 |
|  |  | Inosine-monophosphate | 0.9894 | 0.0222 |
|  | Pyrimidines | Deoxyurbine-diphosphate | 0.7517 | 0.0049 |
|  |  | 5-6-Dihydrouridine | 0.4247 | 0.4329 |
|  |  | Cytidine-diphosphate | 0.5557 | 0.4807 |

| Region | Purine or Pyrimidine | Metabolite | p value |  |
|---|---|---|---|---|
| Plasma | Purines | Adenine | 0.5871 | — |
|  |  | Adenosine monophosphate | 0.8697 | — |
|  |  | Adenosine triphosphate | 0.7528 | — |
|  |  | D-Ribose-5-phosphate | 0.6598 | — |
|  |  | D-Ribulose-5-phosphate | 0.1537 | — |
|  |  | Guanosine monophosphate | 0.2434 | — |
|  |  | Guanosine diphosphate | 0.4332 | — |
|  |  | Hypoxanthine | 0.4893 | — |
|  |  | Inosine | 0.1620 | — |
|  |  | Phosphoribosyl pyrophosphate | 0.1417 | — |
|  | Pyrimidines | 5-6-Dihydrouridine | 0.6810 | — |
|  |  | Cytidine monophosphate | 0.8047 | — |
|  |  | Dihydrothymine | 0.4706 | — |
|  |  | Uridine 5'-monophosphate | 0.1285 | — |
|  |  | Uridine 5'-diphosphate | 0.3336 | — |

TABLE 2

| Common Name | Abbreviation | Class |
|---|---|---|
| Adenosine monophosphate | AMP | Purine ribonucleoside monophosphates |
| Deoxyuridine-diphosphate | dUDP | Pyrimidine 2'-deoxyribonucleoside diphosphates |
| Guanosine diphosphate | GDP | Purine ribonucleoside diphosphates |
| Guanosine triphosphate | GTP | Purine ribonucleoside triphosphates |
| Inosine monophosphate | IMP | Purine ribonucleoside monophosphates |
| Methylmalonic-acid | — | Dicarboxylic acids and derivatives |

TABLE 3

| Name | Abbreviation | Sample | Change | Group | Excitatory/Inhibitory | Receptor | Notes |
|---|---|---|---|---|---|---|---|
| D-Alanine | Ala | HPC | Increase | CFC | Inhibitory | Glycine receptor | Has been shown to increase following anti-depressant treatment. |
| D-Serine | Ser | PFC | Decrease | CFC | Excitatory | NDMA receptors and glycine receptors | Coagonist at the glycine site of NDMA receptors. |
| Gamma-aminobuytric acid | GABA | HPC | Increase | CFC | Inhibitory | GABAA receptors and GABAA-p receptors | Low GABA levels have been linked to depression. |
| Glycine | Gly | PFC | Decrease | CFC | Inhibitory/Excitatory | NDMA receptors and glycine receptors | Often released with GABA. |
| L-Glutamic acid | Glu | HPC | Increase | CFC | Excitatory | NDMA receptors and AMPA receptors | Precursor to GABA as well. |
| L-Tyrosine | Tyr | PFC | Decrease | CFC | Excitatory | CaSR | Precursor to neurotransmitters such as tyrosine, dopamine, norepinephrine, and epinephrine. |
| O-Phosphoethanolamine* | PE | HPC | Increase | CFC | — | — | Shows strong structural similarity to GABA. Co-released with taurine. |
| Phenylalanine | Phe | PFC | Decrease | CFC | Excitatory | CaSR | Precursor to neurotransmitters such as tyrosine, dopamine, norephinephrine, and epinephrine. |
| Taurine | Tau | HPC | Increase | CFC and context exposure | Inhibitory | Glycine receptor | Structural resemblance with GABA. |
| 5-Hydroxy-L-tryptophan | 5-HTP | Plasma | Increase | CFC | — | — | Immediate precursor to serotonin (5-HT), which elevates mood. |
| D-Serine | Ser | Plasma | Decrease | CFC | Excitatory | NDMA receptors and glycine receptors | Enhances glutamatergic signalling via NMDARs. |

TABLE 3-continued

| Name | Abbreviation | Sample | Change | Group | Excitatory/Inhibitory | Receptor | Notes |
|---|---|---|---|---|---|---|---|
| Gamma-aminobuytric acid | GABA | Plasma | Decrease | CFC | Inhibitory | GABAA receptors and GABAA-p receptors | Homeostatic balance of GABAergic inhibition is essential for controlling exitatory neurotransmission. |
| L-Glutamic acid | Glu | Plasma | Decrease | CFC | Excitatory | NDMA receptors and AMPA receptors | Precursor to glutamine, which stabilizes the immune system in times of stress. |
| N-Acetyl-L-tyrosine | NALT | Plasma | Decrease | CFC | — | — | Precursor to tyrosine, which converts to norepinephrine (NE) and dopamine (DA), enhancers of mood. |
| O-Phosphoethanolamine* | PE | Plasma | Increase | CFC | — | — | Inhibits mitochondrial dysfunction, suggested to be involved in the pathophysiology of affective illnesses. |

What is claimed is:

1. A method for treating a subject for a stress-induced affective disorder or stress-induced psychopathology, the method comprising:
   (a) administering or having administered a pharmaceutic composition comprising ketamine to the subject prior to a stressor;
   (b) determining level of cytidine monophosphate in a biological sample obtained from the subject after step (a) and after the stressor; and
   (c) comparing the level of cytidine monophosphate obtained in step (b) with the level of cytidine monophosphate in a control sample;
   wherein the stress-induced affective disorder or stress-induced psychopathology is selected from the group consisting of depressive-like behavior and associated affective disorders, anhedonic behavior and associated affective disorders, anxiety and associated affective disorders, cognitive impairments and deficits and associated disorders, and combinations thereof.

2. The method of claim 1, further comprising maintaining a treatment regime, when the level of cytidine monophosphate increases or decreases by at least 10% compared to its level in the control sample.

3. The method of claim 1, further comprising adjusting a treatment regime, when the level of cytidine monophosphate is unchanged, or increases or decreases by less than 10%, compared to its level in the control sample.

4. The method of claim 1, wherein the pharmaceutic composition is administered to the subject about 48 hours to about 3 weeks prior to the stressor.

5. The method of claim 1, wherein the pharmaceutic composition is administered to the subject about 1 week prior to the stressor.

6. The method of claim 1, wherein the pharmaceutic composition is administered to the subject once prior to the stressor.

7. The method of claim 1, wherein the pharmaceutic composition is administered orally, intravenously, intranasally, or via injection to the subject.

8. The method of claim 2, wherein the increase or decrease in the level of cytidine monophosphate is at least 50%.

9. The method of claim 2, wherein the increase or decrease in the level of cytidine monophosphate ranges from about 30% to about 3-fold.

10. The method of claim 1, wherein the biological sample is a plasma, serum, blood or urine sample.

* * * * *